US012766167B2

(12) United States Patent
Chen

(10) Patent No.: US 12,766,167 B2
(45) Date of Patent: Oct. 20, 2026

(54) COMPOSITIONS AND METHODS OF TREATMENT OF VISION LOSS THROUGH GENERATION OF ROD PHOTORECEPTORS FROM MÜLLER GLIAL CELLS

(71) Applicant: ICAHN SCHOOL OF MEDICINE AT MOUNT SINAI, New York, NY (US)

(72) Inventor: Bo Chen, New York, NY (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 1151 days.

(21) Appl. No.: 17/045,256

(22) PCT Filed: Apr. 5, 2019

(86) PCT No.: PCT/US2019/026048

§ 371 (c)(1),
(2) Date: Oct. 5, 2020

(87) PCT Pub. No.: WO2019/195717

PCT Pub. Date: Oct. 10, 2019

(65) Prior Publication Data

US 2022/0040236 A1 Feb. 10, 2022

Related U.S. Application Data

(60) Provisional application No. 62/654,106, filed on Apr. 6, 2018, provisional application No. 62/654,256, filed on Apr. 6, 2018.

(51) Int. Cl.

| | |
|---|---|
| ***A61P 27/06*** | (2006.01) |
| ***A61K 35/30*** | (2015.01) |
| ***C07K 14/47*** | (2006.01) |
| ***C12N 5/079*** | (2010.01) |

(52) U.S. Cl.

CPC .............. *A61K 35/30* (2013.01); *A61P 27/06* (2018.01); *C07K 14/47* (2013.01); *C12N 5/0622* (2013.01)

(58) Field of Classification Search

None

See application file for complete search history.

(56) References Cited

U.S. PATENT DOCUMENTS

| | | | | |
|---|---|---|---|---|
| 8,663,624 | B2 * | 3/2014 | Schaffer | A61K 38/185 424/93.1 |
| 2006/0122111 | A1 * | 6/2006 | Furukawa | A61P 27/02 514/20.8 |
| 2007/0196919 | A1 | 8/2007 | Reh et al. | |
| 2011/0223140 | A1 | 9/2011 | Park et al. | |
| 2011/0223660 | A1 | 9/2011 | Park et al. | |

FOREIGN PATENT DOCUMENTS

| | | | |
|---|---|---|---|
| EP | 2554662 | A1 | 6/2013 |

OTHER PUBLICATIONS

Yao et al., 2016, Cell Reports 17, 165-178 Sep. 27, 2016 (Year: 2016).*

Xue, K., et al. "Technique of retinal gene therapy: delivery of viral vector into the subretinal space." Eye 31.9 (2017): 1308-1316. (Year: 2017).*

Yao, Kai, et al. "Wnt regulates proliferation and neurogenic potential of Müller glial cells via a Lin28/let-7 miRNA-dependent pathway in adult mammalian retinas." Cell reports 17.1 (2016): 165-178. (Year: 2016).*

Hennig, Anne K., Guang-Hua Peng, and Shiming Chen. "Regulation of photoreceptor gene expression by Crx-associated transcription factor network." Brain research 1192 (2008): 114-133. (Year: 2008).*

Thomas, Biju B., et al. "Animal models for the evaluation of retinal stem cell therapies." Progress in retinal and eye research (2025): 101356. (Year: 2025).*

Elsaeidi, Fairouz, et al. "Notch suppression collaborates with Ascl1 and Lin28 to unleash a regenerative response in fish retina, but not in mice." Journal of Neuroscience 38.9 (2018): 2246-2261. (Year: 2018).*

International Search Report and Written Opinion of the International Searching Authority for International Application No. PCT/US2019/026048 mailed on Jun. 14, 2019.

Yao, Kai et al., "Wnt Regulates Proliferation and Neurogenic Potential of Müller Glial Cells via a Lin28/let-7 miRNA-Dependent Pathway in Adult Mammalian Retinas," Cell Reports, vol. 17, No. 1, p. 165-178 (2016).

Nishida, Akihiro et al., "Otx2 homeobox gene controls retinal photoreceptor cell fate and pineal gland development," Nature Neuroscience, vol. 6, No. 12, p. 1255-1263 (2003).

Chen, Shiming et al., "Crx, a Novel Otx-like Paired-Homeodomain Protein, Binds to and Transactivates Photoreceptor Cell-Specific Genes," Neuron, vol. 19, No. 5, p. 1017-1030 (1997).

Ryback, Agnieszka et al., "A feedback loop comprising lin-28 and let-7 controls pre-let-7 maturation during neural stem-cell commitment," Nature Cell Biology, vol. 10, No. 8, p. 987-993 (2008).

(Continued)

*Primary Examiner* — Anoop K Singh
*Assistant Examiner* — Constantina E Stavrou
(74) *Attorney, Agent, or Firm* — Heslin Rothenberg Farley & Mesiti P.C.

(57) ABSTRACT

The present invention provides methods and compositions for inducing differentiation of Müller glial cells into rod photoreceptors through a two-step process of inducing Müller glial cell proliferation by increasing WNT signaling effectors in the Müller glial cell and then directed differentiation into a rod photoreceptor through activation of rod-specific photoreceptor genes. The methods and compositions are useful in a method of treating vision loss or impairment due to photoreceptor loss. The present invention also provides methods for treating vision loss or impairment in a subject comprising (a) administering to the subject a therapeutically effective amount of a Müller glial(MG) cell proliferation agent; and (b)a period of time after the administering of step (a), administering to the subject a therapeutically effective amount of a MG cell differentiation agent.

4 Claims, 53 Drawing Sheets

Specification includes a Sequence Listing.

(56) References Cited

OTHER PUBLICATIONS

Yao, Kai et al., "Restoraion of vision after de novo genesis of rod photoreceptors in mammalian retinas," Nature, vol. 560, No. 7719, p. 484-488.
Boda, Enrica et al., "Emerging pharmacological approached to promoted neurogenesis from endogenous glial cells," Biochemical Pharmacology, vol. 141, p. 23-41 (2017).
Goldman, Daniel, "Müller glia cell reprogramming and retina regeneration," National Reviews Neuroscience, vol. 15, No. 7, p. 431-442 (2014).
Seko, Yuko et al., "Derivation of human differential photoreceptor cells from adult human dermal fibroblasts by defined combinations of CRX, RAX, OTX2 and Neuro, " Genes to Cells, vol. 19, p. 198-208 (2014).
Ahmad, Iqbal et al., "Müller Glia: A Promising Target for Therapeutic Regeneration," Investigative Opthalmology & Visual Sciences, vol. 52, No. 8, p. 5758-5764 (2011).
Leach, Lyndsay L. et al., "Canoncial/ß-Catenin Wnt Pathway Activation Improves Retinal Pigmented Epithelium Derivation From Human Embryonic Stem Cells," Nanotechnology and Regenerative Medicine, vol. 56, p. 1002-1013 (2015).
Annex to Form PCT/ISA/206 Communication Relating to the Results of the Partial International Search of the International Searching Authority for International Application No. PCT/US2019026048 mailed on Dec. 6, 2021.
Leach, Lyndsay L. et al., "Canoncial/B-Catenin Wnt Pathway Activation Improves Retinal Pigmented Epithelium Derivation From Human Embryonic Stem Cells," Investigative Ophthalmology & Visual Science, vol. 56, p. 1002-1013 (2015).
Klimczak, Ryan R., et al.; "A Novel Adeno-Associated Viral Variant for efficient and Selective Intravitreal Transduction of Rat Nuller Cells"; PLoS ONE 2009; 4(10):1-10.
Kotterman, Melissa A., et al.; "Engineered AAV vectors for improved central nervous system gene delivery"; Neurogenesis 2015; 2(1):e1122700-1-e1122700-6.
Westhaus, Adrian, et al.; "AAV capsid bioengineering in primary human retina models"; Scientific Reports 2023; 13(21946):1-31.
Koerber, James T., et al.; "Molecular Evolution of Adeno-associated Virus for Enhanced Glial Gene Delivery"; Molecular Therapy 2009; 17(12):2088-2095.
Bennett, Jean; "Taking Stock of Retinal Gene Therapy: Looking Back and Moving Forward"; Molecular Therapy 2017; 25(5):1076-1094.
Gonzalez-Cordero, Anai, et al.; "Assessment of AAV Vector Tropisms for Mouse and Human Pluripotent Stem Cell-Derived RPE and Photoreceptor Cells"; Human Gene Therapy 2018; 29(10):1124-1139.

* cited by examiner

Control

β-Catenin

β-Catenin

Control

Lin28a

Lin28b

β-Catenin

β-Catenin
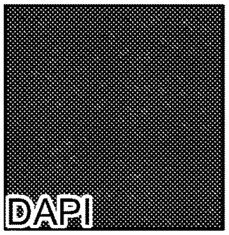
FIG. 17A
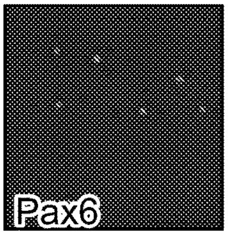
FIG. 17A'
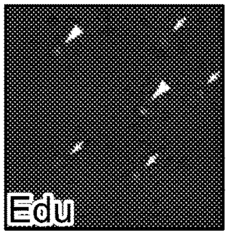
FIG. 17A"
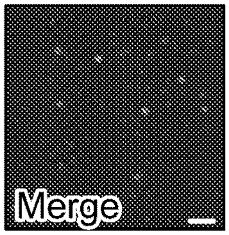
FIG. 17A'"
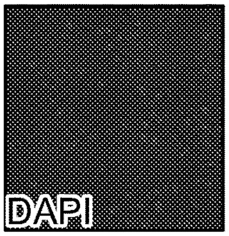
FIG. 17B
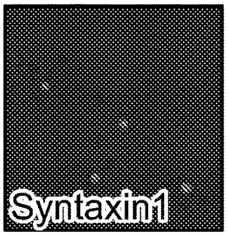
FIG. 17B'
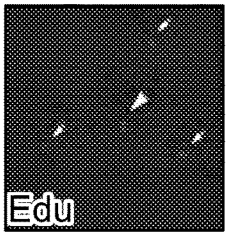
FIG. 17B"
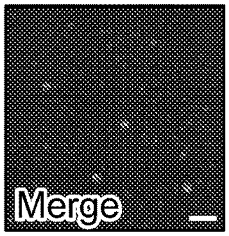
FIG. 17B'"
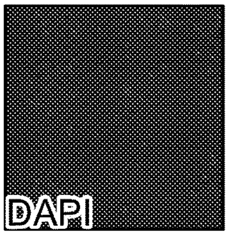
FIG. 17C
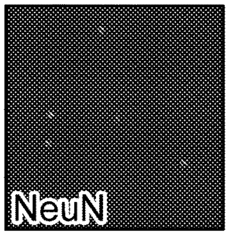
FIG. 17C'
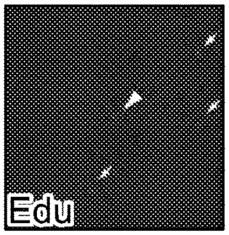
FIG. 17C"
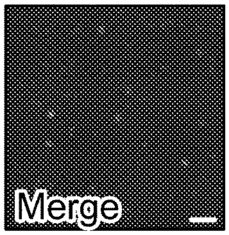
FIG. 17C'"
Lin28a
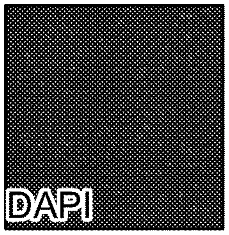
FIG. 17D
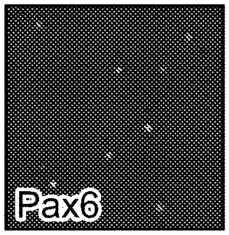
FIG. 17D'
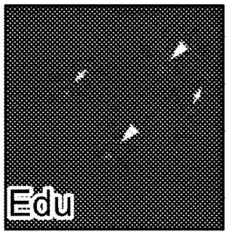
FIG. 17D"
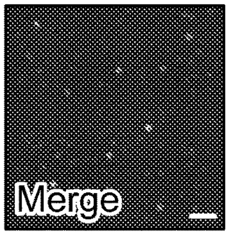
FIG. 17D'"
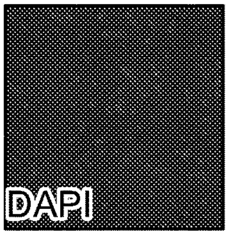
FIG. 17E
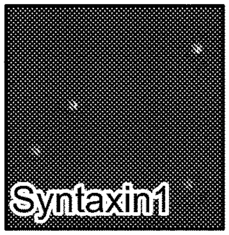
FIG. 17E'
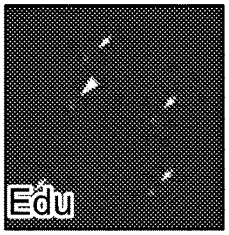
FIG. 17E"
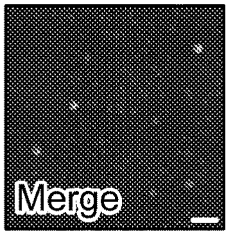
FIG. 17E'"
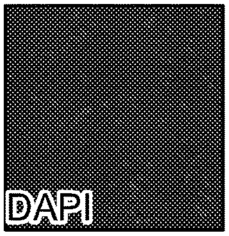
FIG. 17F
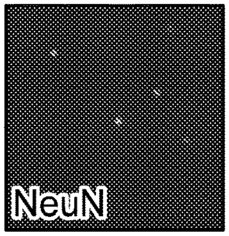
FIG. 17F'
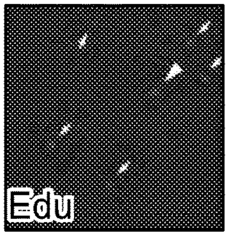
FIG. 17F"
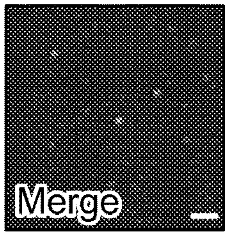
FIG. 17F'"

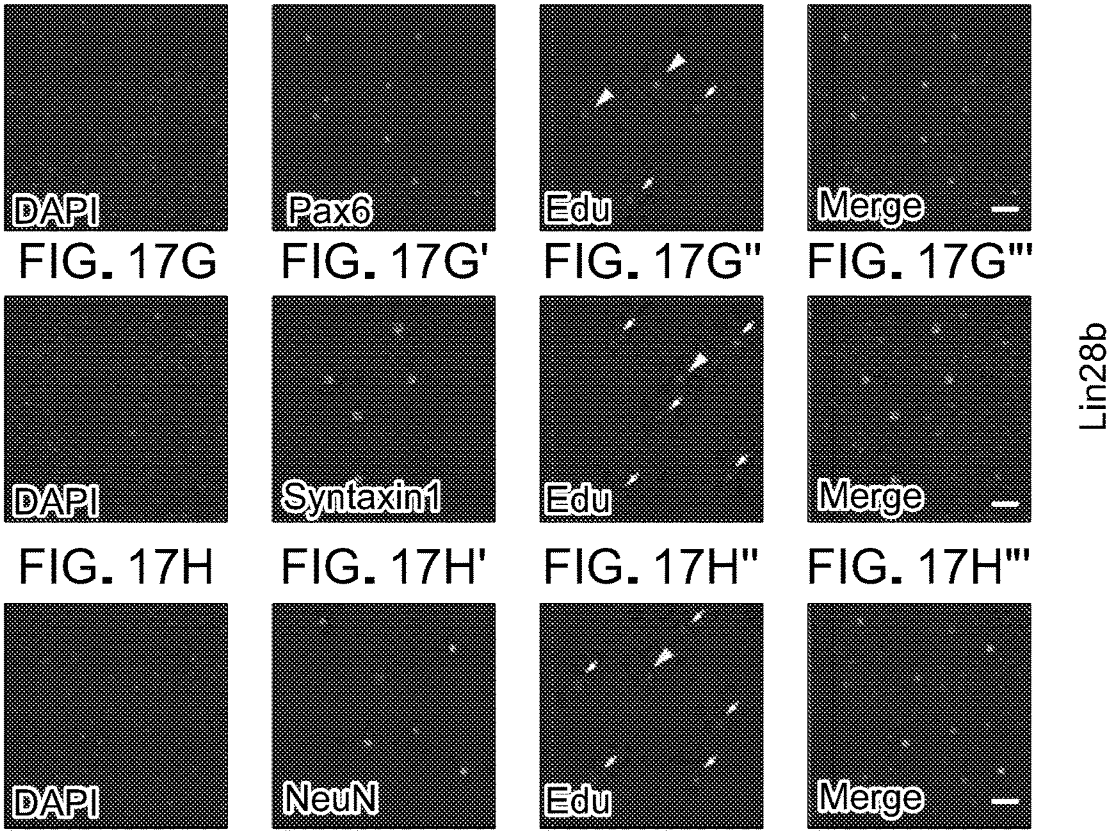
FIG. 17G FIG. 17G' FIG. 17G'' FIG. 17G'''
FIG. 17H FIG. 17H' FIG. 17H'' FIG. 17H'''
FIG. 17I FIG. 17I' FIG. 17I'' FIG. 17I'''
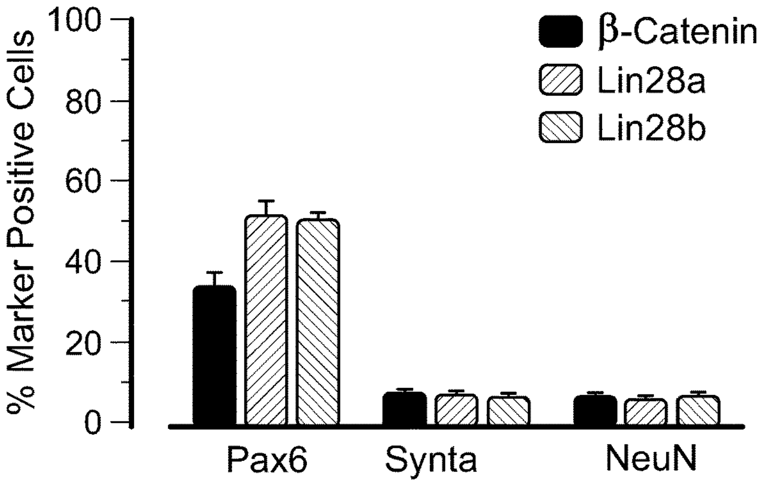
FIG. 17J

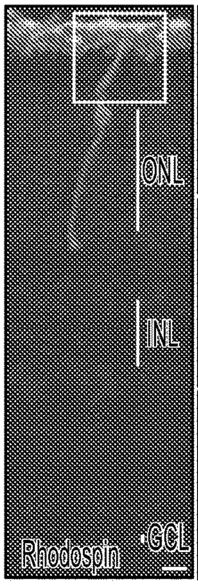
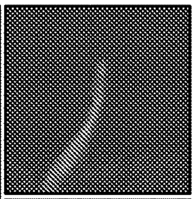
FIG. 29B
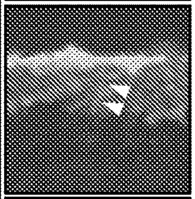
FIG. 29C
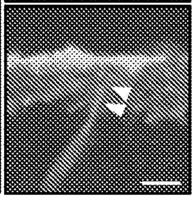
FIG. 29D
FIG. 29A
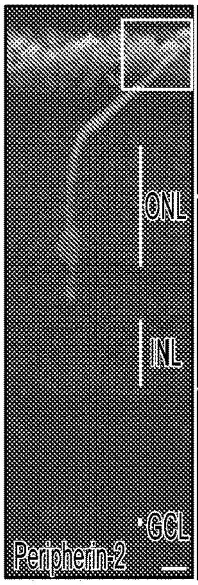
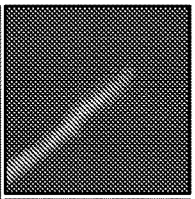
FIG. 29F
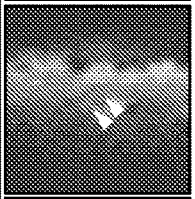
FIG. 29G
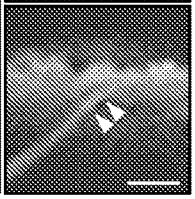
FIG. 29H
FIG. 29E
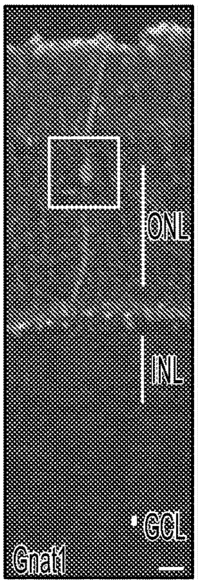
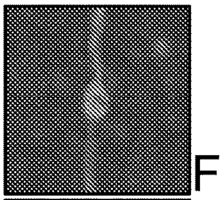
FIG. 29J
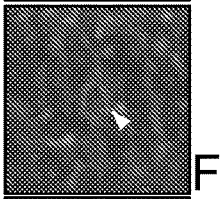
FIG. 29K
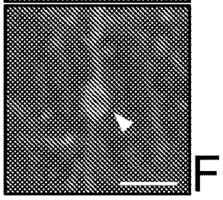
FIG. 29L
FIG. 29I
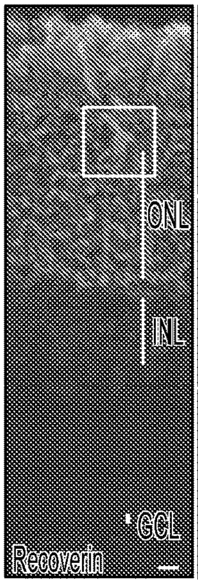
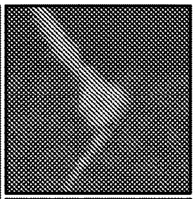
FIG. 29N
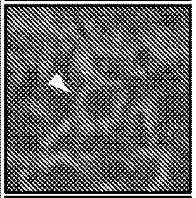
FIG. 29O
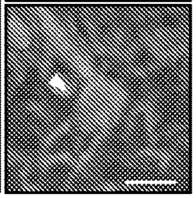
FIG. 29P
FIG. 29M

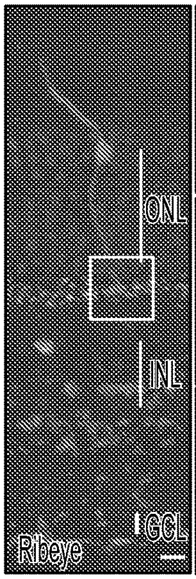
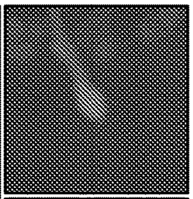
FIG. 29R
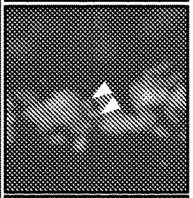
FIG. 29S
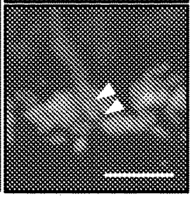
FIG. 29T
FIG. 29Q
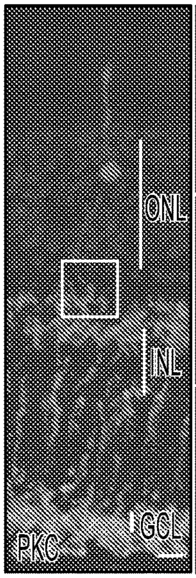
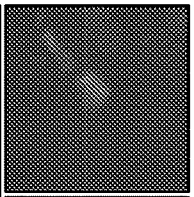
FIG. 29V
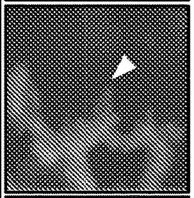
FIG. 29W
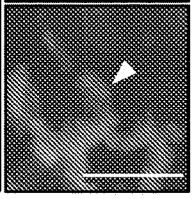
FIG. 29X
FIG. 29U
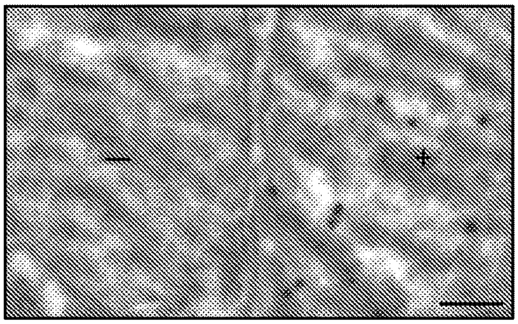
FIG. 29Y
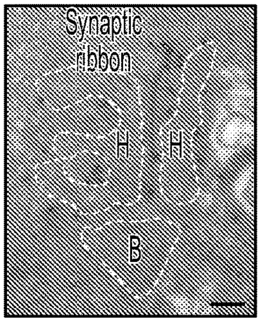
FIG. 29Z'''
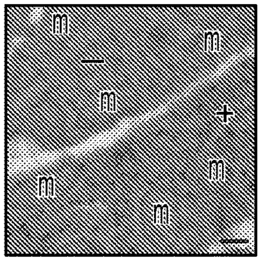
FIG. 29Z
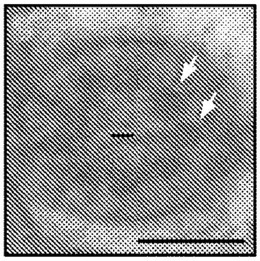
FIG. 29Z'
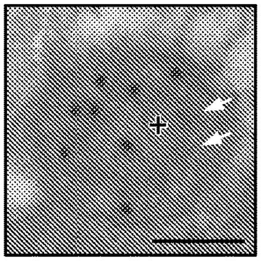
FIG. 29Z"

0 h 24 h

EdU

BrdU

Merge

Otx2

Crx

Nrl

Otx2+Crx

Otx2+Nrl

Crx+Nrl

| Viral constructs | Virus | Titers |
|---|---|---|
| pAAV-GFAP-GFP | ShH10-GFAP-GFP | $2.6 \times 10^{13}$ |
| pAAV-GFAP-β-Catenin | ShH10-GFAP-β-Catenin | $2.9 \times 10^{13}$ |
| pAAV-Rho-tdTomato | ShH10-Rho-tdTomato | $1.8 \times 10^{13}$ |
| pAAV-GFAP-Otx2 | ShH10-GFAP-Otx2 | $4.7 \times 10^{13}$ |
| pAAV-GFAP-Crx | ShH10-GFAP-Crx | $5.0 \times 10^{13}$ |
| pAAV-GFAP-Nrl | ShH10-GFAP-Nrl | $4.8 \times 10^{13}$ |
| pAAV-Rho-Gnat1 | ShH10-Rho-Gnat1 | $1.5 \times 10^{13}$ |
| pAAV-CAG-GFP | 2/5-CAG-GFP | $2.4 \times 10^{13}$ |

FIG. 42

SEQUENCE LISTING

<160> NUMBER OF SEQ ID NOS: 8

<210> SEQ ID NO 1
<211> LENGTH: 781
<212> TYPE: PRT
<213> ORGANISM: Homo sapiens

<400> SEQUENCE: 1

Met Ala Thr Gln Ala Asp Leu Met Glu Leu Asp Met Ala Met Glu Pro
1 5 10 15

Asp Arg Lys Ala Ala Val Ser His Trp Gln Gln Gln Ser Tyr Leu Asp
20 25 30

Ser Gly Ile His Ser Gly Ala Thr Thr Thr Ala Pro Ser Leu Ser Gly
35 40 45

Lys Gly Asn Pro Glu Glu Glu Asp Val Asp Thr Ser Gln Val Leu Tyr
50 55 60

Glu Trp Glu Gln Gly Phe Ser Gln Ser Phe Thr Gln Glu Gln Val Ala
65 70 75 80

Asp Ile Asp Gly Gln Tyr Ala Met Thr Arg Ala Gln Arg Val Arg Ala

-continued

```
                85                  90                  95

Ala Met Phe Pro Glu Thr Leu Asp Glu Gly Met Gln Ile Pro Ser Thr
            100                 105                 110

Gln Phe Asp Ala Ala His Pro Thr Asn Val Gln Arg Leu Ala Glu Pro
        115                 120                 125

Ser Gln Met Leu Lys His Ala Val Val Asn Leu Ile Asn Tyr Gln Asp
    130                 135                 140

Asp Ala Glu Leu Ala Thr Arg Ala Ile Pro Glu Leu Thr Lys Leu Leu
145                 150                 155                 160

Asn Asp Glu Asp Gln Val Val Val Asn Lys Ala Ala Val Met Val His
                165                 170                 175

Gln Leu Ser Lys Lys Glu Ala Ser Arg His Ala Ile Met Arg Ser Pro
            180                 185                 190

Gln Met Val Ser Ala Ile Val Arg Thr Met Gln Asn Thr Asn Asp Val
        195                 200                 205

Glu Thr Ala Arg Cys Thr Ala Gly Thr Leu His Asn Leu Ser His His
    210                 215                 220

Arg Glu Gly Leu Leu Ala Ile Phe Lys Ser Gly Gly Ile Pro Ala Leu
225                 230                 235                 240

Val Lys Met Leu Gly Ser Pro Val Asp Ser Val Leu Phe Tyr Ala Ile
                245                 250                 255

Thr Thr Leu His Asn Leu Leu Leu His Gln Glu Gly Ala Lys Met Ala
            260                 265                 270

Val Arg Leu Ala Gly Gly Leu Gln Lys Met Val Ala Leu Leu Asn Lys
        275                 280                 285

Thr Asn Val Lys Phe Leu Ala Ile Thr Thr Asp Cys Leu Gln Ile Leu
    290                 295                 300

Ala Tyr Gly Asn Gln Glu Ser Lys Leu Ile Ile Leu Ala Ser Gly Gly
305                 310                 315                 320

Pro Gln Ala Leu Val Asn Ile Met Arg Thr Tyr Thr Tyr Glu Lys Leu
                325                 330                 335

Leu Trp Thr Thr Ser Arg Val Leu Lys Val Leu Ser Val Cys Ser Ser
            340                 345                 350

Asn Lys Pro Ala Ile Val Glu Ala Gly Gly Met Gln Ala Leu Gly Leu
        355                 360                 365

His Leu Thr Asp Pro Ser Gln Arg Leu Val Gln Asn Cys Leu Trp Thr
    370                 375                 380

Leu Arg Asn Leu Ser Asp Ala Ala Thr Lys Gln Glu Gly Met Glu Gly
385                 390                 395                 400

Leu Leu Gly Thr Leu Val Gln Leu Leu Gly Ser Asp Asp Ile Asn Val
                405                 410                 415

Val Thr Cys Ala Ala Gly Ile Leu Ser Asn Leu Thr Cys Asn Asn Tyr
            420                 425                 430

Lys Asn Lys Met Met Val Cys Gln Val Gly Gly Ile Glu Ala Leu Val
        435                 440                 445

Arg Thr Val Leu Arg Ala Gly Asp Arg Glu Asp Ile Thr Glu Pro Ala
    450                 455                 460

Ile Cys Ala Leu Arg His Leu Thr Ser Arg His Gln Glu Ala Glu Met
465                 470                 475                 480

Ala Gln Asn Ala Val Arg Leu His Tyr Gly Leu Pro Val Val Val Lys
                485                 490                 495

Leu Leu His Pro Pro Ser His Trp Pro Leu Ile Lys Ala Thr Val Gly
            500                 505                 510
```

```
Leu Ile Arg Asn Leu Ala Leu Cys Pro Ala Asn His Ala Pro Leu Arg
        515                 520                 525

Glu Gln Gly Ala Ile Pro Arg Leu Val Gln Leu Leu Val Arg Ala His
    530                 535                 540

Gln Asp Thr Gln Arg Arg Thr Ser Met Gly Gly Thr Gln Gln Gln Phe
545                 550                 555                 560

Val Glu Gly Val Arg Met Glu Glu Ile Val Glu Gly Cys Thr Gly Ala
                565                 570                 575

Leu His Ile Leu Ala Arg Asp Val His Asn Arg Ile Val Ile Arg Gly
            580                 585                 590

Leu Asn Thr Ile Pro Leu Phe Val Gln Leu Leu Tyr Ser Pro Ile Glu
        595                 600                 605

Asn Ile Gln Arg Val Ala Ala Gly Val Leu Cys Glu Leu Ala Gln Asp
    610                 615                 620

Lys Glu Ala Ala Glu Ala Ile Glu Ala Glu Gly Ala Thr Ala Pro Leu
625                 630                 635                 640

Thr Glu Leu Leu His Ser Arg Asn Glu Gly Val Ala Thr Tyr Ala Ala
                645                 650                 655

Ala Val Leu Phe Arg Met Ser Glu Asp Lys Pro Gln Asp Tyr Lys Lys
            660                 665                 670

Arg Leu Ser Val Glu Leu Thr Ser Ser Leu Phe Arg Thr Glu Pro Met
        675                 680                 685

Ala Trp Asn Glu Thr Ala Asp Leu Gly Leu Asp Ile Gly Ala Gln Gly
    690                 695                 700

Glu Pro Leu Gly Tyr Arg Gln Asp Asp Pro Ser Tyr Arg Ser Phe His
705                 710                 715                 720

Ser Gly Gly Tyr Gly Gln Asp Ala Leu Gly Met Asp Pro Met Met Glu
                725                 730                 735

His Glu Met Gly Gly His His Pro Gly Ala Asp Tyr Pro Val Asp Gly
            740                 745                 750

Leu Pro Asp Leu Gly His Ala Gln Asp Leu Met Asp Gly Leu Pro Pro
        755                 760                 765

Gly Asp Ser Asn Gln Leu Ala Trp Phe Asp Thr Asp Leu
    770                 775                 780
```

<210> SEQ ID NO 2
<211> LENGTH: 209
<212> TYPE: PRT
<213> ORGANISM: Homo sapiens

<400> SEQUENCE: 2

```
Met Gly Ser Val Ser Asn Gln Gln Phe Ala Gly Gly Cys Ala Lys Ala
1               5                   10                  15

Ala Glu Glu Ala Pro Glu Glu Ala Pro Glu Asp Ala Ala Arg Ala Ala
            20                  25                  30

Asp Glu Pro Gln Leu Leu His Gly Ala Gly Ile Cys Lys Trp Phe Asn
        35                  40                  45

Val Arg Met Gly Phe Gly Phe Leu Ser Met Thr Ala Arg Ala Gly Val
    50                  55                  60

Ala Leu Asp Pro Pro Val Asp Val Phe Val His Gln Ser Lys Leu His
65                  70                  75                  80

Met Glu Gly Phe Arg Ser Leu Lys Glu Gly Glu Ala Val Glu Phe Thr
                85                  90                  95

Phe Lys Lys Ser Ala Lys Gly Leu Glu Ser Ile Arg Val Thr Gly Pro
```

```
            100                 105                 110

Gly Gly Val Phe Cys Ile Gly Ser Glu Arg Arg Pro Lys Gly Lys Ser
        115                 120                 125

Met Gln Lys Arg Arg Ser Lys Gly Asp Arg Cys Tyr Asn Cys Gly Gly
    130                 135                 140

Leu Asp His His Ala Lys Glu Cys Lys Leu Pro Pro Gln Pro Lys Lys
145                 150                 155                 160

Cys His Phe Cys Gln Ser Ile Ser His Met Val Ala Ser Cys Pro Leu
                165                 170                 175

Lys Ala Gln Gln Gly Pro Ser Ala Gln Gly Lys Pro Thr Tyr Phe Arg
            180                 185                 190

Glu Glu Glu Glu Glu Ile His Ser Pro Thr Leu Leu Pro Glu Ala Gln
        195                 200                 205

Asn


<210> SEQ ID NO 3
<211> LENGTH: 250
<212> TYPE: PRT
<213> ORGANISM: Homo sapiens

<400> SEQUENCE: 3

Met Ala Glu Gly Gly Ala Ser Lys Gly Gly Gly Glu Glu Pro Gly Lys
1               5                   10                  15

Leu Pro Glu Pro Ala Glu Glu Glu Ser Gln Val Leu Arg Gly Thr Gly
            20                  25                  30

His Cys Lys Trp Phe Asn Val Arg Met Gly Phe Gly Phe Ile Ser Met
        35                  40                  45

Ile Asn Arg Glu Gly Ser Pro Leu Asp Ile Pro Val Asp Val Phe Val
    50                  55                  60

His Gln Ser Lys Leu Phe Met Glu Gly Phe Arg Ser Leu Lys Glu Gly
65                  70                  75                  80

Glu Pro Val Glu Phe Thr Phe Lys Lys Ser Ser Lys Gly Leu Glu Ser
                85                  90                  95

Ile Arg Val Thr Gly Pro Gly Gly Ser Pro Cys Leu Gly Ser Glu Arg
            100                 105                 110

Arg Pro Lys Gly Lys Thr Leu Gln Lys Arg Lys Pro Lys Gly Asp Arg
        115                 120                 125

Cys Tyr Asn Cys Gly Gly Leu Asp His His Ala Lys Glu Cys Ser Leu
    130                 135                 140

Pro Pro Gln Pro Lys Lys Cys His Tyr Cys Gln Ser Ile Met His Met
145                 150                 155                 160

Val Ala Asn Cys Pro His Lys Asn Val Ala Gln Pro Pro Ala Ser Ser
                165                 170                 175

Gln Gly Arg Gln Glu Ala Glu Ser Gln Pro Cys Thr Ser Thr Leu Pro
            180                 185                 190

Arg Glu Val Gly Gly Gly His Gly Cys Thr Ser Pro Pro Phe Pro Gln
        195                 200                 205

Glu Ala Arg Ala Glu Ile Ser Glu Arg Ser Gly Arg Ser Pro Gln Glu
    210                 215                 220

Ala Ser Ser Thr Lys Ser Ser Ile Ala Pro Glu Glu Gln Ser Lys Lys
225                 230                 235                 240

Gly Pro Ser Val Gln Lys Arg Lys Lys Thr
                245                 250
```

<210> SEQ ID NO 4
<211> LENGTH: 2555
<212> TYPE: PRT
<213> ORGANISM: Homo sapiens

<400> SEQUENCE: 4

Met Pro Pro Leu Leu Ala Pro Leu Leu Cys Leu Ala Leu Leu Pro Ala
1 5 10 15

Leu Ala Ala Arg Gly Pro Arg Cys Ser Gln Pro Gly Glu Thr Cys Leu
20 25 30

Asn Gly Gly Lys Cys Glu Ala Ala Asn Gly Thr Glu Ala Cys Val Cys
35 40 45

Gly Gly Ala Phe Val Gly Pro Arg Cys Gln Asp Pro Asn Pro Cys Leu
50 55 60

Ser Thr Pro Cys Lys Asn Ala Gly Thr Cys His Val Val Asp Arg Arg
65 70 75 80

Gly Val Ala Asp Tyr Ala Cys Ser Cys Ala Leu Gly Phe Ser Gly Pro
85 90 95

Leu Cys Leu Thr Pro Leu Asp Asn Ala Cys Leu Thr Asn Pro Cys Arg
100 105 110

Asn Gly Gly Thr Cys Asp Leu Leu Thr Leu Thr Glu Tyr Lys Cys Arg
115 120 125

Cys Pro Pro Gly Trp Ser Gly Lys Ser Cys Gln Gln Ala Asp Pro Cys
130 135 140

Ala Ser Asn Pro Cys Ala Asn Gly Gly Gln Cys Leu Pro Phe Glu Ala
145 150 155 160

Ser Tyr Ile Cys His Cys Pro Pro Ser Phe His Gly Pro Thr Cys Arg
165 170 175

Gln Asp Val Asn Glu Cys Gly Gln Lys Pro Gly Leu Cys Arg His Gly
180 185 190

Gly Thr Cys His Asn Glu Val Gly Ser Tyr Arg Cys Val Cys Arg Ala
195 200 205

Thr His Thr Gly Pro Asn Cys Glu Arg Pro Tyr Val Pro Cys Ser Pro
210 215 220

Ser Pro Cys Gln Asn Gly Gly Thr Cys Arg Pro Thr Gly Asp Val Thr
225 230 235 240

His Glu Cys Ala Cys Leu Pro Gly Phe Thr Gly Gln Asn Cys Glu Glu
245 250 255

Asn Ile Asp Asp Cys Pro Gly Asn Asn Cys Lys Asn Gly Gly Ala Cys
260 265 270

Val Asp Gly Val Asn Thr Tyr Asn Cys Arg Cys Pro Pro Glu Trp Thr
275 280 285

Gly Gln Tyr Cys Thr Glu Asp Val Asp Glu Cys Gln Leu Met Pro Asn
290 295 300

Ala Cys Gln Asn Gly Gly Thr Cys His Asn Thr His Gly Gly Tyr Asn
305 310 315 320

Cys Val Cys Val Asn Gly Trp Thr Gly Glu Asp Cys Ser Glu Asn Ile
325 330 335

Asp Asp Cys Ala Ser Ala Ala Cys Phe His Gly Ala Thr Cys His Asp
340 345 350

Arg Val Ala Ser Phe Tyr Cys Glu Cys Pro His Gly Arg Thr Gly Leu
355 360 365

Leu Cys His Leu Asn Asp Ala Cys Ile Ser Asn Pro Cys Asn Glu Gly
370 375 380

```
Ser Asn Cys Asp Thr Asn Pro Val Asn Gly Lys Ala Ile Cys Thr Cys
385                 390                 395                 400

Pro Ser Gly Tyr Thr Gly Pro Ala Cys Ser Gln Asp Val Asp Glu Cys
                405                 410                 415

Ser Leu Gly Ala Asn Pro Cys Glu His Ala Gly Lys Cys Ile Asn Thr
            420                 425                 430

Leu Gly Ser Phe Glu Cys Gln Cys Leu Gln Gly Tyr Thr Gly Pro Arg
        435                 440                 445

Cys Glu Ile Asp Val Asn Glu Cys Val Ser Asn Pro Cys Gln Asn Asp
    450                 455                 460

Ala Thr Cys Leu Asp Gln Ile Gly Glu Phe Gln Cys Ile Cys Met Pro
465                 470                 475                 480

Gly Tyr Glu Gly Val His Cys Glu Val Asn Thr Asp Glu Cys Ala Ser
                485                 490                 495

Ser Pro Cys Leu His Asn Gly Arg Cys Leu Asp Lys Ile Asn Glu Phe
            500                 505                 510

Gln Cys Glu Cys Pro Thr Gly Phe Thr Gly His Leu Cys Gln Tyr Asp
        515                 520                 525

Val Asp Glu Cys Ala Ser Thr Pro Cys Lys Asn Gly Ala Lys Cys Leu
    530                 535                 540

Asp Gly Pro Asn Thr Tyr Thr Cys Val Cys Thr Glu Gly Tyr Thr Gly
545                 550                 555                 560

Thr His Cys Glu Val Asp Ile Asp Glu Cys Asp Pro Asp Pro Cys His
                565                 570                 575

Tyr Gly Ser Cys Lys Asp Gly Val Ala Thr Phe Thr Cys Leu Cys Arg
            580                 585                 590

Pro Gly Tyr Thr Gly His His Cys Glu Thr Asn Ile Asn Glu Cys Ser
        595                 600                 605

Ser Gln Pro Cys Arg His Gly Gly Thr Cys Gln Asp Arg Asp Asn Ala
    610                 615                 620

Tyr Leu Cys Phe Cys Leu Lys Gly Thr Thr Gly Pro Asn Cys Glu Ile
625                 630                 635                 640

Asn Leu Asp Asp Cys Ala Ser Ser Pro Cys Asp Ser Gly Thr Cys Leu
                645                 650                 655

Asp Lys Ile Asp Gly Tyr Glu Cys Ala Cys Glu Pro Gly Tyr Thr Gly
            660                 665                 670

Ser Met Cys Asn Ile Asn Ile Asp Glu Cys Ala Gly Asn Pro Cys His
        675                 680                 685

Asn Gly Gly Thr Cys Glu Asp Gly Ile Asn Gly Phe Thr Cys Arg Cys
    690                 695                 700

Pro Glu Gly Tyr His Asp Pro Thr Cys Leu Ser Glu Val Asn Glu Cys
705                 710                 715                 720

Asn Ser Asn Pro Cys Val His Gly Ala Cys Arg Asp Ser Leu Asn Gly
                725                 730                 735

Tyr Lys Cys Asp Cys Asp Pro Gly Trp Ser Gly Thr Asn Cys Asp Ile
            740                 745                 750

Asn Asn Asn Glu Cys Glu Ser Asn Pro Cys Val Asn Gly Gly Thr Cys
        755                 760                 765

Lys Asp Met Thr Ser Gly Tyr Val Cys Thr Cys Arg Glu Gly Phe Ser
    770                 775                 780

Gly Pro Asn Cys Gln Thr Asn Ile Asn Glu Cys Ala Ser Asn Pro Cys
785                 790                 795                 800

Leu Asn Gln Gly Thr Cys Ile Asp Asp Val Ala Gly Tyr Lys Cys Asn
```

```
                805                 810                 815

Cys Leu Leu Pro Tyr Thr Gly Ala Thr Cys Glu Val Val Leu Ala Pro
            820                 825                 830

Cys Ala Pro Ser Pro Cys Arg Asn Gly Gly Glu Cys Arg Gln Ser Glu
        835                 840                 845

Asp Tyr Glu Ser Phe Ser Cys Val Cys Pro Thr Gly Trp Gln Gly Gln
    850                 855                 860

Thr Cys Glu Val Asp Ile Asn Glu Cys Val Leu Ser Pro Cys Arg His
865                 870                 875                 880

Gly Ala Ser Cys Gln Asn Thr His Gly Gly Tyr Arg Cys His Cys Gln
                885                 890                 895

Ala Gly Tyr Ser Gly Arg Asn Cys Glu Thr Asp Ile Asp Asp Cys Arg
            900                 905                 910

Pro Asn Pro Cys His Asn Gly Gly Ser Cys Thr Asp Gly Ile Asn Thr
        915                 920                 925

Ala Phe Cys Asp Cys Leu Pro Gly Phe Arg Gly Thr Phe Cys Glu Glu
    930                 935                 940

Asp Ile Asn Glu Cys Ala Ser Asp Pro Cys Arg Asn Gly Ala Asn Cys
945                 950                 955                 960

Thr Asp Cys Val Asp Ser Tyr Thr Cys Thr Cys Pro Ala Gly Phe Ser
                965                 970                 975

Gly Ile His Cys Glu Asn Asn Thr Pro Asp Cys Thr Glu Ser Ser Cys
            980                 985                 990

Phe Asn Gly Gly Thr Cys Val Asp  Gly Ile Asn Ser Phe  Thr Cys Leu
        995                 1000                1005

Cys Pro  Pro Gly Phe Thr Gly  Ser Tyr Cys Gln His  Asp Val Asn
    1010                 1015                 1020

Glu Cys  Asp Ser Gln Pro Cys  Leu His Gly Gly Thr  Cys Gln Asp
    1025                 1030                 1035

Gly Cys  Gly Ser Tyr Arg Cys  Thr Cys Pro Gln Gly  Tyr Thr Gly
    1040                 1045                 1050

Pro Asn  Cys Gln Asn Leu Val  His Trp Cys Asp Ser  Ser Pro Cys
    1055                 1060                 1065

Lys Asn  Gly Gly Lys Cys Trp  Gln Thr His Thr Gln  Tyr Arg Cys
    1070                 1075                 1080

Glu Cys  Pro Ser Gly Trp Thr  Gly Leu Tyr Cys Asp  Val Pro Ser
    1085                 1090                 1095

Val Ser  Cys Glu Val Ala Ala  Gln Arg Gln Gly Val  Asp Val Ala
    1100                 1105                 1110

Arg Leu  Cys Gln His Gly Gly  Leu Cys Val Asp Ala  Gly Asn Thr
    1115                 1120                 1125

His His  Cys Arg Cys Gln Ala  Gly Tyr Thr Gly Ser  Tyr Cys Glu
    1130                 1135                 1140

Asp Leu  Val Asp Glu Cys Ser  Pro Ser Pro Cys Gln  Asn Gly Ala
    1145                 1150                 1155

Thr Cys  Thr Asp Tyr Leu Gly  Gly Tyr Ser Cys Lys  Cys Val Ala
    1160                 1165                 1170

Gly Tyr  His Gly Val Asn Cys  Ser Glu Glu Ile Asp  Glu Cys Leu
    1175                 1180                 1185

Ser His  Pro Cys Gln Asn Gly  Gly Thr Cys Leu Asp  Leu Pro Asn
    1190                 1195                 1200

Thr Tyr  Lys Cys Ser Cys Pro  Arg Gly Thr Gln Gly  Val His Cys
    1205                 1210                 1215
```

```
Glu Ile  Asn Val Asp Asp Cys  Asn Pro Pro Val Asp  Pro Val Ser
    1220                 1225                 1230

Arg Ser  Pro Lys Cys Phe Asn  Asn Gly Thr Cys Val  Asp Gln Val
    1235                 1240                 1245

Gly Gly  Tyr Ser Cys Thr Cys  Pro Pro Gly Phe Val  Gly Glu Arg
    1250                 1255                 1260

Cys Glu  Gly Asp Val Asn Glu  Cys Leu Ser Asn Pro  Cys Asp Ala
    1265                 1270                 1275

Arg Gly  Thr Gln Asn Cys Val  Gln Arg Val Asn Asp  Phe His Cys
    1280                 1285                 1290

Glu Cys  Arg Ala Gly His Thr  Gly Arg Arg Cys Glu  Ser Val Ile
    1295                 1300                 1305

Asn Gly  Cys Lys Gly Lys Pro  Cys Lys Asn Gly Gly  Thr Cys Ala
    1310                 1315                 1320

Val Ala  Ser Asn Thr Ala Arg  Gly Phe Ile Cys Lys  Cys Pro Ala
    1325                 1330                 1335

Gly Phe  Glu Gly Ala Thr Cys  Glu Asn Asp Ala Arg  Thr Cys Gly
    1340                 1345                 1350

Ser Leu  Arg Cys Leu Asn Gly  Gly Thr Cys Ile Ser  Gly Pro Arg
    1355                 1360                 1365

Ser Pro  Thr Cys Leu Cys Leu  Gly Pro Phe Thr Gly  Pro Glu Cys
    1370                 1375                 1380

Gln Phe  Pro Ala Ser Ser Pro  Cys Leu Gly Gly Asn  Pro Cys Tyr
    1385                 1390                 1395

Asn Gln  Gly Thr Cys Glu Pro  Thr Ser Glu Ser Pro  Phe Tyr Arg
    1400                 1405                 1410

Cys Leu  Cys Pro Ala Lys Phe  Asn Gly Leu Leu Cys  His Ile Leu
    1415                 1420                 1425

Asp Tyr  Ser Phe Gly Gly Gly  Ala Gly Arg Asp Ile  Pro Pro Pro
    1430                 1435                 1440

Leu Ile  Glu Glu Ala Cys Glu  Leu Pro Glu Cys Gln  Glu Asp Ala
    1445                 1450                 1455

Gly Asn  Lys Val Cys Ser Leu  Gln Cys Asn Asn His  Ala Cys Gly
    1460                 1465                 1470

Trp Asp  Gly Gly Asp Cys Ser  Leu Asn Phe Asn Asp  Pro Trp Lys
    1475                 1480                 1485

Asn Cys  Thr Gln Ser Leu Gln  Cys Trp Lys Tyr Phe  Ser Asp Gly
    1490                 1495                 1500

His Cys  Asp Ser Gln Cys Asn  Ser Ala Gly Cys Leu  Phe Asp Gly
    1505                 1510                 1515

Phe Asp  Cys Gln Arg Ala Glu  Gly Gln Cys Asn Pro  Leu Tyr Asp
    1520                 1525                 1530

Gln Tyr  Cys Lys Asp His Phe  Ser Asp Gly His Cys  Asp Gln Gly
    1535                 1540                 1545

Cys Asn  Ser Ala Glu Cys Glu  Trp Asp Gly Leu Asp  Cys Ala Glu
    1550                 1555                 1560

His Val  Pro Glu Arg Leu Ala  Ala Gly Thr Leu Val  Val Val Val
    1565                 1570                 1575

Leu Met  Pro Pro Glu Gln Leu  Arg Asn Ser Ser Phe  His Phe Leu
    1580                 1585                 1590

Arg Glu  Leu Ser Arg Val Leu  His Thr Asn Val Val  Phe Lys Arg
    1595                 1600                 1605
```

```
Asp Ala His Gly Gln Gln Met Ile Phe Pro Tyr Tyr Gly Arg Glu
    1610                1615                1620

Glu Glu Leu Arg Lys His Pro Ile Lys Arg Ala Ala Glu Gly Trp
    1625                1630                1635

Ala Ala Pro Asp Ala Leu Leu Gly Gln Val Lys Ala Ser Leu Leu
    1640                1645                1650

Pro Gly Gly Ser Glu Gly Gly Arg Arg Arg Arg Glu Leu Asp Pro
    1655                1660                1665

Met Asp Val Arg Gly Ser Ile Val Tyr Leu Glu Ile Asp Asn Arg
    1670                1675                1680

Gln Cys Val Gln Ala Ser Ser Gln Cys Phe Gln Ser Ala Thr Asp
    1685                1690                1695

Val Ala Ala Phe Leu Gly Ala Leu Ala Ser Leu Gly Ser Leu Asn
    1700                1705                1710

Ile Pro Tyr Lys Ile Glu Ala Val Gln Ser Glu Thr Val Glu Pro
    1715                1720                1725

Pro Pro Pro Ala Gln Leu His Phe Met Tyr Val Ala Ala Ala Ala
    1730                1735                1740

Phe Val Leu Leu Phe Phe Val Gly Cys Gly Val Leu Leu Ser Arg
    1745                1750                1755

Lys Arg Arg Arg Gln His Gly Gln Leu Trp Phe Pro Glu Gly Phe
    1760                1765                1770

Lys Val Ser Glu Ala Ser Lys Lys Lys Arg Arg Glu Pro Leu Gly
    1775                1780                1785

Glu Asp Ser Val Gly Leu Lys Pro Leu Lys Asn Ala Ser Asp Gly
    1790                1795                1800

Ala Leu Met Asp Asp Asn Gln Asn Glu Trp Gly Asp Glu Asp Leu
    1805                1810                1815

Glu Thr Lys Lys Phe Arg Phe Glu Glu Pro Val Val Leu Pro Asp
    1820                1825                1830

Leu Asp Asp Gln Thr Asp His Arg Gln Trp Thr Gln Gln His Leu
    1835                1840                1845

Asp Ala Ala Asp Leu Arg Met Ser Ala Met Ala Pro Thr Pro Pro
    1850                1855                1860

Gln Gly Glu Val Asp Ala Asp Cys Met Asp Val Asn Val Arg Gly
    1865                1870                1875

Pro Asp Gly Phe Thr Pro Leu Met Ile Ala Ser Cys Ser Gly Gly
    1880                1885                1890

Gly Leu Glu Thr Gly Asn Ser Glu Glu Glu Glu Asp Ala Pro Ala
    1895                1900                1905

Val Ile Ser Asp Phe Ile Tyr Gln Gly Ala Ser Leu His Asn Gln
    1910                1915                1920

Thr Asp Arg Thr Gly Glu Thr Ala Leu His Leu Ala Ala Arg Tyr
    1925                1930                1935

Ser Arg Ser Asp Ala Ala Lys Arg Leu Leu Glu Ala Ser Ala Asp
    1940                1945                1950

Ala Asn Ile Gln Asp Asn Met Gly Arg Thr Pro Leu His Ala Ala
    1955                1960                1965

Val Ser Ala Asp Ala Gln Gly Val Phe Gln Ile Leu Ile Arg Asn
    1970                1975                1980

Arg Ala Thr Asp Leu Asp Ala Arg Met His Asp Gly Thr Thr Pro
    1985                1990                1995

Leu Ile Leu Ala Ala Arg Leu Ala Val Glu Gly Met Leu Glu Asp
```

```
    2000                2005                2010

Leu Ile  Asn Ser His Ala Asp  Val Asn Ala Val Asp  Asp Leu Gly
    2015                2020                2025

Lys Ser  Ala Leu His Trp Ala  Ala Ala Val Asn Asn  Val Asp Ala
    2030                2035                2040

Ala Val  Val Leu Leu Lys Asn  Gly Ala Asn Lys Asp  Met Gln Asn
    2045                2050                2055

Asn Arg  Glu Glu Thr Pro Leu  Phe Leu Ala Ala Arg  Glu Gly Ser
    2060                2065                2070

Tyr Glu  Thr Ala Lys Val Leu  Leu Asp His Phe Ala  Asn Arg Asp
    2075                2080                2085

Ile Thr  Asp His Met Asp Arg  Leu Pro Arg Asp Ile  Ala Gln Glu
    2090                2095                2100

Arg Met  His His Asp Ile Val  Arg Leu Leu Asp Glu  Tyr Asn Leu
    2105                2110                2115

Val Arg  Ser Pro Gln Leu His  Gly Ala Pro Leu Gly  Gly Thr Pro
    2120                2125                2130

Thr Leu  Ser Pro Pro Leu Cys  Ser Pro Asn Gly Tyr  Leu Gly Ser
    2135                2140                2145

Leu Lys  Pro Gly Val Gln Gly  Lys Lys Val Arg Lys  Pro Ser Ser
    2150                2155                2160

Lys Gly  Leu Ala Cys Gly Ser  Lys Glu Ala Lys Asp  Leu Lys Ala
    2165                2170                2175

Arg Arg  Lys Lys Ser Gln Asp  Gly Lys Gly Cys Leu  Leu Asp Ser
    2180                2185                2190

Ser Gly  Met Leu Ser Pro Val  Asp Ser Leu Glu Ser  Pro His Gly
    2195                2200                2205

Tyr Leu  Ser Asp Val Ala Ser  Pro Pro Leu Leu Pro  Ser Pro Phe
    2210                2215                2220

Gln Gln  Ser Pro Ser Val Pro  Leu Asn His Leu Pro  Gly Met Pro
    2225                2230                2235

Asp Thr  His Leu Gly Ile Gly  His Leu Asn Val Ala  Ala Lys Pro
    2240                2245                2250

Glu Met  Ala Ala Leu Gly Gly  Gly Gly Arg Leu Ala  Phe Glu Thr
    2255                2260                2265

Gly Pro  Pro Arg Leu Ser His  Leu Pro Val Ala Ser  Gly Thr Ser
    2270                2275                2280

Thr Val  Leu Gly Ser Ser Ser  Gly Gly Ala Leu Asn  Phe Thr Val
    2285                2290                2295

Gly Gly  Ser Thr Ser Leu Asn  Gly Gln Cys Glu Trp  Leu Ser Arg
    2300                2305                2310

Leu Gln  Ser Gly Met Val Pro  Asn Gln Tyr Asn Pro  Leu Arg Gly
    2315                2320                2325

Ser Val  Ala Pro Gly Pro Leu  Ser Thr Gln Ala Pro  Ser Leu Gln
    2330                2335                2340

His Gly  Met Val Gly Pro Leu  His Ser Ser Leu Ala  Ala Ser Ala
    2345                2350                2355

Leu Ser  Gln Met Met Ser Tyr  Gln Gly Leu Pro Ser  Thr Arg Leu
    2360                2365                2370

Ala Thr  Gln Pro His Leu Val  Gln Thr Gln Gln Val  Gln Pro Gln
    2375                2380                2385

Asn Leu  Gln Met Gln Gln Gln  Asn Leu Gln Pro Ala  Asn Ile Gln
    2390                2395                2400
```

Gln Gln Gln Ser Leu Gln Pro Pro Pro Pro Pro Pro Gln Pro His
2405 2410 2415

Leu Gly Val Ser Ser Ala Ala Ser Gly His Leu Gly Arg Ser Phe
2420 2425 2430

Leu Ser Gly Glu Pro Ser Gln Ala Asp Val Gln Pro Leu Gly Pro
2435 2440 2445

Ser Ser Leu Ala Val His Thr Ile Leu Pro Gln Glu Ser Pro Ala
2450 2455 2460

Leu Pro Thr Ser Leu Pro Ser Ser Leu Val Pro Pro Val Thr Ala
2465 2470 2475

Ala Gln Phe Leu Thr Pro Pro Ser Gln His Ser Tyr Ser Ser Pro
2480 2485 2490

Val Asp Asn Thr Pro Ser His Gln Leu Gln Val Pro Glu His Pro
2495 2500 2505

Phe Leu Thr Pro Ser Pro Glu Ser Pro Asp Gln Trp Ser Ser Ser
2510 2515 2520

Ser Pro His Ser Asn Val Ser Asp Trp Ser Glu Gly Val Ser Ser
2525 2530 2535

Pro Pro Thr Ser Met Gln Ser Gln Ile Ala Arg Ile Pro Glu Ala
2540 2545 2550

Phe Lys
2555

<210> SEQ ID NO 5
<211> LENGTH: 805
<212> TYPE: PRT
<213> ORGANISM: Homo sapiens

<400> SEQUENCE: 5

Gly Cys Gly Val Leu Leu Ser Arg Lys Arg Arg Arg Gln His Gly Gln
1 5 10 15

Leu Trp Phe Pro Glu Gly Phe Lys Val Ser Glu Ala Ser Lys Lys Lys
20 25 30

Arg Arg Glu Pro Leu Gly Glu Asp Ser Val Gly Leu Lys Pro Leu Lys
35 40 45

Asn Ala Ser Asp Gly Ala Leu Met Asp Asp Asn Gln Asn Glu Trp Gly
50 55 60

Asp Glu Asp Leu Glu Thr Lys Lys Phe Arg Phe Glu Glu Pro Val Val
65 70 75 80

Leu Pro Asp Leu Asp Asp Gln Thr Asp His Arg Gln Trp Thr Gln Gln
85 90 95

His Leu Asp Ala Ala Asp Leu Arg Met Ser Ala Met Ala Pro Thr Pro
100 105 110

Pro Gln Gly Glu Val Asp Ala Asp Cys Met Asp Val Asn Val Arg Gly
115 120 125

Pro Asp Gly Phe Thr Pro Leu Met Ile Ala Ser Cys Ser Gly Gly Gly
130 135 140

Leu Glu Thr Gly Asn Ser Glu Glu Glu Glu Asp Ala Pro Ala Val Ile
145 150 155 160

Ser Asp Phe Ile Tyr Gln Gly Ala Ser Leu His Asn Gln Thr Asp Arg
165 170 175

Thr Gly Glu Thr Ala Leu His Leu Ala Ala Arg Tyr Ser Arg Ser Asp
180 185 190

Ala Ala Lys Arg Leu Leu Glu Ala Ser Ala Asp Ala Asn Ile Gln Asp

```
        195                 200                 205

Asn Met Gly Arg Thr Pro Leu His Ala Ala Val Ser Ala Asp Ala Gln
    210                 215                 220

Gly Val Phe Gln Ile Leu Ile Arg Asn Arg Ala Thr Asp Leu Asp Ala
225                 230                 235                 240

Arg Met His Asp Gly Thr Thr Pro Leu Ile Leu Ala Ala Arg Leu Ala
                245                 250                 255

Val Glu Gly Met Leu Glu Asp Leu Ile Asn Ser His Ala Asp Val Asn
            260                 265                 270

Ala Val Asp Asp Leu Gly Lys Ser Ala Leu His Trp Ala Ala Ala Val
        275                 280                 285

Asn Asn Val Asp Ala Ala Val Val Leu Leu Lys Asn Gly Ala Asn Lys
    290                 295                 300

Asp Met Gln Asn Asn Arg Glu Glu Thr Pro Leu Phe Leu Ala Ala Arg
305                 310                 315                 320

Glu Gly Ser Tyr Glu Thr Ala Lys Val Leu Leu Asp His Phe Ala Asn
                325                 330                 335

Arg Asp Ile Thr Asp His Met Asp Arg Leu Pro Arg Asp Ile Ala Gln
            340                 345                 350

Glu Arg Met His His Asp Ile Val Arg Leu Leu Asp Glu Tyr Asn Leu
        355                 360                 365

Val Arg Ser Pro Gln Leu His Gly Ala Pro Leu Gly Gly Thr Pro Thr
    370                 375                 380

Leu Ser Pro Pro Leu Cys Ser Pro Asn Gly Tyr Leu Gly Ser Leu Lys
385                 390                 395                 400

Pro Gly Val Gln Gly Lys Lys Val Arg Lys Pro Ser Ser Lys Gly Leu
                405                 410                 415

Ala Cys Gly Ser Lys Glu Ala Lys Asp Leu Lys Ala Arg Arg Lys Lys
            420                 425                 430

Ser Gln Asp Gly Lys Gly Cys Leu Leu Asp Ser Ser Gly Met Leu Ser
        435                 440                 445

Pro Val Asp Ser Leu Glu Ser Pro His Gly Tyr Leu Ser Asp Val Ala
    450                 455                 460

Ser Pro Pro Leu Leu Pro Ser Pro Phe Gln Gln Ser Pro Ser Val Pro
465                 470                 475                 480

Leu Asn His Leu Pro Gly Met Pro Asp Thr His Leu Gly Ile Gly His
                485                 490                 495

Leu Asn Val Ala Ala Lys Pro Glu Met Ala Ala Leu Gly Gly Gly Gly
            500                 505                 510

Arg Leu Ala Phe Glu Thr Gly Pro Pro Arg Leu Ser His Leu Pro Val
        515                 520                 525

Ala Ser Gly Thr Ser Thr Val Leu Gly Ser Ser Ser Gly Gly Ala Leu
    530                 535                 540

Asn Phe Thr Val Gly Gly Ser Thr Ser Leu Asn Gly Gln Cys Glu Trp
545                 550                 555                 560

Leu Ser Arg Leu Gln Ser Gly Met Val Pro Asn Gln Tyr Asn Pro Leu
                565                 570                 575

Arg Gly Ser Val Ala Pro Gly Pro Leu Ser Thr Gln Ala Pro Ser Leu
            580                 585                 590

Gln His Gly Met Val Gly Pro Leu His Ser Ser Leu Ala Ala Ser Ala
        595                 600                 605

Leu Ser Gln Met Met Ser Tyr Gln Gly Leu Pro Ser Thr Arg Leu Ala
    610                 615                 620
```

Thr Gln Pro His Leu Val Gln Thr Gln Gln Val Gln Pro Gln Asn Leu
625 630 635 640

Gln Met Gln Gln Gln Asn Leu Gln Pro Ala Asn Ile Gln Gln Gln Gln
645 650 655

Ser Leu Gln Pro Pro Pro Pro Pro Pro Gln Pro His Leu Gly Val Ser
660 665 670

Ser Ala Ala Ser Gly His Leu Gly Arg Ser Phe Leu Ser Gly Glu Pro
675 680 685

Ser Gln Ala Asp Val Gln Pro Leu Gly Pro Ser Ser Leu Ala Val His
690 695 700

Thr Ile Leu Pro Gln Glu Ser Pro Ala Leu Pro Thr Ser Leu Pro Ser
705 710 715 720

Ser Leu Val Pro Pro Val Thr Ala Ala Gln Phe Leu Thr Pro Pro Ser
725 730 735

Gln His Ser Tyr Ser Ser Pro Val Asp Asn Thr Pro Ser His Gln Leu
740 745 750

Gln Val Pro Glu His Pro Phe Leu Thr Pro Ser Pro Glu Ser Pro Asp
755 760 765

Gln Trp Ser Ser Ser Ser Pro His Ser Asn Val Ser Asp Trp Ser Glu
770 775 780

Gly Val Ser Ser Pro Pro Thr Ser Met Gln Ser Gln Ile Ala Arg Ile
785 790 795 800

Pro Glu Ala Phe Lys
805

<210> SEQ ID NO 6
<211> LENGTH: 236
<212> TYPE: PRT
<213> ORGANISM: Homo sapiens

<400> SEQUENCE: 6

Met Glu Ser Ser Ala Lys Met Glu Ser Gly Gly Ala Gly Gln Gln Pro
1 5 10 15

Gln Pro Gln Pro Gln Gln Pro Phe Leu Pro Pro Ala Ala Cys Phe Phe
20 25 30

Ala Thr Ala Ala Ala Ala Ala Ala Ala Ala Ala Ala Ala Ala Ala Gln
35 40 45

Ser Ala Gln Gln Gln Gln Gln Gln Gln Gln Gln Gln Gln Gln Ala Pro
50 55 60

Gln Leu Arg Pro Ala Ala Asp Gly Gln Pro Ser Gly Gly Gly His Lys
65 70 75 80

Ser Ala Pro Lys Gln Val Lys Arg Gln Arg Ser Ser Ser Pro Glu Leu
85 90 95

Met Arg Cys Lys Arg Arg Leu Asn Phe Ser Gly Phe Gly Tyr Ser Leu
100 105 110

Pro Gln Gln Gln Pro Ala Ala Val Ala Arg Arg Asn Glu Arg Glu Arg
115 120 125

Asn Arg Val Lys Leu Val Asn Leu Gly Phe Ala Thr Leu Arg Glu His
130 135 140

Val Pro Asn Gly Ala Ala Asn Lys Lys Met Ser Lys Val Glu Thr Leu
145 150 155 160

Arg Ser Ala Val Glu Tyr Ile Arg Ala Leu Gln Gln Leu Leu Asp Glu
165 170 175

His Asp Ala Val Ser Ala Ala Phe Gln Ala Gly Val Leu Ser Pro Thr

```
            180                 185                 190

Ile Ser Pro Asn Tyr Ser Asn Asp Leu Asn Ser Met Ala Gly Ser Pro
        195                 200                 205

Val Ser Ser Tyr Ser Ser Asp Glu Gly Ser Tyr Asp Pro Leu Ser Pro
    210                 215                 220

Glu Glu Gln Glu Leu Leu Asp Phe Thr Asn Trp Phe
225                 230                 235


<210> SEQ ID NO 7
<211> LENGTH: 736
<212> TYPE: PRT
<213> ORGANISM: Artificial Sequence
<220> FEATURE:
<223> OTHER INFORMATION: adeno-associated virus ShH10 capsid

<400> SEQUENCE: 7

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Val Gln
```

```
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asp Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Lys Asn Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Ser Thr Asp Pro Ala
            580                 585                 590

Thr Gly Asp Val His Val Met Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys Asn Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735
```

<210> SEQ ID NO 8
<211> LENGTH: 696
<212> TYPE: DNA
<213> ORGANISM: Homo sapiens

<400> SEQUENCE: 8

```
agatctaaca tatcctggtg tggagtaggg gacgctgctc tgacagaggc tcgggggcct     60

gagctggctc tgtgagctgg ggaggaggca gacagccagg cctttgtctg caagcagacc    120

tggcagcatt gggctggccg ccccccaggg cctcctcttc atgcccagtg aatgactcac    180

cttggcacag acacaatgtt cggggtgggc acagtgcctg cttcccgccg caccccagcc    240

cccctcaaat gccttccgag aagcccattg agcagggggc ttgcattgca ccccagcctg    300

acagcctggc atcttgggat aaaagcagca cagcccccta ggggctgccc ttgctgtgtg    360

gcgccaccgg cggtggagaa caaggctcta ttcagcctgt gcccaggaaa ggggatcagg    420

ggatgcccag gcatggacag tgggtggcag ggggggagag gagggctgtc tgcttcccag    480

aagtccaagg acacaaatgg gtgaggggag agctctcccc atagctgggc tgcggcccaa    540

ccccaccccc tcaggctatg ccaggggggtg ttgccagggg cacccgggca tcgccagtct    600

agcccactcc ttcataaagc cctcgcatcc caggagcgag cagagccaga gcaggttgga    660

gaggagacgc atcacctccg ctgctcgcgg ggatcc                              696
```

COMPOSITIONS AND METHODS OF TREATMENT OF VISION LOSS THROUGH GENERATION OF ROD PHOTORECEPTORS FROM MÜLLER GLIAL CELLS

CROSS-REFERENCE TO RELATED APPLICATIONS

This application is a National Stage filing under 35 U.S.C. § 371 of International Application No. PCT/US2019/026048, which was filed on Apr. 5, 2019, and claims the priority benefit of U.S. provisional application Nos. 62/654,256, filed Apr. 6, 2018, and 62/654,106, filed Apr. 6, 2018, each of which application is incorporated by reference herein in its entirety.

STATEMENT OF FEDERALLY SPONSORED RESEARCH

This invention was made with government support under Grant no. EY024986, awarded by the National Institutes of Health. The government has certain rights in the invention.

SEQUENCE LISTING

The present specification is being filed with a computer readable form (CRF) copy of the Sequence Listing. The CRF entitled Sequence_Listing. txt, which was created on Apr. 4, 2019 and is 50,002 bytes in size, is identical to the paper copy of the Sequence Listing and is incorporated herein by reference in its entirety.

BACKGROUND

Müller glial cells (MGs) are the primary support cells in the vertebrate retina. In cold-blooded vertebrates such as zebrafish, MGs are a source of stem cells for they can readily re-enter the cell cycle and replenish lost neurons, establishing a powerful self-repair mechanism (Bernardos et al., J. Neurosci. 2007, 27:7028-7040; Fausett and Goldman, J Neurosci. 2006, 26:6303-6313; Fimbel et al., J Neurosci. 2007, 27:1712-1724; Qin et al., Proc Natl Acad Sci USA, 2009, 106:9310-9315; Ramachandran et al., J Comp Neurol. 2010, 518:4196-4212; Thummel et al., Dev Neurobiol. 2008, 68:392-408). In mammals, however, MGs are naturally quiescent and lack regenerative capability (Sahel et al., Exp Eye Res. 1991, 53:657-664). Recent studies suggest that the regenerative machinery still exists in adult mammalian retina, but to restore the stem cell status of MGs, as evidenced by cell cycle re-entry, requires retinal injury such as neurotoxin treatment (Close et al., Glia, 2006, 54:94-104; Dyer and Cepko, Nat Neurosci. 2000, 3:873-880; Karl et al., Proc Natl Acad Sci USA, 2008, 105:19508-19513; Ooto et al., Proc Natl Acad Sci USA, 2004, 101:13654-13659). This type of injury would be counterproductive for regeneration as it massively kills retinal neurons including retinal ganglion cells and amacrine cells (Dyer and Cepko, Nat Neurosci. 2000, 3:873-880; Karl et al., 2008; Ooto et al., Proc Natl Acad Sci USA, 2004, 101:13654-13659). The molecular nature of injury-induced signals that activates MG proliferation in mammals remains poorly understood.

Photoreceptors are the most abundant cells in the mammalian retina and they mediate the first step in vision. The death of photoreceptors is a leading cause of vision impairment and blindness in major retinal degenerative diseases including age-related macular degeneration (AMD) and retinitis pigmentosa (RP). Extensive research efforts aimed at restoring the regenerative capability of MGs in mammals have met with little success. Current strategies for MG-derived photoreceptor regeneration rely on retinal injury and treatment of the whole retina with various factors. Retinal injury is a prerequisite for restoring the stem/progenitor cell status of adult mammalian MGs, as evidenced by cell cycle re-entry (Close et al., Glia, 2006, 54:94-104; Dyer and Cepko, Nat Neurosci. 2000, 3:873-880; Karl et al., Proc Natl Acad Sci USA, 2008, 105:19508-19513; Osakada et al., J Neurosci. 2007, 27:4210-4219; Takeda et al., Invest Ophtalmol Vis Sci. 2008, 49:1142-1150; Wan et al., Vision Res. 2008, 48:223-234; Wan et al., Biochem Biophys Res Commun. 2007, 363:347-354). However, retinal injury kills retinal neurons in the first place. Neurotoxin-induced retinal injury inevitably causes death of amacrine cells and retinal ganglion cells, and therefore could be counterproductive to the aim of restoring regenerative capabilities in the mammalian retina. Global treatment of the entire retina may lead to undesirable side effects in untargeted cells. There is thus a need in the art for an injury-free strategy of restoring photoreceptor function that would not necessitate inflicting a further damage to a diseased retina. The present invention addresses this unmet need in the art.

SUMMARY

In a first aspect, provided herein is a method of treating vision loss or impairment in a subject, comprising: (a) administering to the subject a therapeutically effective amount of a MG cell proliferation agent; and (b) a period of time after the administering of step (a), administering to the subject a therapeutically effective amount of a MG cell differentiation agent.

In a second aspect, provided herein is a method of treating age-related macular degeneration (AMD), diabetic retinopathy, retrolental fibroplasia, Stargardt disease, retinitis pigmentosa (RP), uveitis, Bardet-Biedl syndrome, or an eye cancer, in a subject, comprising: (a) administering to the subject a therapeutically effective amount of a MG cell proliferation agent; and (b) a period of time after the administering of step (a), administering to the subject a therapeutically effective amount of a MG cell differentiation agent.

In a third aspect, provided herein is a method of generating new rod photoreceptors in a retina in a subject, comprising: (a) administering to the subject a therapeutically effective amount of a MG cell proliferation agent; and (b) a period of time after the administering of step (a), administering to the subject a therapeutically effective amount of a MG cell differentiation agent.

In certain embodiments of the first through third aspects, the proliferation agent comprises a nucleic acid encoding a protein selected from the group consisting of beta-catenin, Lin28a, Lin28b, Notch, and Achaete-Scute family basic helix-loop-helix transcription factor 1 (Ascl1). In certain embodiments, the proliferation agent comprises a nucleic acid encoding beta-catenin. In certain embodiments, the proliferation agent comprises a nucleic acid encoding Ascl1. In certain embodiments, the nucleic acid is operably linked to a promoter, wherein the promoter specifically expresses the nucleic acid in MG cells. In certain embodiments, the promoter is a glial fibrillary acidic protein (GFAP) promoter. In certain embodiments, the GFAP promoter comprises the sequence of SEQ ID NO:8.

In certain embodiments of the first through third aspects, the proliferation agent comprises a vector comprising a protein selected from the group consisting of beta-catenin, Lin28a, Lin28b, Notch, and Ascl1.

In certain embodiments of the first through third aspects, the proliferation agent comprises a vector, wherein the vector comprises a nucleic acid encoding a protein selected from the group consisting of beta-catenin, Lin28a, Lin28b, Notch, and Ascl1. In certain embodiments, the proliferation agent comprises a vector, wherein the vector comprises a nucleic acid encoding beta-catenin. In certain embodiments, the proliferation agent comprises a vector, wherein the vector comprises a nucleic acid encoding Ascl1. In certain embodiments, the nucleic acid is operably linked to a promoter, wherein the promoter specifically expresses the nucleic acid in MG cells. In certain embodiments, the promoter is a GFAP promoter. In certain embodiments, the GFAP promoter comprises the sequence of SEQ ID NO:8.

In certain embodiments, the vector is a virus or a virus-like particle. In certain embodiments, the vector is an adeno-associated virus (AAV). In certain embodiments, the AAV is AAV-ShH10. In certain embodiments, the capsid of the AAV viral vector comprises an amino acid sequence having at least about 85%, at least about 90%, at least about 95%, at least about 98%, at least about 99%, or 100%, amino acid sequence identity to the ShH10 amino acid sequence of SEQ ID NO:7.

In certain embodiments of the first through third aspects, the proliferation agent comprises a protein selected from the group consisting of beta-catenin, Lin28a, Lin28b, Notch, and Ascl1.

In certain embodiments of the first through third aspects, the differentiation agent comprises at least one nucleic acid molecule encoding at least one transcription factor selected from the group consisting of Otx2, Crx, Nrl, Nr2e3, and NueroD. In certain embodiments, the differentiation agent comprises at least one nucleic acid molecule encoding Otx2, Crx, and Nrl. In certain embodiments, the at least one nucleic acid molecule is operably linked to a promoter, wherein the promoter specifically expresses the nucleic acid molecule in MG cells. In certain embodiments, the promoter comprises a GFAP promoter. In certain embodiments, the GFAP promoter comprises the sequence of SEQ ID NO:8.

In certain embodiments of the first through third aspects, the differentiation agent comprises a first nucleic acid molecule, a second nucleic acid molecule, and a third nucleic acid molecule, wherein the first nucleic acid molecule encodes Otx2, wherein the second nucleic acid molecule encodes Crx, and wherein the third nucleic acid molecule encodes Nrl. In certain embodiments, the first nucleic acid molecule is operably linked to a first promoter that specifically expresses the first nucleic acid in an MG cell, the second nucleic acid molecule is operably linked to a second promoter that specifically expresses the second nucleic acid in an MG cell, and the third nucleic acid molecule is operably linked to a third promoter that specifically expresses the third nucleic acid in an MG cell. In certain embodiments, each of the first, second, and/or third promoter comprises a GFAP promoter. In certain embodiments, the GFAP promoter comprises the sequence of SEQ ID NO:8.

In certain embodiments of the first through third aspects, the differentiation agent comprises a first vector, a second vector, and a third vector, wherein the first vector comprises a first nucleic acid molecule, the second vector comprises a second nucleic acid molecule, and the third vector comprises a third nucleic acid molecule, wherein the first nucleic acid molecule encodes a transcription factor selected from the group consisting of Otx2, Crx, Nrl, Nr2e3, and NueroD, the second nucleic acid molecule encodes a transcription factor selected from the group consisting of Otx2, Crx, Nrl, Nr2e3, and NueroD, and the third nucleic acid molecule encodes a transcription factor selected from the group consisting of Otx2, Crx, Nrl, Nr2e3, and NueroD, and wherein each of the first, second, and third nucleic acid molecules encode a different protein. In certain embodiments, the first nucleic acid molecule is operably linked to a first promoter that specifically expresses the first nucleic acid in an MG cell, the second nucleic acid molecule is operably linked to a second promoter that specifically expresses the second nucleic acid in an MG cell, and the third nucleic acid molecule is operably linked to a third promoter that specifically expresses the third nucleic acid in an MG cell. In certain embodiments, each of the first, second, and/or third promoter comprises a GFAP promoter. In certain embodiments, the GFAP promoter comprises the sequence of SEQ ID NO:8. In certain embodiments, the first vector is a first virus or a first virus-like particle, the second vector is a second virus or a second virus-like particle, and the third vector is a third virus or a third virus-like particle. In certain embodiments, the first vector is a first AAV, the second vector is a second AAV, and the third vector is a third AAV. In certain embodiments in which the first vector is a first AAV, the second vector is a second AAV, and the third vector is a third AAV, the capsid of each of the first, second, and third AAV comprises an amino acid sequence having at least about 85%, at least about 90%, at least about 95%, at least about 98%, at least about 99%, or 100%, amino acid sequence identity to the ShH10 amino acid sequence of SEQ ID NO:7. In certain embodiments, the first, second, and/or third AAV is AAV-ShH10. In certain embodiments, the first AAV is AAV-ShH10, the second AAV is AAV-ShH10, and the third AAV is AAV-ShH10.

In certain embodiments of the first through third aspects, the differentiation agent comprises a first vector, a second vector, and a third vector, wherein the first vector comprises a first nucleic acid molecule, the second vector comprises a second nucleic acid molecule, and the third vector comprises a third nucleic acid molecule, wherein the first nucleic acid molecule encodes Otx2, the second nucleic acid molecule encodes Crx, and the third nucleic acid molecule encodes Nrl. In certain embodiments, the first nucleic acid molecule is operably linked to a first promoter that specifically expresses the first nucleic acid in an MG cell, the second nucleic acid molecule is operably linked to a second promoter that specifically expresses the second nucleic acid in an MG cell, and the third nucleic acid molecule is operably linked to a third promoter that specifically expresses the third nucleic acid in an MG cell. In certain embodiments, each of the first, second, and/or third promoter comprises a GFAP promoter. In certain embodiments, the GFAP promoter comprises the sequence of SEQ ID NO:8. In certain embodiments, the first vector is a first virus or a first virus-like particle, the second vector is a second virus or a second virus-like particle, and the third vector is a third virus or a third virus-like particle. In certain embodiments, the first vector is a first AAV, the second vector is a second AAV, and the third vector is a third AAV. In certain embodiments in which the first vector is a first AAV, the second vector is a second AAV, and the third vector is a third AAV, the capsid of each of the first, second, and third AAV comprises an amino acid sequence having at least about 85%, at least about 90%, at least about 95%, at least about 98%, at least about 99%, or 100%, amino acid sequence identity to the ShH10 amino acid sequence of SEQ ID NO:7. In certain embodiments, the first, second, and/or third AAV is AAV- ShH10. In certain embodiments, the first AAV is AAV-ShH10, the second AAV is AAV-ShH10, and the third AAV is AAV-ShH10.

In certain embodiments of the first through third aspects, the differentiation agent comprises Otx2, Crx, and Nrl.

In certain embodiments of the first through third aspects, the differentiation agent comprises a first vector comprising Otx2, a second vector comprising Crx, and a third vector comprising Nrl.

In certain embodiments of the first through third aspects, the administering of step (a) is via intraocular, intravitreal, or topical administration.

In certain embodiments of the first through third aspects, the administering of step (b) is via intraocular, intravitreal, or topical administration.

In certain embodiments of the first through third aspects, the period of time of step (b) is at least one week, at least two weeks, at least three weeks, four weeks. In certain embodiments, the period of time of step (b) is two weeks.

In certain embodiments of the first through third aspects, the subject has a condition associated with vision loss or impairment due to photoreceptor loss. In certain embodiments, the condition is AMD, diabetic retinopathy, retrolental fibroplasia, Stargardt disease, RP, uveitis, Bardet-Biedl syndrome and eye cancers.

In certain embodiments of the first through third aspects, the subject is a human.

In a fourth aspect, provided herein is a nucleic acid molecule encoding at least one transcription factor selected from the group consisting of Otx2, Crx, Nrl, Nr2e3, and NueroD, which is operably linked to a promoter, wherein the promoter expresses the nucleic acid in an MG cell. In certain embodiments, the nucleic acid molecule encodes Otx2. In certain embodiments, the nucleic acid molecule encodes Crx. In certain embodiments, the nucleic acid molecule encodes Nrl. In certain embodiments, the promoter specifically expresses the nucleic acid in an MG cell.

In a fifth aspect, provided herein is a vector comprising a nucleic acid of the fourth aspect. In certain embodiments, the vector is a virus-like particle. In certain embodiments, the vector is a virus. In certain embodiments, the virus is AAV. In certain embodiments, the capsid of the AAV comprises an amino acid sequence having at least about 85%, at least about 90%, at least about 95%, at least about 98%, at least about 99%, or 100%, amino acid sequence identity to the ShH10 amino acid sequence of SEQ ID NO:7. In certain embodiments, the AAV is AAV-ShH10.

In a sixth aspect, provided herein is a composition comprising one or more nucleic acid molecules of the fourth aspect. In certain embodiments, the composition comprises: a first nucleic acid molecule encodes Otx2, a second nucleic acid molecule encodes Crx, and a third nucleic acid molecule encodes Nrl. In certain embodiments, each of the first, second, and third nucleic acid molecules of the composition is operatively bound to a promoter that specifically expresses the nucleic acid in an MG cell. In certain embodiments, each of the first, second, and third nucleic acid molecules of the composition is operatively bound to a GFAP promoter. In certain embodiments, the GFAP promoter comprises the sequence of SEQ ID NO:8.

In a seventh aspect, provided herein is a composition comprising one or more vectors of the fifth aspect. In certain embodiments, the composition comprises: a first vector comprising a first nucleic acid molecule encodes Otx2, a second vector comprising a second nucleic acid molecule encodes Crx, and a third vector comprising a third nucleic acid molecule encodes Nrl. In certain embodiments, each of the first, second, and third vectors is a virus-like particle. In certain embodiments, each of the first, second, and third vectors is a virus. In certain embodiments, the virus is AAV. In certain embodiments, the capsid of the AAV comprises an amino acid sequence having at least about 85%, at least about 90%, at least about 95%, at least about 98%, at least about 99%, or 100%, amino acid sequence identity to the ShH10 amino acid sequence of SEQ ID NO:7. In certain embodiments, each of the first, second, and/or third AAV is AAV-ShH10.

In an eighth aspect, the invention relates to a method for inducing proliferation of a MG cell comprising contacting the MG cell with a composition wherein the composition increases the level or activity of a WNT signaling effector in the cell.

In one embodiment, the method comprises increasing the level or activity of at least one protein selected from the group consisting of β-catenin, Lin28a, and Lin28b.

In one embodiment, the composition comprises at least one nucleic acid molecule encoding at least one protein selected from the group consisting of β-catenin, Lin28a, and Lin28b. In one embodiment, at least one nucleic acid molecule is operationally linked to a promoter for expression in MG cells. In one embodiment, the promoter is the GFAP promoter. In certain embodiments, the GFAP promoter comprises the sequence of SEQ ID NO:8.

In one embodiment, the composition is an inhibitor of GSK3B. In one embodiment, the composition is a let-7 anti-miR.

In a ninth aspect, the invention relates to a method of guiding differentiation of cycling MG cells comprising contacting the MG cells with at least one composition wherein the at least one composition increases the level or activity of at least one protein selected from the group consisting of rhodopsin, rod α-transducin, rod arrestin, phosducin, ROM1, retinal cGMP, Guanylate Cyclase-Activating Protein Photoreceptor 2, Tubby Like Protein 1, Retinoschisin 1, G alpha 1, G gamma 1, cGMP PDE gamma, G beta 1, mUNC119, rod PDE beta, Pleckstrin Homology Domain Retinal Protein 1, Peripherin 2, recoverin, ribeye, bassoon, and CtBP.

In one embodiment, the composition comprises at least one transcription factor selected from the group consisting of Otx2, Crx, Nrl, Nr2e3 and NeuroD. In one embodiment, the composition comprises Otx2, Crx, and Nrl.

In one embodiment, the composition comprises at least one nucleic acid molecule encoding at least one transcription factor selected from the group consisting of Otx2, Crx, Nrl, Nr2e3 and NeuroD. In one embodiment, the nucleic acid molecule is operationally linked to a promoter for expression in MG cells. In one embodiment, the promoter is the GFAP promoter. In certain embodiments, the GFAP promoter comprises the sequence of SEQ ID NO:8.

In one embodiment, the composition comprises a first nucleic acid molecule encoding Otx2, a second nucleic molecule encoding Crx, and a third nucleic acid molecule encoding Nrl. In one embodiment, the first nucleic acid molecule is operationally linked to a promoter for expression in MG cells, the second nucleic acid molecule is operationally linked to a promoter for expression in MG cells, and the third nucleic acid molecule is operationally linked to a promoter for expression in MG cells. In one embodiment, the promoter is the GFAP promoter. In certain embodiments, the GFAP promoter comprises the sequence of SEQ ID NO:8.

In a tenth aspect, the invention relates to a method of treating vision loss or impairment comprising administering to a subject a) a first composition for inducing MG cell proliferation; and b) a second composition for inducing differentiation of proliferating MG cells to rod photoreceptors.

In one embodiment, the first composition increases the level or activity of at least one protein selected from the group consisting of β-catenin, Lin28a, and Lin28b. In one embodiment, the first composition comprises at least one nucleic acid molecule encoding at least one protein selected from the group consisting of β-catenin, Lin28a, and Lin28b. In one embodiment, the at least one nucleic acid molecule is operationally linked to a promoter for expression in MG cells. In one embodiment, the promoter is the GFAP promoter. In certain embodiments, the GFAP promoter comprises the sequence of SEQ ID NO:8.

In one embodiment, the first composition is an inhibitor of GSK3B. In one embodiment, the first composition is a let-7 anti-miR.

In one embodiment, the second composition increases the level or activity of at least one protein selected from the group consisting of rhodopsin, rod α-transducin, rod arrestin, phosducin, ROMI, retinal cGMP, Guanylate Cyclase-Activating Protein Photoreceptor 2, Tubby Like Protein 1, Retinoschisin 1, G alpha 1, G gamma 1, cGMP PDE gamma, G beta 1, mUNC119, rod PDE beta, Pleckstrin Homology Domain Retinal Protein 1, Peripherin 2, recoverin, ribeye, bassoon, and CtBP.

In one embodiment, the second composition comprises at least one transcription factor selected from the group consisting of Otx2, Crx, Nrl, Nr2e3 and NeuroD. In one embodiment, the second composition comprises at least one nucleic acid molecule encoding at least one transcription factor selected from the group consisting of Otx2, Crx, Nrl, Nr2e3 and NeuroD. In one embodiment, at the least one nucleic acid molecule is operationally linked to a promoter for expression in MG cells. In one embodiment, the promoter is the GFAP promoter. In certain embodiments, the GFAP promoter comprises the sequence of SEQ ID NO:8.

In one embodiment, the second composition comprises a first nucleic acid molecule encoding Otx2, a second nucleic acid molecule encoding Crx, and a third nucleic acid molecule encoding Nrl. In one embodiment, the first nucleic acid molecule is operationally linked to a promoter for expression in MG cells, the second nucleic acid molecule is operationally linked to a promoter for expression in MG cells, and the third nucleic acid molecule is operationally linked to a promoter for expression in MG cells. In one embodiment, the promoter is the GFAP promoter. In certain embodiments, the GFAP promoter comprises the sequence of SEQ ID NO:8.

In one embodiment, the first composition and the second composition are administered substantially concurrently. In one embodiment, the first composition is administered at least one week prior to administration of the second composition.

In an eleventh aspect, the invention relates to a composition comprising an expression vector comprising the ShH-10 backbone sequence and the GFAP promoter for expression of the nucleic acid in MG cells. In certain embodiments, the GFAP promoter comprises the sequence of SEQ ID NO:8.

In a twelfth aspect, the invention relates to a composition for inducing proliferation of a MG cell, wherein the composition increases the level or activity of a WNT signaling effector in the cell.

In one embodiment, the composition increases the level or activity of at least one protein selected from the group consisting of β-catenin, Lin28a, and Lin28b. In one embodiment, the composition comprises at least one nucleic acid molecule encoding at least one protein selected from the group consisting of β-catenin, Lin28a, and Lin28b. In one embodiment, the nucleic acid molecule is operationally linked to a promoter for expression in MG cells. In one embodiment, the promoter is the GFAP promoter. In certain embodiments, the GFAP promoter comprises the sequence of SEQ ID NO:8.

In one embodiment, the composition comprises an inhibitor of GSK3B. In one embodiment, the composition comprises a let-7 anti-miR.

In a thirteenth aspect, the invention relates to a composition for guiding differentiation of cycling MG cells, wherein the composition increases the level or activity of at least one protein selected from the group consisting of rhodopsin, rod α-transducin, rod arrestin, phosducin, ROMI, retinal cGMP, Guanylate Cyclase-Activating Protein Photoreceptor 2, Tubby Like Protein 1, Retinoschisin 1, G alpha 1, G gamma 1, cGMP PDE gamma, G beta 1, mUNC119, rod PDE beta, Pleckstrin Homology Domain Retinal Protein 1, Peripherin 2, recoverin, ribeye, bassoon, and CtBP.

In one embodiment, the composition comprises at least one transcription factor selected from the group consisting of Otx2, Crx, Nrl, Nr2e3 and NeuroD. In one embodiment, the composition comprises at least one nucleic acid molecule encoding at least one transcription factor selected from the group consisting of Otx2, Crx, Nrl, Nr2e3 and NeuroD. In one embodiment, the nucleic acid molecule is operationally linked to a promoter for expression in MG cells. In one embodiment, the promoter is the GFAP promoter. In certain embodiments, the GFAP promoter comprises the sequence of SEQ ID NO:8.

In one embodiment, the composition comprises Otx2, Crx, and Nrl. In one embodiment, the composition comprises a first nucleic acid molecule encoding Otx2, a second nucleic acid molecule encoding Crx, and a third nucleic acid molecule encoding Nrl. In one embodiment, the first nucleic acid molecule is operationally linked to a promoter for expression in MG cells, the second nucleic acid molecule is operationally linked to a promoter for expression in MG cells, and the third nucleic acid molecule is operationally linked to a promoter for expression in MG cells. In one embodiment, the promoter is the GFAP promoter. In certain embodiments, the GFAP promoter comprises the sequence of SEQ ID NO:8.

DESCRIPTION OF DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1, comprising FIG. 1A through FIG. 1K, depicts a time course analysis of NMDA-induced cell death. FIG. 1A through FIG. 1J depict adult mouse retinas collected at 0, 3, 6, 12, 18, 24, 36, 48, 60 and 72 hours after NMDA injection respectively and immunostained with an anti-HuC/D antibody. Confocal images of the retinal ganglion cell layer are presented to show the loss of ganglion and amacrine cells after NMDA damage over time. Scale bar: 20 μm. FIG. 1K depicts the number of HuC/D+ cells as a percentage relative to the onset of the treatment. Data are presented as mean±sem, n=4.

FIG. 2, comprising FIG. 2A depicts a time course analysis of MG proliferation by scoring the number of $EdU^+$ cells/$mm^2$ on retinal flat-mount preparations following NMDA-induced neurotoxic injury. Data are presented as mean±sem, n=4. FIG. 2B depicts representative images of EdU detection/anti-CyclinD3 or EdU detection/anti-$p27^{kip1}$ immunohistochemistry at each time point. Arrow heads: $EdU^+$ cells were double positive for CyclinD3 or $p27^{kip1}$ immunoreactivity. Scale bar: 25 μm. FIG. 2C depicts a time course analysis of the RNA levels for Wnt genes, Wnt antagonists Dkk1 and WIF-1 following NMDA-induced neurotoxic injury. FIG. 2D depicts a time course analysis of the RNA levels for Wnt target genes following NMDA-induced neurotoxic injury. Data are presented as mean±sem, n=4. FIG. 2E depicts MGs visualized as tdTomato+ cells in Rosa26-tdTomato reporter mice. ONL: outer nuclear layer; INL: inner nuclear layer; GCL: ganglion cell layer. FIG. 2F depicts the RNA levels for Wnt genes, Wnt antagonists Dkk1 and WIF-1 in FACS-purified MGs and non-MGs at 18 hours after neurotoxic injury. Data are presented as mean±sem, n=3. * p<0.001, Student's t test. FIG. 2G depicts the RNA levels for Wnt target genes in FACS-purified MGs and non-MGs at 18 hours after neurotoxic injury. Data are presented as mean±sem, n=3.  p<0.01, * p<0.001, Student's t test. FIGS. 2H and 2I depict inhibition of Wnt signaling suppresses neurotoxic injury-induced MG proliferation. In comparison to NMDA treatment alone (FIG. 2H), Wnt inhibitor XAV939 treatment (FIG. 2I) significantly reduced the number of $EdU^+$ 60 hours after NMDA injection. Scale bar: 50 μm. FIG. 2J depicts quantification of $EdU^+$ cells after XAV939 treatment. Data are presented as mean±sem, n=4. * p<0.001, Student's t test.

FIG. 3, comprising FIG. 3G-FIG. 3O depict ShH10-GFAP-GFP infected retinas immunostained for MG-specific antigens: glutamine synthase (GS in FIG. 3G-FIG. 3I), $p27^{kip1}$ (FIG. 3J-FIG. 3L), and CyclinD3 (FIG. 3M-FIG. 3O). ShH10-GFAP mediated gene transfer of GFP was detected in the MG processes indicated by arrows in FIG. 3I, as well as in the MG nuclei indicated by arrows in FIG. 3L and FIG. 3O. Scale bars: 25 μm.

FIG. 4, comprising FIG. 4A and FIG. 4B depicts an assay of Wnt reporter activation in the presence (FIG. 4B) or absence (FIG. 4A) of β-catenin. Scale bar: 20 μm. FIG. 4C depicts gene transfer of β-catenin in MGs activates the expression of Wnt target genes: Ccnd1, Lef1, and Axin2. RNA levels were quantified in comparison to ShH10-GFAP-GFP infected retinas as a control using quantitative PCR at 1, 2, and 4 weeks post-viral infection. Data are presented as mean±sem, n=4.  p<0.01, * p<0.001, Student's t test.

FIG. 5Z depicts anti-CyclinD3 immunohistochemistry in untreated and β-catenin treated retinas at 2 weeks after viral infection. The number of CyclinD3+ cells was quantified per 100 μm in retinal sections. Data are presented as mean±sem, n=4. Scale bars in FIG. 5C, FIG. 5O, FIG. 5I, and FIG. 5U: 25 μm; Scale bars in FIG. 5F, FIG. 5R, FIG. 5L, and FIG. 5X: 10 μm. Scale bars in FIG. 5Z: 20 μm.

FIG. 6, comprising FIG. 6A—FIG. 6D depict co-detection of EdU and cell proliferation antigen Ki67. FIG. 6E—FIG. 6H depict co-detection of EdU and cell proliferation antigen phosphohistone H3 (PH3). The boxed areas in FIG. 6A and FIG. 6E are enlarged in FIG. 6B—FIG. 6D and FIG. 6F-FIG. 6H, respectively. FIG. 6I depicts analysis of the percentage of $Ki67^+$ cells that were also $EdU^+$, the percentage of $PH3^+$ cells that were also $EdU^+$, and vice versa. Data are presented as mean±sem, n=5. Scale bars in FIG. 6A and FIG. 6E: 20 μm; Scale bars in FIG. 6D and FIG. 6H: 5 μm.

FIG. 7, comprising FIG. 7A and FIG. 7B depict ShH10-GFAP-GFP infection itself did not lead to detection of $EdU^+$ cells in the whole retina. FIG. 7C and FIG. 7D depict many MGs re-entered the cell cycle two weeks after ShH10-GFAP-mediated gene transfer of β-catenin and GFP (co-infection marker). FIG. 7E depicts the number of $EdU^+$ cells/$mm^2$ in each of the four retinal quadrants (Dorasal, Ventral, Nasal, and Temporal) was quantified at 700 μm, 1400 μm, and 2100 μm from the center of the retina. Data are presented as mean±sem, n=21. FIG. 7F depicts quantification of the number of $EdU^+$ cells/$mm^2$ at different distances from the center of the retina. Data are presented as mean±sem, n=21. * p<0.05, * p<0.001, Student's t test. Scale bar: 1 mm. FIG. 7G through FIG. 7**I depict EdU incorporation analysis performed on retinas that were dissociated two weeks after ShH10-GFAP-mediated gene transfer of β-catenin and GFP (co-infection marker). Arrowheads: $GFP^+$ cells that were also $EdU^+$. Scale bar: 20 μm.

FIG. 8, comprising FIG. 8M and FIG. 8N depict that GSK3ß deletion activates Wnt reporter gene. ShH10-Wnt-GFP reporter was injected intravitreally into adult GSK3B$^{loxp/loxp}$ mice in the absence (FIG. 8M) or presence (FIG. 8N) of ShH10-GFAP-Cre co-infection. Scale bars: 20 μm.

FIG. 9, comprising FIG. 9A through FIG. 9F depict co-detection of EdU and anti-CyclinD3 immunoreactivity in the absence (FIG. 9A-FIG. 9C) or presence (FIG. 9D-FIG. 9F) of ShH10-GFAP-Cre infection. FIG. 9G through FIG. 9L depict co-detection of EdU and anti-p27$^{kip1}$ immunoreactivity in the absence (FIG. 9G-FIG. 91) or presence (FIG. 9J-FIG. 9L) of ShH10-GFAP-Cre infection. The boxed areas in FIG. 9F and FIG. 9L are enlarged to show co-labeling of EdU and MG-specific antigens. Arrows: EdU' cells were also positive for anti-CyclinD3 (FIG. 9F) or anti-p27$^{kip1}$ (FIG. 9L) immunoreactivity. Scale bars: 50 μm.

FIG. 10, comprising FIG. 10A depicts gene transfer of β-catenin, or GFP as a control, resulted in an increase in the RNA levels for Lin28a and Lin28b measured by quantitative PCR. Data are presented as mean±sem, n=5. * p<0.001, Student's t test. FIG. 10B through FIG. 10M depict immunohistochemistry to detect Lin28a (FIG. 10B-FIG. 10G) or Lin28b (FIG. 10H-FIG. 10**M) at two weeks after ShH10-GFAP-β-catenin infection. Scale bars: 20 μm.

FIG. 11, comprising FIG. 11A through FIG. 11F depict Lin28a-GFP promoter reporter analysis in HEK293T cells transfected with pCAG-tdTomato (transfection marker), in the absence (FIG. 11A-FIG. 11C) or presence (FIG. 11D-FIG. 11F) of pCAG-Flag-β-catenin co-transfection. FIG. 11G through FIG. 111 depict mutation of the β-catenin binding sites in the Lin28a promoter abolished the reporter activity. FIG. 11J through FIG. 110 depict Lin28b-GFP reporter analysis in HEK293T cells transfected with pCAG-tdTomato (transfection marker), in the absence (FIG. 11J-FIG. 11L) or presence (FIG. 11M-FIG. 11O) of pCAG-Flag-β-catenin co-transfection. FIG. 11W and FIG. 11X depict quantification of the promoter reporter activity, represented by normalized GFP intensity, for Lin28a (FIG. 11W) and Lin28b (FIG. 11X). Scale bars: 20 μm. Data are presented as mean±sem, n=4. *** p<0.001, One-way ANOVA.

FIG. 12, comprising FIG. 12A through FIG. 12T, depicts results of example experiments demonstrating that Wnt/β-catenin transactivates Lin28a and Lin28b in MGs in adult mouse retina. FIG. 12A through FIG. 12F depict Lin28a-GFP reporter analysis in retinas infected with ShH10-GFAP-tdTomato (infection marker), in the absence (FIG. 12A-FIG. 12C) or presence (FIG. 12D—FIG. 12F) of ShH10-GFAP-β-catenin co-infection. FIG. 12G through FIG. 121 depict mutation of the β-catenin binding sites in the Lin28a promoter abolished the reporter activity. FIG. 12J through FIG. 120 depict Lin28b-GFP reporter analysis in retinas infected with ShH10-GFAP-tdTomato (infection marker), in the absence (FIG. 12J—FIG. 12L) or presence (FIG. 12M-FIG. 120) of ShH10-GFAP-β-catenin co-infection. FIG. 12P through FIG. 12R depict mutation of the β-catenin binding sites on the Lin28b promoter abolished the reporter activity. Scale bars: 20 μm. FIG. 12S and FIG. 12T depict ChIP analysis which reveals direct binding of β-catenin to the Lin28a (FIG. 12S) or the Lin28b (FIG. 12T) promoter. Adult mouse retinas were infected with ShH10-Lin28-GFP or Lin28mut-GFP, in the presence or absence of ShH10-GFAP-β-catenin co-infection. Chromatin, immunoprecipitated with an antibody specific to β-catenin, was assayed by PCR with primers flanking the putative β-catenin binding sites 1 and 2.

FIG. 13, comprising FIG. 13A through FIG. 131, depicts results of example experiments demonstrating that Lin28 plays an essential role in MG proliferation in adult mouse retina. FIG. 13A through FIG. 13C depict Lin28 is sufficient to stimulate MG proliferation without retinal injury. ShH10-GFAP-mediated gene transfer of Lin28a (FIG. 13A) or Lin28b (FIG. 13B) led to proliferative response of MGs, analyzed by EdU incorporation and quantified (FIG. 13C) in comparison to β-catenin gene transfer and GSK3β deletion. FIG. 13G through FIG. 131 depict co-deletion of Lin28a and Lin28b largely suppresses NMDA-induced MG proliferation. Lin28a$^{loxp/loxp}$; Lin28b$^{loxp/loxp}$ double floxed mice were infected with ShH10-GFAP-GFP (FIG. 13G) or ShH10-GFAP-Cre (FIG. 13H) two weeks before NMDA damage. MG proliferation was analyzed and quantified (FIG. 131) by EdU incorporation. Scale bars: 50 μm. Data are presented as mean±sem, n=4. *** p<0.001, Student's t test.

FIG. 14, comprising FIG. 14A depicts ShH10-GFAP-mediated gene transfer of β-catenin downregulates let-7a, let-7b, and let-7f miRNA levels in the adult mouse retina. Data are presented as mean±sem, n=3. * p<0.001, Student's t test. FIG. 14B depicts co-deletion of Lin28a and Lin28b largely neutralizes β-catenin-induced suppression of let-7a, let-7b, and let-7f miRNAs. Data are presented as mean±sem, n=3. * p<0.001, One-way ANOVA analysis. FIG. 14C through FIG. 14E depict co-expression of let-7b miRNA abolishes β-catenin-mediated effects on MG proliferation, analyzed and quantified (FIG. 14E) by EdU incorporation. Scale bar: 25 μm. Data are presented as mean±sem, n=4. *** p<0.001, Student's t test.

FIG. 15, comprising

FIG. 17, comprising FIG. 17A through FIG. 17J, wherein each of FIG. 17A through FIG. 17I comprises four panels demarked as X, X', X" and X'" with X representing the letters A through I respectively, depicts results of example experiments demonstrating that a subset of cell cycle reactivated MGs express markers for amacrine cells. Adult mouse retinas were treated with EdU at 10 days after infection with ShH10-GFAP-β-catenin, Lin28a, or Lin28b. Treated retinas were dissociated 4 days after EdU treatment and analyzed for EdU incorporation and immunohistochemistry for amacrine cell markers: Pax6, Syntaxin1, and NeuN. FIG. 17A through FIG. 17C depict co-detection of EdU and the expression of amacrine cell markers in ShH10-GFAP-β-catenin infected retinas. FIG. 17D through FIG. 17F depict co-detection of EdU and the expression of amacrine cell markers in ShH10-GFAP-Lin28a infected retinas. FIG. 17G through FIG. 17I depict co-detection of EdU and the expression of amacrine cell markers in ShH10-GFAP-Lin28b infected retinas. Arrows: EdU positive but marker negative cells. Arrow heads: cells double positive for EdU and marker. Scale bars: 40 μm. FIG. 17J depicts an analysis of the percentage of $EdU^+$ cells that were also $Pax6^+$, $Syntaxin1^+$ or $NeuN^+$. Data are presented as mean±sem, n=4.

FIG. 21, comprising FIG. 21A depicts GFP expression driven by a CAG promoter. FIG. 21B depicts tdTomato expression driven by a rhodopsin promoter.

FIG. 23, comprising FIG. 23A through FIG. 231, depicts differentiation stages of MG-derived rod photoreceptors. FIG. 23A through FIG. 23C depict the initial stage. FIG. 23D through FIG. 23F depict the intermediate stage. FIG. 23G through FIG. 231 depict the terminal stage. Arrow heads: cell soma. Arrows: rod photoreceptor outer segment. Scale bar: 25 μm.

FIG. 24, comprising FIG. 24A depicts co-injected AAV2/5-CAG-GFP. FIG. 24B depicts ShH10-rhodopsin-tdTomato.

FIG. 25, comprising FIG. 25A depicts untreated MG fate mapping mice with MGs labeled by tdTomato. FIG. 25B depicts MG fate mapping mice treated with the two-step rod induction protocol. Arrow heads: rod soma. Arrows: rod outer segments. Scale bar: 20 μm.

FIG. 26, comprising FIG. 26A depicts regenerated rods labeled by ShH10-rhodopsin-tdTomato. CtBP immunoreactivity. The boxed area in FIG. 26A is amplified in FIG. 26B through FIG. 26D. Arrow: CtBP expression in the rod synapse. Scale bar in FIG. 26A: 25 μm. Scale bar in FIG. 26D: 5 μm.

FIG. 27, comprising FIG. 27A through FIG. 27C depict the localization of Gnat1 in the dark. FIG. 27D through FIG. 27F depict the localization of Gnat1 after light stimulation. Gnat1 immunoreactivity and co-expressed ShH10-rhodopsin-tdTomato. Scale bar: 25 μm.

FIG. 29. MG-derived rod photoreceptors express essential rod genes and are morphologically similar to native rod photoreceptors. a-t, MG-derived rods correctly expressed a set of essential rod genes, including Rhodopsin (a-d), Peripherin-2 (e-h), Gnat1 (i-l), Recoverin (m-p), and Ribeye (q-t). Arrowheads indicate detection of immunoreactivity in MG-derived rods. u-x, MG-derived rods had an enlarged bouton-like synaptic terminal in close apposition to the $PKC\alpha^+$ rod bipolar cells. Arrowheads indicate rod bipolar dendrites in close proximity to the MG-derived rod terminal. Scale bars: 20 μm (a, e, i, m, q, u); 10 μm (b-d, f-h, j-1, n-p); 5 μm (r-t, v-x). y-z", Ultrastructural analysis of MG-derived rods using transmission electron microscopy indicates correct formation of the rod outer segments containing densely packed membrane discs (y), rod inner segments containing long thin mitochondria (z), connecting cilium with microtubule doublets (arrow heads) arranged in a circle (z', z"), and classic triad synapse with horizontal axon terminals (letter H) and bipolar dendritic terminal (letter B) (z"). +, immunogold-labeled MG-derived rods. –, native rods. m, mitochondrion. Scale bar: 200 nm.

FIG. 3O. MG-derived regeneration of rod photoreceptors in adult $Gnat1^{-/-}$: $Gnat2^{epfl3}$ mice. a-f, Gnat1, detected by immunohistochemistry in Rhodopsin-$tdTomato^+$ MG-derived rods (b, e), translocated from the rod outer segments in the dark-adapted retina (a-c) to the rod inner segments, rod soma, and synaptic terminals (d-f) upon light stimulation. Experiments were performed 4 weeks after the second injection for rod induction in adult $Gnat1^{-/-}$:$Gnat2^{epfl3}$ mice. g-k, Effective generation of MG-derived rod photoreceptors in adult $Gnat1^{-/-}$:$Gnat2^{epfl3}$ mice, analyzed by scoring the number of Rhodopsin-$tdTomato^+$ MG-derived rods per $mm^2$ (k) in the Dorsal (g), Nasal (h), Temporal (i), and Ventral (i) quadrants in retinal flat-mount preparations. Scale bar: 20 μm. Data in (k) are presented as mean±SEM, n=4 retinas.

FIG. 42. Table of viral constructs, packaged viruses, and the virus titers after purification and concentration.

DETAILED DESCRIPTION

Figure 1A:
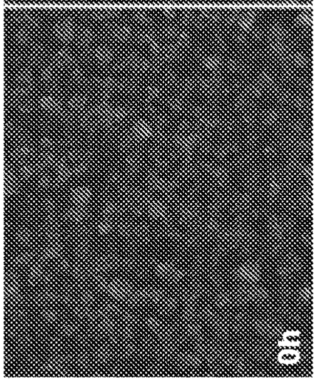
Figure 1B:
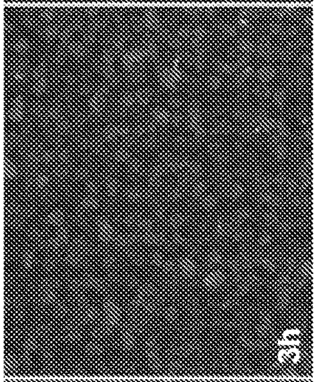
Figure 1C:
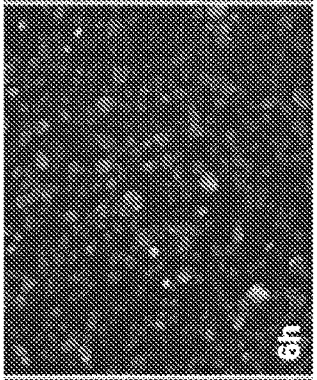
Figure 1D:
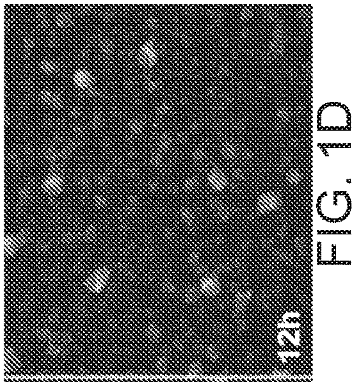
Figure 1E:
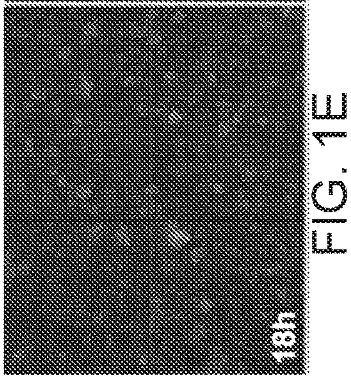
Figure 1F:
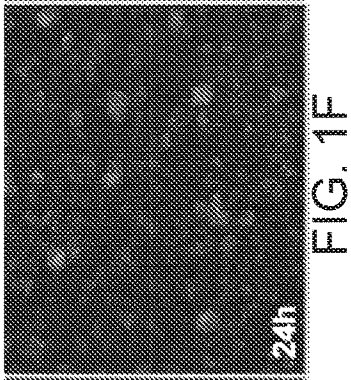
Figure 1G:
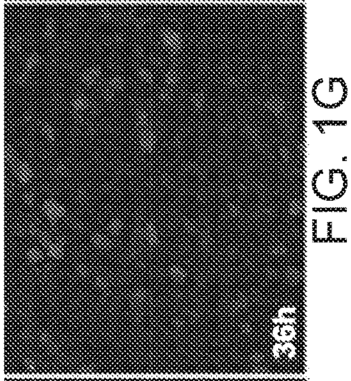
Figure 1H:
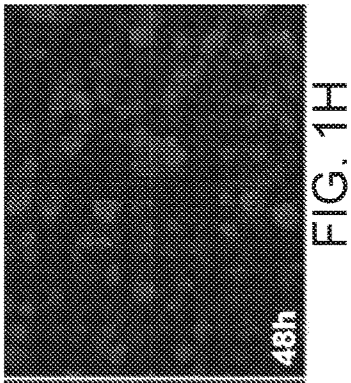
Figure 1I:
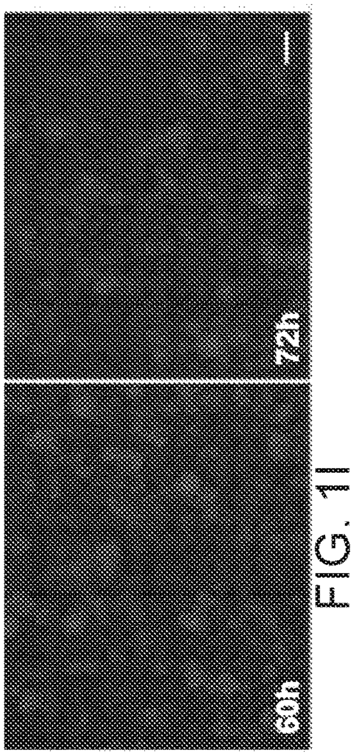
Figure 1K:
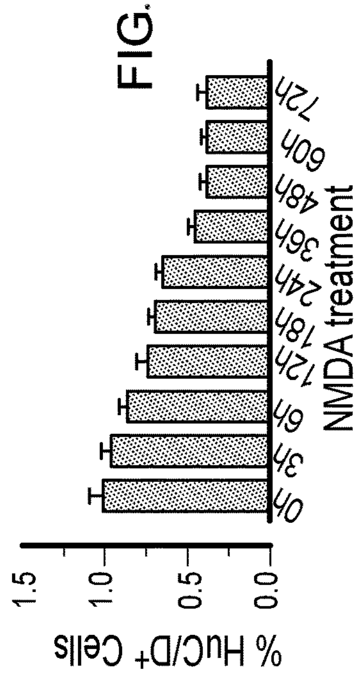

The disclosure is based, in part, on the finding that rod cells can be produced in vivo by carrying out a two-step method: first, an agent (e.g., a composition comprising a nucleic acid encoding beta-catenin, Lin28a, Lin28b, Notch, or Ascl1) that proliferates MG cells is administered to the retina; second, after a period of time to allow proliferation of the MG cells, an agent that differentiates (e.g., into rod cells) the MG cells (e.g., a composition comprising a first nucleic acid encoding Otx2, a second nucleic acid encoding Crx, and a third nucleic acid encoding Nrl) is administered to the retina. To minimize potentially harmful off-target effects, the nucleic acids can be operably linked to a promoter that specifically expresses the nucleic acid in MG cells (e.g., expresses the nucleic acid in MG cells at least 5-fold, at least 10-fold, at least 15-fold, at least 20-fold, at least 25-fold, at least 50-fold, or more than 50-fold more than in non-retinal cells). To further minimize potentially harmful off-target effects, the nucleic acids operably linked to promoters for expression specifically in MG cells can expressed by one or more vectors (e.g., virus or virus-like particle vectors) that specifically target MG cells (e.g., expresses the vector in MG cells at least 5-fold, at least 10-fold, at least 15-fold, at least 20-fold, at least 25-fold, at least 50-fold, or more than 50-fold more than in non-retinal cells).

Thus, the present invention relates generally to compositions and methods of inducing proliferation of MG cells and compositions and methods for inducing differentiation of MG cells to photoreceptor cells or rods. In one embodiment, the method comprises a first step of stimulating MG proliferation and a second step of guiding rod differentiation in the proliferating MG cells. In a specific embodiment, the first step comprises administering to a subject a therapeutically effective amount of a MG cell proliferation agent and the second step comprises, a period of time after the first step, administering to the subject a therapeutically effective amount of a MG cell differentiation agent. In certain embodiments, this two-step method treats vision loss or impairment in a subject. In certain embodiments, this two-step method treats AMD, diabetic retinopathy, retrolental fibroplasia, Stargardt disease, RP, uveitis, Bardet-Biedl syndrome, or eye cancer. In certain embodiments, this two-step method generates new rodphotoreceptors in a retina.

In various embodiments, the method for increasing MG proliferation has the associated effect of increasing expression of amacrine cell markers in MG cells. Amacrine cell markers include, but are not limited to, Pax6, Syntaxin1, and NeuN. Therefore, in one embodiment, the invention relates to methods and compositions for inducing expression of one or more amacrine cell-specific proteins in MG cells.

In one embodiment, stimulation of MG proliferation is accomplished through treatment of MG cells with a WNT signaling effector. In one embodiment, the WNT signaling effector serves to increase β-catenin signaling. In one embodiment, the invention relates to compositions and methods for activating or increasing the level of B-catenin in MG cells. Accordingly, the invention provides activators (e.g., agonists) of β-catenin to increase the expression, activity, or both of β-catenin. In one embodiment, the activator of β-catenin includes but is not limited to a small molecule, a chemical compound, a protein, a peptide, a peptidomemetic, a nucleic acid, and the like. In an embodiment of the present invention, the composition increases the transcription of β-catenin or translation of β-catenin mRNA. In one embodiment of the present invention, the composition increases β-catenin activity.

In one embodiment, the present invention comprises a method for stimulating MG proliferation by increasing one or more of the level, production, and activity of β-catenin comprising administering to a subject an effective amount of a composition comprising an activator of β-catenin.

In one embodiment, the invention relates to compositions and methods for activating or increasing the expression, activity, or both of a downstream β-catenin signaling target. In one embodiment, a downstream β-catenin signaling target is one of Lin28a and Lin28b. Therefore, in one embodiment, the invention relates to methods and compositions for increasing the level of one or more of Lin28a and Lin28b in MG cells. Accordingly, the invention provides activators (e.g., agonists) of one or more of Lin28a and Lin28b. In one embodiment, the activator of one or more of Lin28a and Lin28b includes but is not limited to a small molecule, a chemical compound, a protein, a peptide, a peptidomemetic, a nucleic acid, and the like. In an embodiment of the present invention, the composition increases the transcription of one or more of Lin28a and Lin28b or translation of one or more of Lin28a and Lin28b mRNA. In another embodiment of the present invention, the composition increases one or more of Lin28a and Lin28b activity.

In one embodiment, the present invention comprises a method for stimulating MG proliferation by increasing one or more of the level, production, and activity of one or more of Lin28a and Lin28b comprising administering to a subject an effective amount of a composition comprising an activator of one or more of Lin28a and Lin28b.

In one embodiment, stimulation of MG proliferation is accomplished through inhibiting negative regulators of β-catenin or downstream β-catenin signaling targets. In one embodiment, a negative regulator of β-catenin is GSK3β. Therefore, in one embodiment the invention relates to methods and compositions for inhibiting GSK3β in MG cells. Accordingly, the invention provides inhibitors (e.g., antagonists) of GSK3β. In one embodiment, the inhibitor of GSK3ß includes but is not limited to an antibody or a fragment thereof, a peptide, a nucleic acid, small molecule, a chemical compound, and the like. In an embodiment of the present invention, the composition decreases the transcription of GSK3β or translation of GSK3ß mRNA. In another embodiment of the present invention, the composition inhibits GSK3β activity.

In one embodiment, the present invention comprises a method for stimulating MG proliferation by decreasing one or more of the level, production, and activity of GSK3β comprising administering to a subject an effective amount of a composition comprising an inhibitor of GSK3B.

In one embodiment, stimulating MG proliferation is accomplished through inhibiting one or more let-7 miRNA. In one embodiment, the inhibitor of one or more let-7 miRNA includes but is not limited to an antibody or a fragment thereof, a peptide, a nucleic acid, small molecule, a chemical compound, and the like. In an embodiment of the present invention, the composition decreases the transcription or processing of one or more let-7 miRNA. In another embodiment of the present invention, the composition inhibits one or more let-7 miRNA activity. In one embodiment, the let-7 miRNA is one of let-7a, let-7b, and let-7f miRNA.

In one embodiment, the present invention comprises a method for stimulating MG proliferation by decreasing one or more of the level, production, and activity of one or more let-7 miRNA comprising administering to a subject an effective amount of a composition comprising an inhibitor of one or more let-7 miRNA.

In one embodiment, the present invention relates to compositions and methods for guiding differentiation of MG cells to photoreceptor cells. In one embodiment, a method of guiding MG differentiation comprises activating expression of cell-specific photoreceptor genes in MG cells. Accordingly, the invention provides activators (e.g., agonists) of one or more cell-specific photoreceptor genes. In one embodiment, the activator of one or more cell-specific photoreceptor genes includes but is not limited to a small molecule, a chemical compound, a protein, a peptide, a peptidomemetic, a nucleic acid, and the like. In an embodiment of the present invention, the composition increases the transcription of one or more cell-specific photoreceptor genes or translation of one or more cell-specific photoreceptor genes. In another embodiment of the present invention, the composition increases one or more cell-specific photoreceptor protein activity. Exemplary photoreceptor genes include, but are not limited to rhodopsin, rod a-transducin, rod arrestin, phosducin, ROMI, retinal cGMP, Guanylate Cyclase-Activating Protein Photoreceptor 2, Tubby Like Protein 1, Retinoschisin 1, G alpha 1, G gamma 1, cGMP PDE gamma, G beta 1, mUNC119, rod PDE beta, Pleckstrin Homology Domain Retinal Protein 1, Peripherin 2, recoverin, ribeye, bassoon, and CtBP.

In one embodiment, the activator of one or more cell-specific photoreceptor genes is a transcription factor. Transcription factors that activate one or more one or more cell-specific photoreceptor genes include, but are not limited to Otx2, Crx, Nrl, Nr2e3 and NeuroD. In one embodiment, a composition that increases the transcription of one or more cell-specific photoreceptor genes comprises one of Otx2, Crx, Nrl, Nr2e3 and NeuroD. In one embodiment, a composition that increases the transcription of one or more cell-specific photoreceptor genes comprises Otx2, Crx, and Nrl. In one embodiment, the composition comprises two or more of Otx2, Crx, Nrl, Nr2e3 and NeuroD. In one embodiment, the composition comprises Otx2, Crx, and Nrl.

In one embodiment, the present invention comprises a method for guiding MG differentiation by increasing one or more of the level, production, and activity of one or more cell-specific photoreceptor genes or proteins comprising administering to a subject an effective amount of a composition comprising an activator of one or more cell-specific photoreceptor genes or proteins.

In various embodiments, the invention relates to compositions comprising activators of MG proliferation. In various embodiments, the invention relates to compositions for guiding MG cell differentiation to photoreceptors. In one embodiment, one or more of the compositions of the invention further comprise a MG-specific promoter. In one embodiment, a MG-specific promoter is GFAP. In certain embodiments, the GFAP promoter comprises the sequence of SEQ ID NO:8.

In one embodiment, the invention provides methods of treatment of vision loss or impairment through administration of the compositions of the invention to a subject. In one embodiment, the method of treatment comprises administering to a subject a first composition (e.g., comprising a MG cell proliferation agent) to stimulate MG proliferation and a second composition (e.g., comprising a MG cell differentiation agent) to guide photoreceptor stimulation. In one embodiment, the compositions of the invention are administered concurrently. In one embodiment, the compositions of the invention are administered less than one day, less than two days, less than three days, less than four days, less than five days, less than six days, less than one week, less than two weeks, less than three weeks, less than four weeks, less than one month, or less than two months apart. In one embodiment, the compositions of the invention are administered more than one day, more than two days, more than three days, more than four days, more than five days, more than six days, more than one week, more than two weeks, more than three weeks, more than four weeks, more than one month, or more than two months apart.

In one embodiment, a subject has a condition associated with vision loss or impairment due to photoreceptor loss. Conditions associated with photoreceptor loss include, but are not limited to, age-related macular degeneration (AMD), diabetic retinopathy, retrolental fibroplasia, Stargardt disease, retinitis pigmentosa (RP), uveitis, Bardet-Biedl syndrome and eye cancers.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

The term "activate," as used herein, means to induce or increase a level, activity or function. Preferably, the activity is induced or increased by 50% compared to a comparator value, more preferably by 75%, and even more preferably by 95%.

"Activate," as used herein, also means to increase a molecule, a reaction, an interaction, a gene, an mRNA, and/or a protein's expression, stability, function or activity by a measurable amount or to increase entirely. Activators are compounds that, e.g., bind to, partially or totally induce stimulation, increase, promote, induce activation, activate, sensitize, or up regulate a protein, a gene, and an mRNA stability, expression, function and activity, e.g., agonists.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The an antibody in the present invention may exist in a variety of forms where the antigen binding portion of the antibody is expressed as part of a contiguous polypeptide chain including, for example, a single domain antibody fragment (sdAb), a single chain antibody (scFv) and a humanized antibody (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426).

"Coding sequence" or "encoding nucleic acid" as used herein may refer to the nucleic acid (RNA or DNA molecule) that comprise a nucleotide sequence which encodes an antigen set forth herein. The coding sequence may further include initiation and termination signals operably linked to regulatory elements including a promoter and polyadenylation signal capable of directing expression in the cells of an individual or mammal to whom the nucleic acid is administered. The coding sequence may further include sequences that encode signal peptides.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of at least one sign or symptom of the disease or disorder, the frequency with which such a sign or symptom is experienced by a patient, or both, is reduced.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein, the terms "effective amount," "pharmaceutically effective amount" and "therapeutically effective amount" refer to a nontoxic but sufficient amount of an agent to provide the desired biological result. That result can be reduction and/or alleviation of the frequency and/or severity of signs, symptoms, or causes of a disease, or any other desired alteration of a biological system. An appropriate therapeutic amount in any individual case may be determined by one of ordinary skill in the art using routine experimentation.

The term "expression" as used herein is defined as the transcription and/or translation of a particular nucleotide sequence driven by its promoter.

By "expression cassette" is meant a nucleic acid molecule comprising a coding sequence operably linked to promoter/regulatory sequences necessary for transcription and, optionally, translation of the coding sequence.

The term "expression vector" as used herein refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules, siRNA, ribozymes, and the like. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity may be measured using sequence comparison software or algorithms or by visual inspection. Various algorithms and software that may be used to obtain alignments of amino acid or nucleotide sequences are well-known in the art. These include, but are not limited to, BLAST, ALIGN, Megalign, BestFit, GCG Wisconsin Package, and variants thereof. In some embodiments, two nucleic acids or polypeptides of the disclosure are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. In some embodiments, identity exists over a region of the sequences that is at least about 10, at least about 20, at least about 20-40, at least about 40-60 nucleotides or amino acid residues, at least about 60-80 nucleotides or amino acid residues in length or any integral value there between. In some embodiments, identity exists over a longer region than 60-80 nucleotides or amino acid residues, such as at least about 80-100 nucleotides or amino acid residues, and in some embodiments the sequences are substantially identical over the full length of the sequences being compared, for example, (i) the coding region of a nucleotide sequence or (ii) an amino acid sequence.

The term "inhibit," as used herein, means to diminish, decrease, suppress or block an activity or function, for example, about ten percent relative to a control value. Preferably, the activity is suppressed or blocked by 50% compared to a control value, more preferably by 75%, and even more preferably by 95%. "Inhibit," as used herein, also means to reduce a molecule, a reaction, an interaction, a gene, an mRNA, and/or a protein's expression, stability, function or activity by a measurable amount or to prevent entirely. Inhibitors are compounds that, e.g., bind to, partially or totally block stimulation, decrease, prevent, delay activation, inactivate, desensitize, or down regulate a protein, a gene, and an mRNA stability, expression, function and activity, e.g., antagonists.

As used herein, an "instructional material" includes a publication, a recording, a diagram, or any other medium of expression which can be used to communicate the usefulness of a compound, composition, vector, or delivery system of the invention in the kit for effecting alleviation of the various diseases or disorders recited herein. Optionally, or alternately, the instructional material can describe one or more methods of alleviating the diseases or disorders in a cell or a tissue of a mammal. The instructional material of the kit of the invention can, for example, be affixed to a container which contains the identified compound, composition, vector, or delivery system of the invention or be shipped together with a container which contains the identified compound, composition, vector, or delivery system. Alternatively, the instructional material can be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

The term "microarray" refers broadly to both "DNA microarrays" and "DNA chip(s)," and encompasses all art-recognized solid supports, and all art-recognized methods for affixing nucleic acid molecules thereto or for synthesis of nucleic acids thereon.

By the term "modulating," as used herein, is meant mediating a detectable increase or decrease in the activity and/or level of a mRNA, polypeptide, or a response in a subject compared with the activity and/or level of a mRNA, polypeptide or a response in the subject in the absence of a treatment or compound, and/or compared with the activity and/or level of a mRNA, polypeptide, or a response in an otherwise identical but untreated subject. The term encompasses perturbing and/or affecting a native signal or response thereby mediating a beneficial therapeutic response in a subject, preferably, a human.

The term "operably linked" as used herein refer to the linkage of nucleic acid sequences in such a manner that a nucleic acid molecule capable of directing the transcription of a given gene and/or the synthesis of a desired protein molecule is produced. The term also refers to the linkage of sequences encoding amino acids in such a manner that a functional (e.g., enzymatically active, capable of binding to a binding partner, capable of inhibiting, etc.) protein or polypeptide is produced. As used herein, the terms "operably linked" and "operationally linked" are used interchangeably.

The terms "patient," "subject." "individual," and the like are used interchangeably herein, and refer to any animal, or cells thereof whether in vitro or in situ, amenable to the methods described herein. In certain non-limiting embodiments, the patient, subject or individual is a human.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in an inducible manner.

An "inducible" promoter is a nucleotide sequence which, when operably linked with a polynucleotide which encodes or specifies a gene product, causes the gene product to be produced substantially only when an inducer which corresponds to the promoter is present.

A "constitutive" promoter is a nucleotide sequence which, when operably linked with a polynucleotide which encodes or specifies a gene product, causes the gene product to be produced in a cell under most or all physiological conditions of the cell.

"Polypeptide" refers to a polymer composed of amino acid residues, related naturally occurring structural variants, and synthetic non-naturally occurring analogs thereof linked via peptide bonds. Synthetic polypeptides can be synthesized, for example, using an automated polypeptide synthesizer.

The term "regulating" as used herein can mean any method of altering the level or activity of a substrate. Non-limiting examples of regulating with regard to a protein include affecting expression (including transcription and/or translation), affecting folding, affecting degradation or protein turnover, and affecting localization of a protein. Non-limiting examples of regulating with regard to a protein further include affecting the enzymatic activity. "Regulator" refers to a molecule whose activity includes affecting the level or activity of a substrate. A regulator can be direct or indirect. A regulator can function to activate or inhibit or otherwise modulate its substrate.

As used herein, a "recombinant cell" is a host cell that comprises a recombinant polynucleotide.

"Sample" or "biological sample" as used herein means a biological material from a subject, including but is not limited to organ, tissue, exosome, blood, plasma, saliva, urine and other body fluid. A sample can be any source of material obtained from a subject.

A "therapeutic" treatment is a treatment administered to a subject who exhibits signs of pathology, for the purpose of diminishing or eliminating those signs.

As used herein, "treating a disease or disorder" means reducing the frequency with which a symptom of the disease or disorder is experienced by a patient.

A "vector" is a composition of matter which comprises an isolated nucleic acid and which can be used to deliver the isolated nucleic acid to the interior of a cell.

Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The invention is based on the unexpected result that MG cells can be induced to re-enter the cell cycle and guided to differentiate into nascent rod-photoreceptors that have similar structure and characteristics (e.g., transducing signal from light) of native rods.

Activation and Proliferation of MG Cells

In one embodiment, the invention relates to a method of inducing MG cell proliferation. Generally, the MG cells of the invention are induced to proliferate by contact with a composition (e.g., comprising a MG cell proliferation agent), e.g., a composition that stimulates WNT signaling. Non-limiting examples of MG cell proliferation agents include activators of one or more of β-catenin, Lin28a, Lin28b, Notch, or Ascl1, and inhibitors of a negative regulator of MG cell proliferation (e.g., an inhibitor of GSK3β or let-7 miRNA). In exemplary embodiments, MG cell proliferation may be stimulated as described herein, by contact with an activator of one or more of β-catenin, Lin28a, Lin28b, Notch, and Ascl1. In exemplary embodiments, MG cell proliferation may be stimulated as described herein, by contact with a nucleic acid encoding one or more of β-catenin, Lin28a, Lin28b, Notch, and Ascl1. Alternatively, MG cell proliferation may be stimulated as described herein, by contact with an inhibitor of a negative regulator of MG cell proliferation. In exemplary embodiments, MG cell proliferation may be stimulated through inhibition of one or more of GSK3β and let-7 miRNA. For example, a population of MG cells can be contacted with an anti-let-7 antibody under conditions appropriate for stimulating proliferation of the MG cells.

Differentiation of MG Cells

In one embodiment, the invention relates to a method of inducing MG cells (e.g., proliferating MG cells) to differentiate into rod photoreceptors. In one embodiment, the method comprises contacting a proliferating cell with a composition (e.g., comprising a MG cell differentiation agent) that stimulates expression of rod-specific genes. Non-limiting examples of MG cell differentiation agents include a transcription factor selected from the group consisting of Otx2, Crx, Nrl, Nr2e3, and NeuroD, or a combination thereof, and a composition which activates one or more of rhodopsin, rod a-transducin, rod arrestin, phosducin, ROMI, retinal cGMP, Guanylate Cyclase-Activating Protein Photoreceptor 2, Tubby Like Protein 1, Retinoschisin 1, G alpha 1, G gamma 1, cGMP PDE gamma, G beta 1, mUNC119, rod PDE beta, Pleckstrin Homology Domain Retinal Protein 1, Peripherin 2, recoverin, ribeye, bassoon, and CtBP, or a combination thereof. In one embodiment, a method of inducing MG cell differentiation comprises contacting a proliferating MG cell with a composition which activates one or more of rhodopsin, rod a-transducin, rod arrestin, phosducin, ROM1, retinal cGMP, Guanylate Cyclase-Activating Protein Photoreceptor 2, Tubby Like Protein 1, Retinoschisin 1, G alpha 1, G gamma 1, cGMP PDE gamma, G beta 1, mUNC119, rod PDE beta, Pleckstrin Homology Domain Retinal Protein 1, Peripherin 2, recoverin, ribeye, bassoon, and CtBP. In one embodiment, MG cell differentiation may be stimulated as described herein, by contacting a proliferating MG cell with Otx2, Crx, Nrl, Nr2e3 and NeuroD, or a combination thereof. In one embodiment, MG cell differentiation may be stimulated as described herein, by contacting a proliferating MG cell with Otx2, Crx, and Nrl. In a specific embodiment, MG cell differentiation may be stimulated as described herein, by administering to a subject Otx, Crx, and Nrl.

In a specific embodiment, MG cell differentiation may be stimulated as described herein by administering to a subject a first nucleic acid molecule encoding Otx2, a second nucleic acid molecule encoding Crx, and a third nucleic acid molecule encoding Nrl. In specific embodiments, the first nucleic acid molecule is operably linked to a promoter that specifically expresses the first nucleic acid in MG cells, the second nucleic acid molecule is operably linked to a promoter that specifically expresses the second nucleic acid in MG cells, and the third nucleic acid molecule is operably linked to a promoter that specifically expresses the third nucleic acid in MG cells.

In specific embodiments, MG cell differentiation may be stimulated as described herein, by administering to a subject: a first vector comprising a first nucleic acid operably linked to a promoter that specifically expresses the first nucleic acid in MG cells, a second vector comprising a second nucleic acid operably linked to a promoter that specifically expresses the second nucleic acid in MG cells, and a third vector comprising a third nucleic acid operably linked to a promoter that specifically expresses the third nucleic acid in MG cells. In specific embodiments, the promoter that specifically expresses the nucleic acid in MG cells is the GFAP promoter. In certain embodiments, the GFAP promoter comprises the sequence of SEQ ID NO:8. In specific embodiments, the first vector is a virus or virus-like particle that specifically infects MG cells, the second vector is a virus or virus-like particle that specifically infects MG cells, and the third vector is a virus or virus-like particle that specifically infects MG cells. In specific embodiments, the first vector is AAV-ShH10, the second vector is AAV-ShH10, and the third vector is AAV-ShH10.

Two-Step Method

Provided herein is a two-step method for inducing new rod photoreceptor formation from MG cells. This two-step method can be used to treat vision loss or impairment in a subject, treat AMD, diabetic retinopathy, retrolental fibroplasia, Stargardt disease, RP, uveitis, Bardet-Biedl syndrome, or eye cancer in a subject, or generate new rod photoreceptors in a retina in a subject. Thus, in one embodiment, the invention provides a method to treat vision loss or impairment in a subject. The invention also provides a method to treat AMD, diabetic retinopathy, retrolental fibroplasia, Stargardt disease, RP, uveitis, Bardet-Biedl syndrome, or eye cancer in a subject. The invention also provides a method of inducing new rod-photoreceptor formation from MG cells.

In one embodiment, the method comprises a first step of inducing MG cell proliferation (see, e.g., the section "Activation and Proliferation of MG Cells" above, and the working examples below) and a second step of guiding differentiation of the proliferating MG cells to rod photoreceptors (see, e.g., the section "Differentiation of MG Cells" above, and the working examples below). Therefore, in one embodiment, the method comprises contacting a MG cell with a first composition for inducing MG cell proliferation (e.g., a composition comprising a MG cell proliferation agent) and contacting the MG cell with a second composition that induces differentiation of the MG cells (e.g., proliferating MG cells) to rod photoreceptors (e.g., a composition comprising a MG cell differentiation agent). In one embodiment, a MG cell is contacted with a single composition comprising a first composition for inducing MG cell proliferation and a second composition that induces differentiation of the proliferating MG cells to rod photoreceptors. In an alternative embodiment, a MG cell is contacted with two or more compositions wherein the two or more compositions comprise at least a first composition for inducing MG cell proliferation and a second composition that induces differentiation of the proliferating MG cells to rod photoreceptors. In one embodiment, a MG cell is contacted with two or more compositions substantially concurrently. In certain embodiments, a MG cell is contacted concurrently with a MG cell proliferation agent and a MG cell differentiation agent. In certain embodiments, a MG cell is contacted substantially concurrently (e.g., within 1 minute, within 5 minutes, within 10 minutes, within an hour, within two hours, or within three hours) with a MG cell proliferation agent and a MG cell differentiation agent. In certain embodiments in which the MG cell is contacted concurrently or substantially concurrently with a MG cell proliferation agent and a MG cell differentiation agent, the MG cell differentiation agent is a delayed release agent (e.g., is not released until 1 to 5 days, 5 to 10 days, 10 to 15 days, 15 to 20 days, or 20 to 30 days after the MG cell is contacted with the MG cell differentiation agent). In an alternative embodiment, contacting the MG cell with two or more compositions comprises contacting the MG cell with a first composition, allowing a sufficient amount of time for the MG cell to enter the cell cycle (i.e. begin proliferating), and subsequently contacting the cell with at least a second composition to induce differentiation of the MG cell into a rod photoreceptor.

Activator Compositions

In various embodiments, the present invention includes compositions for use in methods of treating vision loss or impairment in a subject. The compositions of the present invention include compositions comprising a MG cell proliferation agent. In one embodiment, the composition activates WNT signaling in MG cells to induce MG cell proliferation. In one embodiment, the composition activates one or more of β-catenin, Lin28, Notch, and Ascl1 in MG cells to induce cell proliferation. The compositions of the present invention also include compositions comprising a MG cell differentiation agent. In one embodiment, the composition activates transcription of cell-specific genes to induce differentiation of cells to rod photoreceptors.

In one embodiment, the composition for treating vision loss or impairment comprises an activator of WNT signaling. In one embodiment, the composition for treating vision loss or impairment comprises an activator of one or more of β-catenin, Lin28a, Lin28b, Notch, and Ascl1. In one embodiment, the composition for treating vision loss or impairment comprises an activator of one or more of rhodopsin, rod a-transducin, rod arrestin, phosducin, ROMI, retinal cGMP, Guanylate Cyclase-Activating Protein Photoreceptor 2, Tubby Like Protein 1, Retinoschisin 1, G alpha 1, G gamma 1, cGMP PDE gamma, G beta 1, mUNC119, rod PDE beta, Pleckstrin Homology Domain Retinal Protein 1, Peripherin 2, recoverin, ribeye, bassoon, and CtBP.

In one embodiment, the activator of the invention increases the amount of polypeptide, the amount of mRNA, the amount of activity, or a combination thereof of the target (e.g., β-catenin, Lin28a, Lin28b, Notch, or Ascl1).

It will be understood by one skilled in the art, based upon the disclosure provided herein, that an increase in the level of protein encompasses the increase in expression, including transcription, translation, or both. The skilled artisan will also appreciate, once armed with the teachings of the present invention, that an increase in the level of protein includes an increase in protein activity. Thus, increasing the level or activity of a protein includes, but is not limited to, increasing the amount of the polypeptide, increasing transcription, translation, or both, of a nucleic acid encoding the protein, and it also includes increasing any activity of the polypeptide as well.

Thus, in one embodiment, the present invention relates to compositions for treatment of vision loss or impairment including a polypeptide, a recombinant polypeptide, an active polypeptide fragment, or an activator of expression or activity of a polypeptide, where the polypeptide or activator functions to increase, induce or otherwise activate proliferation of MG cells.

In another embodiment, the present invention relates to compositions for treatment of vision loss or impairment including a polypeptide, a recombinant polypeptide, an active polypeptide fragment, or an activator of expression or activity of a polypeptide, where the polypeptide or activator functions to increase, induce or otherwise activate one or more proteins to direct rod photoreceptor differentiation of proliferating MG cells.

It is understood by one skilled in the art, that an increase in the level of a protein encompasses the increase of protein expression. Thus, increasing the level or activity of a protein includes, but is not limited to, increasing transcription, translation, or both, of a nucleic acid encoding the protein; and it also includes increasing the stability of a nucleic acid encoding the protein.

Additionally, the skilled artisan would appreciate, that an increase in the level of a protein includes an increase in one or more enzymatic activity of the protein.

An activator of the invention can include, but should not be construed as being limited to, a chemical compound, a protein, a peptidomemetic, an antibody, or a nucleic acid molecule. In one embodiment, an activator encompasses a chemical compound that increases the level, enzymatic activity, or the like of one or more of WNT signaling, β-catenin, Lin28a, Lin28b, Notch, and Ascl1. In one embodiment, an activator encompasses a chemical compound that increases the level, enzymatic activity, or the like of one or more proteins to direct rod photoreceptor differentiation of proliferating MG cells. In one embodiment, an activator encompasses a chemical compound that increases the level, enzymatic activity, or the like of one or more of rhodopsin, rod a-transducin, rod arrestin, phosducin, ROMI, retinal cGMP, Guanylate Cyclase-Activating Protein Photoreceptor 2, Tubby Like Protein 1, Retinoschisin 1, G alpha 1, G gamma 1, cGMP PDE gamma, G beta 1, mUNC119, rod PDE beta, Pleckstrin Homology Domain Retinal Protein 1, Peripherin 2, recoverin, ribeye, bassoon, and CtBP.

It will be understood by one skilled in the art, based upon the disclosure provided herein, that an increase in the level, enzymatic activity, or the like of one or more proteins to direct rod photoreceptor differentiation of proliferating MG cells encompasses the increase in gene expression, including transcription, translation, or both of one or more proteins to direct rod photoreceptor differentiation of proliferating MG cells. Therefore, in one embodiment, an activator of the invention is a transcription factor. Transcription factors that increase the level of one or more proteins to direct rod photoreceptor differentiation of proliferating MG cells include, but are not limited to Otx2, Crx, Nrl, Nr2e3 and NeuroD. In a specific embodiment, an activator of the invention is the combination of transcription factors Otx2, Crx, and Nrl.

Further, one of skill in the art would, when equipped with this disclosure and the methods exemplified herein, appreciate that an activator includes such activators as discovered in the future, as can be identified by well-known criteria in the art of pharmacology, such as the physiological results of activation of MG proliferation and MG to rod photoreceptor differentiation as described in detail herein and/or as known in the art. Therefore, the present invention is not limited in any way to any particular activator as exemplified or disclosed herein; rather, the invention encompasses those activators that would be understood by the skilled artisan to be useful as are known in the art and as are discovered in the future.

Further methods of identifying and producing an activator are well known to those of ordinary skill in the art, including, but not limited, obtaining an activator from a naturally occurring source. Alternatively, an activator can be synthesized chemically. Further, the skilled artisan would appreciate, based upon the teachings provided herein, that an activator can be obtained from a recombinant organism. Compositions and methods for chemically synthesizing activators and for obtaining them from natural sources are well known in the art and are described in the art.

One of skill in the art will appreciate that an activator can be a small molecule chemical, a protein, a nucleic acid construct encoding a protein, or combinations thereof. In one embodiment, an activator comprises a nucleic acid operably linked to a promoter for MG cell-specific expression. In one embodiment, the promoter is the GFAP promoter. In certain embodiments, the GFAP promoter comprises the sequence of SEQ ID NO:8. Numerous vectors and other compositions and methods are well known for administering a protein or a nucleic acid construct encoding a protein to cells or tissues. In one embodiment, an activator comprising a nucleic acid construct is cloned into the ShH10-GFAP vector for expression in MG cells.

Peptides

The present invention comprises a peptide comprising an activator of WNT signaling or a peptide that induces MG cell proliferation.

In one embodiment the peptide comprises β-catenin. An exemplary amino acid sequence of human-catenin (GenBank Accession No. NP_001091679, encoded by GenBank Accession No. NM_001098209) is provided below:

```
                                          (SEQ ID NO: 1)
  1 matqadlmel dmamepdrka avshwqqqsy ldsgihsgat
    ttapslsgkg npeeedvdts

 61 qvlyeweqgf sqsftqeqva didgqyamtr aqrvraamfp
    etldegmqip stqfdaahpt

121 nvqrlaepsq mlkhavvnli nyqddaelat raipeltkll
    ndedqvvvnk aavmvhqlsk

181 keasrhaimr spqmvsaivr tmqntndvet arctagtlhn
    lshhreglla ifksggipal

241 vkmlgspvds vlfyaittlh nlllhqegak mavrlagglq
    kmvallnktn vkflaittdc

301 lqilaygnqe skliilasgg pqalvnimrt ytyekllwtt
    srvlkvlsvc ssnkpaivea

361 ggmqalglhl tdpsqrlvqn clwtlrnlsd aatkqegmeg
    llgtivqllg sddinvvtca

421 agilsnltcn nyknkmmvcq vggiealvrt vlragdredi
    tepaicalrh ltsrhqeaem
```

-continued 481 agnavrlhyg lpvvvkllhp pshwplikat vglirnlalc panhaplreq gaiprivqll 541 vrahqdtqrr tsmggtqqqf vegvrmeeiv egctgalhil ardvhnrivi rglntiplfv 601 qllyspieni qrvaagvlce laqdkeaaea ieaegatapl tellhsrneg vatyaaavlf 661 rmsedkpqdy kkrlsvelts slfrtepmaw netadlgldi gaqgeplgyr qddpsyrsfh 721 sggygqdalg mdpmmehemg ghhpgadypv dglpdlghaq dlmdglppgd snqlawfdtd 781 l.

In another embodiment, the peptide comprises Lin28a. An exemplary amino acid sequence of human Lin28a (GenBank Accession No. NP_078950, encoded by GenBank Accession No. NM_024674) is provided below:

(SEQ ID NO: 2)

1 mgsysnqqfa ggcakaaeea peeapedaar aadepqllhg agickwfnvr mgfgflsmta 61 ragvaldppv dvfvhqsklh megfrslkeg eaveftfkks akglesirvt gpggvfcigs 121 errpkgksmq krrskgdrcy ncggldhhak ecklppqpkk chfcqsishm vascplkaqq 181 gpsaqgkpty freeeeeihs ptllpeaqn.

In another embodiment, the peptide comprises Lin28b. An exemplary amino acid sequence of human Lin28b (GenBank Accession No. NP_001004317, encoded by GenBank Accession No. NM_001004317) is provided below:

(SEQ ID NO: 3)

1 maeggaskgg geepgklpep aeeesqvlrg tghckwfnvr mgfgfismin regspldipv 61 dvfvhqsklf megfrslkeg epveftfkks skglesirvt gpggspclgs errpkgktlq 121 krkpkgdrcy ncggldhhak ecslppqpkk chycqsimhm vancphknva qppassqgrq 181 eaesqpctst lprevggghg ctsppfpqea raeisersgr spqeasstks siapeeqskk 241 gpsvqkrkkt.

In another embodiment, the peptide comprises Notch. An exemplary amino acid sequence of human Notch (GenBank Accession No. NP_060087, encoded by GenBank Accession No. NM_017617) is provided below:

(SEQ ID NO: 4)

1 mppllapllc lallpalaar gprcsqpget clnggkceaa ngteacvcgg afvgprcqdp 61 npclstpckn agtchvvdrr gvadyacsca lgfsgplclt pldnacltnp crnggtcdll 121 tlteykcrcp pgwsgkscqq adpcasnpca nggqclpfea syichcppsf hgptcrqdvn 181 ecgqkpglcr hggtchnevg syrcvcrath tgpncerpyv pcspspcqng gtcrptgdvt 241 hecaclpgft gqnceenidd cpgnnckngg acvdgvntyn crcppewtgq yctedvdecq -continued 301 lmpnacqngg tchnthggyn cvcvngwtge dcsenidica saacfhgatc hdrvasfyce 361 cphgrtgllc hlndacisnp cnegsncdtn pvngkaictc psgytgpacs qdvdecslga 421 npcehagkci ntlgsfecqc lqgytgprce idvnecvsnp cqndatcldq igefqcicmp 481 gyegvhcevn tdecasspcl hngrcldkin efqcecptgf tghlcqydvd ecastpckng 541 akcldgpnty tcvctegytg thcevdidec dpdpchygsc kdgvatftcl crpgytghhc 601 etninecssq perhggtcqd rdnaylcfcl kgttgpncei nlddcasspc dsgtcldkid 661 gyecacepgy tgsmcninid ecagnpchng gtcedgingf tcrcpegyhd ptclsevnec 721 nsnpcvhgac rdslngykcd cdpgwsgtnc dinnnecesn pcvnggtckd mtsgyvctcr 781 egfsgpncqt ninecasnpc lnqgtciddv agykcncllp ytgatcevvl apcapspern 841 ggecrqsedy esfscvcptg wqgqtcevdi necvlsperh gascqnthgg yrchcqagys 901 grncetdidd crpnpchngg sctdgintaf cdclpgfrgt fceedineca sdperngancn 961 tdcvdsytct cpagfsgihc enntpdctes scfnggtcvd ginsftcicp pgftgsycqh 1021 dvnecdsqpc lhggtcqdgc gsyrctcpqg ytgpncqnlv hwcdsspckn ggkcwqthtq 1081 yrcecpsgwt glycdvpsys cevaaqrqgv dvarlcqhgg lcvdagnthh crcqagytgs 1141 ycedlvdecs pspcqngatc tdylggysck cvagyhgvnc seeideclsh pcqnggtcld 1201 lpntykcscp rgtqgvhcei nvddcnppvd pvsrspkcfn ngtcvdqvgg ysctcppgfv 1261 gercegdvne clsnpcdarg tqncvqrvnd fhcecraght grrcesving ckgkpckngg 1321 tcavasntar gfickcpagf egatcendar tcgslrclng gtcisgprsp tciclgpftg 1381 pecqfpassp clggnpcynq gtceptsesp fyrcicpakf ngllchildy sfgggagrdi 1441 ppplieeace lpecqedagn kvcslqcnnh acgwdggdcs lnfndpwknc tqslqcwkyf 1501 sdghcdsqcn sagclfdgfd cqraegqcnp lydqyckdhf sdghcdqgcn saecewdgld 1561 caehvperla agtivvvvlm ppeqlrnssf hflrelsrvl htnvvfkrda hgqqmifpyy 1621 greeelrkhp ikraaegwaa pdallgqvka sllpggsegg rrrreldpmd vrgsivylei 1681 dnrqcvqass qcfqsatdva aflgalaslg slnipykiea vqsetveppp paqlhfmyva 1741 aaafvllffv gcgvllsrkr rrqhgqlwfp egfkvseask kkrreplged svglkplkna 1801 sdgalmddnq newgdedlet kkfrfeepvv lpdlddqtdh rqwtqqhlda adlrmsamap 1861 tppqgevdad cmdvnvrgpd gftplmiasc sgggletgns eeeedapavi sdfiyqgasl -continued

```
1921 hnqtdrtget alhlaarysr sdaakrllea sadaniqdnm
     grtplhaavs adaqgvfqil

1981 irnratdlda rmhdgttpli laarlavegm ledlinshad
     vnavddlgks alhwaaavnn

2041 vdaavvllkn gankdmqnnr eetplflaar egsyetakvl
     ldhfanrdit dhmdrlprdi

2101 aqermhhdiv rlldeynlvr spqlhgaplg gtptlspplc
     spngylgslk pgvqgkkvrk

2161 psskglacgs keakdlkarr kksqdgkgcl ldssgmlspv
     dslesphgyl sdvasppllp

2221 spfqqspsvp lnhlpgmpdt hlgighlnva akpemaalgg
     ggrlafetgp prlshlpvas

2281 gtstvlgsss ggalnftvgg stslngqcew lsrlqsgmvp
     nqynplrgsv apgplstqap

2341 slqhgmvgpl hsslaasals qmmsyqglps trlatqphlv
     qtqqvqpqnl qmqqqnlqpa

2401 niqqqqslqp pppppqphlg vssaasghlg rsflsgepsq
     advqplgpss lavhtilpqe

2461 spalptslps slvppvtaaq fltppsqhsy sspvdntpsh
     qlqvpehpfl tpspespdqw

2521 ssssphsnvs dwsegvsspp tsmqsqiari peafk.
```

In some embodiments, the peptide comprises the intracellular domain of Notch. An exemplary amino acid sequence of human Notch intracellular domain is provided below:

```
                                          (SEQ ID NO: 5)
  1 gcgvllsrkr rrqhgqlwfp egfkvseask kkrreplged
    svglkplkna sdgalmddnq

 61 newgdedlet kkfrfeepvv lpdlddqtdh rqwtqqhlda
    adlrmsamap tppqgevdad

121 cmdvnvrgpd gftplmiasc sgggletgns eeeedapavi
    sdfiyqgasl hnqtdrtget

181 alhlaarysr sdaakrllea sadaniqdnm grtplhaavs
    adaqgvfqil irnratdlda

241 rmhdgttpli laarlavegm ledlinshad vnavddlgks
    alhwaaavnn vdaavvllkn

301 gankdmqnnr eetplflaar egsyetakvl ldhfanrdit
    dhmdrlprdi aqermhhdiv

361 rlldeynlvr spqlhgaplg gtptlspplc spngylgslk
    pgvqgkkvrk psskglacgs

421 keakdlkarr kksqdgkgcl ldssgmlspv dslesphgyl
    sdvasppllp spfqqspsvp

481 lnhlpgmpdt hlgighlnva akpemaalgg ggrlafetgp
    prlshlpvas gtstvlgsss

541 ggalnftvgg stslngqcew lsrlqsgmvp nqynplrgsv
    apgplstqap slqhgmvgpl

601 hsslaasals qmmsyqglps trlatqphlv qtqqvqpqnl
    qmqqqnlqpa niqqqqslqp

661 pppppqphlg vssaasghlg rsflsgepsq advqplgpss
    lavhtilpqe spalptslps

721 slvppvtaaq fltppsqhsy sspvdntpsh qlqvpehpfl
    tpspespdqw ssssphsnvs

781 dwsegvsspp tsmqsqiari peafk.
```

In another embodiment, the peptide comprises Ascl1. An exemplary amino acid sequence of human Ascl1 (GenBank Accession No. NP_004307, encoded by GenBank Accession No. NM_004316) is provided below:

```
                                          (SEQ ID NO: 6)
  1 messakmesg gagqqpqpqp qqpflppaac ffataaaaaa
    aaaaaaaqsa qqqqqqqqqq

 61 qqapqlrpaa dgqpsggghk sapkqvkrqr ssspelmrck
    rrinfsgfgy slpqqqpaav

121 arrnerernr vklvnlgfat lrehvpngaa nkkmskvetl
    rsaveyiral qqlldehdav

181 saafqagvls ptispnysnd lnsmagspvs syssdegsyd
    plspeeqell dftnwf.
```

The peptide of the present invention may be made using chemical methods. For example, peptides can be synthesized by solid phase techniques (Roberge J Y et al (1995) Science 269:202-204), cleaved from the resin, and purified by preparative high performance liquid chromatography. Automated synthesis may be achieved, for example, using the ABI 431 A Peptide Synthesizer (Perkin Elmer) in accordance with the instructions provided by the manufacturer.

The peptide may alternatively be made by recombinant means or by cleavage from a longer polypeptide. The composition of a peptide may be confirmed by amino acid analysis or sequencing.

The variants of the polypeptides according to the present invention may be (i) one in which one or more of the amino acid residues are substituted with a conserved or non-conserved amino acid residue (preferably a conserved amino acid residue) and such substituted amino acid residue may or may not be one encoded by the genetic code, (ii) one in which there are one or more modified amino acid residues, e.g., residues that are modified by the attachment of substituent groups, (iii) one in which the polypeptide is an alternative splice variant of the polypeptide of the present invention, (iv) fragments of the polypeptides (e.g., the notch intracellular domain with respect to notch) and/or (v) one in which the polypeptide is fused with another polypeptide, such as a leader or secretory sequence or a sequence which is employed for purification (for example, His-tag) or for detection (for example, Sv5 epitope tag). The fragments include polypeptides generated via proteolytic cleavage (including multi-site proteolysis) of an original sequence. Variants may be post-translationally, or chemically modified. Such variants are deemed to be within the scope of those skilled in the art from the teaching herein.

The polypeptides of the invention can be post-translationally modified. For example, post-translational modifications that fall within the scope of the present invention include signal peptide cleavage, glycosylation, acetylation, isoprenylation, proteolysis, myristoylation, protein folding and proteolytic processing, etc. Some modifications or processing events require introduction of additional biological machinery.

The polypeptides of the invention may include unnatural amino acids formed by post-translational modification or by introducing unnatural amino acids during translation. A variety of approaches are available for introducing unnatural amino acids during protein translation. By way of example, special tRNAs, such as tRNAs which have suppressor properties, suppressor (RNAs, have been used in the process of site-directed non-native amino acid replacement (SNAAR). In SNAAR, a unique codon is required on the mRNA and the suppressor IRNA, acting to target a non-native amino acid to a unique site during the protein synthesis (described in WO90/05785). However, the suppressor (RNA must not be recognizable by the aminoacyl tRNA synthetases present in the protein translation system. In certain cases, a non-native amino acid can be formed after the tRNA molecule is aminoacylated using chemical reactions which specifically modify the native amino acid and do not significantly alter the functional activity of the aminoacylated tRNA, These reactions are referred to as post-aminoacylation modifications. For example, the epsilon-amino group of the lysine linked to its cognate IRNA (IRNALYS), could be modified with an amine specific photoaffinity label.

Fusion and Chimeric Polypeptides

A protein of the invention may be conjugated with other molecules, such as proteins, to prepare fusion proteins. This may be accomplished, for example, by the synthesis of N-terminal or C-terminal fusion proteins provided that the resulting fusion protein retains the functionality of increasing WNT signaling.

A protein or fusion protein of the invention may be phosphorylated using conventional methods such as the method described in Reedijk et al. (The EMBO Journal 11 (4): 1365, 1992).

Cyclic derivatives of the peptides or chimeric proteins of the invention are also part of the present invention. Cyclization may allow the peptide or chimeric protein to assume a more favorable conformation for association with other molecules. Cyclization may be achieved using techniques known in the art. For example, disulfide bonds may be formed between two appropriately spaced components having free sulfhydryl groups, or an amide bond may be formed between an amino group of one component and a carboxyl group of another component. Cyclization may also be achieved using an azobenzene-containing amino acid as described by Ulysse, L., et al., J. Am. Chem. Soc. 1995, 117, 8466-8467. The components that form the bonds may be side chains of amino acids, non-amino acid components or a combination of the two. In an embodiment of the invention, cyclic peptides may comprise a beta-turn in the right position. Beta-turns may be introduced into the peptides of the invention by adding the amino acids Pro-Gly at the right position.

It may be desirable to produce a cyclic peptide which is more flexible than the cyclic peptides containing peptide bond linkages as described above. A more flexible peptide may be prepared by introducing cysteines at the right and left position of the peptide and forming a disulphide bridge between the two cysteines. The two cysteines are arranged so as not to deform the beta-sheet and turn. The peptide is more flexible as a result of the length of the disulfide linkage and the smaller number of hydrogen bonds in the beta-sheet portion. The relative flexibility of a cyclic peptide can be determined by molecular dynamics simulations.

(a) Tags

In a particular embodiment of the invention, a polypeptide of the invention further comprises a tag. The tag includes but is not limited to: polyhistidine tags (His-tags) (for example H6 and H10, etc.) or other tags for use in IMAC systems, for example, $Ni^{2+}$ affinity columns, etc., GST fusions, MBP fusions, streptavidine-tags, the BSP biotinylation target sequence of the bacterial enzyme BIRA and tag epitopes that are directed by antibodies (for example c-myc tags, FLAG-tags, among others). As will be observed by a person skilled in the art, the tag peptide can be used for purification, inspection, selection and/or visualization of the fusion protein of the invention. In a particular embodiment of the invention, the tag is a detection tag and/or a purification tag. It will be appreciated that the tag sequence will not interfere in the function of the protein of the invention.

(b) Leader and Secretory Sequences

Accordingly, the polypeptides of the invention can be fused to another polypeptide or tag, such as a leader or secretory sequence or a sequence which is employed for purification or for detection. In a particular embodiment, the polypeptide of the invention comprises the glutathione-S-transferase protein tag which provides the basis for rapid high-affinity purification of the polypeptide of the invention. Indeed, this GST-fusion protein can then be purified from cells via its high affinity for glutathione. Agarose beads can be coupled to glutathione, and such glutathione-agarose beads bind GST-proteins. Thus, in a particular embodiment of the invention, the polypeptide of the invention is bound to a solid support. In a preferred embodiment, if the polypeptide of the invention comprises a GST moiety, the polypeptide is coupled to a glutathione-modified support. In a particular case, the glutathione modified support is a glutathione-agarose bead. Additionally, a sequence encoding a protease cleavage site can be included between the affinity tag and the polypeptide sequence, thus permitting the removal of the binding tag after incubation with this specific enzyme and thus facilitating the purification of the corresponding protein of interest. Suitable protease cleavage sites for incorporation into the polypeptides of the invention include enterokinase, factor Xa, thrombin, TEV protease, PreScission protease, inteins and the like.

(c) Targeting Sequences

The invention also relates to proteins or peptides of the invention fused to, or integrated into, a target protein, and/or a targeting domain capable of directing the chimeric protein to a desired cellular component or cell type or tissue. The chimeric proteins may also contain additional amino acid sequences or domains. The chimeric proteins are recombinant in the sense that the various components are from different sources, and as such are not found together in nature (i.e. are heterologous).

A target protein is a protein that is selected for degradation and for example may be a protein that is mutated or over expressed in a disease or condition. In another embodiment of the invention, a target protein is a protein that is abnormally degraded and for example may be a protein that is mutated or underexpressed in a disease or condition. The targeting domain can be a membrane spanning domain, a membrane binding domain, or a sequence directing the protein to associate with for example vesicles or with the nucleus. The targeting domain can target a protein of the invention to a particular cell type or tissue. For example, the targeting domain can be a cell surface ligand or an antibody against cell surface antigens of a target tissue. A targeting domain may target a protein to a MG cell. In one embodiment, an accessory peptide can be used to enhance interaction of the protein with the target MG cell.

(d) Intracellular Targeting

Combined with certain formulations, peptides can be effective intracellular agents. In order to increase the efficacy of such peptides, the peptide can be provided as a fusion peptide along with a second peptide which promotes "transcytosis", e.g., uptake of the peptide by epithelial cells. To illustrate, the peptide can be provided as a chimeric peptide which includes a heterologous peptide sequence ("internalizing peptide") which drives the translocation of an extracellular form of a peptide across a cell membrane in order to facilitate intracellular localization of the peptide. In this regard, the peptide sequence is one which is active intracellularly. The internalizing peptide, by itself, is capable of crossing a cellular membrane by, e.g., transcytosis, at a relatively high rate. The internalizing peptide is conjugated, e.g., as a fusion protein, to the protein. The resulting chimeric peptide is transported into cells at a higher rate relative to the peptide alone to thereby provide a means for enhancing its introduction into cells to which it is applied.

In one embodiment, the internalizing peptide is derived from the *Drosophila* antennapedia protein, or homologs thereof. The 60 amino acid long homeodomain of the homeo-protein antennapedia has been demonstrated to translocate through biological membranes and can facilitate the translocation of heterologous polypeptides to which it is couples. See for example Derossi et al. (1994) J Biol Chem 269:10444-10450; and Perez et al. (1992) J Cell Sci 102: 717-722. Recently, it has been demonstrated that fragments as small as 16 amino acids long of this protein are sufficient to drive internalization. See Derossi et al. (1996) J Biol Chem 271:18188-18193.

The present invention contemplates a protein sequence for activation of WNT signaling, or a WNT signaling effector, as described herein, and at least a portion of the Antennapedia protein (or homolog thereof) sufficient to promote the transmembrane transport of the chimeric protein.

Another example of an internalizing peptide is the HIV transactivator (TAT) protein. This protein appears to be divided into four domains (Kuppuswamy et al. (1989) Nucl. Acids Res. 17:3551-3561). Purified TAT protein is taken up by cells in tissue culture (Frankel and Pabo, (1989) Cell, 55:1189-1193), and peptides, such as the fragment corresponding to residues 37-62 of TAT, are rapidly taken up by cell in vitro (Green and Loewenstein, (1989) Cell 55:1179-1188). The highly basic region mediates internalization and targeting of the internalizing moiety to the nucleus (Ruben et al., (1989) J. Virol. 63:1-8).

Another exemplary transcellular polypeptide can be generated to include a sufficient portion of mastoparan (T. Higashijima et al., (1990) J. Biol. Chem. 265:14176) to increase the transmembrane transport of the chimeric protein.

While not wishing to be bound by any particular theory, it is noted that hydrophilic polypeptides may be also be physiologically transported across the membrane barriers by coupling or conjugating the polypeptide to a transportable peptide which is capable of crossing the membrane by receptor-mediated transcytosis, e.g., a histone, insulin, transferrin, basic albumin, prolactin and insulin-like growth factor I (IGF-I), insulin-like growth factor II (IGF-II) or other growth factors.

Another class of translocating/internalizing peptides exhibits pH-dependent membrane binding. For an internalizing peptide that assumes a helical conformation at an acidic pH, the internalizing peptide acquires the property of amphiphilicity, e.g., it has both hydrophobic and hydrophilic interfaces. More specifically, within a pH range of approximately 5.0-5.5, an internalizing peptide forms an alpha-helical, amphiphilic structure that facilitates insertion of the moiety into a target membrane. An alpha-helix-inducing acidic pH environment may be found, for example, in the low pH environment present within cellular endosomes. Such internalizing peptides can be used to facilitate transport of peptides, taken up by an endocytic mechanism, from endosomal compartments to the cytoplasm.

A preferred pH-dependent membrane-binding internalizing peptide includes a high percentage of helix-forming residues, such as glutamate, methionine, alanine and leucine. In addition, a preferred internalizing peptide sequence includes ionizable residues having pKa's within the range of pH 5-7, so that a sufficient uncharged membrane-binding domain will be present within the peptide at pH 5 to allow insertion into the target cell membrane.

In various embodiments, internalizing peptides include, but are not limited to, peptides of apo-lipoprotein A-1 and B; peptide toxins, such as melittin, bombolittin, delta hemolysin and the pardaxins; antibiotic peptides, such as alamethicin; peptide hormones, such as calcitonin, corticotrophin releasing factor, beta endorphin, glucagon, parathyroid hormone, pancreatic polypeptide; and peptides corresponding to signal sequences of numerous secreted proteins. In addition, exemplary internalizing peptides may be modified through attachment of substituents that enhance the alpha-helical character of the internalizing peptide at acidic pH.

Yet another class of internalizing peptides suitable for use within the present invention include hydrophobic domains that are "hidden" at physiological pH, but are exposed in the low pH environment of the target cell endosome. Upon pH-induced unfolding and exposure of the hydrophobic domain, the moiety binds to lipid bilayers and effects translocation of the covalently linked polypeptide into the cell cytoplasm. Such internalizing peptides may be modeled after sequences identified in, e.g., *Pseudomonas* exotoxin A, clathrin, or Diphtheria toxin.

Pore-forming proteins or peptides may also serve as internalizing peptides herein. Pore-forming proteins or peptides may be obtained or derived from, for example, C9 complement protein, cytolytic T-cell molecules or NK-cell molecules. These moieties are capable of forming ring-like structures in membranes, thereby allowing transport of attached polypeptide through the membrane and into the cell interior.

Mere membrane intercalation of an internalizing peptide may be sufficient for translocation of the proteins of the invention across cell membranes. However, translocation may be improved by attaching to the internalizing peptide a substrate for intracellular enzymes (i.e., an "accessory peptide"). It is preferred that an accessory peptide be attached to a portion(s) of the internalizing peptide that protrudes through the cell membrane to the cytoplasmic face. The accessory peptide may be advantageously attached to one terminus of a translocating/internalizing moiety or anchoring peptide. An accessory moiety of the present invention may contain one or more amino acid residues. In one embodiment, an accessory moiety may provide a substrate for cellular phosphorylation (for instance, the accessory peptide may contain a tyrosine residue).

Suitable accessory peptides include peptides that are kinase substrates, peptides that possess a single positive charge, and peptides that contain sequences which are glycosylated by membrane-bound glycotransferases. Accessory peptides that are glycosylated by membrane-bound glycotransferases may include the sequence x-NLT-x, where "x" may be another peptide, an amino acid, coupling agent or hydrophobic molecule, for example. When this hydrophobic tripeptide is incubated with microsomal vesicles, it crosses vesicular membranes, is glycosylated on the luminal side, and is entrapped within the vesicles due to its hydrophilicity (C. Hirschberg et al., (1987) Ann. Rev. Biochem. 56:63-87). Accessory peptides that contain the sequence x-NLT-x thus will enhance target cell retention of corresponding polypeptide.

In certain instances, it may also be desirable to include a nuclear localization signal as part of the protein or fusion protein.

As described above, the internalizing and accessory peptides can each, independently, be added to the protein of the invention by either chemical cross-linking or in the form of a fusion protein. In the instance of fusion proteins, unstructured polypeptide linkers can be included between each of the peptide moieties.

In the generation of fusion proteins, it may be necessary to include unstructured linkers in order to ensure proper folding of the various peptide domains. Many synthetic and natural linkers are known in the art and can be adapted for use in the present invention.

(e) Expression System

Peptides of the invention may be developed using a biological expression system. The use of these systems allows the production of large libraries of random peptide sequences and the screening of these libraries for peptide sequences that bind to particular proteins. Libraries may be produced by cloning synthetic DNA that encodes random peptide sequences into appropriate expression vectors. (see Christian et al 1992, J. Mol. Biol. 227:711; Devlin et al, 1990 Science 249:404; Cwirla et al 1990, Proc. Natl. Acad, Sci. USA, 87:6378). Libraries may also be constructed by concurrent synthesis of overlapping peptides (see U.S. Pat. No. 4,708,871).

The peptides and chimeric proteins of the invention may be converted into pharmaceutical salts by reacting with inorganic acids such as hydrochloric acid, sulfuric acid, hydrobromic acid, phosphoric acid, etc., or organic acids such as formic acid, acetic acid, propionic acid, glycolic acid, lactic acid, pyruvic acid, oxalic acid, succinic acid, malic acid, tartaric acid, citric acid, benzoic acid, salicylic acid, benzenesulfonic acid, and toluenesulfonic acids.

Nucleic Acids

The invention also includes nucleic acids encoding the peptides described herein. In one embodiment, the invention includes an isolated nucleic acid comprising a coding sequence which encodes an activator of WNT signaling. In one embodiment the nucleotide sequence comprises a coding sequence which encodes β-catenin. In another embodiment, the nucleotide sequence comprises a coding sequence which encodes Lin28a. In another embodiment, the nucleotide sequence comprises a coding sequence which encodes Lin28b. In another embodiment, the nucleotide sequence comprises a coding sequence which encodes Notch. In another embodiment, the nucleotide sequence comprises a coding sequence which encodes Ascl1.

The nucleotide sequences encoding β-catenin, Lin28a Lin28b, Notch, or Ascl1 can alternatively comprise sequence variations with respect to the original nucleotide sequences, for example, substitutions, insertions and/or deletions of one or more nucleotides, with the condition that the resulting polynucleotide encodes a polypeptide according to the invention which has the effect of increasing or activating WNT signaling.

In another embodiment, the invention includes a nucleic acid molecule encoding at least one transcription factor selected from the group consisting of Otx2, Crx, Nrl, Nr2e3, and NueroD. In specific embodiments, the nucleic acid molecule encodes Otx2. In specific embodiments, the nucleic acid molecule encodes Crx. In specific embodiments, the nucleic acid molecule encodes Nrl.

The nucleic acid molecules encoding Otx2, Crx, Nrl, Nr2e3, or NueroD can alternatively comprise sequence variations with respect to the original (e.g., wild type) nucleic acid molecules encoding Otx2, Crx, Nrl, Nr2e3, or NueroD, respectively, for example, substitutions, insertions and/or deletions of one or more nucleotides, with the condition that the resulting polynucleotide encodes a polypeptide according to the invention which has the effect of expressing Otx2, Crx, Nrl, Nr2e3, or NueroD capable of causing MG cell differentiation as described here.

In one embodiment, the invention relates to a construct, comprising a nucleotide sequence encoding Otx2, Crx, Nrl, Nr2e3, NueroD, or an activator of WNT signaling, or derivative thereof. In a particular embodiment, the construct is operatively bound to transcription (e.g., a promoter), and optionally translation, control elements. The construct can incorporate an operatively bound regulatory sequence of the expression of the nucleotide sequence of the invention, thus forming an expression cassette. In certain embodiments, the transcription control element (e.g., a promoter), is specific to particular cell type (e.g., MG cells). For example, nucleic acids described herein can be operably linked to a promoter for specific expression (i.e., transcription) of the nucleic acid in MG cells. A nonlimiting example of a promoter for specific expression of a nucleic acid in MG cells is the GFAP promoter (see, e.g., Brenner et al., J Neurosci 14 (3): 1070-7, 1994; Kuzmanovic et al., Retinal Cell Biology 44 (8): 3606-3613, 2003). In certain embodiments, the GFAP promoter comprises the sequence:

```
                                          (SEQ ID NO: 8)
agATctaACATATcCtggtGTgGAGTAGGGGACGCTGcTCTGACAGAGGc

TCGGGGGCCtGAGCTGgcTCTGTGAGCTGGGGAGGAGGCAGACAgCCAGG

CCtTTGTcTGCAAGCAGACCTGGCAGCATTGGGCTGgCCGCCCCCCAGGg

CCTCCTCTTCATGCCCAGTGAATGACTCACCTTGGCACAGACACAATGTT

CGGGGTGGGCACAGTGCCTGCTTCCCGCCGCACCCCAGCCCCCCTCAAAT

GCCTTCCGAGAAGCCCATTGAGCAGGGGGCTTGCATTGCACCCCAGCCTG

ACAGCCTGGCATCTTGGGATAAAAGCAGCACAGCCCCCTAGGGGCTGCCC

TTGCTGTGTGGCGCCACCGGCGGTGGAGAACAAGGCTCTATTCAGCCTGT

GCCCAGGAAAGGGGATCAGGGGATGCCCAGGCATGGACAGTGGGTGGCAG

GGGGGGAGAGGAGGGCTGTCTGCTTCCCAGAAGTCCAAGGACACAAATGG

GTGAGGGGAGAGCTCTCCCCATAGCTGGGCTGCGGCCCAACCCCACCCCC

TCAGGCTATGCCAGGGGGTGTTGCCAGGGGCACCCGGGCATCGCCAGTCT

AGCCCACTCCTTCATAAAGCCCTCGCATCCCAGGAGCGAGCAGAGCCAGA

GCAGGTTGGAGAGGAGACGCATCACCTCCGCTGCTCGCGGGGATCC.
```

A nucleic acid sequence of the invention may be prepared using recombinant DNA methods. Accordingly, a nucleic acid molecule which encodes an activator of WNT signaling, including, but not limited to β-catenin, Lin28a, and Lin28b, or which encodes Otx2, Crx, Nrl, Nr2e3, or NueroD, Notch, or Ascl1, may be incorporated in a known manner into an appropriate expression vector which ensures good expression of the protein. In specific embodiments, the expression vector is specifically expressed in retinal cells (e.g., AAV-ShH10 (see, e.g., Klimczak et al., PLOS One, 2009 and U.S. Pat. No. 8,663,624, each of which is incorporated by reference herein in its entirety)). In specific embodiments, the expression vector is a vector described in U.S. Pat. No. 8,663,624, which is incorporated by reference herein in its entirety.

Therefore, in another aspect, the invention relates to a vector, comprising the nucleotide sequence of the invention or the construct of the invention. The choice of the vector will depend on the host cell in which it is to be subsequently introduced. In a particular embodiment, the vector of the invention is an expression vector. Suitable host cells include a wide variety of prokaryotic and eukaryotic host cells. In specific embodiments, the expression vector is selected from the group consisting of a viral vector, a bacterial vector and a mammalian cell vector. Prokaryote- and/or eukaryote-vector based systems can be employed for use with the present invention to produce polynucleotides, or their cognate polypeptides. Many such systems are commercially and widely available.

Further, the expression vector may be provided to a cell in the form of a viral vector. Viral vector technology is well known in the art and is described, for example, in Sambrook et al. (2001), and in Ausubel et al. (1997), and in other virology and molecular biology manuals. Viruses, which are useful as vectors include, but are not limited to, retroviruses, adenoviruses, adeno-associated viruses (e.g., ShH10), herpes viruses, and lentiviruses. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193).

In specific embodiments, the viral vector is a viral vector that specifically infects a retinal cell. In certain embodiments, a viral vector specifically infects a retinal cell if exhibits at least S-fold, at least 10-fold, at least 15-fold, at least 20-fold, at least 25-fold, at least 50-fold, or more than 50-fold, increased infectivity of a retinal cell compared to the infectivity of a non-retinal cell. In specific embodiments, the viral vector that specifically infects a retinal cell is an AAV. In specific embodiments, the viral vector that specifically infects a retinal cell is an AAV described in U.S. Pat. No. 8,663,624, which is incorporated by reference herein in its entirety. In specific embodiments in which the viral vector is an AAV, the capsid of the AAV viral vector comprises an amino acid sequence having at least about 85%, at least about 90%, at least about 95%, at least about 98%, at least about 99%, or 100%, amino acid sequence identity to the ShH10 amino acid sequence of SEQ ID NO:7:

```
                                                  (SEQ ID NO: 7)
  1  MAADGYLPDW LEDNLSEGIR EWWDLKPGAP KPKANQQKQD
     DGRGLVLPGY KYLGPFNGLD

 61  KGEPVNAADA AALEHDKAYD QQLKAGDNPY LRYNHADAEF
     QERLQEDTSF GGNLGRAVFQ

121  AKKRVLEPFG LVEEGAKTAP GKKRPVEQSP QEPDSSSGIG
     KTGQQPAKKR LNFGQTGDSE

181  SVPDPQPLGE PPATPAAVGP TTMASGGGAP MADNNEGADG
     VGNASGNWHC DSTWLGDRVI

241  TTSTRTWALP TYNNHLYKQI SSASTGASND NHYFGYSTPW
     GYFDFNRFHC HFSPRDWQRL

301  INNNWGFRPK RLNFKLFNVQ VKEVTTNDGV TTIANNLTST
     VQVFSDSEYQ LPYVLGSAHQ

361  GCLPPFPADV FMIPQYGYLT LNNGSQAVGR SSFYCLEYFP
     SQMLRTGNNF TFSYTFEDVP

421  FHSSYAHSQS LDRLMNPLID QYLYYLNRTQ DQSGSAQNKD
     LLFSRGSPAG MSVQPKNWLP

481  GPCYRQQRVS KTKTDNNNSN FTWTGASKYN LNGRESIINP
     GTAMASHKDD KNKFFPMSGV

541  MIFGKESAGA SNTALDNVMI TDEEEIKATN PVATERFGTV
     AVNLQSSSTD PATGDVHVMG
```

-continued

```
601  ALPGMVWQDR DVYLQGPIWA KIPHTDGHFH PSPLMGGFGL
     KNPPPQILIK NTPVPANPPA

661  EFSATKFASF ITQYSTGQVS VEIEWELQKE NSKRWNPEVQ
     YTSNYAKSAN VDFTVDNNGL

721  YTEPRPIGTR YLTRPL.
```

In specific embodiments, the viral vector is AAV-ShH10.

Vectors suitable for the insertion of the polynucleotides are vectors derived from expression vectors in prokaryotes such as pUC18, pUC19, Bluescript and the derivatives thereof, mp18, mp19, pBR322, pMB9, ColE1, pCR1, RP4, phages and "shuttle" vectors such as pSA3 and pAT28, expression vectors in yeasts such as vectors of the type of 2 micron plasmids, integration plasmids, YEP vectors, centromere plasmids and the like, expression vectors in insect cells such as vectors of the pAC series and of the pVL, expression vectors in plants such as pIBI, pEarley Gate, pAVA, pCAMBIA, pGSA, pGWB, pMDC, pMY, pORE series and the like, and expression vectors in eukaryotic cells based on viral vectors (adenoviruses, viruses associated to adenoviruses such as retroviruses and, particularly, lentiviruses) as well as non-viral vectors such as pSilencer 4.1-CMV (Ambion), pcDNA3, pcDNA3.1/hyg, pHMCV/Zeo, pCR3.1, pEFI/His, pIND/GS, pRc/HCMV2, pSV40/Zeo2, pTRACER-HCMV, PUB6/V5-His, pVAX1, pZeoSV2, pCI, pSVL and PKSV-10, pBPV-1, pML2d and pTDT1. In a preferred embodiment, the vector is the MG cell specific ShH10 vector.

By way of illustration, the vector in which the nucleic acid sequence is introduced can be a plasmid which is or is not integrated in the genome of a host cell when it is introduced in the cell. Illustrative, non-limiting examples of vectors in which the nucleotide sequence of the invention or the gene construct of the invention can be inserted include a tet-on inducible vector for expression in eukaryote cells.

The vector may be obtained by conventional methods known by persons skilled in the art (Sambrook et al., "Molecular cloning, a Laboratory Manual", 2nd ed., Cold Spring Harbor Laboratory Press, N.Y., 1989 Vol 1-3]. In a particular embodiment, the vector is a vector useful for transforming animal cells.

The recombinant expression vectors may also contain nucleic acid molecules which encode a portion which provides increased expression of the recombinant protein; increased solubility of the protein; and/or aid in the purification of the protein by acting as a ligand in affinity purification. For example, a proteolytic cleavage site may be inserted in the recombinant peptide to allow separation of the recombinant protein from the fusion portion after purification of the fusion protein. Examples of fusion expression vectors include pGEX (Amrad Corp., Melbourne, Australia), pMAL (New England Biolabs, Beverly, Mass.) and pRIT5 (Pharmacia, Piscataway, N.J.) which fuse glutathione S-transferase (GST), maltose E binding protein, or protein A, respectively, to the recombinant protein.

Additional promoter elements, i.e., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either co-operatively or independently to activate transcription.

A promoter may be one naturally associated with a gene or polynucleotide sequence, as may be obtained by isolating the 5' non-coding sequences located upstream of the coding segment and/or exon. Such a promoter can be referred to as "endogenous." Similarly, an enhancer may be one naturally associated with a polynucleotide sequence, located either downstream or upstream of that sequence. Alternatively, certain advantages will be gained by positioning the coding polynucleotide segment under the control of a recombinant or heterologous promoter, which refers to a promoter that is not normally associated with a polynucleotide sequence in its natural environment. A recombinant or heterologous enhancer refers also to an enhancer not normally associated with a polynucleotide sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (U.S. Pat. Nos. 4,683,202, 5,928,906). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know how to use promoters, enhancers, and cell type combinations for protein expression, for example, see Sambrook et al. (2001). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

A promoter sequence exemplified in the experimental examples presented herein is the GFAP (glial fibrillary acidic protein) promoter (e.g., SEQ ID NO:8). This promoter sequence is capable of driving high levels of expression of any polynucleotide sequence operatively linked thereto in MG cells. However, other constitutive promoter sequences may also be used, including, but not limited to the cytomegalovirus (CMV) promoter, simian virus 40 (SV40) early promoter, mouse mammary tumor virus (MMTV), human immunodeficiency virus (HIV) long terminal repeat (LTR) promoter, Moloney virus promoter, the avian leukemia virus promoter, Epstein-Barr virus immediate early promoter, Rous sarcoma virus promoter, as well as human gene promoters such as, but not limited to, the actin promoter, the myosin promoter, the hemoglobin promoter, and the muscle creatine promoter. Further, the invention should not be limited to the use of constitutive promoters. Inducible promoters are also contemplated as part of the invention. The use of an inducible promoter in the invention provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter. Further, the invention includes the use of a tissue specific promoter, which promoter is active only in a desired tissue. MG specific promoters include, but are not limited to, the RLBP1 promoter, the CD44 promoter and the GFAP promoter sequences.

In one embodiment, the expression of the nucleic acid may be externally controlled. For example, the expression may be externally controlled using a doxycycline Tet-On system.

The recombinant expression vectors may also contain a selectable marker gene which facilitates the selection of transformed or transfected host cells. Suitable selectable marker genes are genes encoding proteins such as G418 and hygromycin which confer resistance to certain drugs, B-galactosidase, chloramphenicol acetyltransferase, firefly luciferase, or an immunoglobulin or portion thereof such as the Fc portion of an immunoglobulin preferably IgG. The selectable markers may be introduced on a separate vector from the nucleic acid of interest.

Reporter genes are used for identifying potentially transfected cells and for evaluating the functionality of regulatory sequences. Reporter genes that encode for easily assayable proteins are well known in the art. In general, a reporter gene is a gene that is not present in or expressed by the recipient organism or tissue and that encodes a protein whose expression is manifested by some easily detectable property, e.g., enzymatic activity. Expression of the reporter gene is assayed at a suitable time after the DNA has been introduced into the recipient cells.

Suitable reporter genes may include genes encoding luciferase, beta-galactosidase, chloramphenicol acetyl transferase, secreted alkaline phosphatase, or the green fluorescent protein gene (see, e.g., Ui-Tei et al., 2000 FEBS Lett. 479:79-82). Suitable expression systems are well known and may be prepared using well known techniques or obtained commercially. Internal deletion constructs may be generated using unique internal restriction sites or by partial digestion of non-unique restriction sites. Constructs may then be transfected into cells that display high levels of siRNA polynucleotide and/or polypeptide expression. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Recombinant expression vectors may be introduced into host cells to produce a recombinant cell. The cells can be prokaryotic or eukaryotic. The vector of the invention can be used to transform eukaryotic cells such as yeast cells, *Saccharomyces cerevisiae*, or mammal cells for example epithelial kidney 293 cells or U2OS cells, or prokaryotic cells such as bacteria, *Escherichia coli* or *Bacillus subtilis*, for example. Nucleic acid can be introduced into a cell using conventional techniques such as calcium phosphate or calcium chloride co-precipitation, DEAE-dextran-mediated transfection, lipofectin, electroporation or microinjection. Suitable methods for transforming and transfecting host cells may be found in Sambrook et al. (Molecular Cloning: A Laboratory Manual, 2nd Edition, Cold Spring Harbor Laboratory press (1989)), and other laboratory textbooks.

For example, a protein of the invention may be expressed in bacterial cells such as *E. coli*, insect cells (using baculovirus), yeast cells or mammalian cells. Other suitable host cells can be found in Goeddel, Gene Expression Technology: Methods in Enzymology 185, Academic Press, San Diego, Calif. (1991).

Inhibitor Compositions

One of skill in the art will realize that diminishing the amount or activity of a molecule that itself diminishes the amount or activity of WNT signaling can serve to increase the amount or activity of WNT signaling. Therefore, in one embodiment, the invention provides an inhibitor of one or more negative regulators of WNT signaling or WNT signaling effectors. In various embodiments, the compositions of the invention decrease the amount of polypeptide, the amount of mRNA, the amount of enzymatic activity, or a combination thereof of one or more negative regulators of WNT signaling. In one embodiments, the compositions of the invention decrease the amount of polypeptide, the amount of mRNA, the amount of enzymatic activity, or a combination thereof of GSK3B. In one embodiment, the composition inhibits one or more let-7 miRNA.

It will be understood by one skilled in the art, based upon the disclosure provided herein, that a decrease in the level of one or more negative regulators of WNT signaling encompasses the decrease in the expression, including transcription, translation, or both. The skilled artisan will also appreciate, once armed with the teachings of the present invention, that a decrease in the level of one or more negative regulators of WNT signaling includes a decrease in the activity of the protein. Thus, decrease in the level or activity of one or more negative regulators of WNT signaling includes, but is not limited to, decreasing the amount of polypeptide of one or more negative regulators of WNT signaling, and decreasing transcription, translation, or both, of a nucleic acid encoding one or more negative regulators of WNT signaling; and it also includes decreasing any activity of one or more negative regulators of WNT signaling.

In one embodiment, the present invention provides a composition for inducing MG proliferation, wherein the composition inhibits a negative regulator of WNT signaling. In certain embodiments, the composition inhibits the expression, activity, or both of a WNT signaling regulator. In one embodiment, a negative regulator of WNT signaling is GSK3B. Therefore, in one embodiment an inhibitor of the invention inhibits GSK3B. In one embodiment, a negative regulator of Lin28, a protein in the WNT signaling pathway, is let-7 miRNA. Therefore, in various embodiments, the composition inhibits the expression, activity, or both of one or more let-7 miRNA. Human let-7 miRNA include, but are not limited to, hsa-let-7a-1, hsa-let-7a-2, hsa-let-7a~3, hsa-let-7b, hsa-let-7c, hsa-let-7d, hsa-let-7e, hsa-let-7f-1, hsa-let-7f-2, hsa-let-7g and hsa-let-7i. In one embodiment, the composition inhibits hsa-let-7b.

An inhibitor may be one of, but is not limited to, a small interfering RNA (siRNA), a microRNA, an antisense nucleic acid, a ribozyme, an expression vector encoding a transdominant negative mutant, an intracellular antibody, a peptide and a small molecule. In one embodiment, one or more of a negative regulator of WNT signaling can be inhibited by way of inactivating and/or sequestering the protein. As such, inhibiting the effects of a negative regulator of WNT signaling can be accomplished by using a transdominant negative mutant. Alternatively an antibody specific for one or more negative regulator of WNT signaling, otherwise known as an inhibitor of one or more negative regulator of WNT signaling may be used. In another embodiment, the inhibitor is a protein and/or compound having the desirable property of interacting with one or more negative regulator of WNT signaling and thereby sequestering the protein. In one embodiment, the composition of the invention is used in combination with other therapeutic agents.

siRNA

In one embodiment, siRNA is used to decrease the level of one or negative regulator of WNT signaling. RNA interference (RNAi) is a phenomenon in which the introduction of double-stranded RNA (dsRNA) into a diverse range of organisms and cell types causes degradation of the complementary mRNA. In the cell, long dsRNAs are cleaved into short 21-25 nucleotide small interfering RNAs, or siRNAs, by a ribonuclease known as Dicer. The siRNAs subsequently assemble with protein components into an RNA-induced silencing complex (RISC), unwinding in the process. Activated RISC then binds to complementary transcript by base pairing interactions between the siRNA antisense strand and the mRNA. The bound mRNA is cleaved and sequence specific degradation of mRNA results in gene silencing. See, for example, U.S. Pat. No. 6,506,559; Fire et al., 1998, Nature 391 (19): 306-311; Timmons et al., 1998, Nature 395:854; Montgomery et al., 1998, TIG 14 (7): 255-258; David R. Engelke, Ed., RNA Interference (RNAi) Nuts & Bolts of RNAi Technology, DNA Press, Eagleville, PA (2003); and Gregory J. Hannon, Ed., RNAi A Guide to Gene Silencing, Cold Spring Harbor Laboratory Press, Cold Spring Harbor, NY (2003). Soutschek et al. (2004, Nature 432:173-178) describe a chemical modification to siRNAs that aids in intravenous systemic delivery. Optimizing siRNAs involves consideration of overall G/C content, C/T content at the termini, Tm and the nucleotide content of the 3' overhang. See, for instance, Schwartz et al., 2003, Cell, 115:199-208 and Khvorova et al., 2003, Cell 15 115:209-216. Therefore, the present invention also includes methods of decreasing levels of one or more of a negative regulator of WNT signaling at the protein level using RNAi technology.

In other related aspects, the invention includes an isolated nucleic acid encoding an inhibitor, wherein an inhibitor such as an siRNA or antisense molecule, inhibits the desired negative regulator of WNT signaling, operably linked to a nucleic acid comprising a promoter/regulatory sequence such that the nucleic acid is preferably capable of directing expression of the protein encoded by the nucleic acid. Thus, the invention encompasses expression vectors and methods for the introduction of exogenous DNA into cells with concomitant expression of the exogenous DNA in the cells such as those described, for example, in Sambrook et al. (2001, Molecular Cloning: A Laboratory Manual, Cold Spring Harbor Laboratory, New York), and in Ausubel et al. (1997, Current Protocols in Molecular Biology, John Wiley & Sons, New York) and as described elsewhere herein.

In another aspect, the invention includes a vector comprising an siRNA or antisense polynucleotide. Preferably, the siRNA or antisense polynucleotide is capable of inhibiting the expression of the desired negative regulator of WNT signaling. The incorporation of a desired polynucleotide into a vector and the choice of vectors is well-known in the art as described in, for example, Sambrook et al., supra, and Ausubel et al., supra, and elsewhere herein.

The siRNA or antisense polynucleotide can be cloned into a number of types of vectors as described elsewhere herein. For expression of the siRNA or antisense polynucleotide, at least one module in each promoter functions to position the start site for RNA synthesis. In one embodiment, a promoter for expression in MG cells is the GFAP promoter. In certain embodiments, the GFAP promoter comprises the sequence of SEQ ID NO:8. In one embodiment, the siRNA or antisense polynucleotide can be cloned into the ShH10-GFAP vector for expression in MG cells.

In order to assess the expression of the siRNA or antisense polynucleotide, the expression vector to be introduced into a cell can also contain either a selectable marker gene or a reporter gene or both to facilitate identification and selection of expressing cells from the population of cells sought to be transfected or infected through viral vectors. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neomycin resistance and the like.

In one embodiment, the invention encompasses methods for delivery of a siRNA or a combination of siRNAs of the invention to a cell in need thereof.

Antisense Nucleic Acids

In one embodiment of the invention, an antisense nucleic acid sequence which is expressed by a plasmid vector is used to inhibit one or more negative regulator of WNT signaling. The antisense expressing vector is used to transfect a mammalian cell or the mammal itself, thereby causing reduced endogenous expression of one or more negative regulator of WNT signaling.

Antisense molecules and their use for inhibiting gene expression are well known in the art (see, e.g., Cohen, 1989, In: Oligodeoxyribonucleotides, Antisense Inhibitors of Gene Expression, CRC Press). Antisense nucleic acids are DNA or RNA molecules that are complementary, as that term is defined elsewhere herein, to at least a portion of a specific mRNA molecule (Weintraub, 1990, Scientific American 262:40). In the cell, antisense nucleic acids hybridize to the corresponding mRNA, forming a double-stranded molecule thereby inhibiting the translation of genes.

The use of antisense methods to inhibit the translation of genes is known in the art, and is described, for example, in Marcus-Sakura (1988, Anal. Biochem. 172:289). Such antisense molecules may be provided to the cell via genetic expression using DNA encoding the antisense molecule as taught by Inoue, 1993, U.S. Pat. No. 5,190,931.

Alternatively, antisense molecules of the invention may be made synthetically and then provided to the cell. Antisense oligomers of between about 10 to about 30, and more preferably about 15 nucleotides, are preferred, since they are easily synthesized and introduced into a target cell. Synthetic antisense molecules contemplated by the invention include oligonucleotide derivatives known in the art which have improved biological activity compared to unmodified oligonucleotides (see U.S. Pat. No. 5,023,243).

Ribozymes

Ribozymes and their use for inhibiting gene expression are also well known in the art (see, e.g., Cech et al., 1992, J. Biol. Chem. 267:17479-17482; Hampel et al., 1989, Biochemistry 28:4929-4933; Eckstein et al., International Publication No. WO 92/07065; Altman et al., U.S. Pat. No. 5,168,053). Ribozymes are RNA molecules possessing the ability to specifically cleave other single-stranded RNA in a manner analogous to DNA restriction endonucleases. Through the modification of nucleotide sequences encoding these RNAs, molecules can be engineered to recognize specific nucleotide sequences in an RNA molecule and cleave it (Cech, 1988, J. Amer. Med. Assn. 260:3030). A major advantage of this approach is the fact that ribozymes are sequence-specific.

There are two basic types of ribozymes, namely, tetrahymena-type (Hasselhoff, 1988, Nature 334:585) and hammerhead-type. Tetrahymena-type ribozymes recognize sequences which are four bases in length, while hammerhead-type ribozymes recognize base sequences 11-18 bases in length. The longer the sequence, the greater the likelihood that the sequence will occur exclusively in the target mRNA species. Consequently, hammerhead-type ribozymes are preferable to tetrahymena-type ribozymes for inactivating specific mRNA species, and 18-base recognition sequences are preferable to shorter recognition sequences which may occur randomly within various unrelated mRNA molecules.

In one embodiment of the invention, a ribozyme is used to inhibit a negative regulator of WNT signaling. Ribozymes useful for inhibiting the expression of a target molecule may be designed by incorporating target sequences into the basic ribozyme structure which are complementary, for example, to the mRNA sequence of the negative regulator of WNT signaling of the present invention. Ribozymes targeting a desired negative regulator of WNT signaling may be synthesized using commercially available reagents (Applied Biosystems, Inc., Foster City, CA) or they may be genetically expressed from DNA encoding them.

Small Molecules

When the inhibitor of the invention is a small molecule, a small molecule inhibitor of one or more negative regulator of WNT signaling may be obtained using standard methods known to the skilled artisan. Such methods include chemical organic synthesis or biological means. Biological means include purification from a biological source, recombinant synthesis and in vitro translation systems, using methods well known in the art.

Combinatorial libraries of molecularly diverse chemical compounds potentially useful in treating a variety of diseases and conditions are well known in the art as are method of making the libraries. The method may use a variety of techniques well-known to the skilled artisan including solid phase synthesis, solution methods, parallel synthesis of single compounds, synthesis of chemical mixtures, rigid core structures, flexible linear sequences, deconvolution strategies, tagging techniques, and generating unbiased molecular landscapes for lead discovery vs. biased structures for lead development.

In a general method for small library synthesis, an activated core molecule is condensed with a number of building blocks, resulting in a combinatorial library of covalently linked, core-building block ensembles. The shape and rigidity of the core determines the orientation of the building blocks in shape space. The libraries can be biased by changing the core, linkage, or building blocks to target a characterized biological structure ("focused libraries") or synthesized with less structural bias using flexible cores.

In one embodiment, the small molecule is able to inhibit one or more negative regulator of WNT signaling. In one embodiment, the small molecule is able to inhibit GSK3B. The inhibitor may also be a hybrid or fusion composition to facilitate, for instance, delivery to target cells or efficacy. In one embodiment, a hybrid composition may comprise a cell-specific targeting sequence. For example, in one embodiment, the inhibitor is targeted to MG cells.

Antibodies

As will be understood by one skilled in the art, any antibody that can recognize and bind to an antigen of interest is useful in the present invention. In one embodiment, an antigen of interest is a negative regulator of WNT signaling. In one embodiment, an antigen is GSK3B. In one embodiment, an antigen is let-7 miRNA, and an antibody that can recognize let-7 miRNA is an anti-miR.

Methods of making and using antibodies are well known in the art. For example, polyclonal antibodies useful in the present invention are generated by immunizing rabbits according to standard immunological techniques well-known in the art (see, e.g., Harlow et al., 1988, In: Antibodies, A Laboratory Manual, Cold Spring Harbor, NY).

The generation of polyclonal antibodies is accomplished by inoculating the desired animal with the antigen and isolating antibodies which specifically bind the antigen therefrom using standard antibody production methods such as those described in, for example, Harlow et al. (1988, In: Antibodies, A Laboratory Manual, Cold Spring Harbor, NY).

Monoclonal antibodies directed against full length or peptide fragments of a protein or peptide may be prepared using any well-known monoclonal antibody preparation procedures, such as those described, for example, in Harlow et al. (1988, In: Antibodies, A Laboratory Manual, Cold Spring Harbor, NY) and in Tuszynski et al. (1988, Blood, 72:109-115). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

Nucleic acid encoding the monoclonal antibody obtained using the procedures described herein may be cloned and sequenced using technology which is available in the art, and is described, for example, in Wright et al. (1992, Critical Rev. Immunol. 12:125-168), and the references cited therein. Further, the antibody of the invention may be "humanized" using the technology described in, for example, Wright et al., and in the references cited therein, and in Gu et al. (1997, Thrombosis and Hematocyst 77:755-759), and other methods of humanizing antibodies well-known in the art or to be developed.

The present invention also includes the use of humanized antibodies specifically reactive with epitopes of an antigen of interest. The humanized antibodies of the invention have a human framework and have one or more complementarity determining regions (CDRs) from an antibody, typically a mouse antibody, specifically reactive with an antigen of interest. When the antibody used in the invention is humanized, the antibody may be generated as described in Queen, et al. (U.S. Pat. No. 6,180,370), Wright et al., (supra) and in the references cited therein, or in Gu et al. (1997, Thrombosis and Hematocyst 77 (4): 755-759). The method disclosed in Queen et al. is directed in part toward designing humanized immunoglobulins that are produced by expressing recombinant DNA segments encoding the heavy and light chain complementarity determining regions (CDRs) from a donor immunoglobulin capable of binding to a desired antigen, such as an epitope on an antigen of interest, attached to DNA segments encoding acceptor human framework regions. Generally speaking, the invention in the Queen patent has applicability toward the design of substantially any humanized immunoglobulin. Queen explains that the DNA segments will typically include an expression control DNA sequence operably linked to the humanized immunoglobulin coding sequences, including naturally-associated or heterologous promoter regions. The expression control sequences can be eukaryotic promoter systems in vectors capable of transforming or transfecting eukaryotic host cells or the expression control sequences can be prokaryotic promoter systems in vectors capable of transforming or transfecting prokaryotic host cells. Once the vector has been incorporated into the appropriate host, the host is maintained under conditions suitable for high level expression of the introduced nucleotide sequences and as desired the collection and purification of the humanized light chains, heavy chains, light/heavy chain dimers or intact antibodies, binding fragments or other immunoglobulin forms may follow (Beychok, Cells of Immunoglobulin Synthesis, Academic Press, New York, (1979), which is incorporated herein by reference).

The invention also includes functional equivalents of the antibodies described herein. Functional equivalents have binding characteristics comparable to those of the antibodies, and include, for example, hybridized and single chain antibodies, as well as fragments thereof. Methods of producing such functional equivalents are disclosed in PCT Application WO 93/21319 and PCT Application WO 89/09622.

Functional equivalents include polypeptides with amino acid sequences substantially the same as the amino acid sequence of the variable or hypervariable regions of the antibodies. "Substantially the same" amino acid sequence is defined herein as a sequence with at least 70%, preferably at least about 80%, more preferably at least about 90%, even more preferably at least about 95%, and most preferably at least 99% homology to another amino acid sequence (or any integer in between 70 and 99), as determined by the FASTA search method in accordance with Pearson and Lipman, 1988 Proc. Nat'l. Acad. Sci. USA 85:2444-2448. Chimeric or other hybrid antibodies have constant regions derived substantially or exclusively from human antibody constant regions and variable regions derived substantially or exclusively from the sequence of the variable region of a monoclonal antibody from each stable hybridoma.

Single chain antibodies (scFv) or Fv fragments are polypeptides that consist of the variable region of the heavy chain of the antibody linked to the variable region of the light chain, with or without an interconnecting linker. Thus, the Fv comprises an antibody combining site.

Functional equivalents of the antibodies of the invention further include fragments of antibodies that have the same, or substantially the same, binding characteristics to those of the whole antibody. Such fragments may contain one or both Fab fragments or the F(ab') 2 fragment. The antibody fragments contain all six complement determining regions of the whole antibody, although fragments containing fewer than all of such regions, such as three, four or five complement determining regions, are also functional. The functional equivalents are members of the IgG immunoglobulin class and subclasses thereof, but may be or may combine with any one of the following immunoglobulin classes: IgM, IgA, IgD, or IgE, and subclasses thereof. Heavy chains of various subclasses, such as the IgG subclasses, are responsible for different effector functions and thus, by choosing the desired heavy chain constant region, hybrid antibodies with desired effector function are produced. Exemplary constant regions are gamma 1 (IgG1), gamma 2 (IgG2), gamma 3 (IgG3), and gamma 4 (IgG4). The light chain constant region can be of the kappa or lambda type.

The immunoglobulins of the present invention can be monovalent, divalent or polyvalent. Monovalent immunoglobulins are dimers (HL) formed of a hybrid heavy chain associated through disulfide bridges with a hybrid light chain. Divalent immunoglobulins are tetramers (H2L2) formed of two dimers associated through at least one disulfide bridge.

Inhibitors of miRNA

In an exemplary embodiment, a negative regulator of Lin28 is let-7 miRNA. Therefore, in this embodiment, the invention relates to methods of inhibiting let-7 miRNA. However, the invention is not restricted to regulating a let-7 miRNA and therefore relates to methods of inhibiting any miRNA which functions to inhibit WNT signaling. Methods of inhibiting miRNA are generally known in the art. In one embodiment, a composition that inhibits miRNA is an anti-miR. Anti-miR antibodies appropriate for use in inhibiting miRNA are discussed elsewhere herein. In various alternative embodiments, a composition that inhibits a miRNA may be, but is not limited to, one of a miRNA sponge, a competing endogenous RNA (ceRNA), or circular RNA (circRNA) which serve to sequester the mature miRNA, disrupting endogenous miRNA: mRNA target binding.

Treatment Methods

Vision loss or impairment is often due to loss or death of rod photoreceptors, and can be a concern associated with aging or a complication of disease such as diabetes. The current invention provides compositions and methods to induce formation of new rod photoreceptor cells and therefore any individual having vision loss or impairment associated with loss of rod photoreceptors can benefit from the method of the invention. Therefore, in one embodiment, the method of the invention relates to administering one or more activator and/or inhibitor compositions (e.g., a composition comprising a MG cell proliferation agent and/or a composition comprising a MG cell differentiation agent) of the invention to a subject identified as having vision loss or impairment. In one embodiment, a subject identified as having vision loss or impairment is a subject having an ophthalmic disease or degenerative eye condition. In one embodiment, an ophthalmic diseases or degenerative eye condition is one of macular degeneration, including age-related macular degeneration (AMD) and exudative or wet AMD, diabetic retinopathy, retrolental fibroplasia, Stargardt disease, retinitis pigmentosa (RP), uveitis, Bardet-Biedl syndrome and eye cancers.

In one embodiment, the present invention provides methods of treating vision loss or impairment comprising administering an effective amount of a composition comprising an activator of WNT signaling to a subject. In one embodiment, the composition induces the proliferation of MG cells.

In one embodiment, the present invention provides methods of treating vision loss or impairment comprising administering an effective amount of a composition comprising an activator of rod photoreceptor genes to a subject. In one embodiment, the composition directs the differentiation of MG cells into rod photoreceptors.

In certain embodiments, the method comprises administering one or more compositions, where each composition comprises one or more activators or inhibitors. For example, in one embodiment, the method comprises administering a first composition comprising β-catenin and a second composition comprising one or more of Otx2, Crx, Nrl, Nr2e3 and NeuroD. In another embodiment, the method comprises administering a first composition comprising β-catenin and a second composition comprising Otx2, Crx, and Nrl. In an alternative embodiment, the method comprises administering a first composition comprising let-7 anti-miR and a second composition comprising one or more of Otx2, Crx, Nrl, Nr2e3 and NeuroD. In an alternative embodiment, the method comprises administering a first composition comprising let-7 anti-miR and a second composition comprising Otx2, Crx, and Nrl. In an alternative embodiment, the method comprises administering a first composition comprising Notch and a second composition comprising one or more of Otx2, Crx, Nrl, Nr2e3 and NeuroD. In an alternative embodiment, the method comprises administering a first composition comprising Notch and a second composition comprising Otx2, Crx, and Nrl. In an alternative embodiment, the method comprises administering a first composition comprising Ascl1 and a second composition comprising one or more of Otx2, Crx, Nrl, Nr2e3 and NeuroD. In an alternative embodiment, the method comprises administering a first composition comprising Ascl1 and a second composition comprising Otx2, Crx, and Nrl.

In certain embodiments, the method comprises administering one or more compositions, where each composition comprises one or more nucleic acid molecules encoding one or more activators or inhibitors. For example, in one embodiment, the method comprises administering a first composition comprising a nucleic acid molecule encoding β-catenin and a second composition comprising one or more nucleic acid molecules encoding one or more of Otx2, Crx, Nrl, Nr2e3 and NeuroD. In another embodiment, the method comprises administering a first composition comprising a nucleic acid molecule encoding β-catenin and a second composition comprising one or more nucleic acid molecules encoding Otx2, Crx, and Nrl. In another embodiment, the method comprises administering a first composition comprising a nucleic acid molecule encoding β-catenin and a second composition comprising a first nucleic acid molecule encoding Otx2, a second nucleic acid molecule encoding Crx, and a third nucleic acid molecule encoding Nrl. In certain embodiments, the second composition comprises a first vector comprising the first nucleic acid molecule, a second vector comprising the second nucleic acid molecule, and a third vector comprising the third nucleic acid molecule.

In an alternative embodiment, the method comprises administering a first composition comprising let-7 anti-miR and a second composition comprising one or more nucleic acid molecules encoding one or more of Otx2, Crx, Nrl, Nr2e3 and NeuroD. In an alternative embodiment, the method comprises administering a first composition comprising let-7 anti-miR and a second composition comprising one or more nucleic acid molecules encoding one or more of Otx2, Crx, and Nrl. In an alternative embodiment, the method comprises administering a first composition comprising let-7 anti-miR and a second composition comprising a first nucleic acid molecule encoding Otx2, a second nucleic acid molecule encoding Crx, and a third nucleic acid molecule encoding Nrl. In certain embodiments, the second composition comprises a first vector comprising the first nucleic acid molecule, a second vector comprising the second nucleic acid molecule, and a third vector comprising the third nucleic acid molecule.

In certain embodiments, the method comprises administering one or more compositions, where each composition comprises one or more nucleic acid molecules encoding one or more activators or inhibitors. For example, in one embodiment, the method comprises administering a first composition comprising a nucleic acid molecule encoding Notch and a second composition comprising one or more nucleic acid molecules encoding one or more of Otx2, Crx, Nrl, Nr2e3 and NeuroD. In another embodiment, the method comprises administering a first composition comprising a nucleic acid molecule encoding Notch and a second composition comprising one or more nucleic acid molecules encoding Otx2, Crx, and Nrl. In another embodiment, the method comprises administering a first composition comprising a nucleic acid molecule encoding Notch and a second composition comprising a first nucleic acid molecule encoding Otx2, a second nucleic acid molecule encoding Crx, and a third nucleic acid molecule encoding Nrl. In certain embodiments, the second composition comprises a first vector comprising the first nucleic acid molecule, a second vector comprising the second nucleic acid molecule, and a third vector comprising the third nucleic acid molecule.

The different compositions may be administered to the subject in any order and in any suitable interval. For example, in certain embodiments, the one or more compositions are administered simultaneously or near simultaneously. In certain embodiments, the method comprises a staggered administration of the one or more compositions, where a first composition is administered and a second composition administered at some later time point. Any suitable interval of administration which produces the desired therapeutic effect may be used.

Also provided herein is a method of treating vision loss or impairment in a subject, comprising: (a) administering to the subject a therapeutically effective amount of a Müller glial (MG) cell proliferation agent; and (b) a period of time after the administering of step (a), administering to the subject a therapeutically effective amount of a MG cell differentiation agent.

In specific embodiments, the MG cell proliferation agent comprises a composition described herein that activates WNT signaling in MG cells to induce MG cell proliferation. In specific embodiments, the MG cell proliferation agent activates one or more of β-catenin and Lin28 in MG cells to induce cell proliferation. In specific embodiments, the MG cell proliferation agent comprises a protein selected from the group consisting of beta-catenin, Lin28a, and Lin28b. In specific embodiments, the MG cell proliferation agent comprises a beta-catenin protein. In specific embodiments, the MG cell proliferation agent comprises a nucleic acid encoding a protein selected from the group consisting of beta-catenin, Lin28a, and Lin28b. In specific embodiments, the MG cell proliferation agent comprises a nucleic acid encoding beta-catenin. In specific embodiments, the MG cell proliferation agent comprises a vector, wherein the vector comprises a nucleic acid encoding a protein selected from the group consisting of beta-catenin, Lin28a, and Lin28b. In specific embodiments, the MG cell the proliferation agent comprises a vector, wherein the vector comprises a nucleic acid encoding beta-catenin.

In specific embodiments, the MG cell proliferation agent activates Notch in MG cells to induce cell proliferation. In specific embodiments, the MG cell proliferation agent comprises a Notch protein. In specific embodiments, the MG cell proliferation agent comprises a nucleic acid encoding Notch. In specific embodiments, the MG cell proliferation agent comprises a vector, wherein the vector comprises a nucleic acid encoding Notch.

In specific embodiments, the MG cell proliferation agent activates Ascl1 in MG cells to induce cell proliferation. In specific embodiments, the MG cell proliferation agent comprises an Ascl1 protein. In specific embodiments, the MG cell proliferation agent comprises a nucleic acid encoding Ascl1. In specific embodiments, the MG cell proliferation agent comprises a vector, wherein the vector comprises a nucleic acid encoding Ascl1.

In specific embodiments in which the MG cell proliferation agent comprises a nucleic acid, the nucleic acid is operably linked to a promoter, wherein the promoter specifically expresses the nucleic acid in MG cells. In specific embodiments, the promoter that specifically expresses the nucleic acid in MG cells comprises a glial fibrillary acidic protein (GFAP) promoter. In certain embodiments, the GFAP promoter comprises the sequence of SEQ ID NO:8.

In specific embodiments in which the MG cell proliferation agent comprises a vector, the vector is a virus or a virus-like particle. In specific embodiments in which the MG cell proliferation agent comprises a vector, the vector is an adeno-associated virus (AAV). In specific embodiments, the AAV is ShH10.

In specific embodiments, the MG cell differentiation agent comprises a composition described herein that activates transcription of cell-specific genes to induce differentiation of cells to rod photoreceptors. In specific embodiments, the MG cell differentiation agent comprises one or more compositions that activates one or more of rhodopsin, rod a-transducin, rod arrestin, phosducin, ROMI, retinal cGMP, Guanylate Cyclase-Activating Protein Photoreceptor 2, Tubby Like Protein 1, Retinoschisin 1, G alpha 1, G gamma 1, cGMP PDE gamma, G beta 1, mUNC119, rod PDE beta, Pleckstrin Homology Domain Retinal Protein 1, Peripherin 2, recoverin, ribeye, bassoon, and CtBP, or a combination thereof. In specific embodiments, the MG cell differentiation agent comprises one or more compositions that activates one or more transcription factors selected from the group consisting of Otx2, Crx, Nrl, Nr2e3, and NeuroD, or a combination thereof. In specific embodiments, the MG cell differentiation agent comprises one or more compositions that activates Otx2, Crx, and Nrl.

In specific embodiments, the MG cell differentiation agent comprises at least one nucleic acid molecule encoding at least one transcription factor selected from the group consisting of Otx2, Crx, Nrl, Nr2e3, and NueroD. In specific embodiments, the differentiation agent comprises at least one nucleic acid molecule encoding Otx2, Crx, and Nrl. In specific embodiments, the MG cell differentiation agent comprises a first nucleic acid molecule, a second nucleic acid molecule, and a third nucleic acid molecule, wherein the first nucleic acid molecule encodes Otx2, wherein the second nucleic acid molecule encodes Crx, and wherein the third nucleic acid molecule encodes Nrl. In specific embodiments in which the MG cell differentiation agent comprises a nucleic acid molecule(s), the nucleic acid molecule is operably linked to a promoter, wherein the promoter specifically expresses the nucleic acid molecule in MG cells. In a specific embodiment, the promoter that specifically expresses the nucleic acid molecule in MG cells comprises a glial fibrillary acidic protein (GFAP) promoter. In certain embodiments, the GFAP promoter comprises the sequence of SEQ ID NO:8.

In specific embodiments, the MG cell differentiation agent comprises a first vector, a second vector, and a third vector, wherein the first vector comprises a first nucleic acid molecule, the second vector comprises a second nucleic acid molecule, and the third vector comprises a third nucleic acid molecule, wherein the first nucleic acid m encodes a transcription factor selected from the group consisting of Otx2, Crx, Nrl, Nr2e3, and NueroD, the second nucleic acid molecule encodes a transcription factor selected from the group consisting of Otx2, Crx, Nrl, Nr2e3, and NueroD, and the third nucleic acid molecule encodes a transcription factor selected from the group consisting of Otx2, Crx, Nrl, Nr2e3, and NueroD, and wherein each of the first, second, and third nucleic acid molecules encode a different protein. For example, if the first nucleic acid molecule encodes Otx2, then neither the second nor the third nucleic acid molecule encodes Otx2. In another example if the first nucleic acid molecule encodes Otx2 and the second nucleic acid molecule encodes Crx, then the third nucleic acid molecule does not encode Otx2 or Crx. In specific embodiments, the differentiation agent comprises a first vector, a second vector, and a third vector, wherein the first vector comprises a first nucleic acid molecule, the second vector comprises a second nucleic acid molecule, and the third vector comprises a third nucleic acid molecule, wherein the first nucleic acid molecule encodes Otx2, the second nucleic acid molecule encodes Crx, and the third nucleic acid molecule encodes Nrl. In specific embodiments, the first nucleic acid molecule is operably linked to a first promoter, the second nucleic acid molecule is operably linked to a second promoter, and the third nucleic acid molecule is operably linked to a third promoter, and wherein the first, second, and third promoters express the nucleic acid molecule in MG cells. In specific embodiments, the first, second, and/or third promoters comprise a glial fibrillary acidic protein (GFAP) promoter. In certain embodiments, the GFAP promoter comprises the sequence of SEQ ID NO:8. In specific embodiments, the first vector is a first virus or a first virus-like particle, the second vector is a second virus or a second virus-like particle, and the third vector is a third virus or a third virus-like particle. In specific embodiments, the first vector is a first adeno-associated virus (AAV), the second vector is a second AAV, and the third vector is a third AAV. In specific embodiments, the first, second, and/or third AAV is ShH10.

In specific embodiments, the period of time of step (b) is at least one week, at least two weeks, at least three weeks, four weeks. In specific embodiments, the period of time of step (b) is two weeks.

In certain embodiments, the period of time of step (b) is less than 1 minute, less than 5 minutes, less than 10 minutes, less than one hour, less than two hours, or less than three hours. In certain embodiments in which the time of step (b) is less than three hours, the MG cell differentiation agent is formulated as a delayed release agent (e.g., the MG cell differentiation agent is not released until 1 to 5 days, 5 to 10 days, 10 to 15 days, 15 to 20 days, or 20 to 30 days after the subject is administered the MG cell differentiation agent).

In a specific embodiment, the subject is a subject identified as having vision loss or impairment. In a specific embodiment, the subject has a condition associated with vision loss or impairment due to photoreceptor loss. Non-limiting examples of conditions associated with vision loss or impairment due to photoreceptor loss include the condition is age-related macular degeneration (AMD), diabetic retinopathy, retrolental fibroplasia, Stargardt disease, retinitis pigmentosa (RP), uveitis, Bardet-Biedl syndrome and eye cancers. In a specific embodiment, the subject is a human.

Treatment Regimens

In one embodiment, the invention relates to a method of treating vision impairment or loss in a subject through administering to the individual a treatment regimen to induce MG cell differentiation into rod photoreceptor cells. In one embodiment, a composition to induce MG cell proliferation is administered to a subject prior to administration of one or more composition to induce differentiation of proliferating MG cells into rod photoreceptor cells. Thus, in specific embodiments, provided herein is a method of treating vision loss or impairment in a subject, comprising: (a) administering to the subject a therapeutically effective amount of a Müller glial (MG) cell proliferation agent; and (b) a period of time after the administering of step (a), administering to the subject a therapeutically effective amount of a MG cell differentiation agent. In one embodiment, a treatment regimen comprises administering a composition to induce MG cell proliferation (e.g., a composition comprising a MG cell proliferation agent) at least one day, at least 2 days, at least 3 days, at least 4 days, at least 5 days, at least 6 days, at least 1 week, at least 2 weeks, at least 3 weeks, at least 4 weeks, at least one month, at least two months or more than two months prior to an administration of one or more composition to induce differentiation of MG cells (e.g., a composition comprising a MG cell differentiation agent). In one embodiment, a treatment regimen comprises administering a composition to induce MG cell proliferation (e.g., a composition comprising a MG cell proliferation agent) less than one day, less than 2 days, less than 3 days, less than 4 days, less than 5 days, less than 6 days, less than 1 week, less than 2 weeks, less than 3 weeks, less than 4 weeks, less than one month, less than two months or less than two months prior to administration of one or more composition to induce differentiation of MG cells (e.g., a composition comprising a MG cell differentiation agent). In one embodiment, a treatment regimen comprises administering a composition to induce MG cell proliferation (e.g., a composition comprising a MG cell proliferation agent) less than 1 minute, less than 5 minutes, less than 10 minutes, less than one hour, less than two hours, or less than three hours prior to administration of one or more composition to induce differentiation of MG cells (e.g., a composition comprising a MG cell differentiation agent). In certain embodiments in which the composition to induce MG cell proliferation is administered less than 1 minute, less than 5 minutes, less than 10 minutes, less than one hour, less than two hours, or less than three hours prior to administration of one or more composition to induce differentiation of MG cells, the MG cell differentiation agent is formulated as a delayed release agent (e.g., the MG cell differentiation agent is not released until 1 to 5 days, 5 to 10 days, 10 to 15 days, 15 to 20 days, or 20 to 30 days after the subject is administered the MG cell differentiation agent).

In one embodiment, a treatment regimen comprises administering a composition to induce MG cell proliferation at least once prior to administration of one or more compositions to induce differentiation of MG cells. In one embodiment, a treatment regimen comprises administering a composition to induce MG cell proliferation at least once daily for at least 1 day, at least 7 days, at least 10 days, at least 1 month, at least 2 months, at least 3 months or more than 3 months prior to administration of one or more compositions to induce differentiation of MG cells.

In one embodiment, a treatment regimen comprises administering one or more compositions to induce differentiation of MG cells at least once following administration of a composition to induce MG cell proliferation. In one embodiment, a treatment regimen comprises administering a composition to induce differentiation of MG cells at least once daily for at least 1 day, at least 7 days, at least 10 days, at least 1 month, at least 2 months, at least 3 months or more than 3 months following administration of a composition to induce MG cell proliferation.

In one embodiment, a treatment regimen includes multiple intravitreal injections of the compositions spaced over several days, weeks, months, a year, or even several years. Therefore, in one embodiment, a treatment regimen includes administering a composition to induce MG cell proliferation to the same subject multiple times spaced over several days, weeks, months, a year, or several years. In one embodiment, a treatment regimen includes administering a composition to induce MG cell proliferation to the same eye multiple times spaced over several days, weeks, months, a year, or several years.

In one embodiment, a treatment regimen includes administering a composition to induce differentiation of MG cells to the same subject multiple times spaced over several days, weeks, months, a year, or several years. In one embodiment, a treatment regimen includes administering a composition to induce differentiation of MG cells to the same eye multiple times spaced over several days, weeks, months, a year, or several years.

In one embodiment, a treatment regimen may include a single administration of a composition to induce MG cell proliferation and multiple administrations of a composition to induce differentiation of MG cells. In one embodiment, a treatment regimen may include multiple administrations of a composition to induce MG cell proliferation and a single administration of a composition to induce differentiation of MG cells. In one embodiment, a treatment regimen may include multiple administrations of a composition to induce MG cell proliferation and multiple administrations of a composition to induce differentiation of MG cells.

In some embodiments, a therapeutically effective amount of a MG cell proliferation is an amount that, when administered to a subject (e.g., administered via intravitreal injection into an eye) in one or more doses, is effective to proliferate MG cells such that, subsequent administration of a therapeutically effective amount of a MG cell differentiation agent slows the progression of retinal degeneration in the subject. In some cases, a therapeutically effective amount of a MG cell differentiation agent is an amount that, when administered to a subject (e.g., administered via intravitreal injection into an eye) in one or more doses, is effective to slow the progression of retinal degeneration in the subject. For example, a therapeutically effective amount of a MG cell proliferation agent can be an amount, when administered to a subject (e.g., administered via intravitreal injection to a subject) in one or more doses, in combination with subsequent administration of a therapeutically effective amount of a MG cell differentiation agent, is effective to slow the progression of retinal degeneration by at least about 15%, at least about 20%, at least about 25%, at least about 30%, at least about 40%, at least about 50%, at least about 60%, at least about 70%, at least about 80%, or more than 80%, compared to the progression of retinal degeneration in the absence of treatment with the MG cell proliferation agent and the MG cell differentiation agent.

In some embodiments, a therapeutically effective amount of a MG cell proliferation is an amount that, when administered to a subject (e.g., administered via intravitreal injection into an eye) in one or more doses, is effective to proliferate MG cells such that, subsequent administration of a therapeutically effective amount of a MG cell differentiation agent is effective to improve vision in the subject. In some cases, a therapeutically effective amount of a MG cell differentiation agent is an amount that, when administered to a subject (e.g., administered via intravitreal injection into an eye) in one or more doses, is effective to improve vision in the subject. For example, a therapeutically effective amount of a MG cell proliferation agent can be an amount, when administered to a subject (e.g., administered via intravitreal injection to a subject) in one or more doses, in combination with subsequent administration of a therapeutically effective amount of a MG cell differentiation agent, is effective to improve vision by at least about 15%, at least about 20%, at least about 25%, at least about 30%, at least about 40%, at least about 50%, at least about 60%, at least about 70%, at least about 80%, or more than 80%, compared to the subject's vision in the absence of treatment with the MG cell proliferation agent and the MG cell differentiation agent.

In some embodiments, a therapeutically effective amount of a MG cell proliferation is an amount that, when administered to a subject (e.g., administered via intravitreal injection into an eye) in one or more doses, is effective to proliferate MG cells such that, subsequent administration of a therapeutically effective amount of a MG cell differentiation agent is effective to increase the number of rod cells in the subject. In some cases, a therapeutically effective amount of a MG cell differentiation agent is an amount that, when administered to a subject (e.g., administered via intravitreal injection into an eye) in one or more doses, is effective to increase the number of rod cells in the subject. An increase in the number of rod cells can be evaluated by looking at improvement of one or more clinical symptoms known in the art, such as, e.g., tests of functional vision, such as visual acuity, visual field, contrast sensitivity, color vision, mobility, and light sensitivity.

In some embodiments, a therapeutically effective amount of a MG cell proliferation is an amount that, when administered to a subject (e.g., administered via intravitreal injection into an eye) in one or more doses, is effective to decrease the rate of vision loss in an eye with impaired vision. In some cases, a therapeutically effective amount of a MG cell differentiation agent is an amount that, when administered to a subject (e.g., administered via intravitreal injection into an eye) in one or more doses, is effective to decrease the rate of vision loss in an eye with impaired vision.

Improvement of clinical symptoms are monitored by one or more methods known to the art, for example, tests of functional vision, such as visual acuity, visual field, contrast sensitivity, mobility, and light sensitivity. Clinical symptoms may also be monitored by anatomical or physiological means, such as indirect ophthalmoscopy, fundus photography, fluorescein angiopathy, optical coherence tomography, electroretinography (full-field, multifocal, or other), external eye examination, slit lamp biomicroscopy, applanation tonometry, pachymetry, autorefraction, or other measures of functional vision.

Pharmaceutical Formulations and Administration

Administration of the compositions of the present invention to a subject, preferably a mammal, more preferably a human, may be carried out using known procedures, at dosages and for periods of time effective to prevent or treat vision loss or impairment in the subject. An effective amount of the therapeutic compositions necessary to achieve a therapeutic effect may vary according to factors such as the state of the disease or disorder in the subject; the age, sex, and weight of the subject; and the ability of the therapeutic compound to cross the blood-brain barrier and the blood-retina barrier The regimen of administration may affect what constitutes an effective amount. In one embodiment, two or more compositions may be administered to the subject concurrently. In another embodiment, two or more compositions may be administered to the subject at different times to constitute a course of treatment. Further, the dosages of the compositions may be proportionally increased or decreased as indicated by the exigencies of the therapeutic situation. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular subject, composition, and mode of administration, without being toxic to the subject.

In particular, the selected dosage level will depend upon a variety of factors including the activity of the particular composition employed, the time of administration, the rate of excretion of the composition, the duration of the treatment, other drugs, compounds or materials used in combination with the composition, the age, sex, weight, condition, general health and prior medical history of the subject being treated, and like factors well known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

Typically, dosages which may be administered in a method of the invention to a mammal, preferably a human, range in amount from 0.5 ng to about 50 mg per kilogram of body weight of the mammal, while the precise dosage administered will vary depending upon any number of factors, including but not limited to, the type of mammal and type of disease state being treated, the age of the mammal and the route of administration. Preferably, the dosage of the compound will vary from about 1 ng to about 10 mg per kilogram of body weight of the mammal. More preferably, the dosage will vary from about 3 ng to about 1 mg per kilogram of body weight of the mammal.

Eye drops and intravitreal or periocular (Sub-Tenon or subconjunctival) injections are the conventional dosage forms that account for greater than ninety percent of the currently available ophthalmic formulations. To improve bioavailability and reduce the complications associated with repeated injections, the present invention contemplates sustained delivery of the compositions of the invention alone or in combination with other medications. The sustained delivery in the present invention can be achieved through a number of different delivery systems, including but not limited to polymeric gels, colloidal systems including liposomes and nanoparticles, cyclodextrins, collagen shields, diffusion chambers, flexible carrier strips, and intravitreal implants.

In the present invention, ocular and intraocular drug delivery systems deliver the compositions to the back of the eye. These drug delivery systems include: using the sclera itself as a drug delivery reservoir, "prodrug" formulations that pass through the tissue, tiny biodegradable pellets that release the combinations over time, intravitreal implants, intravitreal silicone inserts, intravitreal and transscleral poly (lactic-co-glycolic acid) microspheres, calcium-alginate inserts, encapsulated cells, transscleral iontophoresis, nanoparticles (e.g., calcium phosphate), and genetically modified viruses that can deliver therapeutic proteins into therapy.

In one embodiment, one or more composition of the invention is administered using intraocular or intravitreal injection. For administration of a composition using intraocular injection, anesthesia may be administered via methods known to those of skill in the art including, but not limited to, topical administration of proparacaine or tetracaine drops, 2% lidocaine gel or subconjunctival injection of 2% lidocaine solution. In general, intravitreal injections are administered under controlled aseptic conditions, using mask, sterile gloves, a sterile drape, and a sterile lid speculum. Prior to injection the periocular area is cleaned. Solutions for use in cleaning the periocular area are known to those of skill in the art and may include a povidone-iodine preparation. Following intravitreal injection, irrigation of the eyes may be performed with an appropriate solution. In one embodiment, a solution appropriate for use is a balanced salt solution.

The compositions of the present invention can be in the form of solutions. Solutions can be administered topically by applying them to the cul-de-sac of the eye from a dropper controlled bottle or dispenser. A typical dose regimen for an adult human may range from about 2 to about 8 drops per day, applied at bed-time or throughout the day. Dosages for adult humans may, however, be higher, in which case the drops are administered by "bunching", e.g., 5 doses administered over a 5 minute period, repeated about 4 times daily. A topical solution in accordance with one embodiment of the invention comprises a therapeutic dose of a composition of the invention in an artificial tear formulation. Such artificial tear formulations are used for restoring the normal barrier function of damaged corneal epithelium following surgery. Typically, artificial tear compositions contain ionic components found in normal human tear film, as well as various combinations of one or more of tonicity agents (e.g., soluble salts, such as Na, Ca, K, and Mg chlorides, and dextrose and sorbitol), buffers (e.g., alkali metal phosphate buffers), viscosity/lubricating agents (e.g., alkyl and hydroxyalkyl celluloses, dextrans, polyacrylamides), nonionic surfactants, sequestering agents (e.g., disodium edetate, citric acid, and sodium citrate), and preservatives (e.g., benzalkonium chloride, and thimerosal). In one embodiment, artificial tear compositions are preservative free. The quantities and relative proportions of each of these components incorporated into an artificial tear composition are readily determinable by the skilled formulation chemist. The ionic species bicarbonate is used in artificial tear compositions, e.g., U.S. Pat. No. 5,403,598 and Ubels, J L, et al, Arch. Ophthalmol. 1995, 113:371-8.

Alternatively, compositions of the present invention can be in the form of ophthalmic ointments. Ophthalmic ointments have the benefit of providing prolonged drug contact time with the eye surface. Ophthalmic ointments will generally include a base comprised of, for example, white petrolatum and mineral oil, often with anhydrous lanolin, polyethylene-mineral oil gel, and other substances recognized by the formulation chemist as being non-irritating to the eye, which permit diffusion of the drug into the ocular fluid, and which retain activity of the medicament for a reasonable period of time under storage conditions.

Therapeutic amounts of a composition of the invention can be administered orally. For these oral dosage forms, the composition may be formulated with a pharmaceutically acceptable solid or liquid carrier. Solid form preparations include powders, tablets, pills, capsules, cachets, and dispersible granules. The concentration or effective amount of the composition to be administered per dosage is widely dependent on the actual composition. However, a total oral daily dosage normally ranges from about 50 mg to 30 g, and more preferably from about 250 mg to 25 g. A solid carrier can be one or more substances which may also function as a diluent, a flavoring agent, a solubilizer, a lubricant, a suspending agent, a binder, a preservative, a tablet disintegrating aid, or an encapsulating material. Suitable carriers include magnesium carbonate, magnesium stearate, talc, sugar, lactose, pectin, dextrin, starch gelatin, tragacanth, methylcellulose, sodium carboxymethylcellulose, microcrystalline cellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills cachets, and lozenges can be used as solid dosage forms suitable for oral administration.

A composition may also be administered surgically as an ocular implant. As one example, a reservoir container having a diffusible wall of polyvinyl alcohol or polyvinyl acetate and containing milligram quantities of a composition may be implanted in the sclera. As another example, a composition in milligram quantities may be incorporated into a polymeric matrix having dimensions of about 2 mm by 4 mm, and made of a polymer such as polycaprolactone, poly(glycolic) acid, poly(lactic) acid, or a polyanhydride, or a lipid such as sebacic acid, and may be implanted on the sclera or in the eye. This is usually accomplished with the subject receiving either a topical or local anesthetic and using a small (3-4 mm incision) made behind the cornea. The matrix, containing a composition, is then inserted through the incision and sutured to the sclera using 9-0 nylon.

A composition may also be contained within an inert matrix for either topical application or injection into the eye. As one example of an inert matrix, liposomes may be prepared from dipalmitoyl phosphatidylcholine (DPPC), preferably prepared from egg phosphatidylcholine (PC) since this lipid has a low heat transition. Liposomes are made using standard procedures as known to one skilled in the art. A composition, in amounts ranging from nanogram to microgram quantities, is added to a solution of egg PC, and the lipophilic drug binds to the liposome.

A time-release drug delivery system may be implanted intraocularly to result in sustained release of the active agent over a period of time. The implantable formation may be in the form of a capsule of a polymer (e.g., polycaprolactone, poly(glycolic) acid, poly(lactic) acid, polyanhydride) or lipids that may be formulation as microspheres. As an illustrative example, a composition may be mixed with polyvinyl alcohol (PVA), the mixture then dried and coated with ethylene vinyl acetate, then cooled again with PVA. The composition bound with liposomes may be applied topically, either in the form of drops or as an aqueous based cream, or may be injected intraocularly. In a formulation for topical application, the drug is slowly released overtime as the liposome capsule degrades due to wear and tear from the eye surface. In a formulation for intraocular injection, the liposome capsule degrades due to cellular digestion. Both of these formulations provide advantages of a slow release drug delivery system, allowing the subject a constant exposure to the drug over time.

In a time-release formulation, the microsphere, capsule, liposome, etc. may contain a concentration of a composition that could be toxic if administered as a bolus dose. The time-release administration, however, is formulated so that the concentration released at any period of time does not exceed a toxic amount. This is accomplished, for example, through various formulations of the vehicle (coated or uncoated microsphere, coated or uncoated capsule, lipid or polymer components, unilamellar or multilamellar structure, and combinations of the above, etc.). Other variables may include the subject's pharmacokinetic-pharmacodynamic parameters (e.g., body mass, gender, plasma clearance rate, hepatic function, etc.). The formation and loading of microspheres, microcapsules, liposomes, etc. and their ocular implantation are standard techniques known by one skilled in the art, for example, the use a ganciclovir sustained-release implant to treat cytomegalovirus retinitis, disclosed in Vitreoretinal Surgical Techniques, Peyman et al., Eds. (Martin Dunitz. London 2001, chapter 45); Handbook of Pharmaceutical Controlled Release Technology, Wise, Ed. (Marcel Dekker, New York 2000), the relevant sections of which are incorporated by reference herein in their entirety.

Multiple compositions of the invention may be administered simultaneously, separately or spaced out over a period of time so as to obtain the maximum efficacy of the combination; it being possible for each administration to vary in its duration from a rapid administration to a continuous perfusion. As a result, for the purposes of the present invention, the combinations are not exclusively limited to those which are obtained by physical association of the constituents, but also to those which permit a separate administration, which can be simultaneous or spaced out over a period of time.

The administration of a nucleic acid or peptide inhibitor of the invention to the subject may be accomplished using gene therapy. Gene therapy is based on inserting a therapeutic gene into a cell by means of an ex vivo or an in vivo technique. Suitable vectors and methods have been described for genetic therapy in vitro or in vivo, and are known as expert on the matter; see, for example, Giordano, Nature Medicine 2 (1996), 534-539; Schaper, Circ. Res 79 (1996), 911-919; Anderson, Science 256 (1992), 808-813; Isner, Lancet 348 (1996), 370-374; Muhlhauser, Circ. Res 77 (1995), 1077-1086; Wang, Nature Medicine 2 (1996), 714-716; WO94/29469; WO97/00957 or Schaper, Current Opinion in Biotechnology 7 (1996), 635-640 and the references quoted therein. A polynucleotide, or a polynucleotide encoding a peptide of the invention, can be designed for direct insertion or by insertion through liposomes or viral vectors (for example, adenoviral or retroviral vectors) in the cell. Suitable gene distribution systems that can be used according to the invention may include liposomes, distribution systems mediated by receptor, naked DNA and viral vectors such as the herpes virus, the retrovirus, the adenovirus and adeno-associated viruses, among others. The distribution of nucleic acids to a specific site in the body for genetic therapy can also be achieved by using a biolistic distribution system, such as that described by Williams (Proc. Natl. Acad. Sci. USA, 88 (1991), 2726-2729). The standard methods for transfecting cells with recombining DNA are well known by an expert on the subject of molecular biology, see, for example, WO94/29469. Genetic therapy can be carried out by directly administering the recombining DNA molecule or the vector of the invention to a patient. In one embodiment, a DNA molecule is administered to the patient through intravitreal injection.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compositions of the present invention and practice the claimed methods. The following working examples therefore, specifically point out the preferred embodiments of the present invention, and are not to be construed as limiting in any way the remainder of the disclosure.

Example 1

Wnt Regulates Proliferation and Neurogenic Potential of Müller Glial Cells Through a Lin28/Let-7 miRNA-Dependent Pathway in Adult Mammalian Retina The experiments presented herein examined whether retinal injury may induce signaling events, which in turn stimulate MG proliferation, and that by directly activating these signals, MGs can be stimulated to re-enter the cell cycle without the need to introduce retinal injury. Wnt signaling regulates proliferation of adult hippocampal stem cells (Lie et al., Nature, 2005, 437:1370-1375). In the adult mammalian retina, injury enhances Wnt signaling and Wnt activation promotes injury-induced MG proliferation (Das et al., Dev Biol. 2006, 299:283-302; Liu et al., Invest Opthalmol Vis Sci. 2013, 54:444-453). The canonical Wnt signaling pathway involves the binding of Wnt proteins to cell surface receptors of the Frizzled family, causing the receptors to activate Disheveled family proteins and ultimately resulting in stabilization and nuclear accumulation of β-catenin, a key effector of Wnt signaling that regulates gene transcription (Logan and Nusse, Annu Rev Cell Dev Biol. 2004, 20:781-810).

Experimental data presented herein demonstrate that retinal injury elicited an early and transient activation of Wnt signaling, prior to eliciting a proliferative response of MGs. Activation of Wnt signaling was manifested by an upregulation of multiple Wnt genes, downregulation of the Wnt antagonist Dkk1 and WIF-1, and transcriptional activation of Wnt target genes (Cond1, Lef1, and Axin2). Furthermore, pharmacological Inhibition of Wnt signaling by XAV939 significantly reduced injury-induced MG proliferation. Consistent with studies in zebrafish that demonstrate that Wnt signaling plays an indispensable role in injury-induced proliferation of MG-derived retinal progenitors (Ramachandran et al., Proc Natl Acad Sci USA, 2011, 108:15858-15863; Wan et al., Cell Rep. 2014, 9:285-297), these results indicate that Wnt signaling is a conserved pathway that is a critical determinant for the proliferative response of MGs in mammals.

Furthermore, a MG-specific gene transfer tool (ShH10-GFAP) has been developed to deliver wild-type β-catenin and observed a robust proliferative response of MGs that was equivalent to retinal injury in combination with mitogenic growth factor treatment (Karl et al., Proc Natl Acad Sci USA, 2008). In addition to the high efficiency in inducing MG proliferation, targeting the intracellular signaling pathway(s) of MGs also eliminates the need for a global treatment of the entire retina with growth factors, which could cause undesirable side effects from untargeted cells.

GSK3 regulates Wnt signaling by promoting β-catenin degradation. GSK3 plays an important role in the maintenance and self-renewal of human and mouse embryonic stem cells (Bone et al., Chem Biol. 2009, 16:15-27; Sato et al., Nat Med. 2004, 10:55-63; Ying et al., Nature, 2008, 453:519-523). Genetic deletion of GSK3 in mice leads to expanded proliferation of neural progenitors in the brain (Kim et al., Nat Neurosci. 2009, 12:1390-1397). Genetic evidence is required to determine whether GSK3 participates in regulating the progenitor/stem cell status of MGs in mammals. The experimental results presented herein show that deletion of GSK3ß resulted in β-catenin stabilization, transcriptional activation of the Wnt reporter, and as a result, MG proliferation in uninjured adult mouse retina. Controlling GSK3β kinase activity therefore appears to be an additional regulatory mechanism that tunes the proliferative response of MGs in adult mammalian retina.

Upon re-entering the cell cycle after Wnt activation, proliferating MGs migrate along their radial processes with a majority of them moving to the ONL where photoreceptors are located. Photoreceptors (rods and cones) are the primary sensory neurons mediating the first step in vision. They are also most vulnerable cells in retinal degenerative diseases, such as retinitis pigmentosa and age-related macular degeneration. However, expression of photoreceptor genes was not detected in the $EdU^+$ cells. Without being bound by a particular theory, it is likely that further re-programming is needed to guide the differentiation of cycling MGs to photoreceptors. During early retinal development, the differentiation of retinal progenitor cells is regulated by both extrinsic cues and the intrinsic properties of progenitor cells (Cepko et al., Proc Natl Acad Sci USA, 1996, 93:589-595; Harris, Curr Opin Genet Dev. 1997, 7:651-658; Livesey and Cepko, Nat Rev Neurosci. 2001, 2:109-118), that impinge on the transcription network of progenitors for determining their cell fates (Swaroop et al., Nat Rev Neurosci. 2010, 11:563-576). ShH10-GFAP-mediated gene transfer provides a practical tool for MG-specific delivery of transcription factors that may guide the differentiation of cycling MGs to specific cell fates. This approach may prove useful in replenishing photoreceptors that typically die in retinal degenerative diseases.

Lin28 has emerged as a master control gene that defines "stemness" in multiple tissue lineages (Shyh-Chang and Daley, Cell Stem Cell, 2013, 12:395-406). As an RNA-binding protein, Lin28 represses let-7 miRNA biogenesis, and thus regulates the self-renewal of mammalian embryonic stem cells. Upstream factors regulating Lin28 remain largely unexplored relative to the effectors and targets downstream of Lin28/let-7 miRNAs. In breast cancer cells, Wnt/β-catenin activates the expression of Lin28a, but not Lin28b, through direct binding to the Lin28a promoter and activating its transcription (Cai et al., J Cell Sci. 2013, 126:2877-2889). Experimental results presented herein demonstrate that gene transfer of β-catenin in MGs induced the expression of both Lin28a and Lin28b. Using ChIP assays, distinct β-catenin binding sites were identified in the proximal region of Lin28a and Lin28b promoters that are critical for transcriptional activation. Mutation of these binding sites abolished β-catenin-induced Lin28a/Lin28b-GFP reporter activity. The two β-catenin binding sites in the Lin28a promoter identified are different from the one reported for augmenting cancer cell expansion (Cai et al., J Cell Sci. 2013, 126:2877-2889), suggesting that distinct β-catenin binding sites may be used to drive Lin28a transcription in progenitor/stem cells. Further, it is demonstrated that Lin28a and Lin28b are essential factors in regulating MG proliferation in vivo, as gene transfer of Lin28a or Lin28b was sufficient to stimulate MG proliferation; and co-deletion of Lin28a and Lin28b abolished β-catenin-induced MG proliferation. Navigating further downstream, both β-catenin and Lin28 suppressed let-7 miRNA expression, and co-deletion of Lin28a and Lin28b neutralized β-catenin-mediated effects on let-7 miRNA expression, indicating that Wnt/β-catenin acts through Lin28 to suppress let-7 miRNA biogenesis. Importantly, let-7 miRNA regulation is functionally relevant for Wnt-activated MG proliferation as β-catenin-mediated proliferation effects were nearly completely suppressed by let-7b miRNA overexpression.

Previous studies in mice used retinal injury, in combination with growth factor treatment (Karl et al., Proc Natl Acad Sci USA, 2008, 105:19508-19513) or transgenic expression of the proneural transcription factor Ascl1 (Ueki et al., Proc Natl Acad Sci USA, 2015, 112:13717-13722), to stimulate the proliferation of MGs, reprogramming these cells to a neurogenic competent state. The neurogenic competence of cell cycle reactivated MGs after injury decreases in an age-dependent manner (Loffler et al., Glia, 2015, 63:1809-1824). Intriguingly, without retinal injury, after gene transfer of β-catenin, Lin28a, or Lin28b, a subset of MGs migrated to the lower part of the inner nuclear layer and expressed markers for amacrine cells: Pax6, Syntaxin 1, and NeuN, indicating that the cell cycle reactivated MGs possess neurogenic potential in an uninjured retina. Taken together, these results provide evidence that GSK3-Wnt-Lin28-let-7miRNA constitutes a central signaling pathway in regulating the proliferative response and neurogenic potential of MGs in adult mammalian retina.

The materials and methods employed in these experiments are now described.

Materials and Methods

Cell Culture and Transfection

HEK293T cells were cultured in Dulbecco's Modified Eagle Medium (DMEM, Invitrogen, Grand Island, NY), supplemented with 10% (v/v) fetal bovine serum (FBS, Sigma, St. Louis, MO) and antibiotics (100 unit/ml penicillin and 100 mg/ml streptomycin) in a 37° C. incubator with 5% $CO_2$. Cells were transfected 24 hours after seeding in a 24-well plate. For Lin28 promoter analysis, cells were transfected with pLin28-GFP and pCAG-β-catenin or pCA-GEN, together with a pCAG-tdTomato for normalization. Cells were collected 48 hours after transfection.

Animals

Wild-type mice (strain C57BL/6J), Rosa26-tdTomato reporter mice and Lin28a$^{loxp/loxp}$; Lin28b$^{loxp/loxp}$ mice were obtained from The Jackson Laboratory (Bar Harbor, ME). GSK3β$^{loxp/loxp}$ mice obtained.

Intravitreal Injection

Adult mice at 4 weeks of age were anesthetized with an intraperitoneal injection of ketamine (50 mg/kg mouse body weight) and xylazine (5 mg/kg mouse body weight). Intravitreal injection was performed using a microsyringe equipped with a 33 gauge needle. The tip of the needle was passed through the sclera, at the equator and next to the dorsal limbus of the eye, into the vitreous cavity. Injection volume is 1 μl per eye for AAVs or other chemicals including NMDA (Acros Organics, 100 mM) and XAV939 (Sigma, 10 μM).

AAV Production

Adeno-associated virus (AAV) was produced by the plasmid co-transfection method, and the cell lysates were purified via iodixanol gradient ultracentrifugation as previously reported (Grieger et al., Nat Protoc. 2006, 1:1412-1428). Purified AAVs were concentrated with Amicon Ultra-15 Centrifugal Filter Units (Millipore, Bedford, MA) to a final titer of 1.0-5.0×1013 genome copies/mL, determined by real-time PCR.

Retinal Cell Dissociation and Fluorescence-Activated Cell Sorting (FACS)

Retinal dissection was performed in HBSS. Dissected retinas were incubated at 37° C. for 20 minutes in the activated Papain mix composed of 40 μl Papain (Worthington, 500 U/mL), 40 μl Cysteine/EDTA mix (25m M cysteine+5 mM EDTA, pH 6~7) and 320 μl HBSS/HEPES (normal HBSS+10 mM HEPES). Cell pellet was collected after centrifugation for 3 minutes at 3000 rpm, and treated with 10 μl DNase I (Roche, 10 U/μl) in 400 μl HBSS at room temperature for 3 minutes with gentle trituration. Dissociated cells were collected after another centrifugation and resuspended in an appropriate volume of HBSS for further experiments. To purify tdTomato$^+$ MGs, retinas were isolated from MG-specific reporter mice with vehicle or NMDA treatment. After retinal dissociation, single-cell resuspension was washed in DPBS before cell sorting using a BD FACS Aria cell sorter. After cell sorting, both tdTomato$^+$ MGs and non-MGs were subject to RNA isolation and reverse transcription.

Immunohistochemistry and Imaging

Retinas were fixed with 4% paraformaldehyde in PBS for 30 minutes at room temperature, followed by overnight incubation at 4° C. in PBS containing 30% sucrose. Retinas were placed in Tissue-Tek OCT Compound (Sakura Fintek, Torrance, CA) and sectioned using a Leica CM1850 cryostat at the thickness of 20 μm. Sample slides were washed with PBS before incubation with a blocking buffer containing 5% normal donkey serum, 0.1% surfactant TRITON X-100™, and 0.1% NaN3 in PBS for 2 hours at room temperature. Primary antibodies were added for overnight incubation at 4° C. Primary antibodies used: mouse anti-CyclinD3 (1:300 dilution; Thermo Scientific), mouse anti-rhodopsin (1:200 dilution; Thermo Scientific), mouse anti-NeuN (1:100 dilution; Millipore), mouse anti-p27$^{kip1}$ (1:100 dilution; BD Transduction Laboratories), mouse anti-GS (1:500 dilution; Millipore), rabbit anti-Ki67 (1:200 dilution; Thermo Scientific), rabbit anti-phospho-histone H3 (PH3) (1:100; Millipore), mouse anti-HuC/D (1:500 dilution; Thermo Scientific), rabbit anti-Pax6 (1:500 dilution; BioLegend), and mouse anti-Syntaxin1 (1:400 dilution; Santa Cruz). Sections were washed with PBS and incubated with secondary antibodies (1:500 dilution; Jackson ImmunoResearch) for 2 hours at room temperature. Cell nuclei were counterstained with DAPI (Sigma, St. Louis, MO). Confocal Images were acquired using a Zeiss LSM 510 EXCITER microscope.

RNA Isolation, RT-PCR, and Real-Time qPCR

Total RNA was extracted from retinas using TRIzol (Invitrogen, Grand Island, NY) according to the manufacture's protocol. Reverse transcription (RT) was then performed at 42° C. for 2 hours in a volume of 20 μl containing 0.5 μg of oligo (dT), 1×RT buffer, 0.5 mM each deoxyribonucleotide triphosphate, 0.1 mM dithiothreitol, and 200 U of Superscript II reverse transcriptase (Invitrogen, Grand Island, NY). Real-Time quantitative PCR (qPCR) was performed in triplicate with SsoFast™ EvaGreen supermix (Bio-Rad, Hercules, CA) using an iCycler real-time PCR detection system (Bio-Rad, Hercules, CA). The amplification protocol was 30 seconds at 94° C., 30 seconds at 56° C., and 30 seconds at 72° C., with a signal detection period of 7 seconds at 80° C. A melt curve analysis was performed at the end of the reaction to check the reaction specificity. Results were obtained after normalization to the expression level of the housekeeping gene, B-actin. All experiments were performed at least twice to ensure repeatable results.

EdU Injection and Incorporation Assay

EdU solution (1 μl) was intravitreally injected into the vitreous chamber at the concentration of 1 mg/ml. Analysis of EdU incorporation was performed using a kit CLICK-IT EDU KIT™ (Invitrogen, Grand Island, NY). In brief, retinal cryostat sections or flatmount preparations were washed in PBS first for 10 min and then washed twice in PBS containing 3% BSA, followed by permeabilization in PBS containing 0.5% surfactant TRITON X-100™ for 20 min. After washing twice in PBS containing 3% BSA, EdU detection components were resuspended according to manufacturer's instructions and applied directly to retinal samples. The solution for each EdU reaction has a total volume of 250 μl composed of 215 μl buffer 1X CLICK-IT™Click-iT reaction buffer, 10 μl CuSO4, 0.6 μl dye ALEXA FLUOR™ azide, and 25 μl 1X Reaction buffer additive. After incubation in the reaction solution for 30 minutes at room temperature, samples were washed with PBS and mounted with Fluoromount-G for detection.

miRNA Analysis

Small RNAs were extracted with the mir Vana™ miRNA Isolation Kit and reverse transcribed using TaqMan MicroRNA Reverse Transcription Kit (Invitrogen, Grand Island, NY) according to the manufacturer's instructions. Quantitative RT-PCR was performed using specific primers and probes for snoRNA-202, has-let-7a, 7b, and 7f supplied in Taqman MicroRNA Assay Kits (Invitrogen, Grand Island, NY). Fold changes were determined using the A (ACT) method after normalization to mouse snoRNA-202 endogenous controls.

Chromatin Immunoprecipitation Assays

HEK293T cells were transfected with the corresponding promoter and expression constructs using PEI (Polysciences, Inc., Warrington, PA). After incubation for 48 hours, cells were fixed using 1% formaldehyde for 10 minutes at room temperature. Cross-linking reactions were terminated by adding glycine to a final concentration of 0.125 M. After washing with PBS, cells were resuspended in 6 ml Lysis Buffer (Santa Cruz Biotechnology, Dallas, TX), Crude nuclear extract was collected after centrifugation and resuspended in 1.9 ml Lysis Buffer High Salt (Santa Cruz Biotechnology, Dallas, TX). Chromatin resuspension was sonicated on ice using Branson Sonifier (power output setting=5, 4 times at an interval of 30 seconds, continuous mode). The Supernatant, collected after centrifugation at 10,000 rpm for 15 minutes at 4° C., was pre-cleared by protein A/G PLUS-Agrose beads (Santa Cruz Biotechnology, Dallas, TX) and then incubated with the primary antibody overnight at 4° C. After incubation with beads for 2 hours at 4° C., beads were washed twice with 1 ml Lysis Buffer High Salt and Wash Buffer (Santa Cruz Biotechnology, Dallas, TX) and resuspended in 400 μl Elution Buffer (Santa Cruz Biotechnology, Dallas, TX). The resuspension was incubated overnight at 65° C. for reverse crosslinking. DNA was isolated using Qiagen Qiaquick PCR purification Kit (Qiagen, Valencia, CA) and analyzed by PCR.

Statistical Analysis

Statistical differences between different experimental groups were analyzed by a Student's t-test or one-way ANOVA test using Prism 6 (GraphPad Software, San Diego, CA). Data are presented as mean±SEM. A value of $p<0.05$ is considered significant, The results of the experiments are now described.

Results

Neurotoxic Injury Leads to Transient Proliferation of MGs in Adult Mouse Retina

Figure 2A:
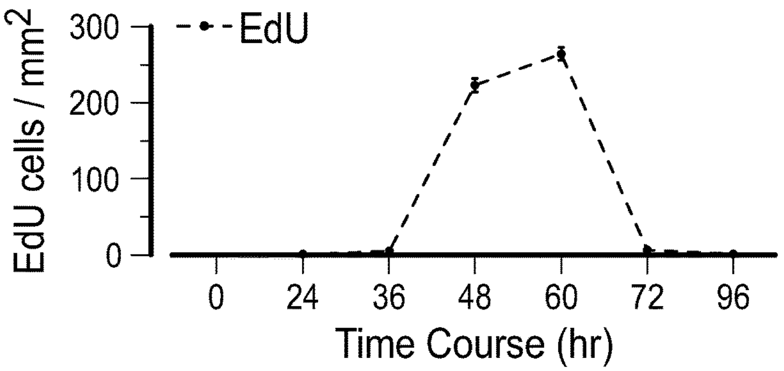
FIG. 2A through FIG. 2J, depicts results of example experiments demonstrating that neurotoxic injury activates Wnt signaling and MG proliferation.
Figure 2B:
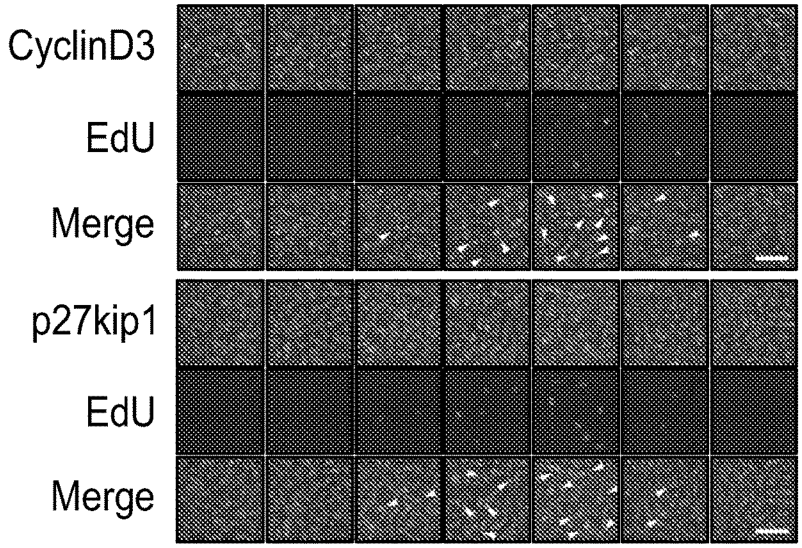

To examine MG proliferation induced by neurotoxic injury in the adult mammalian retina, 200 nmol was injected NMDA into the vitreous chamber of the mouse retina at 4 weeks of age. The same dosage of NMDA was previously used to introduce retinal injury leading to MG proliferation in adult rat and mouse retina (Karl et al., Proc Natl Acad Sci USA, 2008, 105:19508-19513; Ooto et al., Proc Natl Acad Sci USA, 2004, 101: 13654-13659). Anti-HuC/D immunohistochemistry was used to assay the time course of NMDA-induced cell death in the ganglion cell layer (GCL). A progressive loss of retinal ganglion cells and amacrine cells was observed with only ~45% of HuC/D$^+$ cells remaining 36 hours post-NMDA injection (FIG. 1). To assay cell proliferation, 1 μl of 1 mg/ml of EdU, a nucleoside analog of thymidine that is incorporated into DNA during active DNA synthesis, was injected into the vitreous chamber 5 hours before tissue collection at 24, 36, 48, 60, 72, and 96 hours post-NMDA injection. NMDA-induced cell proliferation was quantified by scoring the number of EdU$^+$ cells/mm$^2$ in retinal flatmount preparations. A small number (4.7±0.8) of EdU$^+$ cells appeared 36 hours post-NMDA injection. The number of EdU$^+$ cells continued to increase, reaching 223.3±8.3 and 264.5±8.4 at 48 and 60 hours, respectively, before it was reduced to 5.8±1.1 at 72 hours post-NMDA injection (FIG. 2A). The EdU cells were also immunoreactive for CyclinD3 and p27$^{kip1}$ (FIG. 2B), MG-specific nuclear antigens (Dyer and Cepko, Nat Neurosci. 2000, 3:873-880). These results indicate that NMDA-induced neurotoxic injury transiently stimulated MG proliferation within a time window of 36-72 hours after NMDA-induced neurotoxic injury.

Figure 2C:
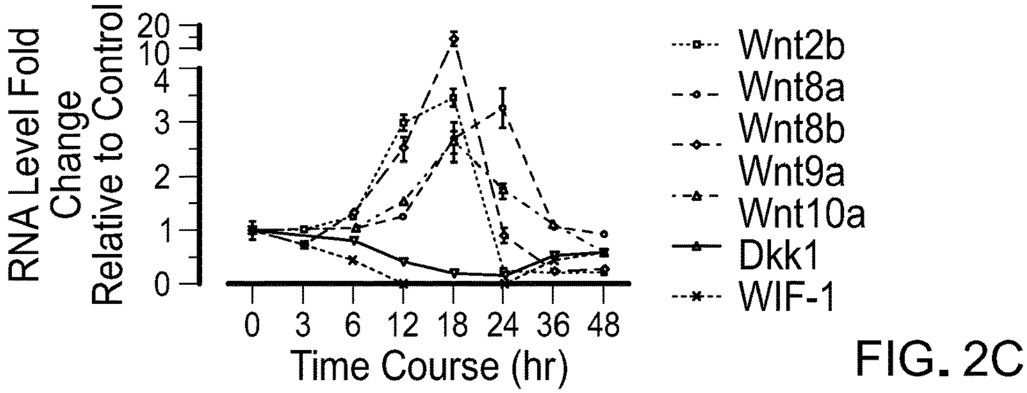
Figure 2D:
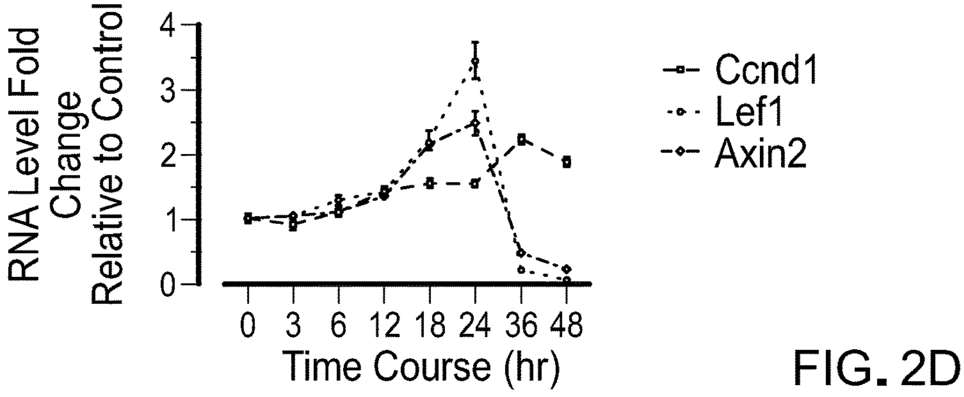

Wnt Signaling is a Molecular Determinant for MG Proliferation Induced by Neurotoxic Injury To examine whether Wnt signaling is activated by NMDA-induced neurotoxic injury, quantitative PCR was performed to assay the RNA levels of Wnt genes at 3, 6, 12, 18, 24, 36, and 48 hours post-NMDA injection, relative to the PBS injected retina as a control. Significantly, the RNA levels for several Wnt genes, including Wnt2b, Wnt8a, Wnt8b, Wnt9a, and Wnt10a, were upregulated at least 3-fold between 6-24 hours post-NMDA injection (FIG. 2C), a time frame before MGs re-entered the cell cycle at 36-72 hours post-NMDA injection (FIG. 2A). Whereas the RNA levels for Dkk1, a Wnt signaling antagonist, were downregulated to 13.2±0.6% of the control 24 hours post-NMDA injection (FIG. 2C). Interestingly, the RNA levels for WIF-1, a secreted protein that binds to Wnt proteins and inhibits their activities (Hsieh et al., Nature, 1999, 398:431-436), were also reduced to 1.6±0.2% of the control 12 hours post-NMDA injection (FIG. 2C). The upregulation of Wnt genes and a concomitant downregulation of WIF-1 and Dkk1 would predict activation of the canonical Wnt/β-catenin signaling pathway. Indeed, 24 hours post-NMDA injection, a 3.4-fold upregulation of CyclinD1 (Cond1, FIG. 2D), a target gene of the Wnt signaling pathway (Shtutman et al., Proc Natl Acad Sci USA, 1999, 96:5522-5527; Tetsu and McCormick, Nature, 1999, 398:422-426) and key regulator of the cell cycle progression from the G1 to S phase (Resnitzky et al., Mol Cell Biol. 1994, 14:1669-1679), was detected. There was also significant upregulation of Lefl and Axin2 (FIG. 2D), two other target genes activated by Wnt signaling (Filali et al., J Biol Chem. 2002, 277:33398-33410; Hovanes et al., Nat Genet. 2001, 28:53-57). These results indicate that NMDA-induced neurotoxic injury led to activation of the Wnt signaling pathway, which preceded the proliferative response of MGs.

Figure 2E:
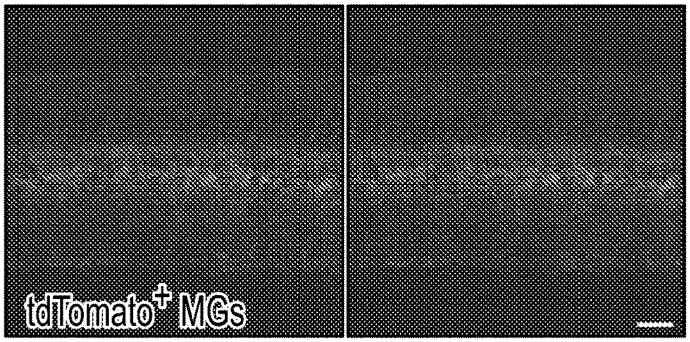
Figure 2F:
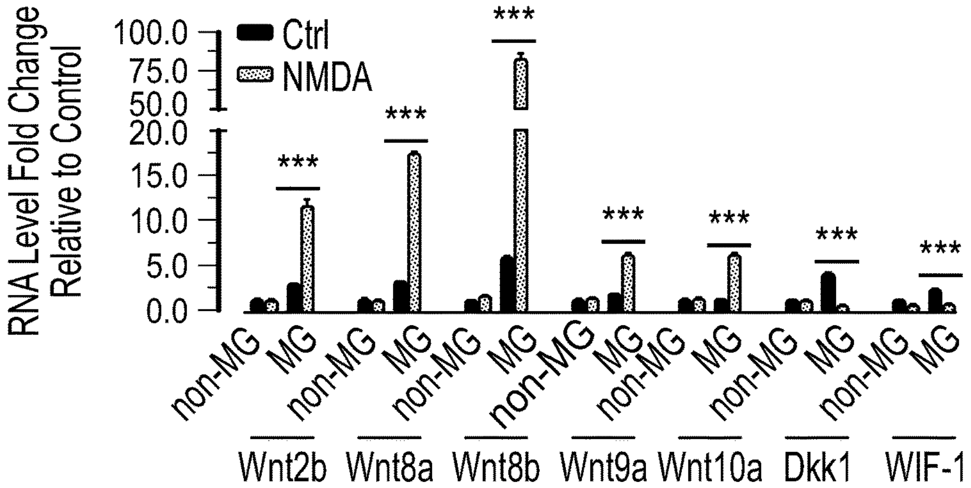
Figure 2G:
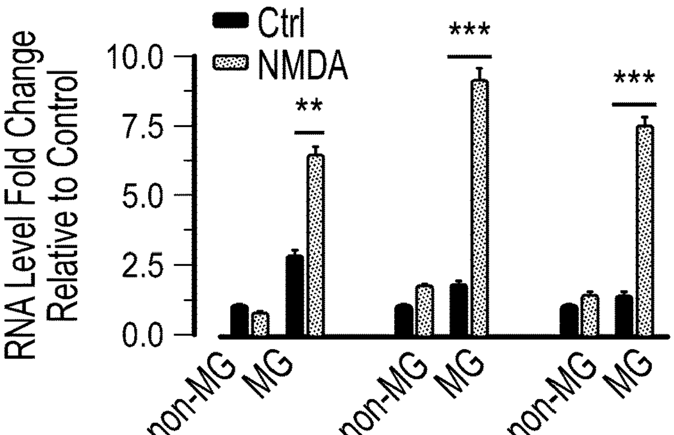

To examine whether NMDA-induced activation of Wnt is a cell-autonomous response of MGs or an indirect effect mediated through non-MGs, a MG-specific reporter mouse line was generated by crossing the GFAP-Cre line to the Rosa26-tdTomato reporter line (Kuzmanovic et al., Invest Ophthalmol Vis Sci. 2003, 44:3606-3613; Madisen et al., Nat Neurosci. 2010, 13:133-140), resulting in cell-type-specific labeling of MGs with tdTomato (FIG. 2E), and used fluorescence-activated cell sorting (FACS) to isolate tdTomato+MGs after NMDA treatment. The RNA levels for Wnt genes and Wnt antagonists were assayed in tdTomato+MGs and the non-MG population at 18 hours post-NMDA injection, when significant fold changes were observed for Wnt genes using total retinal RNA (FIG. 2C). While the RNAs levels for Wnt genes (Wnt2b, Wnt&a, Wnt8b, Wnt9a, and Wnt10a) and Wnt antagonists (Dkk1 and WIF-1) remained largely unchanged in the non-MG group, even greater fold changes were detected for these genes in MGs (FIG. 2F). Consistently, robust activation of Wnt target genes (CyclinD1, Lef1, and Axin2) was also detected in MGs (FIG. 2G).

Figure 2H:
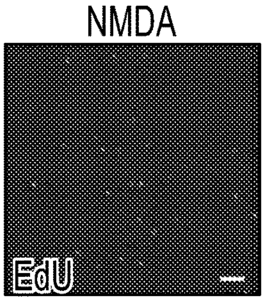
Figure 2I:
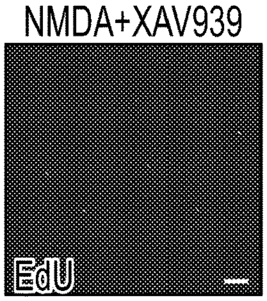
Figure 2J:
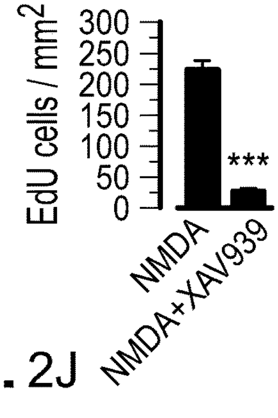

To examine the ability of inhibition of Wnt signaling to suppress NMDA-induced MG proliferation, NMDA was co-injected with XAV939, a selective Wnt signaling antagonist (Huang et al., Nature, 2009, 461:614-620), and the number of EdU$^+$ cells per mm$^2$ in retinal flatmount preparations was quantified 60 hours post-injection, when the maximum number of EdU$^+$ cells were detected (FIG. 2A). The number of EdU$^+$ cells was significantly reduced when Wnt signaling was inhibited by XAV939, in comparison to NMDA injection alone (FIGS. 2H-2J). To assay whether XAV939 treatment affects NMDA-induced retinal damage, the number of HuC/D+ cells was quantified in the GCL at 60 hours post-injection. A similar level of cell death was observed in retinas co-injected with XAV939, in comparison to NMDA injection alone. Taken together, these results indicate that Wnt signaling is a critical molecular determinant for MG proliferation induced by neurotoxic injury.

MG-Specific Gene Transfer in Adult Mouse Retina

Figure 3A:
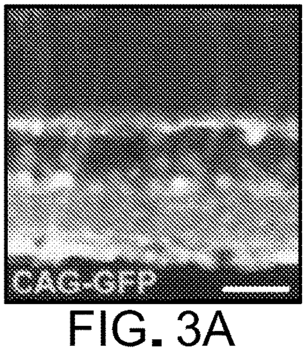
FIG. 3A through FIG. 3O, depicts results of example experiments demonstrating that ShH10-GFAP (glial fibrillary acidic protein) promoter-mediated gene transfer is specific for MGs. Transduction of retinal cells by ShH10-CAG-GFP (FIG. 3A-FIG. 3C) or ShH10-GFAP-GFP (FIG. 3D-FIG. 3F) via intravitreal injections in adult mouse retina at 4-weeks of age. ShH10-CAG-mediated gene transfer resulted in transduction of NeuN immunoreactive retinal neurons indicated by arrows in FIG. 3C. By contrast, ShH10-GFAP-mediated gene transfer confers MG-specific transduction, eliminating GFP expression in NeuN-labeled cells. Scale bar: 20 μm.
Figure 3B:
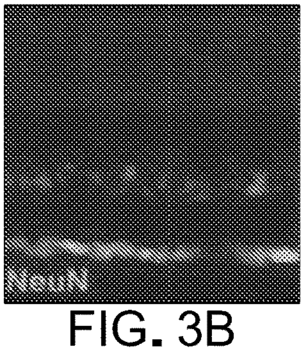
Figure 3C:
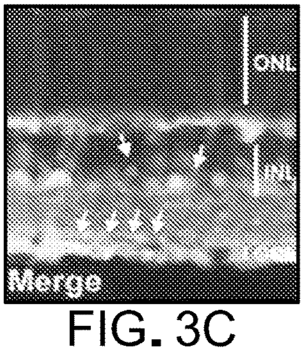
Figure 3D:
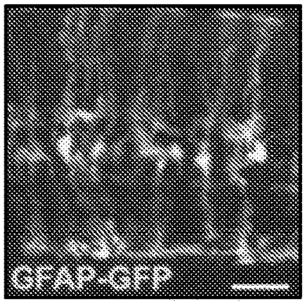
Figure 3E:
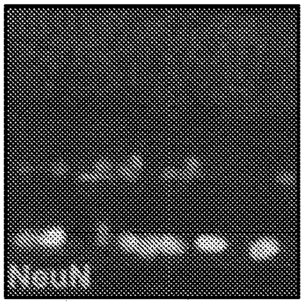
Figure 3F:
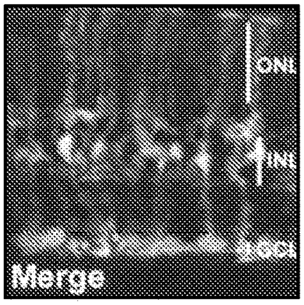
Figure 3G:
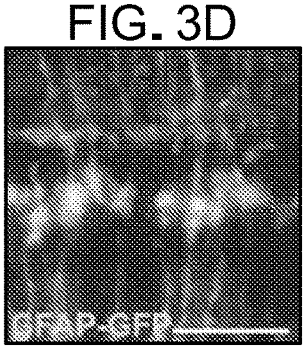
Figure 3H:
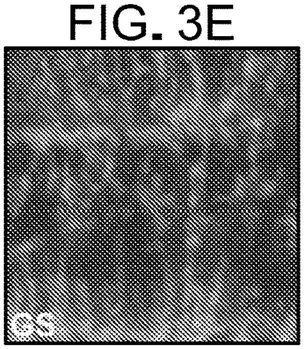
Figure 3I:
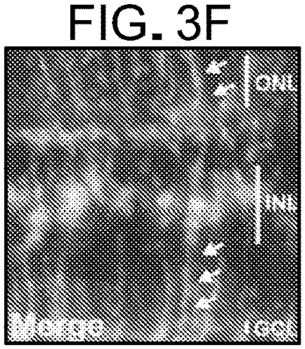
Figure 3J:
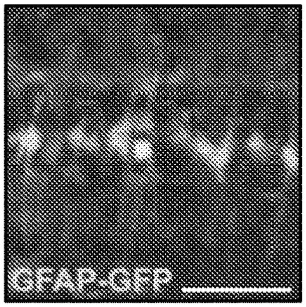
Figure 3K:
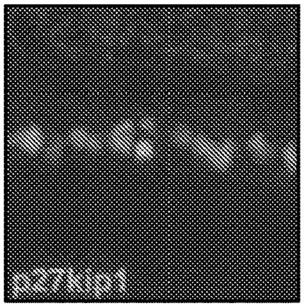
Figure 3L:
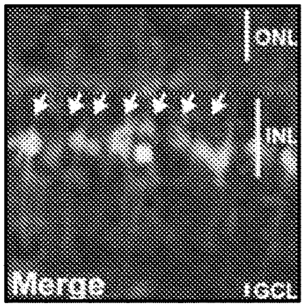
Figure 3M:
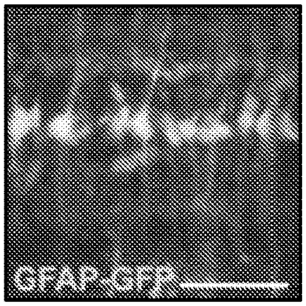
Figure 3N:
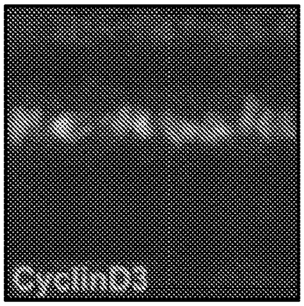
Figure 3O:
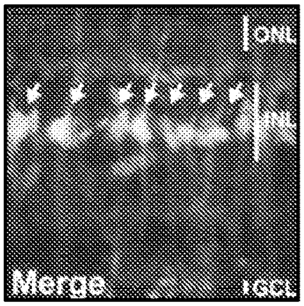

To develop a gene transfer method specifically for MGs in the adult mouse retina, an adeno-associated virus (AAV) variant, known as ShH10 (Klimczak et al., PLOS One, 2009, 4: e7467; Koerber et al., Mol Ther. 2009, 17:2088-2095) was modified by replacing the ubiquitous CAG promoter with the MG-specific promoter GFAP (Kuzmanovic et al., Invest Ophthalmol Vis Sci. 2003, 44:3606-3613). ShH10-CAG-mediated gene transfer of the green fluorescence protein (GFP), via intravitreal injections in the adult mouse eye, resulted in transgene expression predominantly in MGs as well as a subset of retinal ganglion cells and amacrine cells labeled by NeuN immunoreactivity (FIGS. 3A-3C), a transduction pattern similar to that observed in the adult rat retina (Klimczak et al., PLOS One, 2009, 4: e7467). By contrast, ShH10-GFAP-mediated gene transfer was highly specific for MGs as GFP expression was not detected in retinal ganglion cells or amacrine cells (FIGS. 3D-3F). Neither ShH10-CAG nor ShH10-GFAP led to photoreceptor transduction. In addition, ShH10-GFAP-mediated gene transfer was also highly efficient to transduce MGs as assessed by immunohistochemistry to detect MG-specific antigens in the cytoplasm, such as glutamine synthetase (FIGS. 3G-3I), or in the nucleus such as p27$^{kip1}$ (FIGS. 3J-3L) and CyclinD3 (FIGS. 3M-3O). Most MGs were transduced in the infection area as GFP expression was detected in both MG processes labeled by glutamine synthetase immunoreactivity (arrows in FIG. 3I), as well as in MG nuclei labeled by p27$^{kip1}$ (arrows in FIG. 3L) or CyclinD3 (arrows in FIG. 3O) immunoreactivity. To further assess the specificity of ShH10-GFAP-mediated gene transfer, ShH10-GFAP-GFP infected retinas were dissociated into single cells and analyze the percentage of GFP$^+$ cells that express MG-specific nuclear antigens CyclinD3 and p27$^{kip1}$. Out of 524 GFP$^+$ cells analyzed from 6 retinas, all of them (100%) were immunoreactive for CyclinD3 or p27$^{kip1}$, indicating that ShH10-GFAP may only transduce MGs.

Figure 4A:
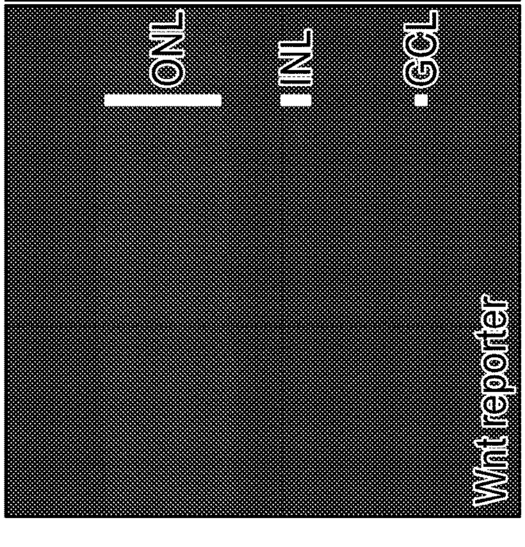
FIG. 4A through FIG. 4C, depicts results of example experiments demonstrating that ShH10-GFAP-mediated gene transfer of β-catenin activates the canonical Wnt signaling pathway in MGs.
Figure 4B:
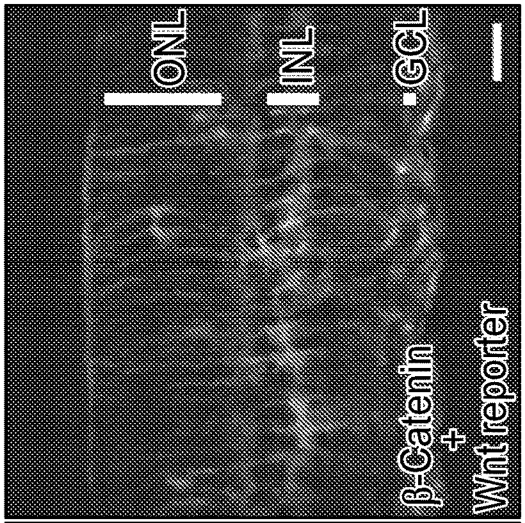
Figure 4C:
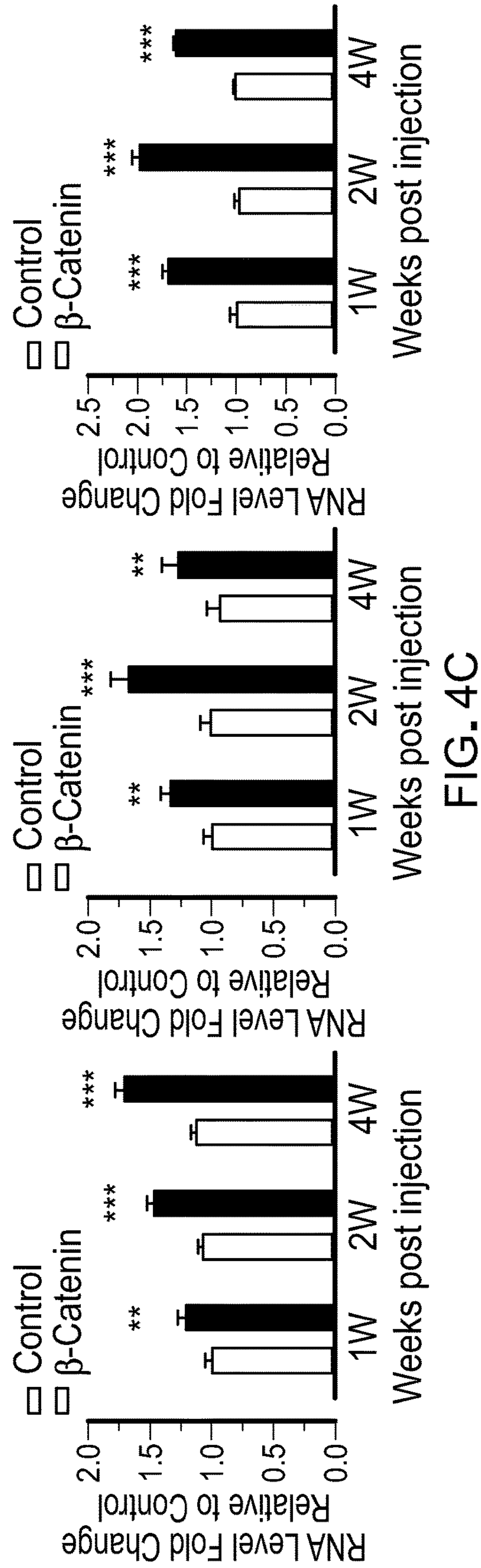

Gene Transfer of β-Catenin Activates Wnt Signaling and Stimulates MG Proliferation without Retinal Injury Previous reports indicate that retinal injury is a prerequisite to stimulate the proliferative response of MGs in adult mammalian retina. Therefore, the ability of direct activation of Wnt signaling, without retinal injury, to stimulate MG proliferation using ShH10-GFAP-mediated gene transfer of wild-type-catenin was examined. To assess the activation of the canonical Wnt pathway, a ShH10-Wnt reporter in which the GFP reporter gene is driven by Tcf/Lef-mediated transcriptional activation was developed. Two weeks after viral infection in the adult mouse retina, significant activation of the reporter gene was observed in MGs co-infected with ShH10-GFAP-β-catenin, in comparison to those infected with the ShH10-Wnt reporter alone (FIGS. 4A and 4B). Using quantitative PCR, a time course study of Wnt target gene activation was performed, following gene transfer of β-catenin in MGs, in comparison to ShH10-GFAP-GFP infected retinas as a control (FIG. 4C). One week post-viral infection, a significant increase in the RNA level was readily detectable for Ccnd1 (121.8±2.9%), Lef1 (134.8±3.0%), and Axin2 (169.5±2.6%). The expression of Wnt target genes continued to increase two weeks post-viral infection, reaching the peak level for Lef1 (167.7±7.0%) and Axin2 (198.8±3.7%) except for Ccnd1 (147.7±2.4%) whose expression increased further (171.5±3.4%) at four weeks post-viral infection.

Figures 5A, 5B, 5C:
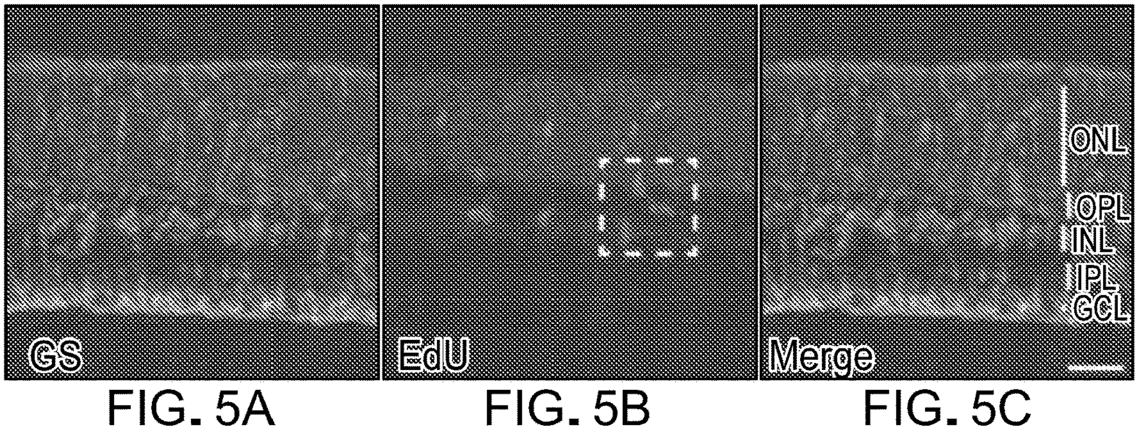
FIG. 5A through FIG. 5Z, depicts results of example experiments demonstrating that MGs re-enter the cell cycle following ShH10-GFAP-mediated gene transfer of β-catenin without retinal injury. Figure SA through Figure SR depict an analysis of EdU incorporation by immunohistochemistry co-labeling for MG-specific antigens: glutamine synthase (GS in FIG. 5A-FIG. 5F), CyclinD3 (FIG. 5G-FIG. 5L), and $p27^{kip1}$ (FIG. 5M-FIG. 5R). The boxed areas in FIG. 5B, Figure SH, and Figure SN are enlarged in FIG. 5D-FIG. 5F, FIG. 5J-FIG. 5L, and FIG. 5P-FIG. 5R, respectively. Arrow heads in FIG. 5F, FIG. 5L, and FIG. 5R show that EdU signals were detected specifically in MGs.
Figures 5D, 5E, 5F:
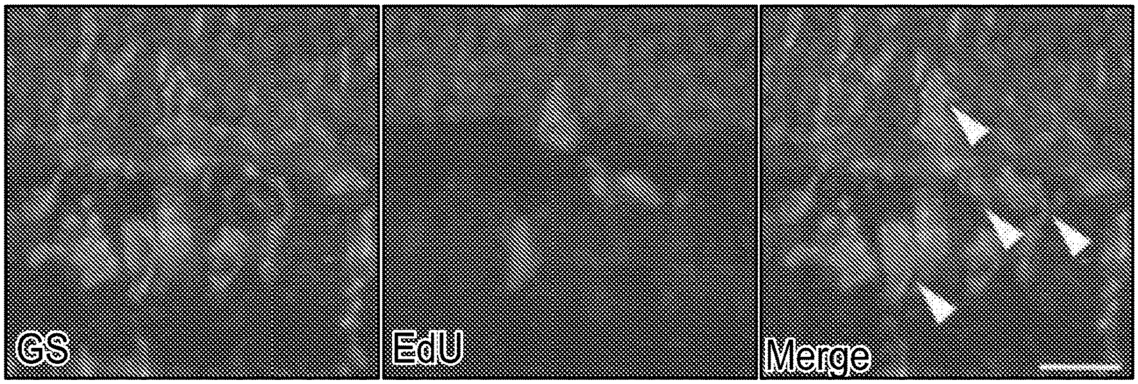
FIG. 5, comprising
FIG. 5S through FIG. 5X depict EdU incorporation in the MG-specific reporter mice. The boxed area in Figure ST is enlarged in FIG. 5V-FIG. 5X. Arrow heads in FIG. 5X show that the EdU signals were detected in the tdTomato-labeled MGs in the ONL. Figure SY depicts the distribution of EdU' cells in retinal layers. ONL: outer nuclear layer; OPL: outer plexiform layer; INL: inner nuclear layer; IPL: inner plexiform layer; GCL: ganglion cell layer. Data are presented as mean±sem, n=38.
Figures 5G, 5H, 5I:
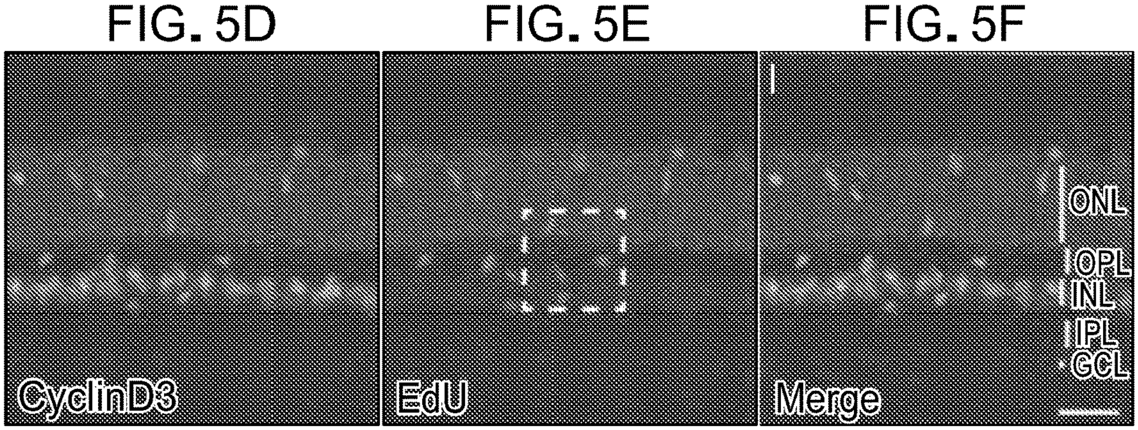
Figures 5J, 5K, 5L:
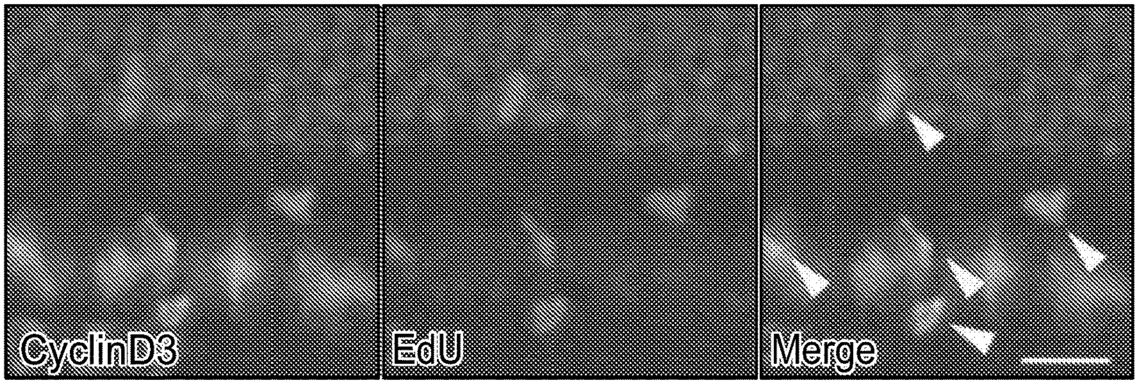
Figure 5M:
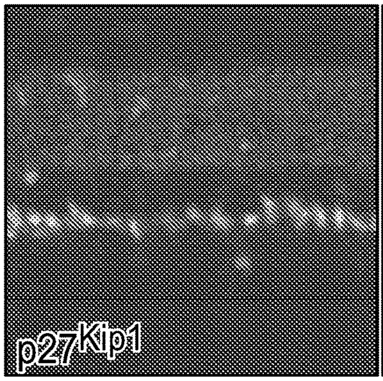
Figure 5N:
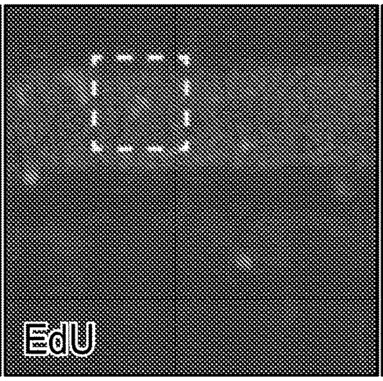
Figure 5O:
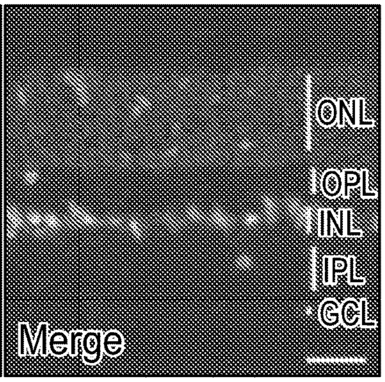
Figure 5P:
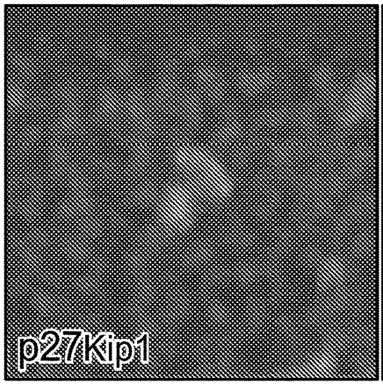
Figure 5Q:
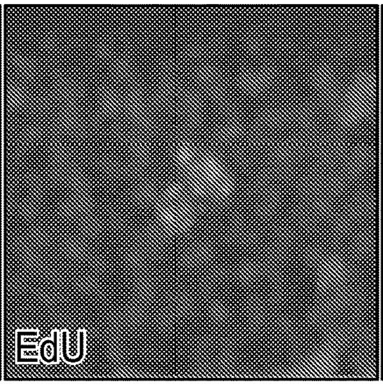
Figure 5R:
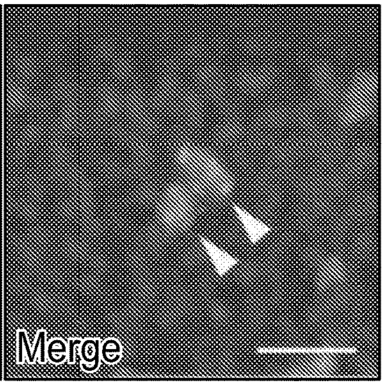
Figure 5S:
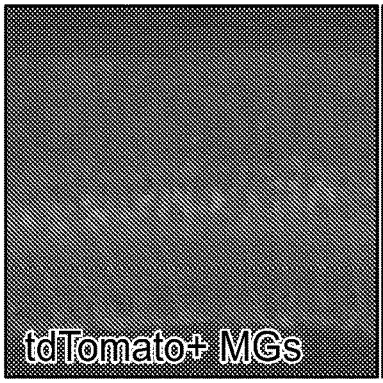
Figure 5T:
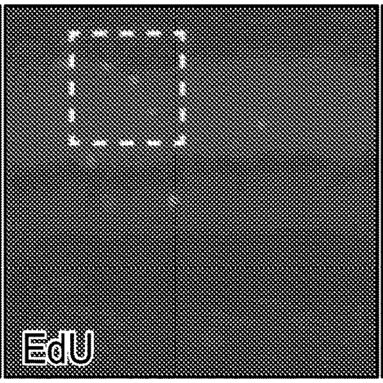
Figure 5U:
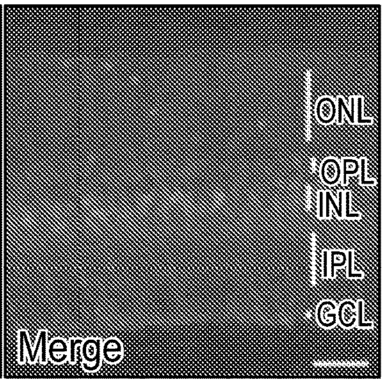
Figure 5V:
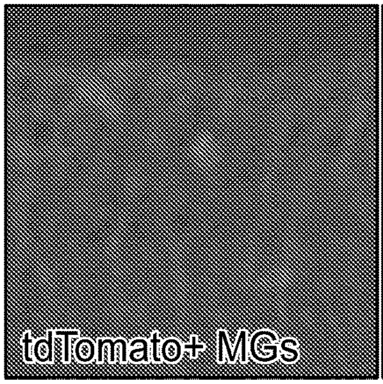
Figure 5W:
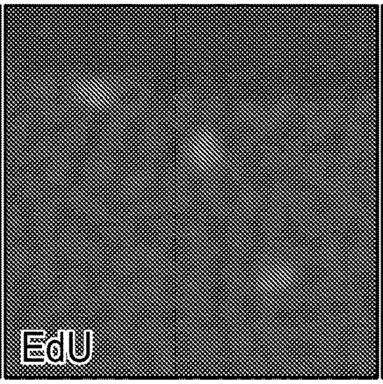
Figure 5X:
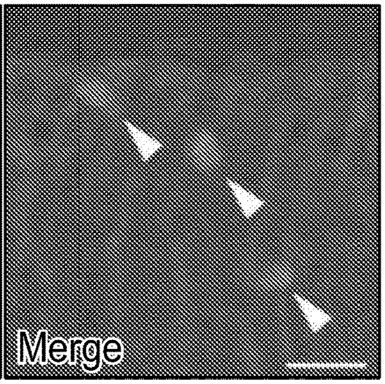
Figure 5Y:
Figure 5Z:
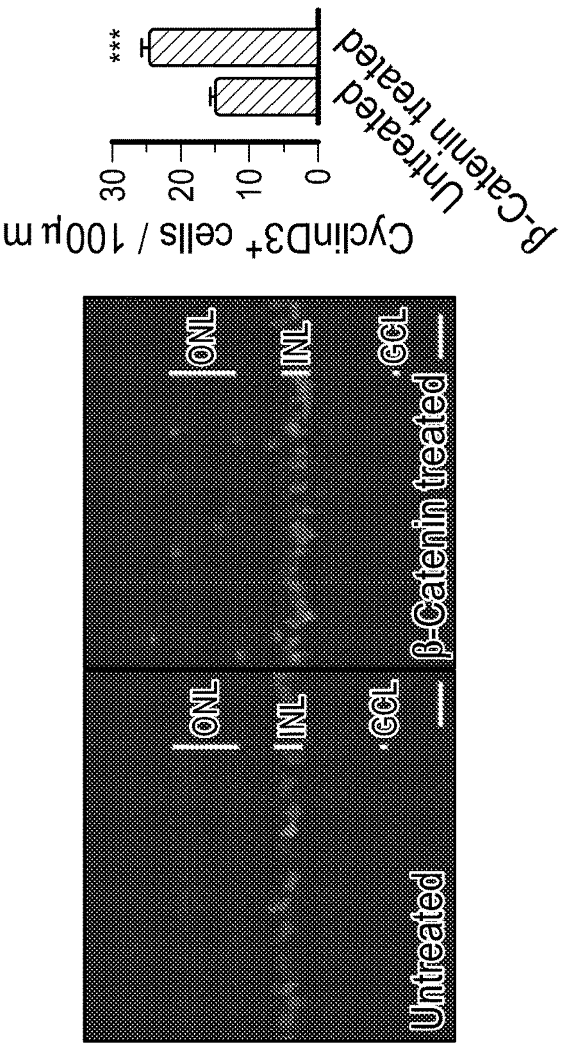

To examine whether Wnt activation leads to MG proliferation, EdU incorporation was analyzed following ShH10-GFAP-mediated gene transfer of wild-type β-catenin in adult mouse retina at 4 weeks of age. Intravitreal injection of EdU was performed 10 days post-viral infection, and the treated retinas were collected 4 days later for the analysis of EdU incorporation. EdU$^+$ cells were detected in retinal sections co-labeled by immunohistochemistry for MG-specific antigens including glutamine synthetase (FIGS. 5A-5F), CyclinD3 (FIGS. 5G-5L), and p27$^{kip1}$ (FIGS. 5M-5R). Many EdU$^+$ cells were detected following β-catenin gene transfer, indicating that these cells re-entered the cell cycle. The nuclear-localizing EdU signals were surrounded by the MG cytoplasm labeled by glutamine synthetase immunoreactivity (FIG. 5F), and were co-localized with MG nuclear antigens CyclinD3 (FIG. 5L) or p27$^{kip1}$ (FIG. 5R). In these co-labeling experiments, all EdU$^+$ cells were positive for MG-specific antigens, indicating that the proliferating cells were MGs. Noticeably, when MGs re-entered the cell cycle, their somas migrated along their radial processes instead of being localized in the middle of the inner nuclear layer (INL) as they normally do. A quantitative analysis (FIG. 5Y) showed that the EdU$^+$ cells were unevenly distributed in retinal layers, with a majority of them (66.2±2.1%) migrating to the outer nuclear layer (ONL) where photoreceptors are localized. The migration of cell cycle reactivated MGs to the ONL was further confirmed by ShH10-GFAP-β-catenin infection in the MG-specific reporter mice (FIG. 1E), where EdU signals were detected in the tdTomato$^+$ MGs in the ONL (FIGS. 5S-5X). About 25.9±1.1% of the EdU$^+$ cells were in the INL, and 12.5±0.6% of them in the outer plexiform layer (OPL), possibly in the course of migrating to the ONL. Many fewer EdU$^+$ cells migrated to the inner plexiform layer (IPL) and ganglion cell layer (GCL). As a result of Wnt-induced cell proliferation, more CyclinD3$^+$ MGs were present relative to the untreated retina (FIG. 5Z).

Figure 6A:
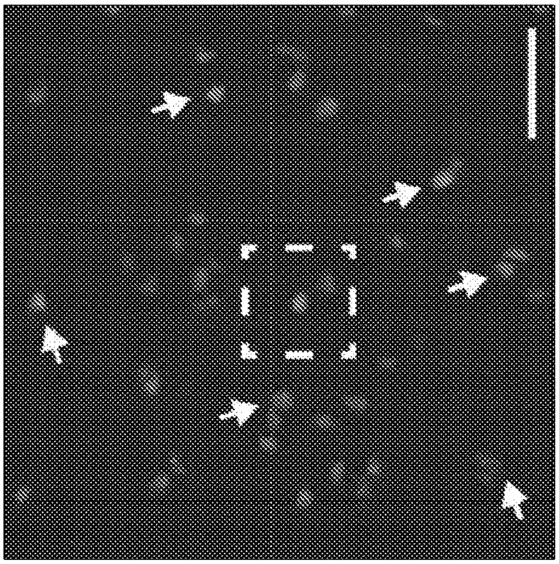
FIG. 6A through FIG. 6I, depicts an analysis of cycle progression of MGs following ShH10-GFAP-mediated gene transfer of β-catenin in adult mouse retina.
Figure 6B:
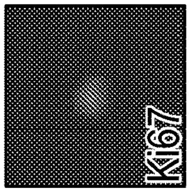
Figure 6C:
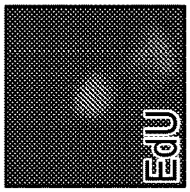
Figure 6D:
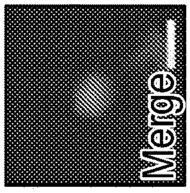
Figure 6E:
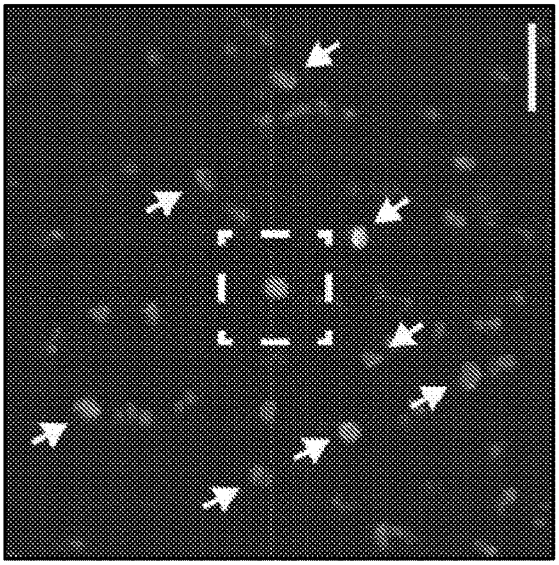
Figure 6F:
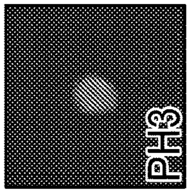
Figure 6G:
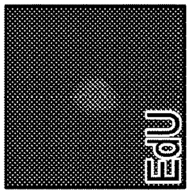
Figure 6H:
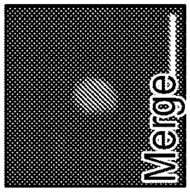
Figure 6I:
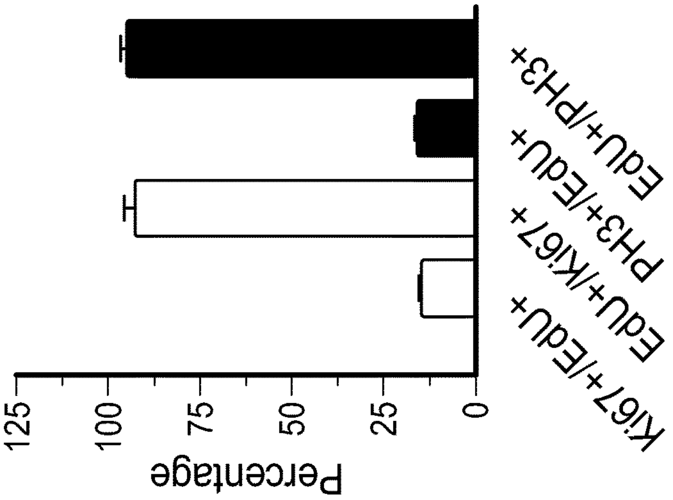

Characterization of Cell Cycle Progression, Distribution and Efficiency of MG Proliferation Following β-Catenin Gene Transfer EdU is incorporated into the newly synthesized DNA during the S phase of the cell cycle. To examine the progression of EdU-labeled MGs through other active phases of the cell cycle, co-labeling experiments were performed (FIG. 6) for EdU detection and immunohistochemical analysis of cell proliferation antigens: Ki67 (FIGS. 6A-6D) and phospho-histone H3 (PH3) (FIGS. 6E-6H), expressed in the nucleus of cells in the active phases (G1, S, G2, and Mitosis) of the cell cycle for Ki67 (Scholzen and Gerdes, J Cell Physiol. 2000, 182:311-322), and late G2 and the actual phases of Mitosis for PH3 (Hendzel et al., Chromosoma, 1997, 106:348-360). The percentages of Ki67 or PH3 positive cells that were also EdU positive, and vice versa (FIG. 6I) were quantified. The vast majority of Ki67 or PH3 positive cells were EdU positive, 92.8±3.4% and 94.7±2.3%, respectively. On the other hand, only a small portion of EdU positive cells were labeled positive for Ki67 or PH3, 14.5 ±0.7% and 15.6±0.9%, respectively, indicating that most $EdU^+$ MGs hadn't proceeded to the later phases of the cell cycle in the 4-day time frame between EdU injection and tissue collection.

Figure 7A:
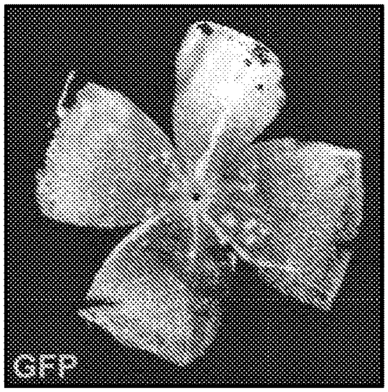
FIG. 7A through FIG. 7I, depicts results of example experiments demonstrating that ShH10-GFAP-mediated gene transfer of β-catenin is highly efficient to stimulate MG proliferation in adult mouse retina.
Figure 7B:
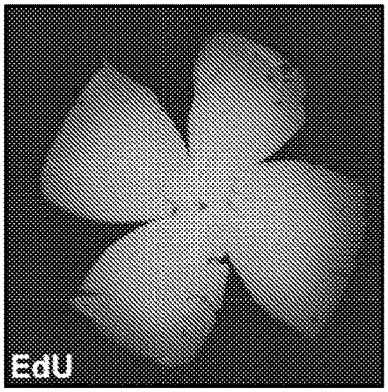
Figure 7F:
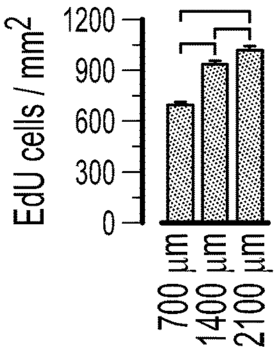
Figure 7C:
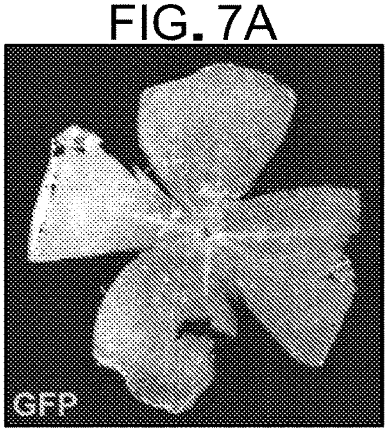
Figure 7D:
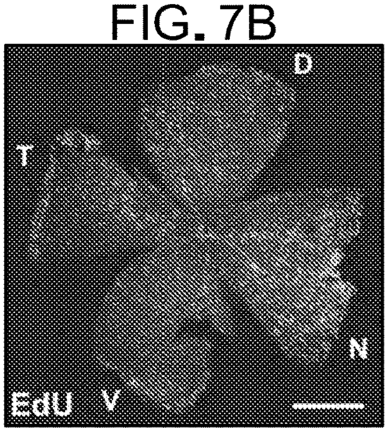
Figure 7G:
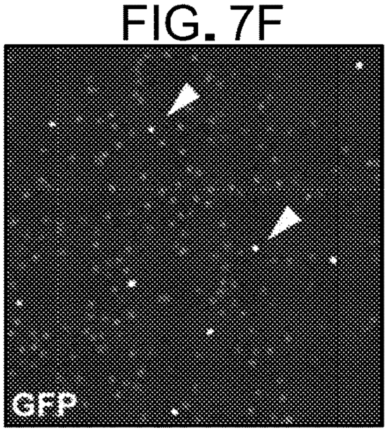
Figure 7E:
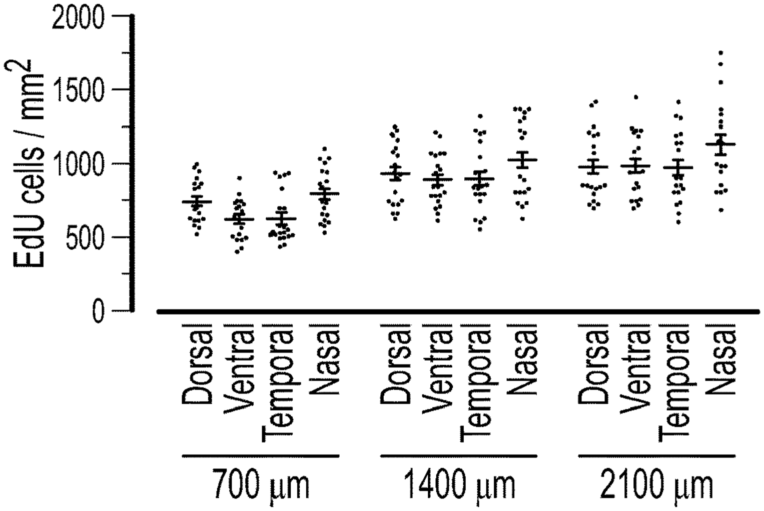

To further analyze the efficiency and distribution pattern of MG proliferation following β-catenin gene transfer, EdU-labeled cells were examined in retinal flatmount preparations. In the ShH10-GFAP-GFP infected retina as a control, neither the viral infection nor the injection procedure itself led to cell proliferation (FIGS. 7A and 7B). By contrast, many MGs re-entered the cell cycle in the β-catenin treated retina, labeled by ShH10-GFAP-GFP co-infection (FIGS. 7C and 7D). The numbers of $EdU^+$ cells/$mm^2$ were quantified in four retinal quadrants (dorsal, ventral, temporal, and nasal) at three distances (700, 1400, and 2100 μm) from the center of the retina (FIG. 7E). Although the number of EdU' cells in each of the four quadrants was not significantly different from one another as long as their distance from the center remained the same, it appeared that there was a slight gradient of an increasing number of $EdU^+$ cells from the center to the periphery (FIG. 7F), with 695.2±18.7 $EdU^+$ cells at 700 μm, 935.8±24.2 $EdU^+$ cells at 1400 μm, and 1019.5±28.3 $EdU^+$ cells at 2100 μm to the center. The results show that Wnt activation was highly efficient to stimulate MG proliferation in an uninjured retina as the number of $EdU^+$ was comparable to that obtained by retinal injury in combination with mitogenic growth factor treatment (Karl et al., Proc Natl Acad Sci USA, 2008, 105:19508-19513).

Figure 7H:
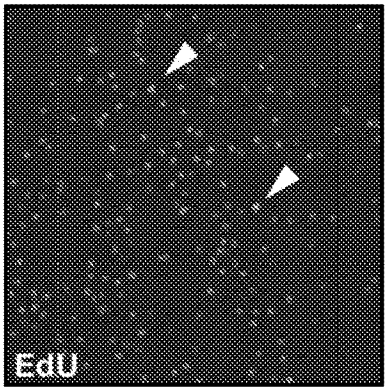
Figure 7I:
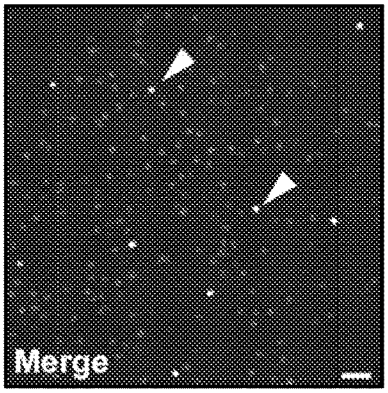

EdU incorporation assay can only label a small fraction of cell cycle reactivated MGs when they are proceeding through the S phase of the cell cycle at the time of EdU injection. The number of $EdU^+$ cells was quantified as a percentage of all Wnt-activated MGs labeled by ShH10-GFAP-GFP co-infection after retinal dissociation (FIGS. 7G-7I). All $EdU^+$ cells were $GFP^+$, however, only ~8% of $GFP^+$ cells were labeled by EdU, indicating that the majority of Wnt-activated MGs were not at the S phase of the cell cycle at the time of EdU injection. Interestingly, gene transfer of a dominant active form of β-catenin did not result in a significant increase in MG proliferation relative to wild-type β-catenin.

GSK3β Deletion Stabilizes β-Catenin and Activates Wnt Signaling

Figure 8A:
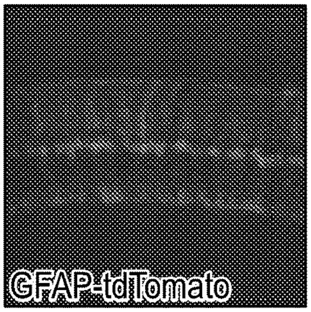
FIG. 8A through FIG. 8N, depicts results of example experiments demonstrating that GSK3β deletion stabilizes β-catenin and activates Wnt signaling in MGs. Adult GSK3B$^{loxp/loxp}$ mouse retinas were infected by ShH10-GFAP-tdTomato (infection marker) in the absence (FIG. 8A-FIG. 8F) or presence (FIG. 8G-FIG. 8L) of ShH10-GFAP-Cre co-infection. Retinal tissues were analyzed two weeks after viral infection by β-catenin immunohistochemistry. The boxed area in FIG. 8B is enlarged in FIG. 8D-FIG. 8F, and the boxed area in FIG. 8H is enlarged in FIG. 8J-FIG. 8L. Arrows in FIG. 8K show stabilized β-catenin in transduced MGs labeled by tdTomato (FIG. 8J).
Figure 8B:
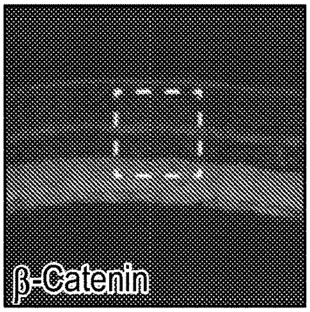
Figure 8C:
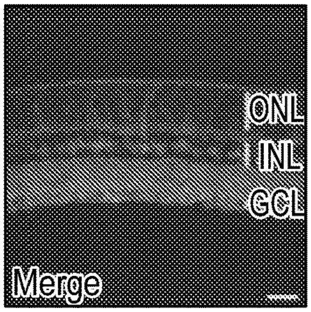
Figure 8D:
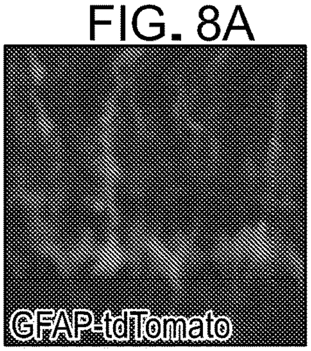
Figure 8E:
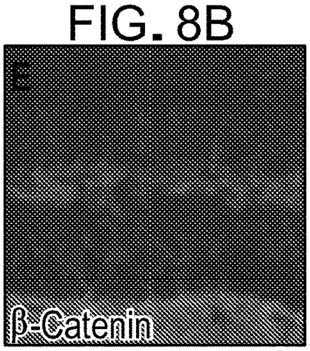
Figure 8F:
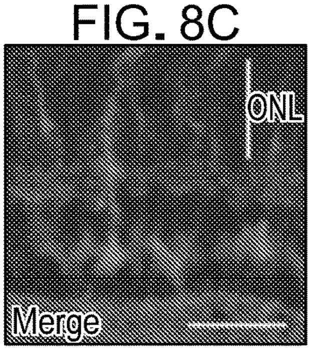
Figure 8G:
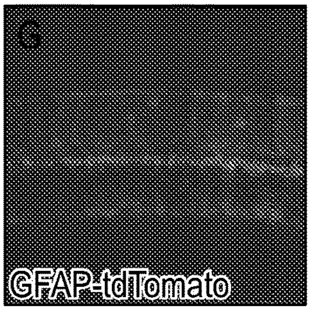
Figure 8H:
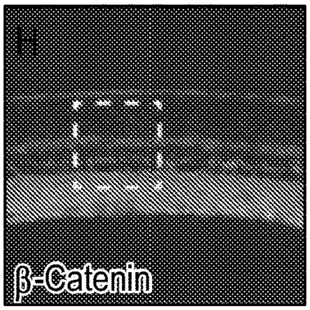
Figure 8I:
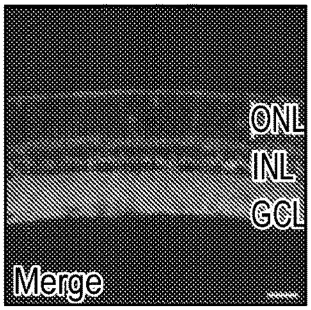
Figure 8J:
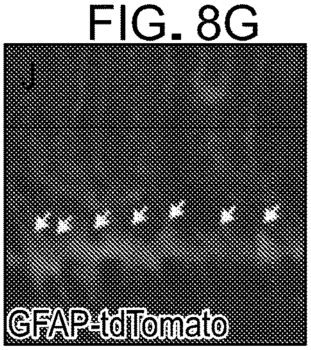
Figure 8K:
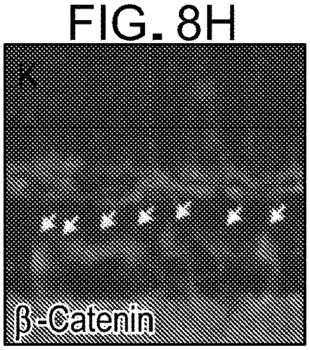
Figure 8L:
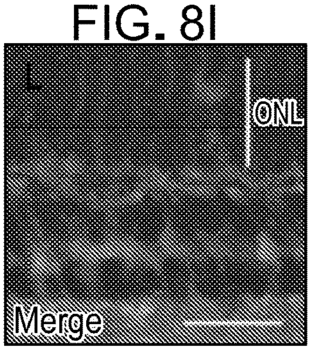
Figure 8M:
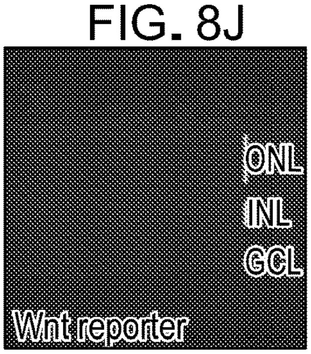
Figure 8N:
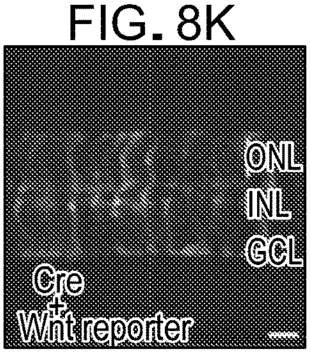

GSK3β regulates Wnt signaling by phosphorylation of β-catenin, resulting in its degradation by the ubiquitin-proteasome system (Logan and Nusse, 2004). To investigate whether GSK3β plays a role in regulating Wnt signaling and MG proliferation in adult mammalian retina, GSK3β was deleted by infecting $GSK3B^{loxp/loxp}$ mice at 4 weeks of age with ShH10-GFAP-Cre, resulting in Cre-recombinase expression specifically in MGs as indicated in the Rosa26 reporter mouse line. In comparison to $GSK3B^{loxp/loxp}$ mice infected with ShH10-GFAP-tdTomato alone as a control (FIGS. 8A-8F), deletion of GSK3β resulted in stabilization and nuclear accumulation of β-catenin in MGs, labeled by ShH10-GFAP-tdTomato co-infection (FIGS. 8G-8L). To further assess whether GSK3β deletion activates Wnt signaling, $GSK3\beta^{loxp/loxp}$ mouse retina were infected with ShH10-GFAP-Cre and the ShH10-Wnt reporter. In comparison to $GSK3B^{loxp/loxp}$ mice infected with the ShH10-Wnt reporter alone (FIG. 8M), significant activation of the reporter gene was observed 2 weeks after ShH10-GFAP-Cre co-injection (FIG. 8N). These results indicate that GSK3β deletion resulted in the activation of the canonical Wnt signaling pathway in MGs.

GSK3β Deletion Stimulates MG Proliferation without Retinal Injury

Figure 9A:
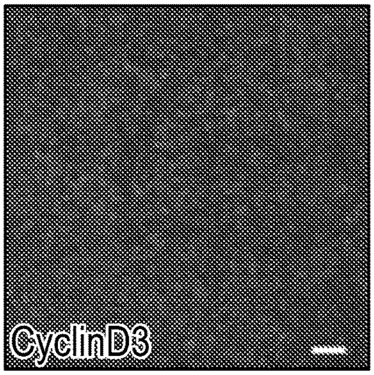
FIG. 9A through FIG. 9L, depicts results of example experiments demonstrating that GSK3β deletion stimulates MG proliferation without retinal injury. ShH10-GFAP-Cre was injected intravitreally in adult GSK3B$^{loxp/loxp}$ mice. EdU was injected 10 days after viral infection. Retinal tissues were collected 4 days later for co-detection of EdU and immunohistochemistry for MG-specific antigens.
Figure 9B:
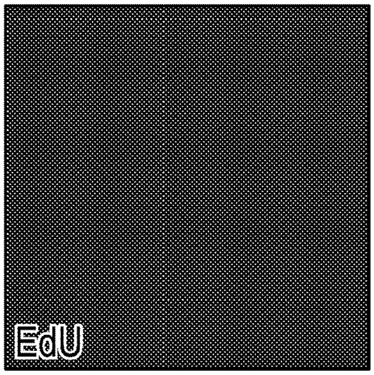
Figure 9C:
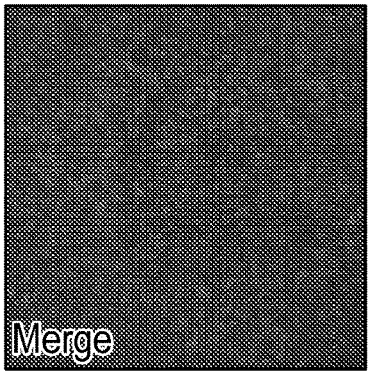
Figure 9D:
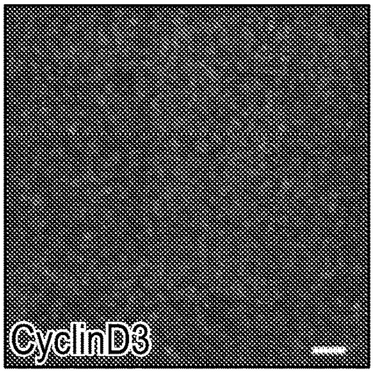
Figure 9E:
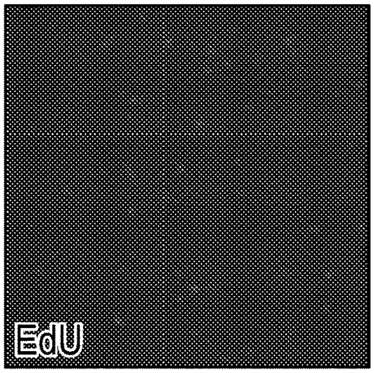
Figure 9F:
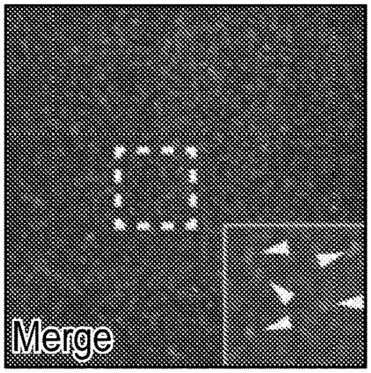
Figure 9G:
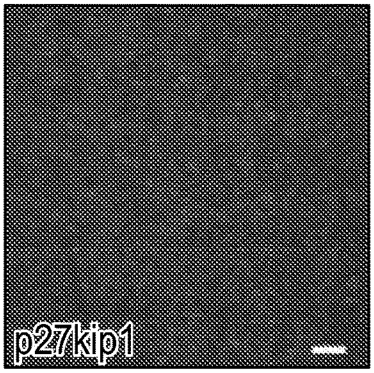
Figure 9H:
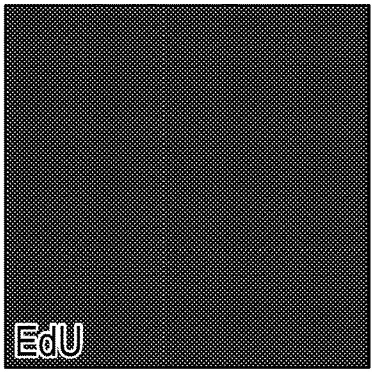
Figure 9I:
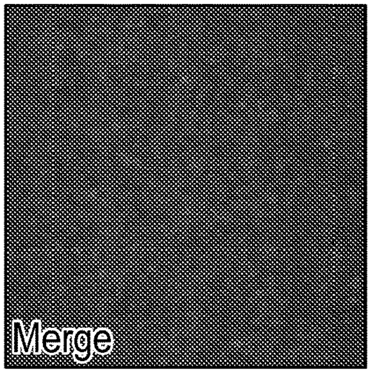
Figure 9J:
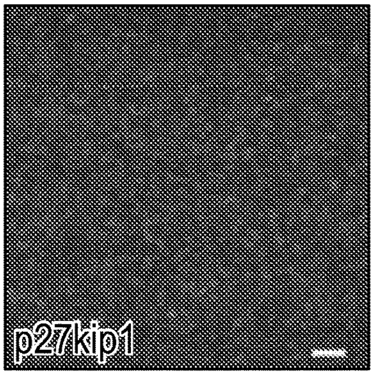
Figure 9K:
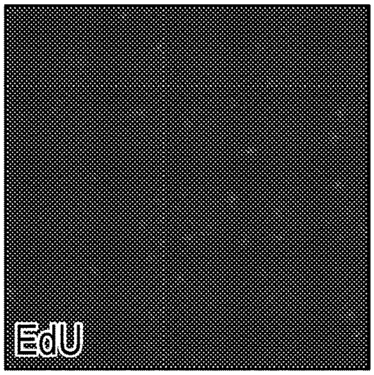
Figure 9L:
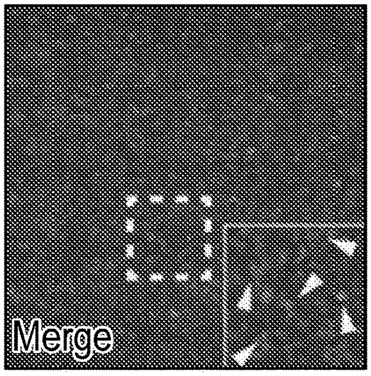

In zebrafish, pharmacological inhibition of GSK3β leads to β-catenin stabilization and MG proliferation (Ramachandran et al., 2011). In cultured mouse retinal explants, GSK3 inhibitor treatment enhances MG proliferation in SvJ129 mice (Suga et al., PLOS One, 2014, 9: e94556). To investigate whether GSK3ß deletion is sufficient to stimulate MG proliferation without retinal injury, EdU incorporation was assayed in the $GSK3\beta^{loxp/loxp}$ mouse retina infected with ShH10-GFAP-Cre at 4 weeks of age. While no EdU signal was detected in the $GSK3\beta^{loxp/loxp}$ mouse retina with sham injection (FIGS. 9A-9C and 9G-9I), 374.3±27.3/$mm^2$ $EdU^+$ cells were scored two weeks after ShH10-GFAP-Cre injection, co-labeled by immunohistochemistry for MG-specific nuclear antigens CyclinD3 (FIGS. 9D-9F) and $p27^{kip1}$ (FIGS. 9J-9L). The results demonstrate that GSK3β deletion, and thus stabilization of endogenous β-catenin, is sufficient to stimulate the proliferative response of MGs without retinal injury.

Wnt Activation Induces Lin28 Expression in Adult MGs

Figure 10A:
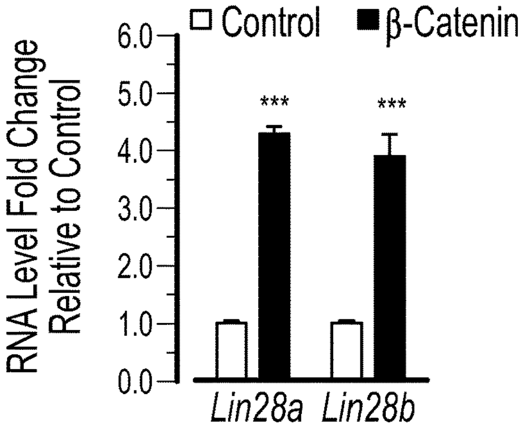
FIG. 10A through FIG. 10M, depicts results of example experiments demonstrating that ShH10-GFAP-mediated gene transfer of β-catenin induces Lin28a and Lin28b expression in MGs.
Figure 10B:
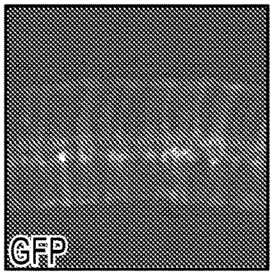
Figure 10C:
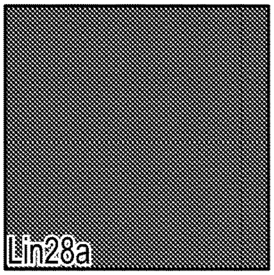
Figure 10D:
Figure 10E:
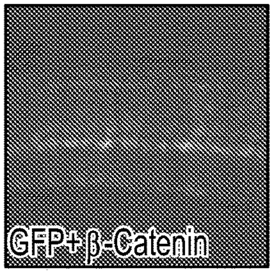
Figure 10F:
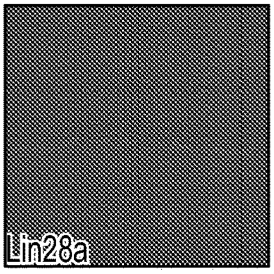
Figure 10G:
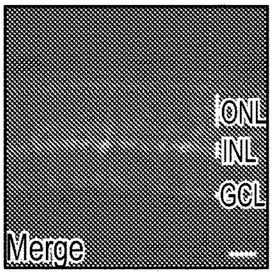
Figure 10H:
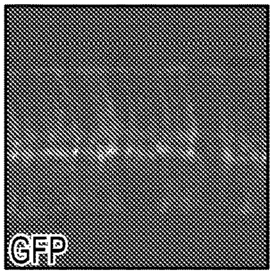
Figure 10I:
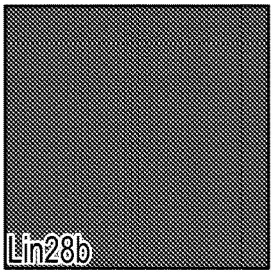
Figure 10J:
Figure 10K:
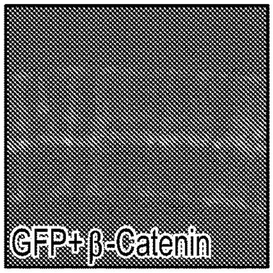
Figure 10L:
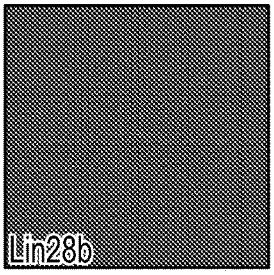
Figure 10M:
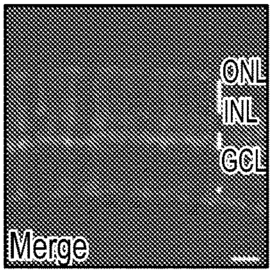

The pluripotency factor Lin28 is highly expressed in mammalian embryonic stem cells and cancer cells (Moss and Tang, Dev Biol. 2003, 258:432-442). Lin28 was used together with Oct4, Sox2, and Nanog to reprogram human somatic fibroblasts to pluripotent stem cells (Yu et al., Science, 2007, 318:1917-1920). In zebrafish, Lin28 regulates MG proliferation in response to retinal injury (Ramachandran et al., Nat Cell Biol. 2010, 12:1101-1107). To determine the role of Lin28 in MG proliferation in mammals, the ability of Wnt signaling to regulate Lin28 expression was examined by analyzing Lin28 RNA levels following gene transfer of β-catenin in adult mouse retina. In comparison to ShH10-GFAP-GFP infection as a control, the RNA levels for both Lin28a and Lin28b were significantly upregulated at two weeks after ShH10-GFAP-β-catenin infection (FIG. 10A). Lin28 protein levels were assessed using immunohistochemistry in retinal sections. In the ShH10-GFAP-GFP infected retina as a control, Lin28a (FIG. 10B-10D) or Lin28b (FIGS. 10H-10J) was not detected. By contrast, ShH10-GFAP-mediated gene transfer of β-catenin resulted in detection of Lin28a (FIGS. 10E-10G) and Lin28b (FIGS. 10K-10M) immunoreactivity in MGs, labeled by ShH10-GFAP-GFP co-infection. The detection of Lin28a and Lin28b immunoreactivity was specific as co-deletion of Lin28a and Lin28b by ShH10-GFAP-Cre infection in $Lin28a^{loxp/loxp}$; $Lin28b^{loxp/loxp}$ double floxed mice completely abolished β-catenin-induced Lin28a or Lin28b expression. The results indicate that activation of Wnt signaling induces the expression of both Lin28a and Lin28b in adult mouse MGs.

Wnt/β-Catenin Directly Regulates Lin28 Transcription

Figure 11A:
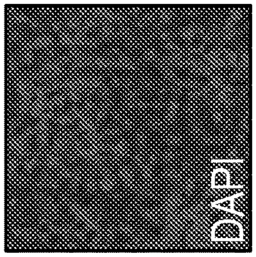
FIG. 11A through FIG. 11X, depicts results of example experiments demonstrating that Wnt/β-catenin transactivates Lin28a and Lin28b through direct binding to their promoters in HEK293T cells.
Figure 11B:
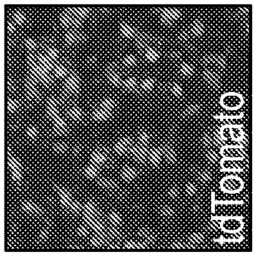
Figure 11C:
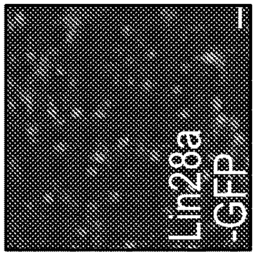
Figure 11D:
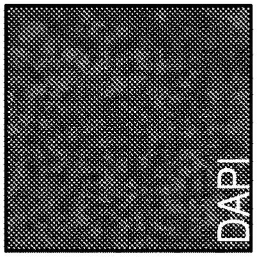
Figure 11E:
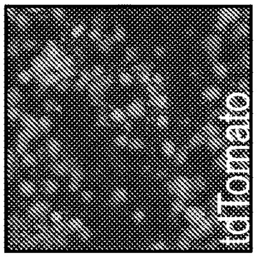
Figure 11F:
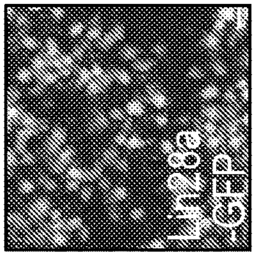
Figure 11G:
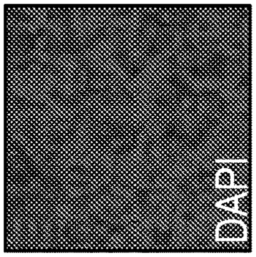
Figure 11H:
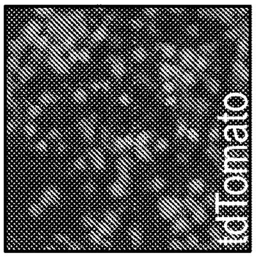
Figure 11I:
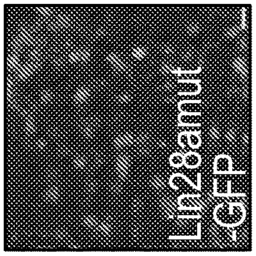
Figure 11J:
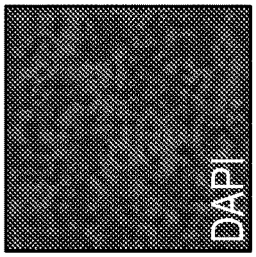
Figure 11K:
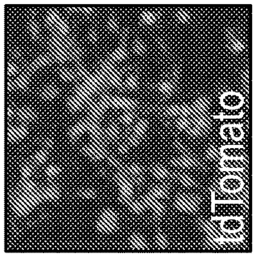
Figure 11L:
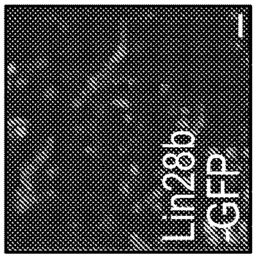
Figure 11M:
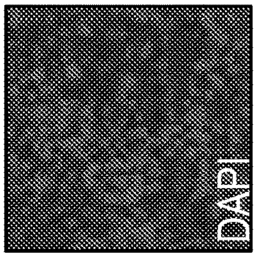
Figure 11N:
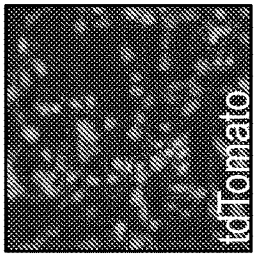
Figure 11O:
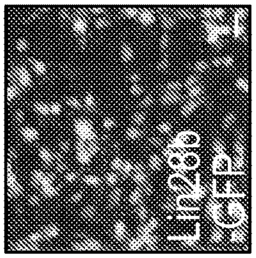
Figure 11P:
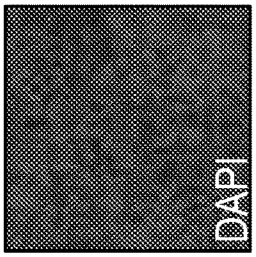
FIG. 11P through FIG. 11R depict mutation of the β-catenin binding sites in the Lin28b promoter abolished the reporter activity.
Figure 11Q:
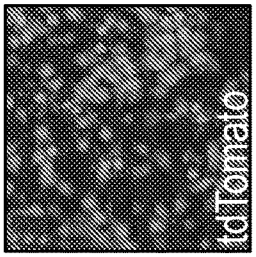
Figure 11R:
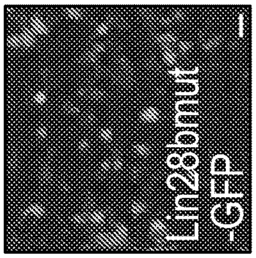
Figure 11S:
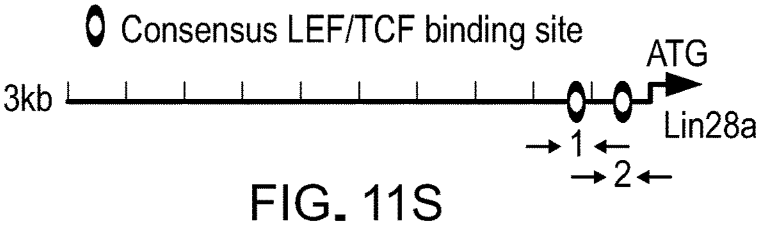
FIG. 11S and FIG. 11T depict schematic illustrations of the putative β-catenin binding sites in the Lin28a (FIG. 11S) and Lin28b (FIG. 11T) promoter, which were mutated to generate Lin28amut-GFP and Lin28bmut-GFP in the promoter reporter analysis.
Figure 11T:
Figure 11U:
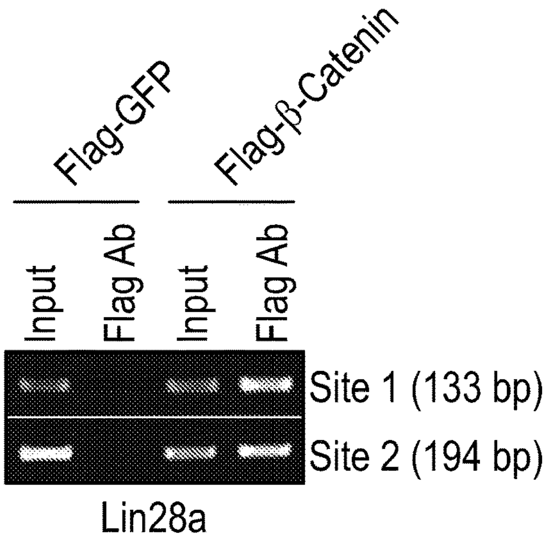
FIG. 11U and FIG. 11V depict the results of ChIP analysis, which reveals direct binding of β-catenin to the Lin28a (FIG. 11U) or the Lin28b (FIG. 11V) promoter. Chromatin, immunoprecipitated with an antibody specific to Flag, was assayed by PCR with primers flanking the putative β-catenin binding sites 1 and 2.
Figure 11V:
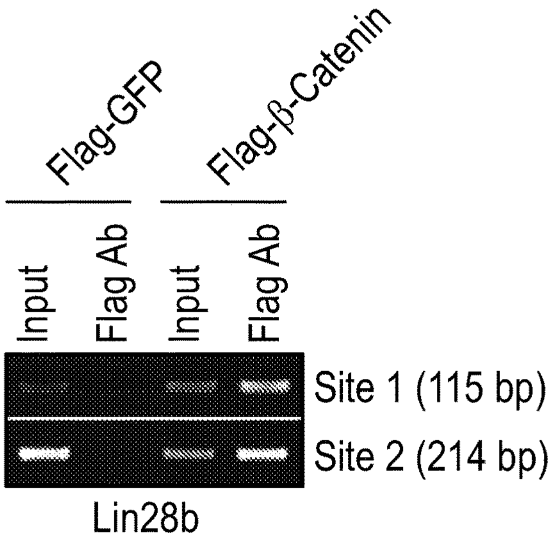
Figure 11W:
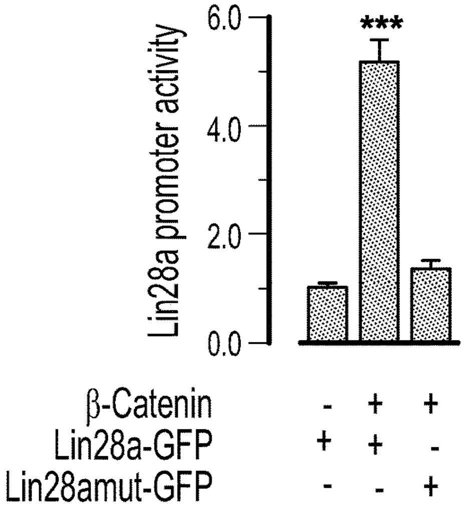
Figure 11X:
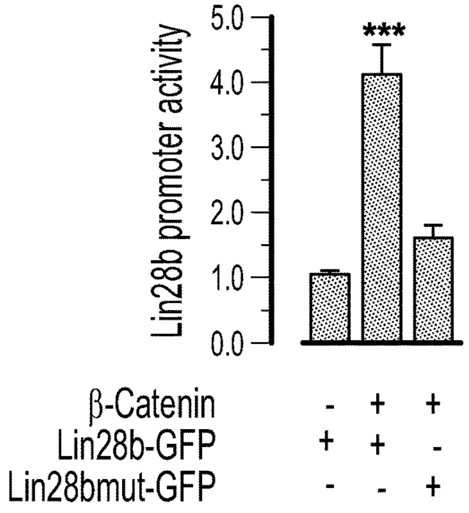

To determine whether Lin28 is a direct transcriptional target of Wnt/B-catenin signaling, 3 kb promoter sequence of the mouse Lin28 was cloned to drive the expression of a GFP reporter, namely Lin28a-GFP and Lin28b-GFP. The promoter activity was tested in HEK293T cells transfected with Lin28a-GFP or Lin28b-GFP and CAG-tdTomato (a transfection marker), with or without a Flag-tagged β-catenin. In the absence of β-catenin, the reporter gene expression was barely detectable for either Lin28a-GFP (FIG. 11A-11C) or Lin28b-GFP (FIGS. 11J-11L). In the presence of β-catenin, however, the reporter gene expression markedly increased for both Lin28a (FIGS. 11D-11F) and Lin28b (FIGS. 11M-11O). To further examine whether B-Catenin activates Lin28a and Lin28b transcription by direct binding to their promoters as a co-activator of LEF/TCF in the canonical Wnt/β-catenin pathway, chromatin immunoprecipitation (ChIP) assays were performed in HEK293T cells transfected with an expression vector encoding a Flag-tagged β-catenin or a Flag-tagged GFP as a control, together with the Lin28 promoter construct. Analysis of multiple independent clones from the ChIP assay using an anti-Flag antibody revealed β-catenin-specific binding to both Lin28a and Lin28b promoters, proximally located within 500 bp upstream of the ATG start codon. Examination of the proximal promoter sequences using MatInspector (Cartharius et al., Bioinformatics, 2005, 21:2933-2942) led to the identification of two putative β-catenin binding sites for Lin28a (FIG. 11S) and Lin28b (FIG. 11T), which were confirmed by additional ChIP assay experiments using primers flanking the putative binding sites for Lin28a (FIG. 11U) and Lin28b (FIG. 11V). To further validate these binding sites, Lin28-GFP reporter constructs were generated with the binding sites mutated (FIGS. 11S and 11T), dubbed Lin28amut-GFP and Lin28bmut-GFP. Mutation of these binding sites abolished β-catenin-activated reporter gene expression for Lin28a (FIGS. 11G-11I and 11W) and Lin28b (FIGS. 11P-11R and 11X). Taken together, these results demonstrate that β-catenin activates the transcription of Lin28a and Lin28b through direct binding to the cis-regulatory elements of their promoters.

Figures 12A, 12B, 12C, 12D, 12E, 12F, 12G, 12H, 12I, 12J, 12K, 12L, 12M, 12N, 12O, 12P, 12Q, 12R:
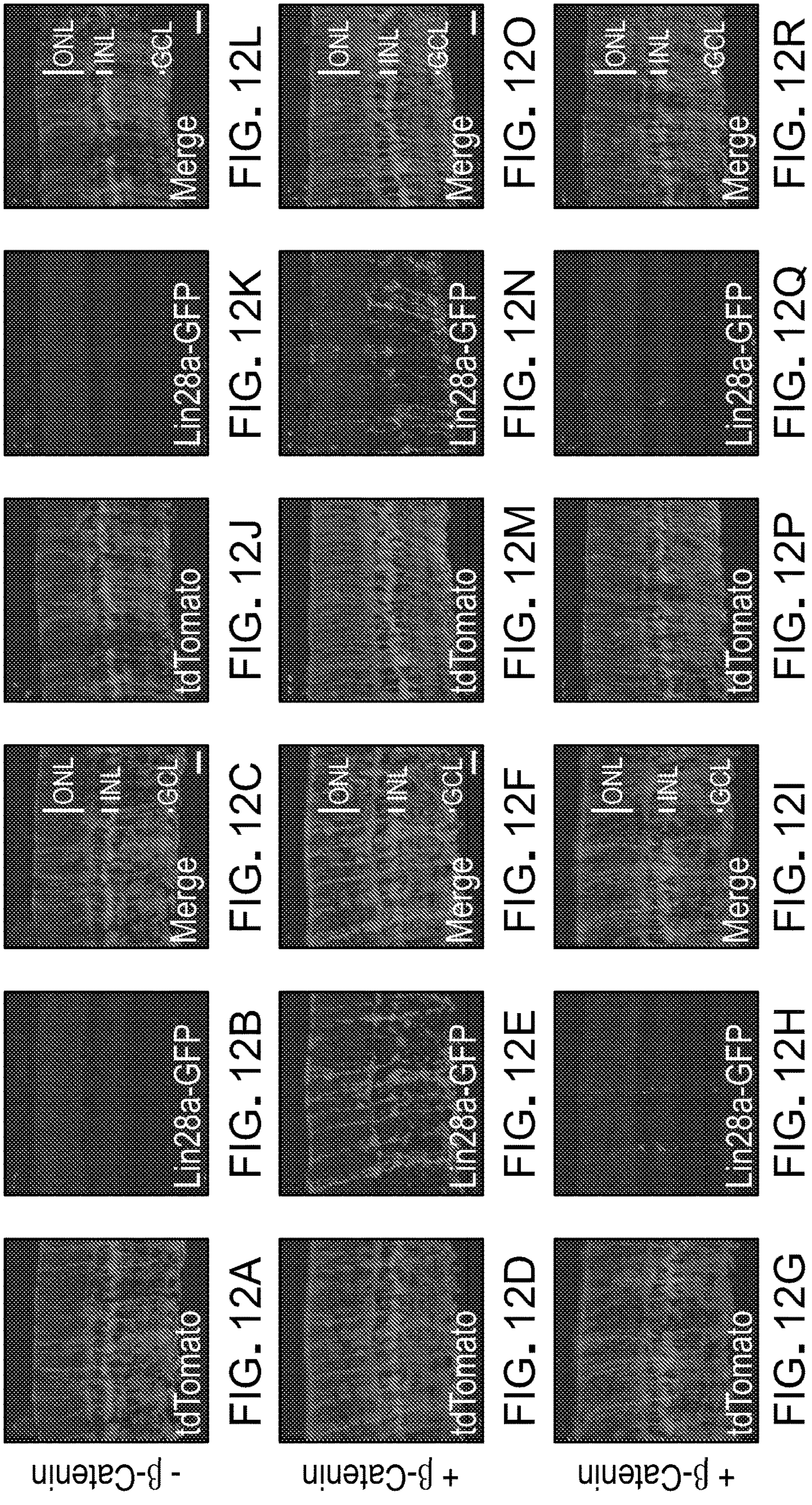
Figure 12S:
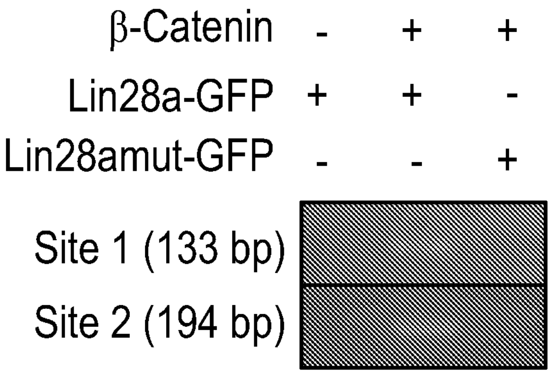
Figure 12T:
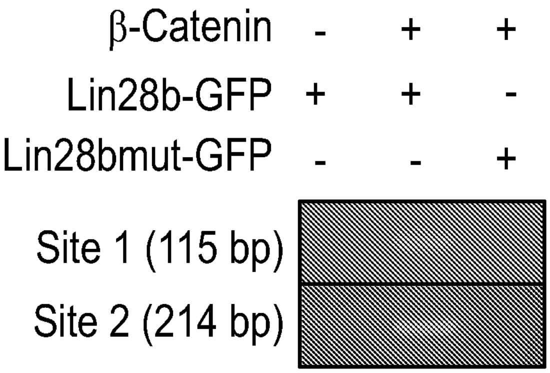

To further test whether β-catenin activates the promoters of Lin28a and Lin28b in MGs, adult mouse retinas were infected at 4 weeks of age with ShH10-Lin28a-GFP or ShH10-Lin28b-GFP, in the presence or absence of ShH10-GFAP-B-catenin co-infection. Two weeks after viral infection, the reporter gene expression was detected only in the presence of β-catenin for Lin28a (FIGS. 12A-12F) and Lin28b (FIGS. 12J-12O). Mutation of the binding sites abolished β-catenin-activated reporter gene expression for Lin28a (FIGS. 12G-12I) and Lin28b (FIGS. 12P-12R). The binding of β-catenin to the Lin28 promoters was further confirmed by ChIP assays using viral infected retinal tissues for Lin28a (FIG. 12S) and Lin28b (FIG. 12T).

Lin28 Plays an Essential Role in Controlling MG Proliferation Via Let-7 miRNAs

Figure 13A:
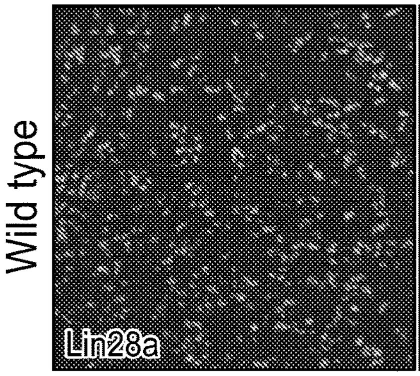
Figure 13B:
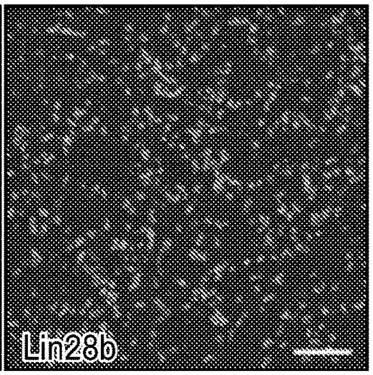
Figure 13C:
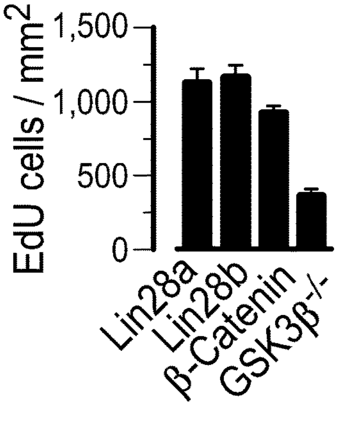
Figure 13D:
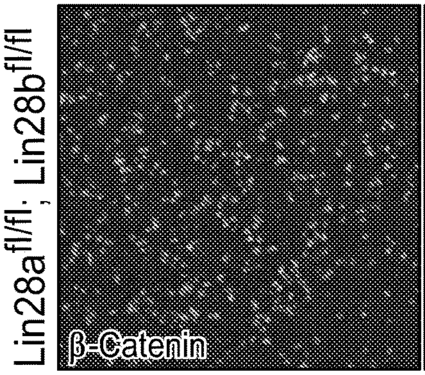
FIG. 13D through FIG. 13F depict eo-deletion of Lin28a and Lin28b abolishes β-catenin-induced MG proliferation, Lin28a$^{loxp/loxp}$; Lin28b$^{loxp/loxp}$ double floxed mice were infected with ShH10-GFAP-β-catenin, in the absence (FIG. 13D) or presence (FIG. 13E) of ShH10-GFAP-Cre co-infection. MG proliferation was analyzed and quantified (FIG. 13F) by EdU incorporation.
Figure 13E:
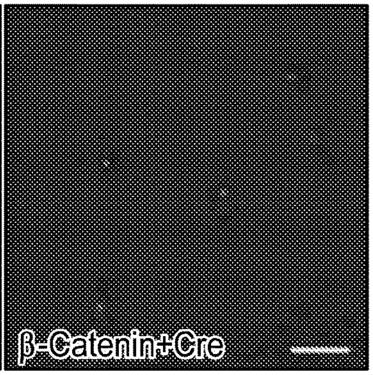
Figure 13F:
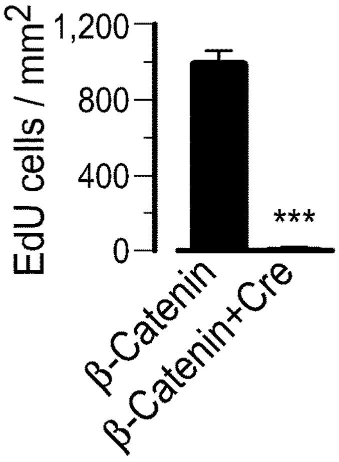
Figure 13G:
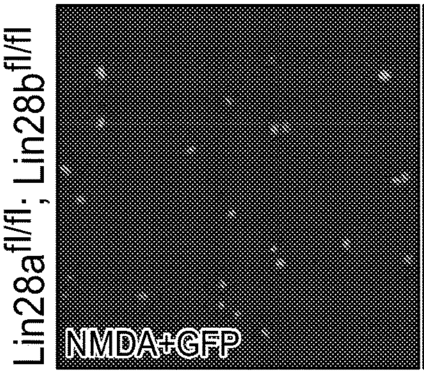
Figure 13H:
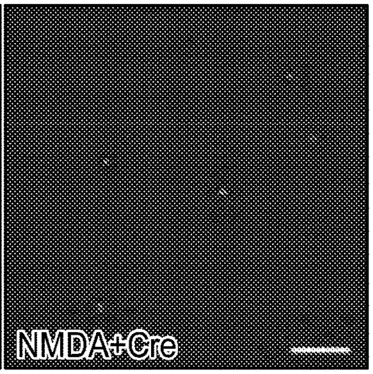
Figure 13I:
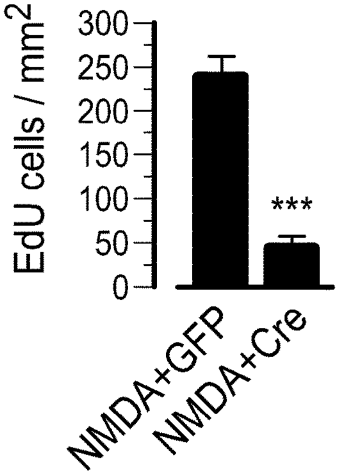

Lin28 is a direct transcriptional target of Wnt/β-catenin signaling. To determine whether gene transfer of Lin28 is sufficient to stimulate MG proliferation without retinal injury, EdU incorporation analysis was performed on adult mouse retinas infected with ShH10-GFAP-Lin28a (FIG. 13A) or ShH10-GFAP-Lin28b (FIG. 13B). Two weeks after viral infection, many MGs re-entered the cell cycle with greater than 1000 $EdU^+$ cells per $mm^2$ at 1400 μm from the retinal center in Lin28a or Lin28b infected retinas, a robust proliferation effect relative to β-catenin gene transfer or GSK3β deletion (FIG. 13C). To determine whether Lin28 was required for β-catenin-induced MG proliferation, co-deletion of Lin28a and Lin28b in $Lin28a^{loxp/loxp}$; $Lin28b^{loxp/loxp}$ double floxed mice was performed. MG proliferation induced by gene transfer of β-catenin was largely neutralized in ShH10-GFAP-Cre infected retinas (FIGS. 13D-13F). To determine if Lin28 plays a role in NMDA-induced MG proliferation, ShH10-GFAP-Cre was injected intravitreally into the retinas of $Lin28a^{loxp/loxp}$; $Lin28b^{loxp/loxp}$ double floxed mice two weeks before NMDA injection. EdU injection was performed 5 hours before tissue collection at 60 hours post-NMDA injection. The number of $EdU^+$ MGs induced by NMDA damage was largely reduced when Lin28a and Lin28b were co-deleted (FIG. 13G-13I). These results demonstrate that Lin28 serves as a key molecular switch downstream of the canonical Wnt signaling pathway to regulate MG proliferation in both injured and uninjured retinas.

Figure 14A:
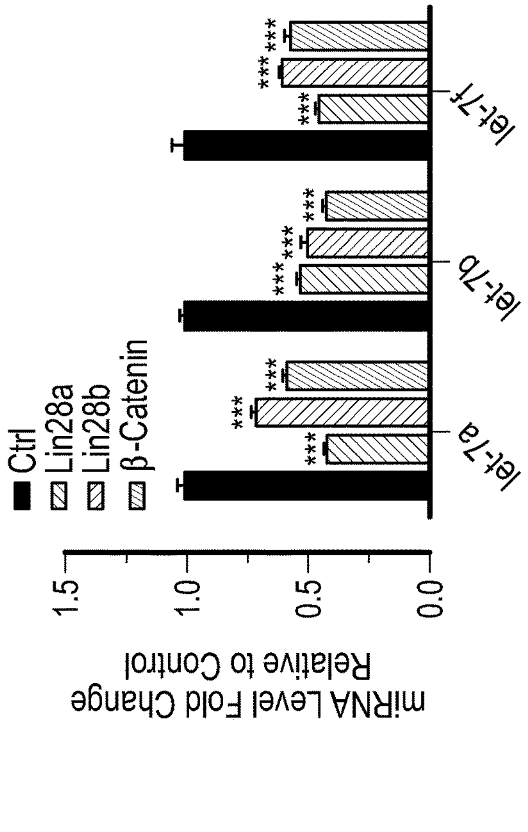
FIG. 14A through FIG. 14E, depicts results of example experiments demonstrating that Wnt/β-catenin acts through let-7 miRNAs to regulate MG proliferation.
Figure 14B:
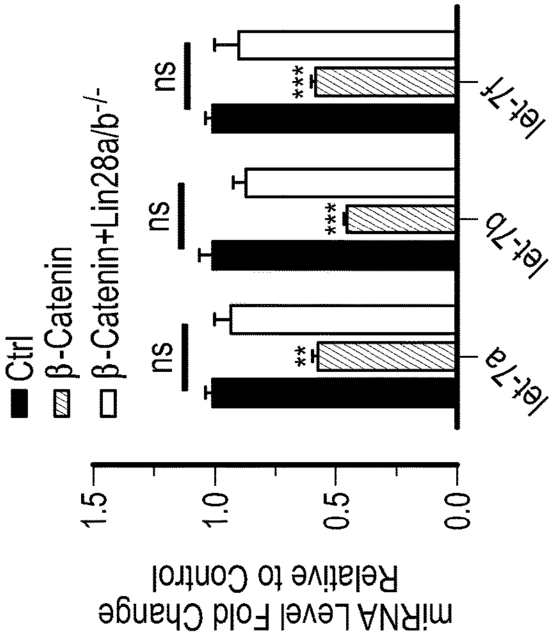
Figure 15A:
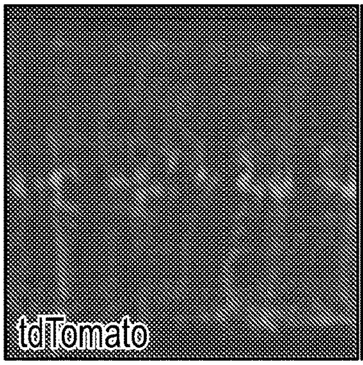
FIG. 15A through FIG. 15L, depicts results of example experiments demonstrating that Wnt/Lin28 signaling regulates let-7 miRNAs specifically in MGs. Adult mouse retinas were infected with ShH10-GFAP-GFP-let-7 miRNA sensor, ShH10-GFAP-tdTomato (infection marker), and in the absence (FIG. 15A-FIG. 15C) or presence of ShH10-GFAP-Lin28a (FIG. 15D-FIG. 15F), ShH10-GFAP-Lin28b (FIG. 15G—FIG. 15I), or ShH10-GFAP-β-catenin (FIG. 15J—FIG. 15L) co-infection, and analyzed two weeks later by confocal microscopy. Scale bar: 20 μm.
Figure 15B:
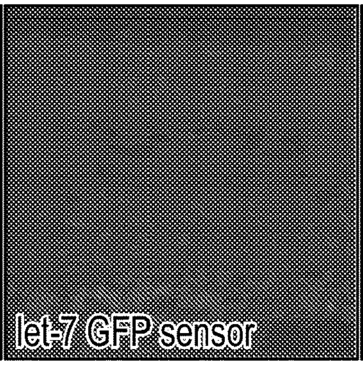
Figure 15C:
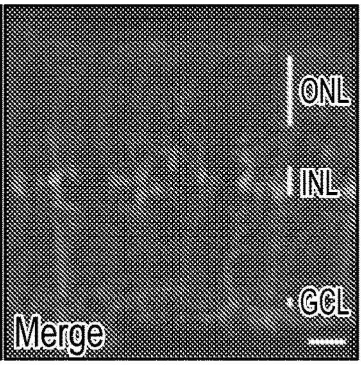
Figure 15D:
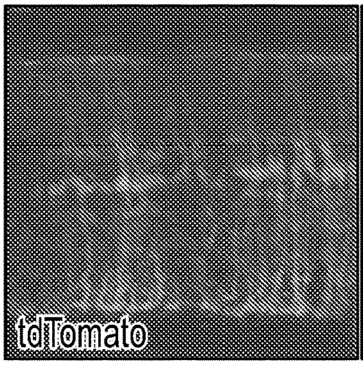
Figure 15E:
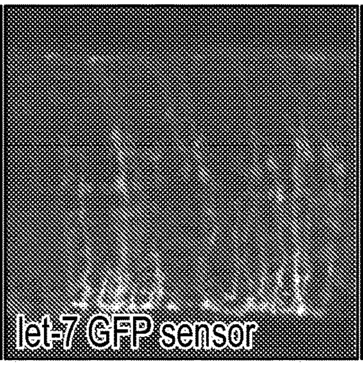
Figure 15F:
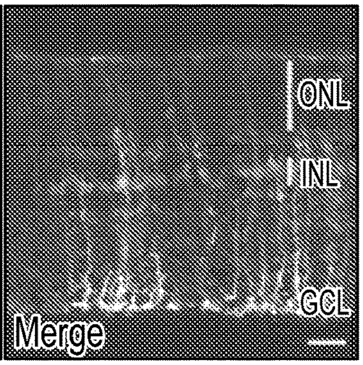
Figure 15G:
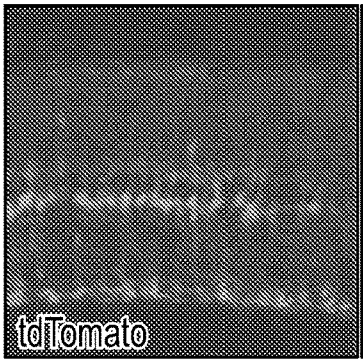
Figure 15H:
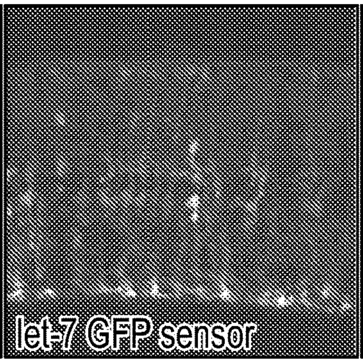
Figure 15I:
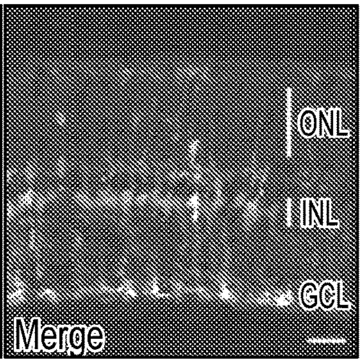
Figure 15J:
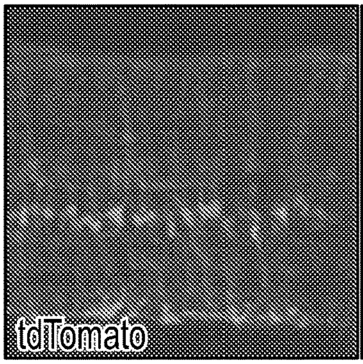
Figure 15K:
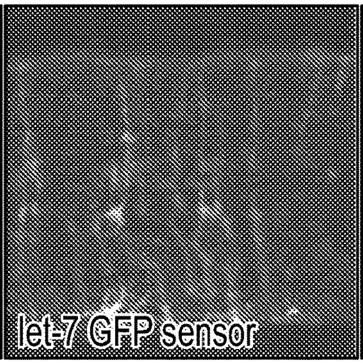
Figure 15L:
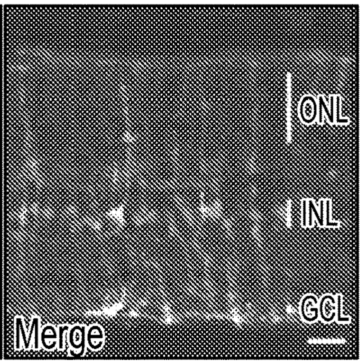

Lin28 plays a central role in regulating proliferative growth of cancer cells and embryonic stem cells through inhibition of posttranscriptional maturation of let-7 miRNAs (Heo et al., Mol Cell, 2008, 32:276-284; Newman et al., RNA, 2008, 14; 1539-1549; Rybak et al., Nat Cell Biol. 2008, 10:987-993; Viswanathan et al., Science, 2008, 320: 97-100). let-7 miRNAs suppress cell proliferation pathways through mRNA degradation or translation inhibition of a network of cell-cycle regulators (Shyh-Chang and Daley, Cell Stem Cell, 2013, 12:395-406). Therefore, Lin28 promotes cell proliferation through let-7 repression (Viswanathan et al., Nat Genet. 2009, 41:843-848). As a further downstream effector of Wnt signaling, let-7 miRNA levels were examined using quantitative PCR assays. ShH10-GFAP-mediated gene transfer of Lin28a or Lin28b in the adult mouse retina, compared to ShH10-GFAP-GFP infection as a control, led to a significant reduction in let-7a, 7b, and 7f miRNA levels two weeks after viral infection (FIG. 14A). Significantly, a marked decrease in let-7a, 7b, and 7f miRNA levels was also observed in retinas infected by ShH10-GFAP-β-catenin (FIG. 14A). To determine whether β-catenin-induced downregulation of let-7 miRNAs is mediated by Lin28, Lin28a and Lin28b were co-deleted by injection of ShH10-GFAP-Cre together with ShH10-GFAP-β-catenin in $Lin28a^{loxp/loxp}$; $Lin28b^{loxp/loxp}$ double floxed mice. Co-deletion of Lin28a and Lin28b largely neutralized β-catenin-mediated effects on let-7 miRNA downregulation (FIG. 14B), indicating that Wnt/β-catenin acts through Lin28 to regulate let-7 miRNA expression. To determine whether Wnt/Lin28-regulated let-7 miRNA expression occurs in MGs, a let-7 miRNA-responsive GFP sensor was constructed, with 3 perfectly complementary let-7 binding sites inserted in the 3'-UTR of the GFP sensor (Cimadamore et al., Proc Natl Acad Sci USA, 2013, 110: E3017-3026; Rybak et al., Nat Cell Biol. 2008, 10:987-993), and packaged into ShH10-GFAP for MG-specific delivery. In the viral transduction area labeled by ShH10-GFAP-tdTomato co-infection, the GFP sensor expression was barely detectable, indicating a high level of let-7 miRNAs present in MGs to suppress proliferation under normal conditions (FIGS. 15A-15C). Co-infection with ShH10-GFAP-Lin28a (FIG. 15D-25F) or ShH10-GFAP-Lin28b (FIGS. 15G-15I) activated the GFP sensor expression in MGs. Significantly, ShH10-GFAP-mediated gene transfer of β-catenin also activated the GFP senor expression in MGs (FIGS. 15J-15L), indicating that Wnt/Lin28-mediated regulation of let-7 miRNAs takes place in MGs.

Figure 14C:
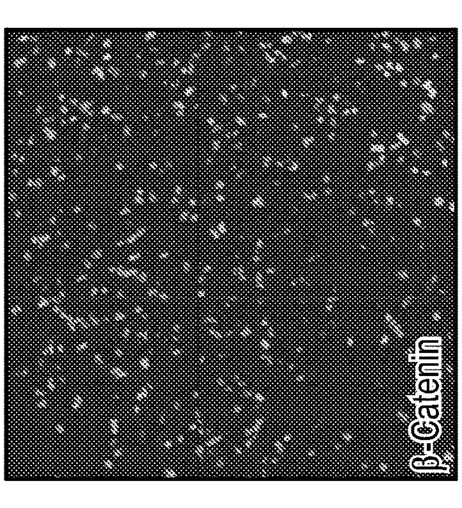
Figure 14D:
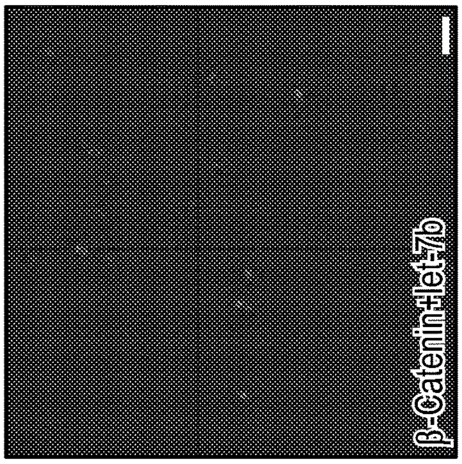
Figure 14E:
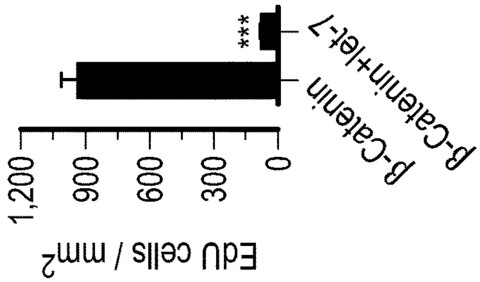

To examine whether let-7 miRNA is critically involved in Wnt/β-catenin-mediated effects on MG proliferation, let-7b miRNA was co-expressed with β-catenin in MGs using ShH10-GFAP-mediated gene transfer in the adult mouse retina at 4 weeks of age. β-catenin-induced MG proliferation was largely suppressed (FIGS. 14C-14E). Taken together, these results delineate a key role of the Wnt/Lin28/let-7 signaling module in regulating the proliferative response of MGs in adult mouse retina.

Neurogenic Potential of Wnt/Lin28-Activated MGs

Figure 16:
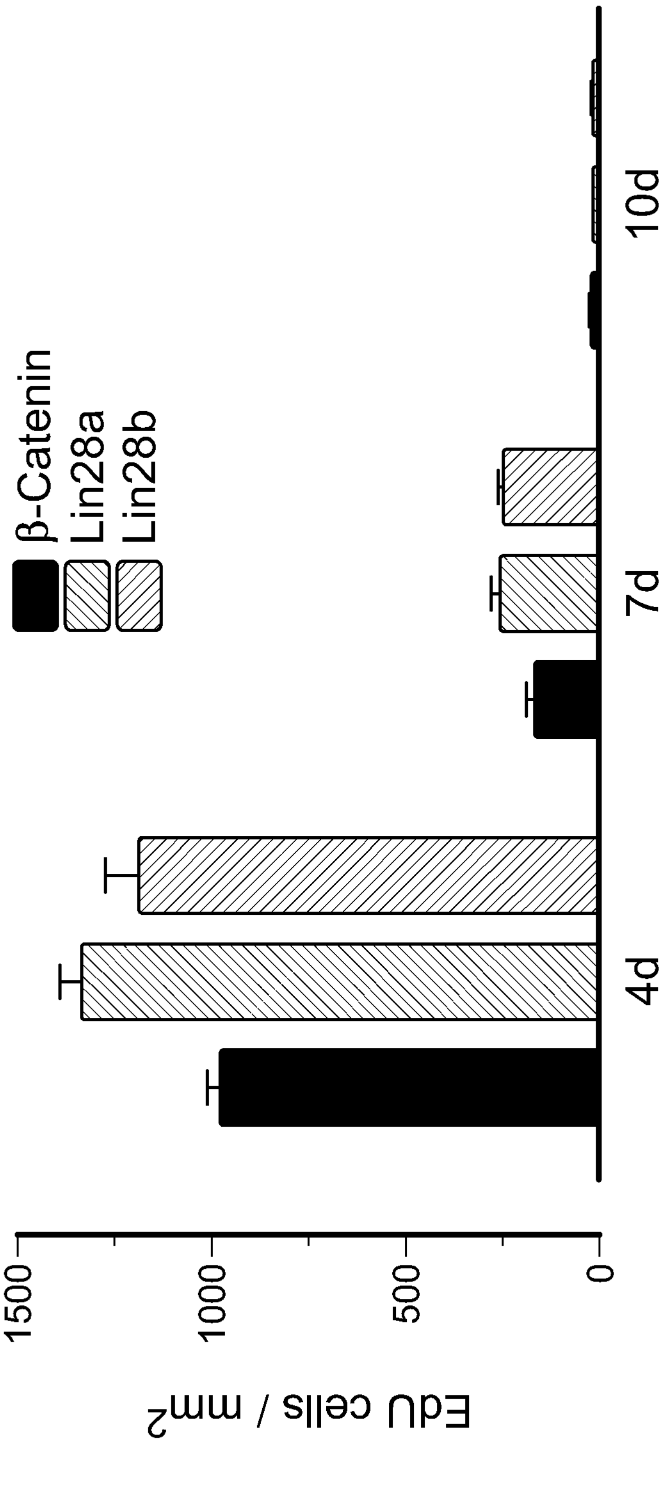
FIG. 16 depicts a time course analysis of cell cycle reactivated MGs. Adult mouse retinas infected with ShH10-GFAP-β-catenin, Lin28a, or Lin28b were treated with EdU 10 days after viral infection. Treated retinas were collected at 4, 7, 10 days after EdU injection for analysis in retinal flatmount preparations. Data are presented as mean±sem, n=3.
Figures 18A, 18B, 18C:
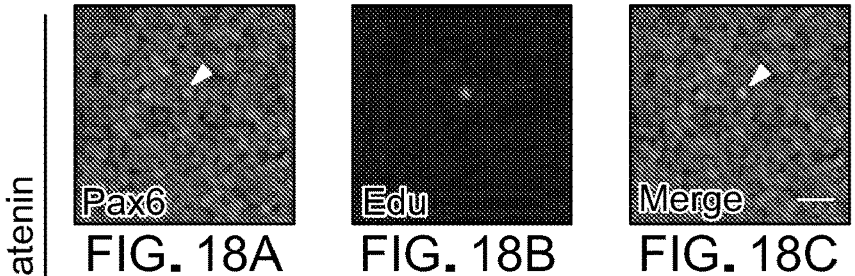
FIG. 18A through FIG. 18R, depicts results of example experiments demonstrating that Wnt-activated MGs express amacrine cell markers. Adult mouse retinas infected with ShH10-GFAP-β-catenin (FIG. 18A-FIG. 18F), ShH10-GFAP-Lin28a (FIG. 18G-FIG. 18L), or ShH10-GFAP-Lin28b (FIG. 18M-FIG. 18R) were treated with EdU 10 days after viral infection. Treated retinas were collected 4 days after EdU injection for immunohistochemistry and confocal microscopy analysis. Confocal images of the amacrine cell layer showing that a subset of EdU MGs express amacrine cell markers: Pax6 and NeuN. Arrowheads show that $EdU^+$ cells were also Pax6 or $NeuN^+$. Arrows show that $EdU^+$ cells were NeuN-. Scale bar: 20 μm.
Figures 18D, 18E, 18F:
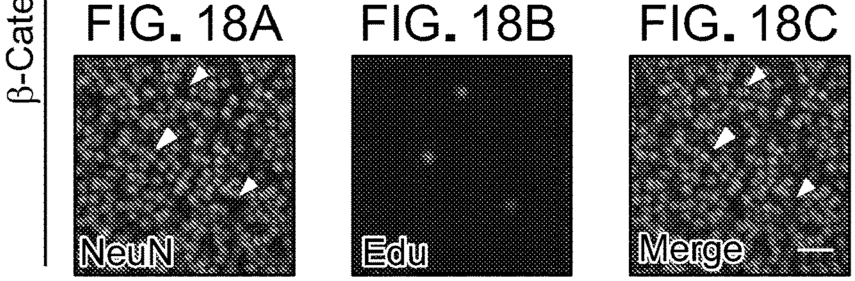
FIG. 18, comprising
Figures 18G, 18H, 18I:
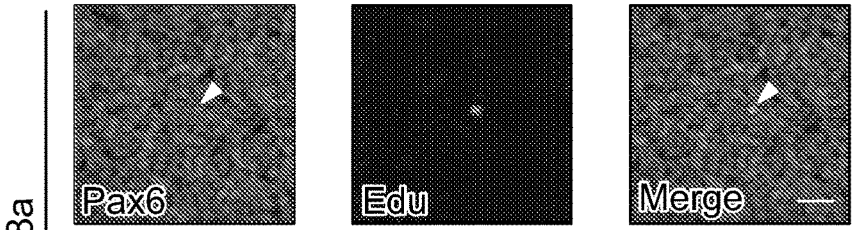
Figures 18J, 18K, 18L:
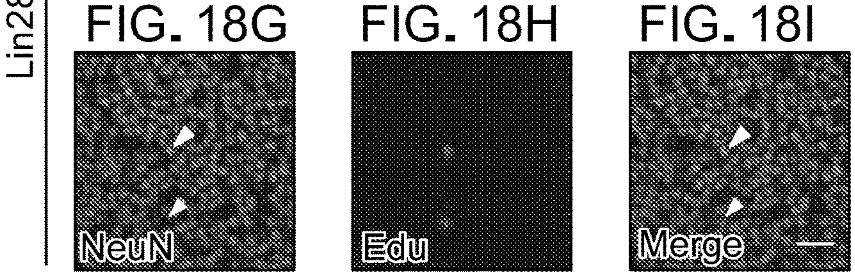
Figures 18M, 18N, 18O:
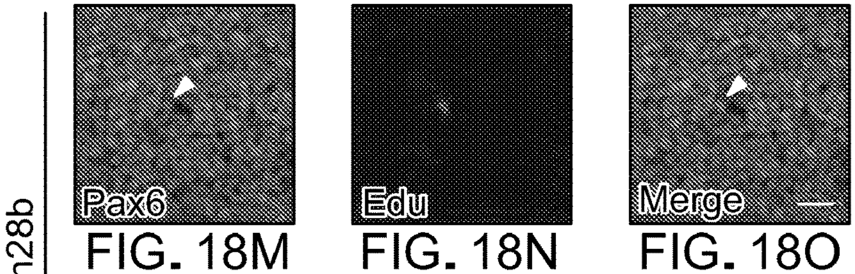
Figures 18P, 18Q, 18R:
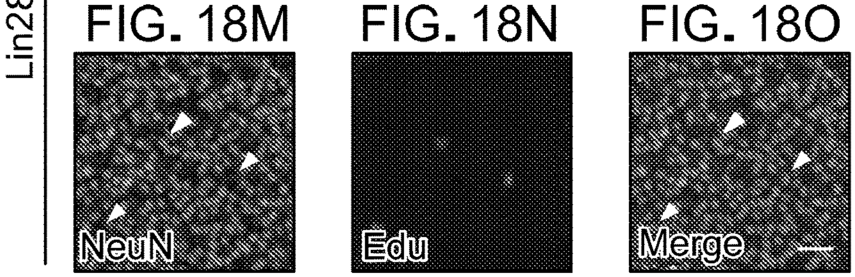
Figure 19:
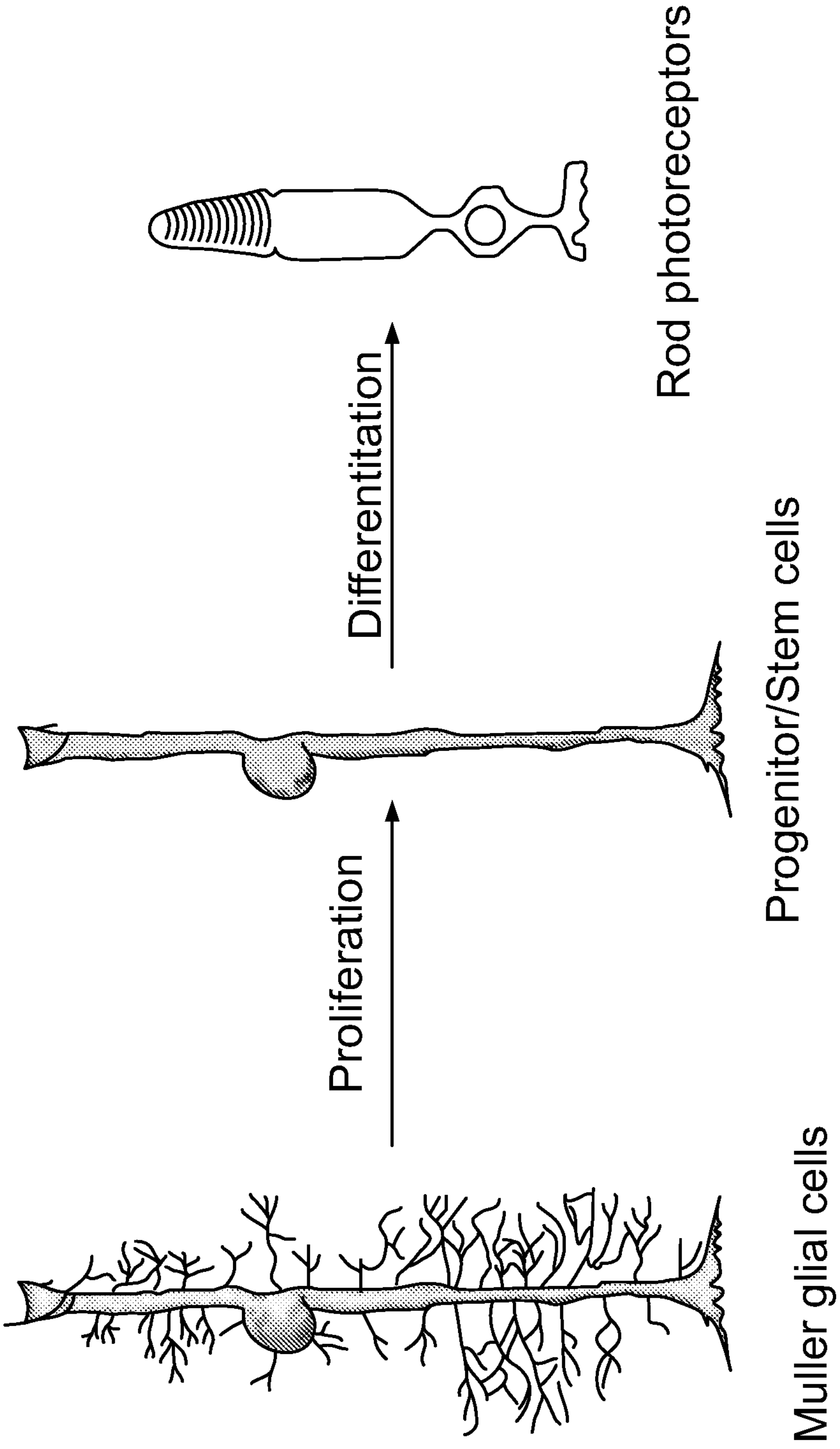
FIG. 19 depicts a schematic illustration of Müller glial cell (MG) reprogramming in adult mouse retina. Step 1: MGs are reprogrammed to become retinal progenitor/stem cells, evidenced by cell cycle re-entry. Step 2: Differentiation of cycling MGs is guided to generate rod photoreceptors using a combination of transcription factors that are essential for photoreceptor cell fate determination during early retinal development.
Figure 20:
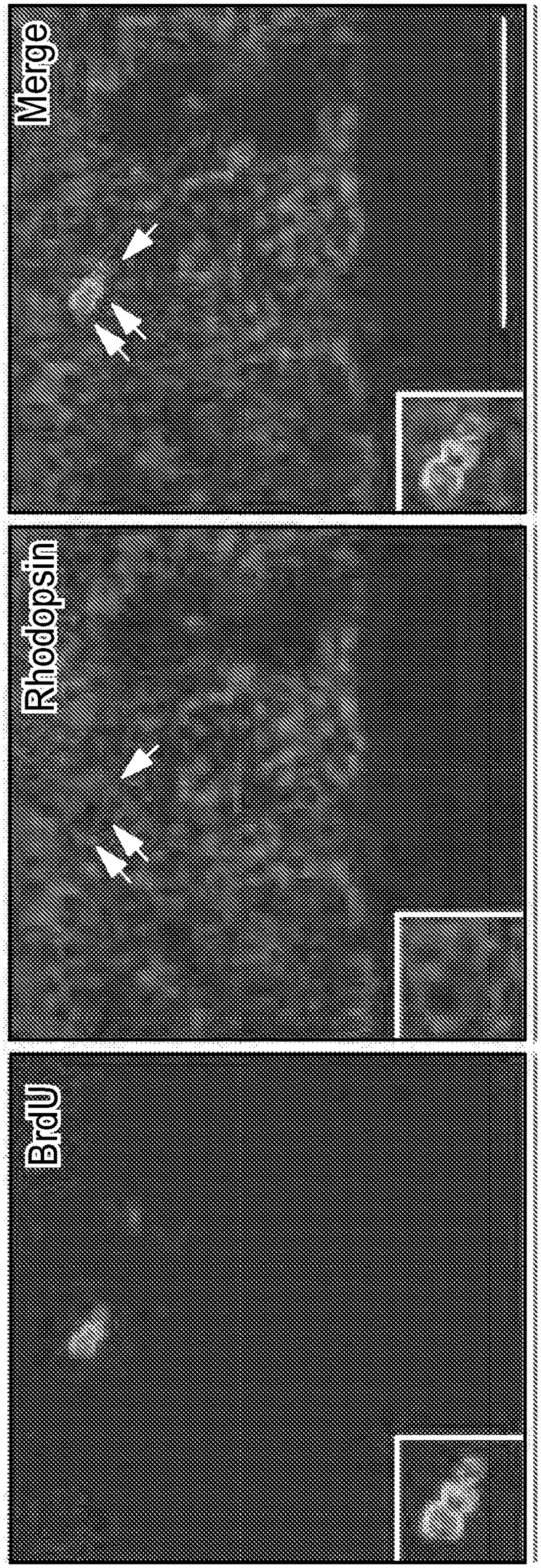
FIG. 20 depicts results of example experiments demonstrating that BrdU labeled MG-derived cells are embedded in the rhodopsin expressing old rods. Left panel, BrdU detection. Middle panel, Rhodopsin immunostaining. Right panel, overlay. Images cited from Ooto S. et al. Proc Natl Acad Sci USA. 2004, 101:13654-13659.

To analyze the fates of cell cycle reactivated MGs, EdU was injected at 10 days after ShH10-GFAP-mediated gene transfer of β-catenin, Lin28a, or Lin28b in the 4-week-old adult mouse retina, and the number of $EdU^+$ cells was quantified at 4, 7, and 10 days after EdU injection. Although many $EdU^+$ cells were scored per $mm^2$ in retinas treated with β-catenin (970.3±40), Lin28a (1325.3±64.4), or Lin28b (1177.3±94.2) at 4 days after EdU injection, the number of $EdU^+$ cells declined over time for all three treatment groups with only a very small number of $EdU^+$ cells remaining at 10 days after EdU injection (FIG. 16). These results are consistent with the previous report on injury-induced MG proliferation (Ooto et al., Proc Natl Acad Sci USA, 2004, 101:13654-13659) that the majority of cell cycle reactivated MGs die, resulting in a time-dependent decrease in the number of BrdU labeled cells. To examine neurogenic potential of the cell cycle reactivated MGs, the expression of cell-type-specific markers by $EdU^+$ cells after retinal dissociation was evaluated at 4 days after EdU injection in retinas infected with ShH10-GFAP-β-catenin, Lin28a, or Lin28b. Expression of markers for rods (rhodopsin), cones (red/green or blue cone opsins), bipolar cells (PKCα), and ganglion cells (Tuj1 or Bm3) was not detected in $EdU^+$ cells for all three treatment groups. Intriguingly, a small number of $EdU^+$ cells were immunoreactive for amacrine cell markers (FIG. 17). In β-catenin-treated retinas (FIGS. 17A-17C and 17J), 33.1±4.3% of $EdU^+$ cells were positive for Pax6 (progenitors and amacrine cells), 6.5±1.5% were positive for Syntaxin1 (amacrine cells), and 6.0±0.9% were positive for NeuN (amacrine and ganglion cells). In Lin28a-treated retinas (FIGS. 17D-17F and 17J), 51.0±4.0% of $EdU^+$ cells were positive for Pax6, 6.1±1.1% were positive for Syntaxin1, and 5.1±1.0% were positive for NeuN. In Lin28b-treated retinas (Figures, 17G-17I and 17J), 49.5±2.6% of $EdU^+$ cells were positive for Pax6, 5.5±0.9% were positive for Syntaxin1, and 5.9±2.0% were positive for NeuN. Using confocal microscopy in intact retina, the expression of amacrine cell markers was confirmed in a small subset of the cell cycle reactivated MGs located in the lower part of the inner nuclear layer where the amacrine cell somas are located, following ShH10-GFAP-mediated gene transfer of β-catenin, Lin28a, or Lin28b (Figure S18). These results signify neurogenic potential of Wnt/Lin28-activated MGs in adult mammalian retina.

Example 2

Gene Transfer of β-Catenin Activates MG Proliferation without Retinal Injury in a Mouse Model of Retinal Degeneration Photoreceptors (rods and cones) are particularly vulnerable to various degenerative conditions. Retinitis pigmentosa (RP) refers to a major group of hereditary retinal degenerative diseases commonly caused by mutations in rod-specific genes. These genetic defects cause rods to die followed by gradual degeneration of cones (Ferrari et al., Curr Genomics, 2011, 12:238-249). A major challenge to restoring vision in RP is the heterogeneous nature of the disease, as it is caused by many mutations; thus, each mutation may require a unique therapy. MG-derived retinal regeneration may represent a general therapeutic strategy regardless of disease-causing mutation(s). Rd1 mice, a widely used mouse model of RP, carry a recessive mutation in the rod-specific gene phosphodiesterase-6B, which is mutated in about 4-5% of human RP patients in the US (Hartong et al., Lancet, 2006, 368:1795-1809). In rd1 mice, rods die rapidly followed by a slower phase of cone degeneration. Previous studies have attempted to protect photoreceptors in rd1 mice, with treatments including neurotrophic factors (LaVail et al., Invest Ophthalmol Vis Sci. 1998, 39:592-602), calcium channel blockers (Frasson et al., Nat Med. 1999, 5:1183-1187), or anti-apoptosis gene transfer (Bennett et al., Gene Ther. 1998, 5:1156-1164). Neuroprotection-based therapeutic intervention would benefit RP patients at an early/intermediate stage of the disease when most photoreceptors are alive. Generation of new photoreceptors from reprogrammed MGs will provide an alternative therapeutic strategy to repopulate photoreceptors even at advanced stages of disease when most photoreceptors have died.

Experiments have been designed to investigate ShH10-GFAP-mediated gene transfer of β-catenin activation of MG proliferation in rd1 mice. ShH10-GFAP-mediated gene transfer of β-catenin is performed in rd1 mice by intravitreal injection at postnatal day 14, 21, or 35, representing early, intermediate, and late stage of photoreceptor degeneration respectively. Activation of Wnt target genes (CyclinD1, Lef1, and Axin2) are examined at 1, 2 and 4 weeks after viral injection. EdU administration and proliferation analysis are performed as described elsewhere herein for the wild-type retina.

Example 3

Regeneration of Rod Photoreceptors from Müller Glial Cells in Adult Mouse Retina Activation of MGs has potential for ultimately restoring the regenerative capability in humans in order to treat blinding diseases. Elsewhere herein, the injury-induced signaling pathway(s) that are responsible for activating the proliferative response of MGs are identified and it was demonstrated that MG proliferation can be activated to generate retinal progenitor/stem cells, without retinal injury (see Example 1). Differentiation of MG-derived progenitor/stem cells to rod photoreceptors (FIG. 19) can be guided by gene transfer of pro-rod transcription factors to generate MG-derived new rods with the molecular, structural, and functional properties of native rods.

The experiments are now described.

Guide the Differentiation of MG-Derived Retinal Progenitor/Stem Cells to Rod Photoreceptors.

Upon injury and growth factor treatment, a subset of mammalian MGs re-enter the cell cycle, but only a very small number of MG-derived retinal progenitors differentiate into retinal neurons, including rods (Ooto et al., Proc Natl Acad Sci US A, 2004, 101:13654-13659; Del Debbio et al., PLOS One, 2010, 5: e12425) and amacrine cells (Karl et al., Proc Natl Acad Sci USA, 2008, 105:19508-19513). Efficient production of MG-derived photoreceptors represents a major challenge to restoring the regenerative capability in the mammalian retina. To achieve high efficiency in regeneration of rod photoreceptors, the differentiation of MG-derived retinal progenitors is guided by delivering a set of pro-rod transcription factors that play an essential role in rod photoreceptor differentiation during retinal development, involving the proliferation and terminal differentiation of retinal progenitor cells into specific cell types. Differentiation of retinal progenitors is regulated by both extrinsic cues and the intrinsic properties of progenitor cells (Cepko et al., Proc Natl Acad Sci USA, 1996, 93:589-595; Harris, Curr Opin Genet Dev. 1997, 7:651-658; Livesey and Cepko, Nat Rev Neurosci. 2001, 2:109-118; Yang, Semin Cell Dev Biol. 2004, 15:91-103), that impinge on the transcription network of retinal progenitor cells for their cell fate determination (Swaroop et al., Nat Rev Neurosci. 2010, 11:563-576). Retinal progenitor cells go through a progression of competency states, each controlled by a distinct network of transcription factors to make particular cell types in a specific time window. For example, a specific set of transcription factors may allow a retinal progenitor cell to produce a rod instead of a bipolar cell or an amacrine cell. Transcription factors, which are known to play an important role in the specification and differentiation of rod photoreceptors during retinal development, h tested and used to guide the differentiation of MG-derived progenitor cells. ShH10-GFAP-mediated gene transfer provides a practical tool for MG-specific delivery of these transcription factors. This approach may prove useful in replenishing photoreceptors that typically die in retinal degenerative diseases.

Construction of a Reporter to Track the Differentiation of MG-Derived Retinal Progenitors to Rod Photoreceptors.

Attempts to stimulate mammalian MGs for photoreceptor regeneration have met with little success. Very few rods were generated when the mammalian retina was first injured and subsequently treated with growth factors. Not only were these newly generated rods limited in number, they were imbedded in an overwhelming majority of native rods, generated from retinal progenitor cells during retinal development. Anti-rhodopsin immunohistochemistry was used to identify these MG-derived new rods (Ooto et al., Proc Natl Acad Sci USA, 2004, 101:13654-13659). However, it was not clear whether the EdU' MGs had rhodopsin expression, because the sparsely scattered EdU' cells were surrounded by native rods that all express rhodopsin protein (FIG. 20 from Ooto et al., Proc Natl Acad Sci USA, 2004, 101:13654-13659).

Figure 21A:
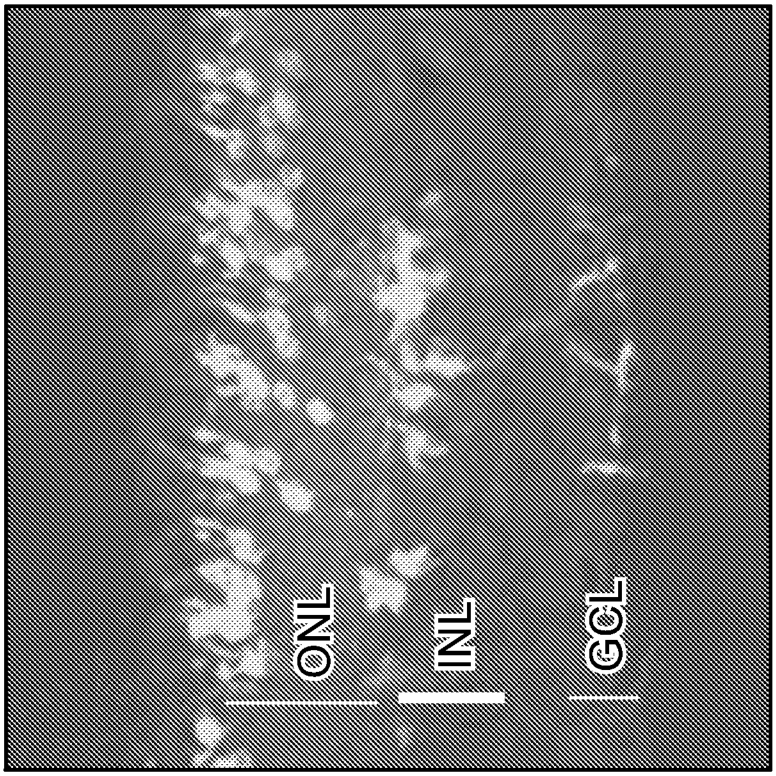
FIG. 21A through FIG. 21B, depicts analysis of the rhodopsin-tdTomato reporter by electroporation in neonatal mouse retina. Retinal sections were analyzed at postnatal day 21.
Figure 21B:
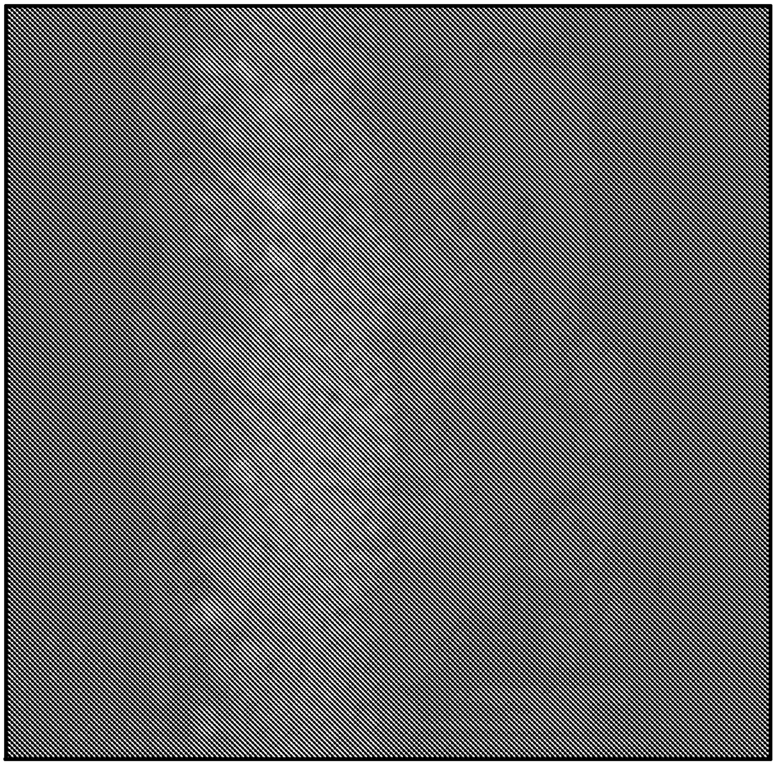

To overcome the above limitation, MG-derived new rods are exclusively labeled using a method that does not detect the native rods. Importantly, this approach allows tracking and characterization of the differentiation of MG-derived retinal progenitors to rods at progressive stages. A reporter for cell-type-specific delivery to MGs is turned on when MG-derived retinal progenitors undergo rod differentiation. The reporter construct contains a 2. 1 kb rhodopsin promoter driving the expression of tdTomato specifically in rods (Matsuda and Cepko, Proc Natl Acad Sci USA, 2004, 101:16-22). The reporter construct was tested by in vivo electroporation to co-transfect a ubiquitous pCAG-GFP plasmid and the rhodopsin-tdTomato reporter plasmid in the newborn mouse retina. The results show that the rhodopsin-tdTomato reporter exclusively labels rods while GFP expression driven by the ubiquitous CAG promoter labels multiple retinal cell types including rods, bipolar cells, amacrine cells, and MGs (FIG. 21). The rhodopsin-tdTomato cassette cloned into the ShH10 vector is used for delivery to MGs. This reporter is referred to as ShH10-rhodopsin-tdTomato hereafter.

Guide the Differentiation of MG-Derived Retinal Progenitors to Rod Photoreceptors.

To guide the differentiation of MG-derived retinal progenitors to rod photoreceptors, the major consideration was the choice of pro-rod transcription factors. Three transcription factors (Otx2, Crx, and Nrl) are essential for determining the rod cell fate of retinal progenitor cells during early retinal development. Otx2 is an early transcription factor for photoreceptor cell fate determination. Otx2 deficiency leads to overproduction of amacrine-like cells at the expense of both rod and cone photoreceptors (Nishida et al., Nat Neurosci. 2003, 6:1255-1263). Crx is another transcription factor required for terminal differentiation and maintenance of photoreceptors (Chen et al., Neuron, 1997, 19:1017-1030; Furukawa et al., Cell, 1997, 91:531-541). Nrl is a basic motif-leucine zipper transcription factor that promotes rod cell fate by transcriptional activation of important rod genes including rhodopsin (Rehemtulla et al., Proc Natl Acad Sci USA, 1996, 93:191-195). Nrl also suppresses cone photoreceptor cell fate by transcriptional activation of Nr2e3 (Mears et al., Nat Genet. 2001, 29:447-452, Mitton et al., J Biol Chem. 2000, 275:29794-29799).

Figure 22:
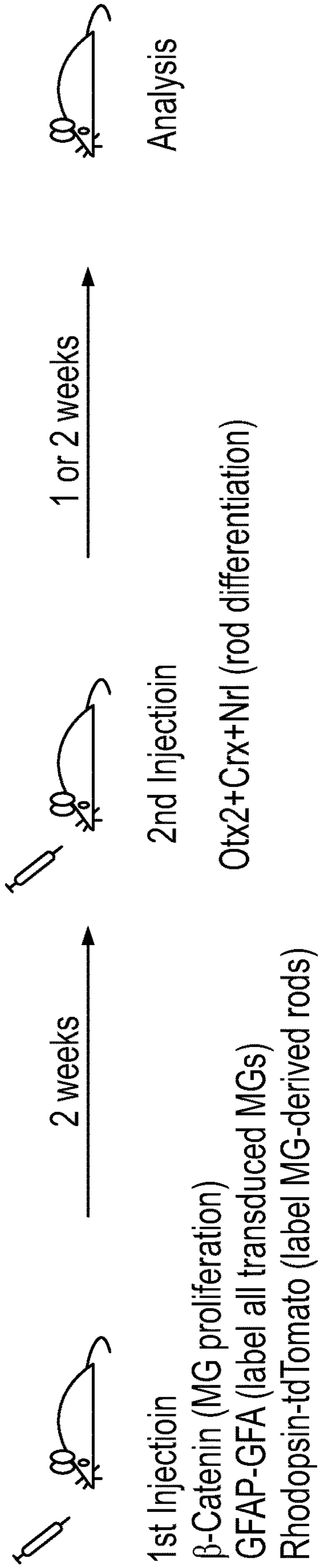
FIG. 22 depicts a schematic illustration of the two-step rod induction protocol.

CDNAs encoding Otx2, Crx, and Nrl were cloned into ShH10-GFAP for MG-specific gene transfer. A two-step protocol for rod induction was used to guide the differentiation of MG-derived retinal progenitors to rod photoreceptors (FIG. 22). First, MG proliferation was stimulated by injection of ShH10-GFAP-β-catenin in adult mouse retina at 4-5 weeks of age, followed by the second injection of ShH10-GFAP-Otx2, ShH10-GFAP-Crx, and ShH10-GFAP-Nrl to guide rod differentiation with a two-week time interval between the two injections. Also included in the first injection were ShH10-GFAP-GFP (as a viral infection marker to label all transduced MGs) and the ShH10-rhodopsin-tdTomato reporter to monitor the differentiation of MGs to rod photoreceptors. Recombinant viruses were purified and concentrated to the titer of $1.0\times10^{13}$ cfu/ml and mixed at the ratio of 1:1:1 for a total volume of 1 μl intravitreal injection. Greater than 90% of co-transduction efficiency was achieved by injection of a mix of multiple high titer adeno-associated viruses to restore color vision in red-green color blind primates (Mancuso et al., Nature, 2009, 461:784-787).

Figures 23A, 23B, 23C, 23D, 23E, 23F, 23G, 23H, 23I:
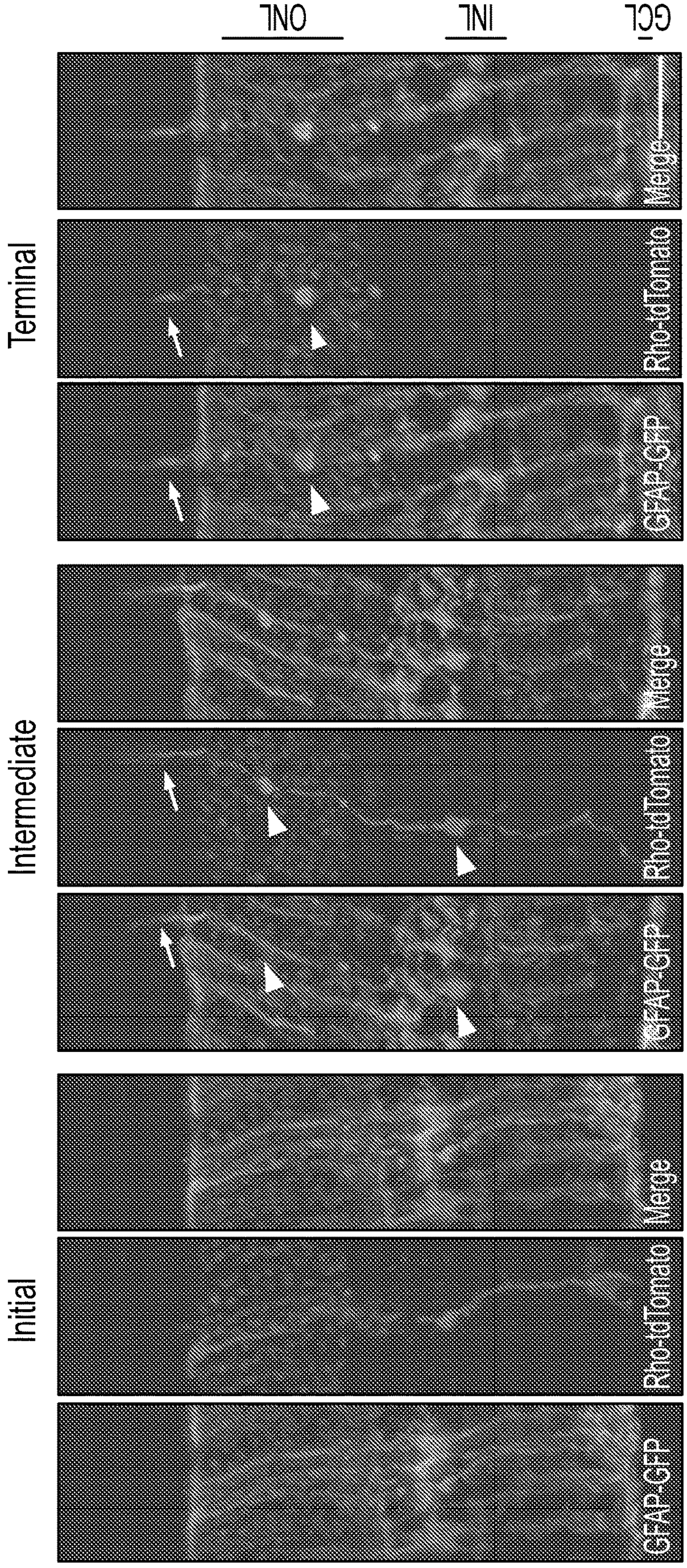

One week after ShH10-GFAP-mediated gene transfer of Otx2, Crx, and Nrl, the ShH10-rhodopsin-tdTomato reporter was turned on in a subset of MGs, and all of rhodopsin-tdTomato positive cells were labeled by co-injected ShH10-GFAP-GFP, indicating that the MG-derived retinal progenitors were undergoing rod differentiation. Based on the morphological changes, the differentiation of MGs was categorized according to three stages: the initial, intermediate, and terminal stage. Initial stage: A majority (close to 75%) of the rhodopsin-tdTomato+ cells appeared morphologically similar to MGs with the upper processes ending at the outer limiting membrane, and the lower processes (MG end feet) extending to the fiber layer of retinal ganglion cells (FIG. 23A-23C). Intermediate stage: A number of (about 20%) of the rhodopsin-tdTomato cells were undergoing morphological changes after the last cell division, one daughter cell was differentiating to the rod as evidenced by the soma migration to the outer nuclear layer while the other daughter cell maintained the MG morphology; and most intriguingly, the MG-derived rod cell developed photoreceptor outer/inner segments (FIG. 23D-23F), a specialized structure for rod phototransduction. Terminal stage: A small portion (about 5%) of the rhodopsin-tdTomato positive cells appeared to have differentiated to mature rods, morphologically identical to the native rods (FIG. 23G-23I). Two weeks after the second injection for rod induction, the majority (about 75%) of the rhodopsin-tdTomato$^+$ cells differentiated to mature rods at the terminal stage. About 25% of the rhodopsin-tdTomato$^+$ cells at the intermediate stage, and very few (<1%) of them were MG-like at the initial stage. The differentiation process of MGs through progressive stages to rod photoreceptors mimicked the developmental stages of rod photoreceptor differentiation from retinal progenitor cells.

ShH10-Rhodopsin-Mediated Gene Transfer does not Transduce Native Photoreceptors.

Figure 24A:
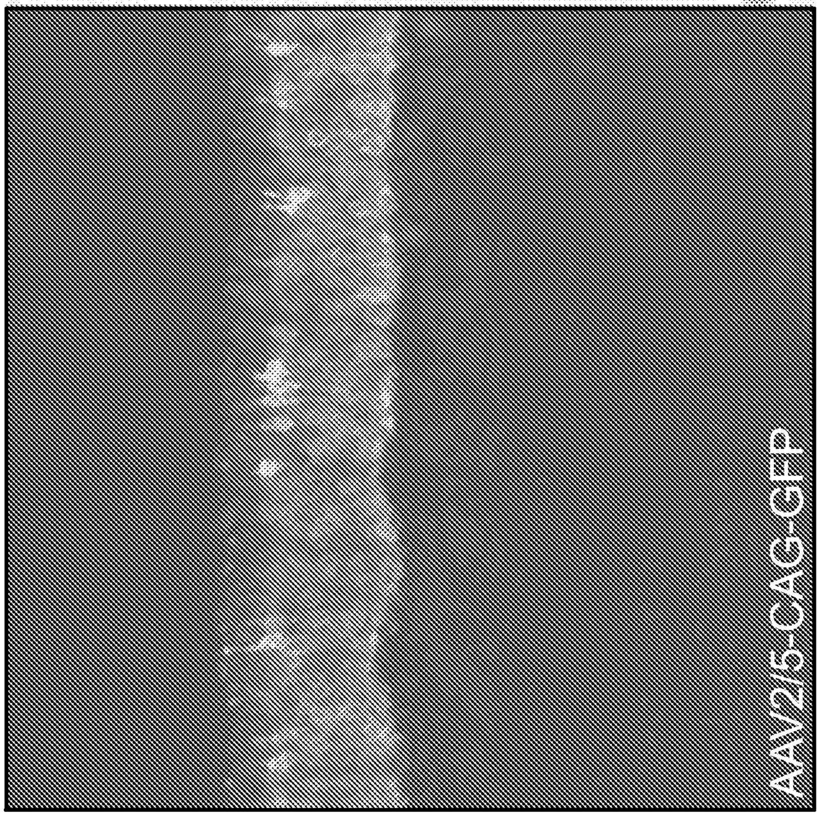
FIG. 24A and FIG. 24B, depicts results of example experiments demonstrating that ShH10-rhodopsin-tdTomato does not transduce photoreceptors even through the subretinal injection route.
Figure 24B:
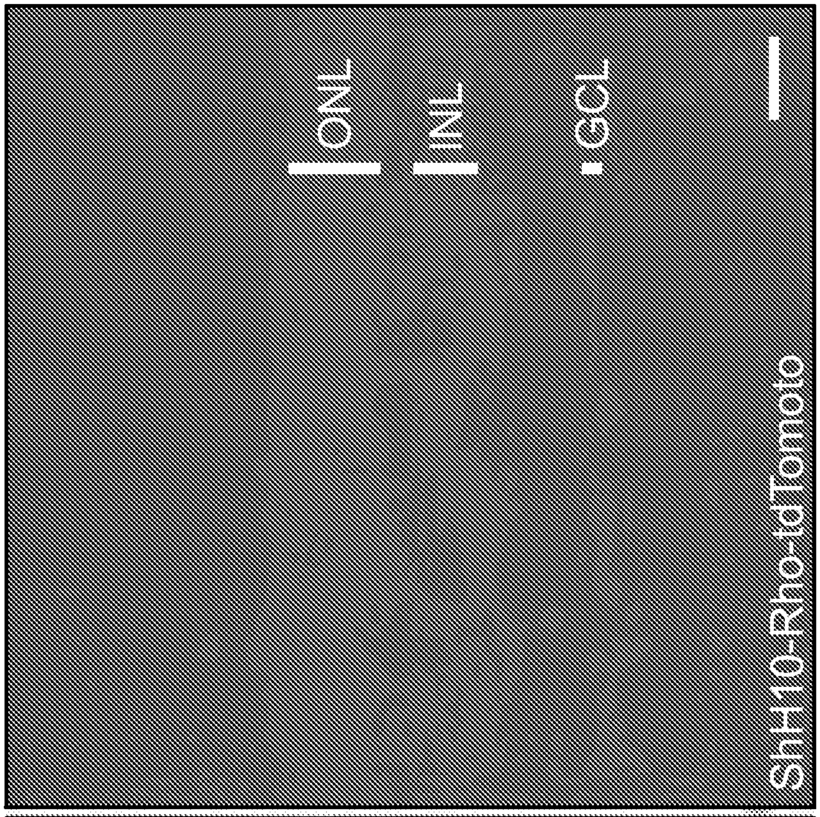

All rhodopsin-tdTomato$^+$ cells were also positive for GFAP-GFP, indicating that no native rods were transduced by ShH10-rhodopsin-tdTomato. To further examine whether ShH10-rhodopsin-mediated gene transfer could transduce native rods, ShH10-rhodopsin-tdTomato was injected into the subretinal space to give the virus maximum chance to infect photoreceptors. While the co-injected AAV2/5-CAG-GFP showed transduction of photoreceptors in the ONL, no tdTomato signal was detected (FIG. 24). These results confirm that ShH10-rhodopsin-mediated gene transfer does not transduce native photoreceptors.

Experiments have been designed to determine whether newly generated rods incorporate EdU by intravitreal injection of EdU 10 days after p-catenin gene transfer, and to analyze EdU incorporation 2 weeks after the second injection.

Experiments have been designed to characterize and quantify the percentage of MG-derived rods at different differentiation stages over time, specifically, 1 or 2 weeks after the second injection.

Experiments have been designed to induce rod differentiation by ShH10-GFAP-mediated gene transfer of Otx2, Crx, and Nrl individually or Otx2+Crx, Otx2+Nrl, and Crx+Nrl combinations for the second injection. Gene transfer of fewer number of transcription factors may lead to higher rod differentiation efficiency.

Fate Mapping for Tracing the Cell Lineage of MG-Derived Rod Photoreceptors.

Figure 25B:
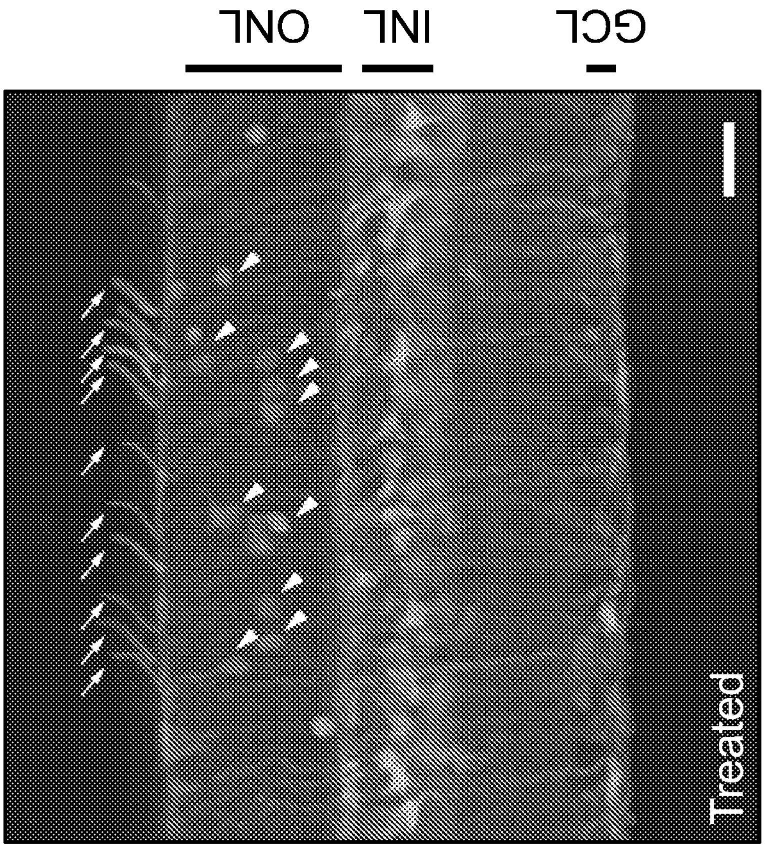
FIG. 25A and FIG. 25B, depicts a rate mapping study to trace MG-derived rod photoreceptors.
Figure 25A:
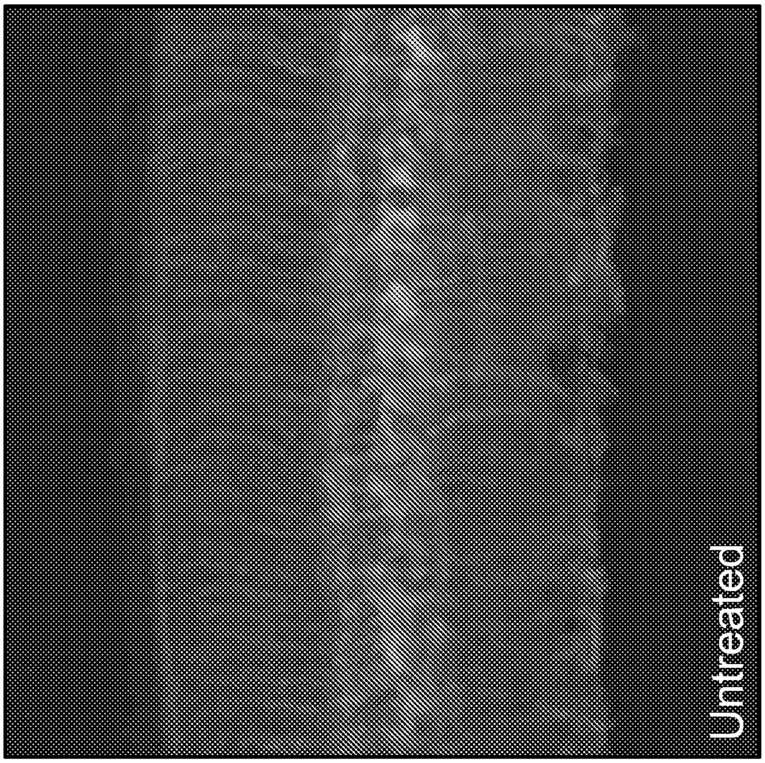

As an alternative approach to demonstrate that the new rods are generated from MGs, fate mapping studies were used to trace the cell fate of MGs following the two-step rod induction protocol (FIG. 22). To this end, a MG fate mapping mouse line was generated by crossing the GFAP-Cre line to the Rosa26-tdTomato reporter line (Kuzmanovic et al., Invest Ophthalmol Vis Sci. 2003, 44:3606-3613; Madisen et al., Nat Neurosci. 2010, 13:133-140), resulting in permanently labeling MGs with tdTomato (FIG. 25A). MG-derived cells were traced with tdTomato labeling. The results show that new rods were generated from MGs after the treatment with the first injection of B-catenin followed by the second injection of Otx2, Crx, and Nrl (FIG. 25B).

Characterize the Cellular Structure and Molecular Features of MG-Derived New Rods.

The rod is a primary sensory neuron consisting of the outer and inner segments, soma, axon and axon terminal. With these specialized structures, rods are highly efficient photon detectors that transmit signals to second-order retinal neurons. Expression of a cohort of rod-specific genes is required for the formation and maintenance of these structures as well as serving as signaling molecules for rod phototransduction, which is initiated by rhodopsin, a G protein-coupled receptor enriched in the rod outer segment. Upon photon absorption, rhodopsin changes conformation from a resting state to an enzymatically active state to catalyze the activation of the rod a-transducin, which in turn, activates cGMP phosphodiesterase, resulting in a decrease in free cGMP and closure of CNG cation channels. The resultant hyperpolarization decreases the open probability of $Ca^{++}$ channels near rod synaptic ribbons, decreasing glutamate release. To shut off the rod phototransduction cascade, photoactivated rhodopsin is silenced by its binding to rod arrestin (Krupnick et al., J Biol Chem. 1997, 272:18125-18131), which regulates rhodopsin photochemistry (Sommer and Farrens, Vision Res. 2006, 46:4532-4546). A variety of techniques are used to characterize the regenerated rods and demonstrate that the cellular structure and molecular features of the MG-derived new rods are similar to native rods.

Figures 26A, 26B, 26C, 26D:
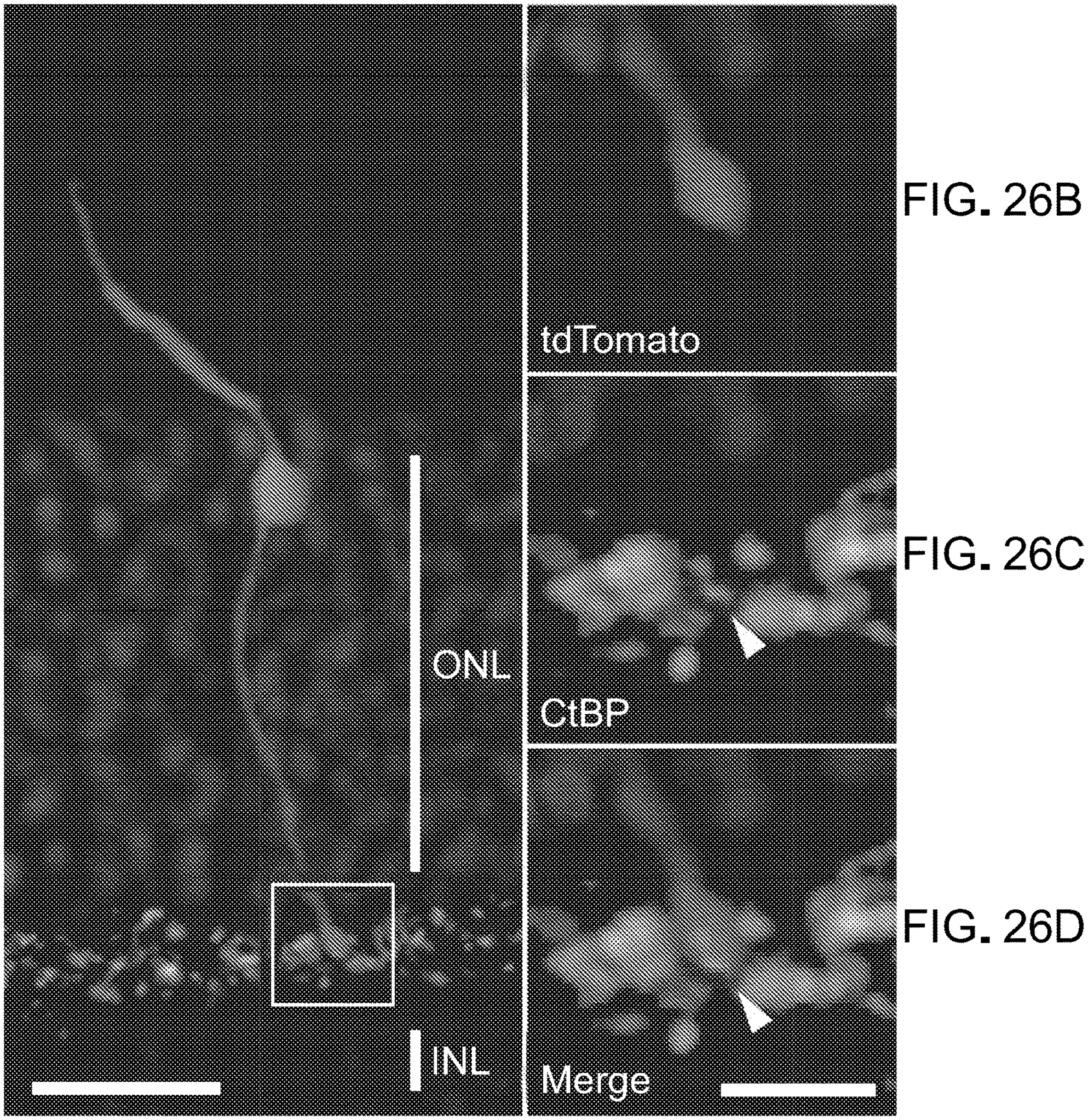
FIG. 26A through FIG. 26D, depicts results of example experiments demonstrating that MG-derived rods morphologically resemble native rods, and develop rod specializations for synaptic transmission.

Using immunohistochemistry and confocal microscopy, MG-derived new rods were investigated for the expression of a cohort of rod-specific genes, such as rhodopsin, rod a-transducin, rod arrestin, and recoverin critical for rod phototransduction, as well as genes critical for the maintenance of the rod synaptic terminal structure (such as ribeye, bassoon, and CtBP) in close apposition to the post-synaptic specialization of rod bipolar cells (PKCα and mGluR6). The results showed that MG-derived new rods, labeled by rhodopsin-tdTomato, were appropriately located in the outer nuclear layer and morphologically similar to native rods (FIG. 26A). These regenerated rods not only developed outer and inner segments, the axon terminal was also enlarged to form a synaptic bouton (FIG. 26B), inside of which the rod ribbon synapse protein CtBP was expressed (FIG. 26C, 26D).

Ultrastructural Analysis of MG-Derived Rod Photoreceptors.

Using electron microscopy (EM), ultrastructural analysis is performed on MG-derived new rods, including the outer segment, synaptic ribbon, and rod-triad synapse. The rod makes postsynaptic contacts with horizontal cells and rod bipolar cells to form the classic triad synapse. The rod synaptic ribbon is an electron-dense specialization where several rows of glutamate-packed vesicles are tethered for release. MG-derived new rods are identified by immunogold labeling with an anti-tdTomato antibody for scanning EM.

Investigate Whether MG-Derived Rods Integrate into the Existing Neural Circuits in the Retina Vision is initiated by light-responsive photoreceptors, propagated through synaptic transmission to second-order neurons (bipolar and amacrine cells). The information is integrated by retinal ganglion cells (RGCs), the output neurons in the retina, and transmitted to the brain. Regenerative therapy is of great interest because of its potential to replenish lost photoreceptors and restore vision. Recent advances in photoreceptor transplantation suggest that new photoreceptors can respond to light, integrate into the existing retinal circuitry (MacLaren et al., Nature, 2006, 444:203-207; Pearson et al., Nature, 2012, 485:99-103). MG-derived rods integrate into retinal circuits and have potential to restore visual function. Without introduction of retinal injury, the results demonstrate that MG-derived rods appear morphologically similar to wild-type rods, and form cellular specializations for phototransduction, and further, MG-derived rods activate photoreceptor-mediated light response in RGCs.

Figure 27C:
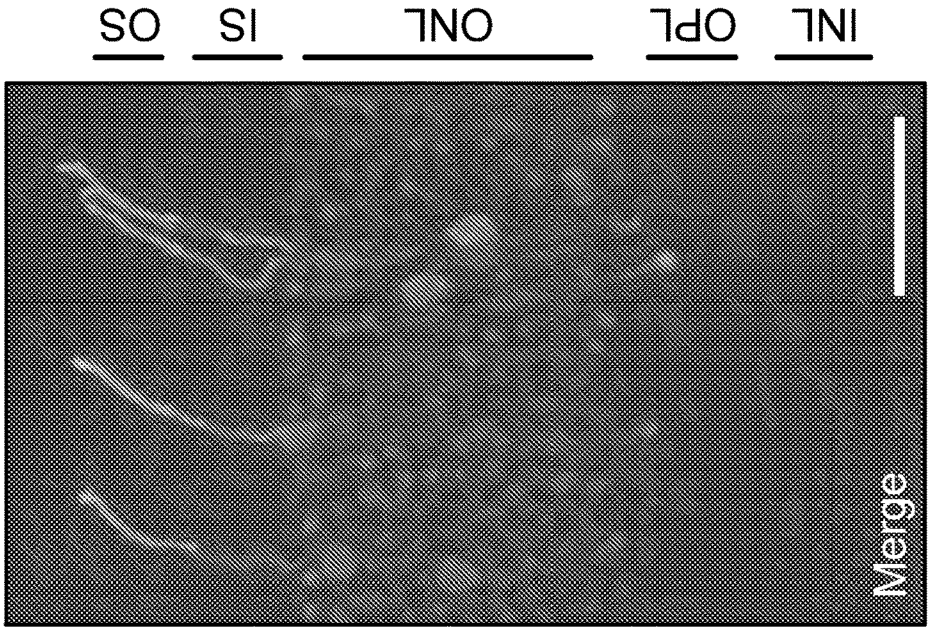
FIG. 27A through FIG. 27F, depicts results of example experiments demonstrating light-driven translocation of Gnat1 (rod a-transducin) in the reconstituted $Gnat1^{-/-}$:$Gnat2^{cpfl3}$ mice.
Figure 27B:
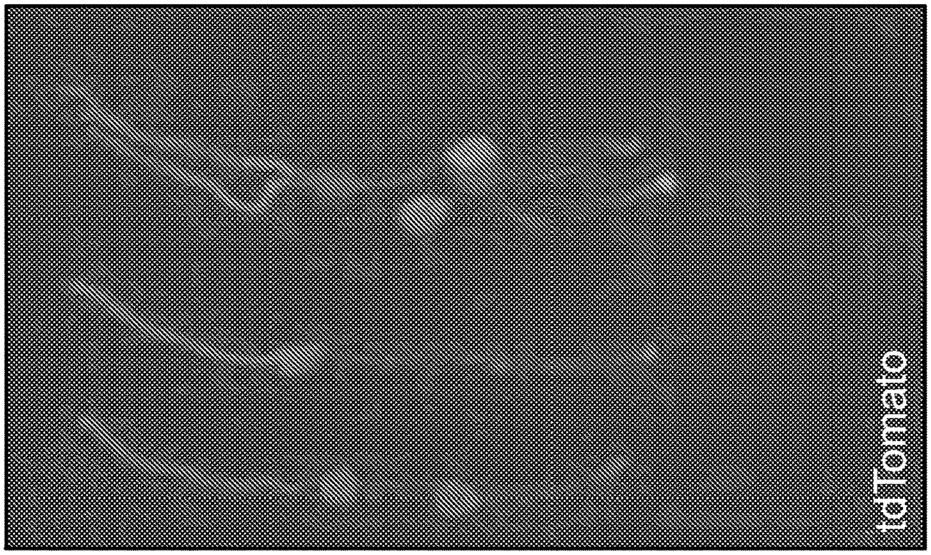
Figure 27A:
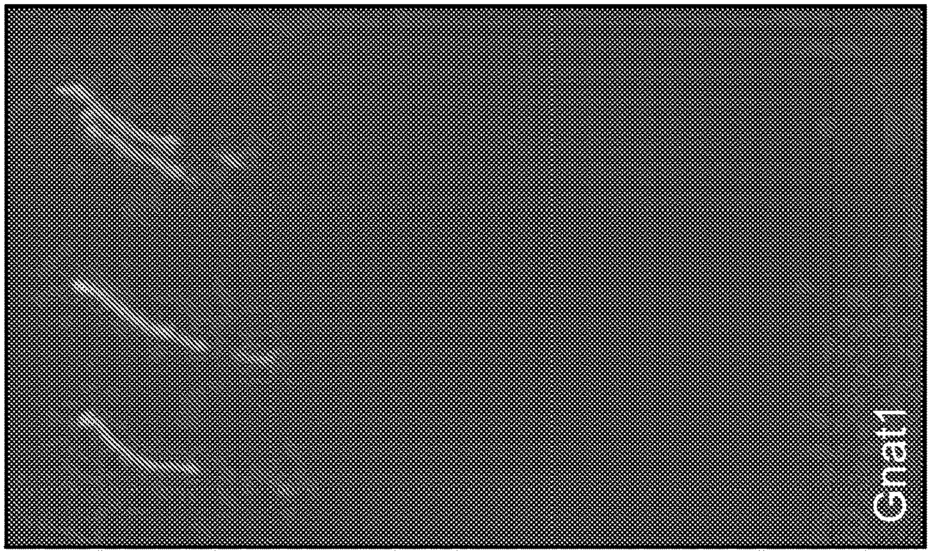
Figures 27D, 27E, 27F:
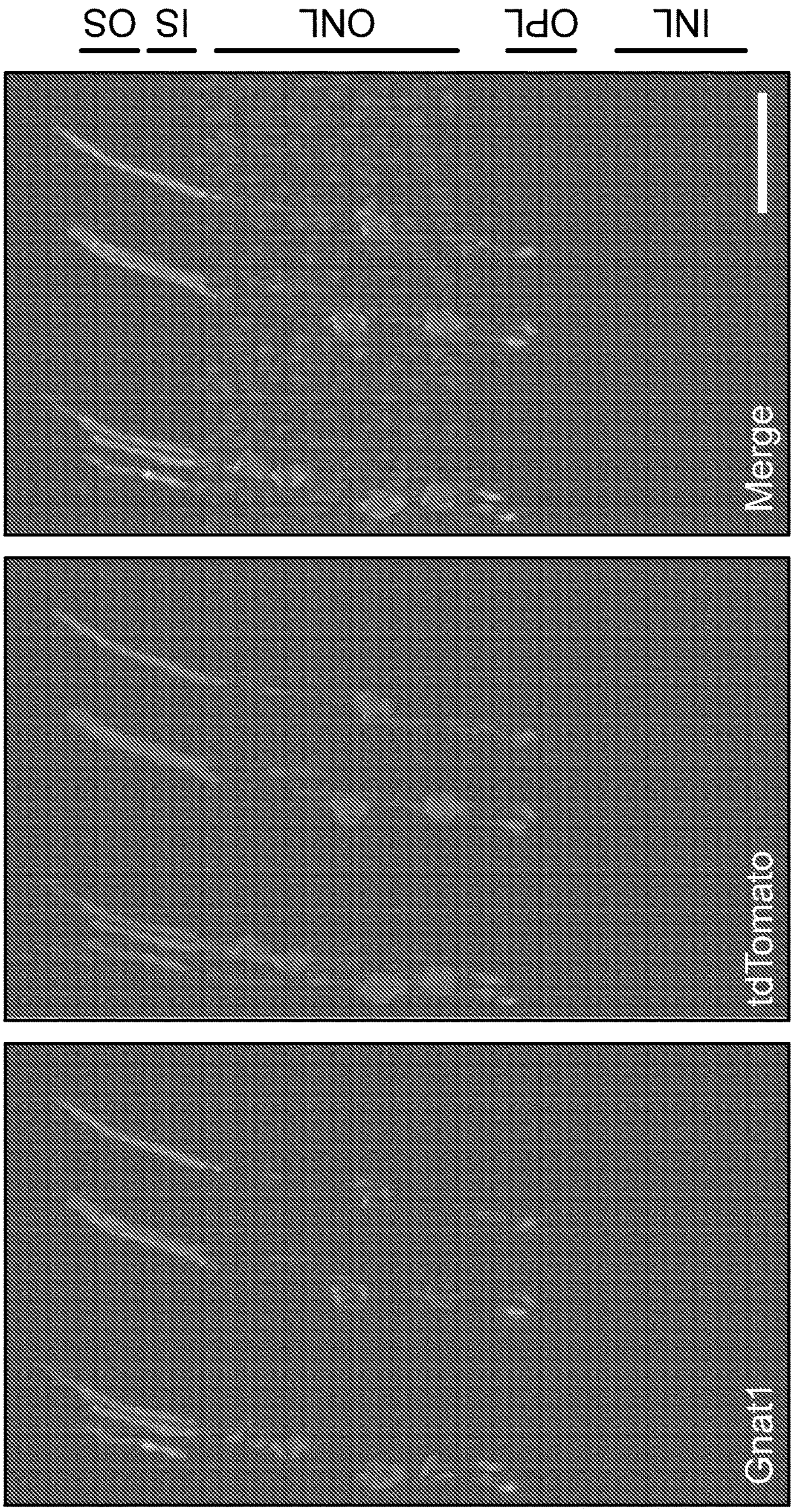

A mouse model was utilized in which newly gained rod function can be assessed unambiguously. $Gnat1^{-/-}$ have no rod function due to the absence of rod a-transducin, an essential component for rod phototransduction (Calvert et al., Proc Natl Acad Sci USA, 2000, 97:13913-13918). $Gnat2^{cpfl3}$ homozygotes have poor cone-mediated responses evident by 3 weeks of age and completely lack cone-mediated responses at 9 weeks of age (Chang et al., Invest Ophthalmol Vis Sci. 2006, 47:5017-5021). $Gnat1^{-/-}$:

Gnat2$^{cpfl3}$ double mutant mice lack photoreceptor-mediated light response and were used for functional assessment of MG-derived new rods. Phototransduction occurs in the outer segment of photoreceptors. Light-dependent translocation of rod photoreceptor-specific G protein, Gnat1 (rod a-transducin), between the outer segment and the other functional compartments of photoreceptors allows these cells to adapt to a wide range of light intensities (Sokolov et al., Neuron, 2002, 34:95-106). Recent studies show that transducin translocation also contributes to rod survival and synaptic transmission to rod bipolar cells (Majumder et al., Proc Natl Acad Sci USA, 2013, 110:12468-12473). To reconstitute rod phototransduction in MG-derived rods in Gnat1$^{-/-}$: Gnat2$^{cpfl3}$ mice, ShH10-rhodopsin-mediated gene transfer of wild-type rod a-transducin in MGs, which does not transduce native rods (FIG. 24) was utilized. The results (FIG. 27) indicate that Gnat1 (rod α-transducin) was localized in the rod outer segments in the dark (FIG. 27A); upon light stimulation (10,000 lux for 2 hours) it translocated to other cellular compartments including the inner segments and synaptic terminals (FIG. 27D), while the localization of co-expressed ShH10-rhodopsin-tdTomato (FIG. 27B, 27E) was not affected by the light stimulation.

Retinal ganglion cells were recorded from the ventral retina of Gnat1$^{-/-}$: Gnat2$^{cpfl3}$ mice, using an in vitro preparation described previously (Wang et al., J Neurosci. 2011, 31:7670-7681; Ke et al., Neuron, 2014, 81:388-401). In the ventral mouse retina, cones express primarily UV-sensitive opsin, with peak sensitivity at 360 nm, whereas rods express the typical green-sensitivity with peak at 500 nm (Wang et al., J Neurosci. 2011, 31:7670-7681; Applebury et al., Neuron, 2000, 27:513-523; Nikonov et al., J Gen Physiol. 2006, 127:359-374; Baden et al., Neuron, 2013, 80:1206-1217). Large somas (diameter, >20 μm) in the ganglion cell layer were targeted for loose-patch recordings of action potentials using IR imaging to minimize photobleaching. Control retinas, receiving either no β-catenin or three pro-rod differentiation factors, lacked any light responses; whereas treated retinas with rescued rod function show responses to dim light with green >UV sensitivity. Whole-cell voltage-clamp recordings of membrane currents were used to assay the integrity of synaptic inputs in these ganglion cells, as described in wild-type retinas (Ke et al., Neuron, 2014, 81:388-401; Murphy and Rieke, Neuron, 2006, 52:511-524).

Example 4

Restoration of Vision after De Novo Genesis of Rod Photoreceptors in Mammalian Retinas

SUMMARY

In zebrafish, Müller glial cells (MGs) are a source of retinal stem cells that can replenish damaged retinal neurons and restore vision[1]. In mammals, however, MGs lack regenerative capability as they do not spontaneously re-enter the cell cycle to generate a population of stem/progenitor cells that differentiate into retinal neurons. The regenerative machinery may exist in the mammalian retina, however, as retinal injury can stimulate MG proliferation followed by limited neurogenesis[2-7]. The fundamental question remains whether MG-derived regeneration can be exploited to restore vision in mammalian retinas. Previously, we showed that gene transfer of β-catenin stimulates MG proliferation in the absence of injury in mouse retinas[8]. Here, we report that following gene transfer of β-catenin, cell-cycle-reactivated MGs can be reprogrammed into rod photoreceptors via a subsequent gene transfer of transcription factors that are essential for rod cell fate specification and determination. MG-derived rods restored visual responses in Gnat1$^{-/-}$: Gnat2$^{cpfl3}$ double mutant mice, a model of congenital blindness[9,10], throughout the visual pathway from the retina to the primary visual cortex in the brain. Together, our results provide evidence of vision restoration after de novo MG-derived genesis of rod photoreceptors in mammalian retinas.

Results and Discussion

In cold-blooded vertebrates such as zebrafish, Müller glial cells (MGs) are retinal stem cells as they readily proliferate to replenish damaged retinal neurons, establishing a powerful self-repair mechanism[11-17]. In mammals, however, MGs lack regenerative capability as they do not spontaneously re-enter the cell cycle[18]. Injuring the mammalian retina does activate the proliferation of MGs, but with limited neurogenesis[2-7]. The necessity for retinal injury to activate MG proliferation is obviously counterproductive for regeneration as it massively kills retinal neurons. Furthermore, there has been no convincing evidence that MG-derived regeneration restores vision in the mammalian retina. To test whether MG-derived neurogenesis improves vision without the necessity for retinal injury, we reprogrammed MGs in vivo to generate new rod photoreceptors in mature mouse retinas. We previously reported that ShH10-GFAP-mediated gene transfer of β-catenin in MGs stimulates these cells to re-enter the cell cycle in the uninjured mouse retina[8]. To reprogram the cell-cycle-reactivated MGs into rod photoreceptors, we tested a combination of three transcription factors (Otx2, Crx, and Nrl) that are essential for determining rod cell fate during retinal development. Otx2 is an early expressed homeodomain transcription factor, deficiency of which leads to overproduction of amacrine-like cells at the expense of both rod and cone photoreceptors[19]. Crx is another homeodomain transcription factor required for terminal differentiation and maintenance of both rod and cone photoreceptors[20,21]. Nrl is a basic motif leucine zipper transcription factor that promotes rod cell fate by transcriptional activation of rod-specific genes while repressing expression of cone-specific genes[22].

In the developing mouse retina, generation of retinal cell types is completed by the first two weeks after birth[23]. To examine whether new rod photoreceptors could be generated from MGs in the mature mouse retina, we used a two-step reprogramming method to first stimulate MG proliferation by intravitreal injection of ShH10-GFAP-β-catenin in the mouse retina at 4 weeks of age. This was followed two weeks later by a second injection of ShH10-GFAP-mediated gene transfer of Otx2, Crx, and Nrl. We first examined whether MGs could undergo successive rounds of cell division after the initial gene transfer of β-catenin. Following an EdU/BrdU double-labeling procedure previously used to analyze the clonal expansion of horizontal cells[24], proliferating MGs were labeled with EdU at 10 days after the injection of ShH10-GFAP-β-catenin, and 24 hours later the S phase cells were labeled with BrdU. Retinas were harvested 4 days later and were assayed to determine whether the EdU$^{+}$ cells progressed through another cell division into a second round of S phase. Very few cells were co-labeled by EdU and BrdU (FIG. 32), indicating that the vast majority of MGs may undergo only one cell division after β-catenin gene transfer.

Figures 28A, 28B, 28C, 28D, 28E, 28F, 28G, 28H, 28I, 28J:
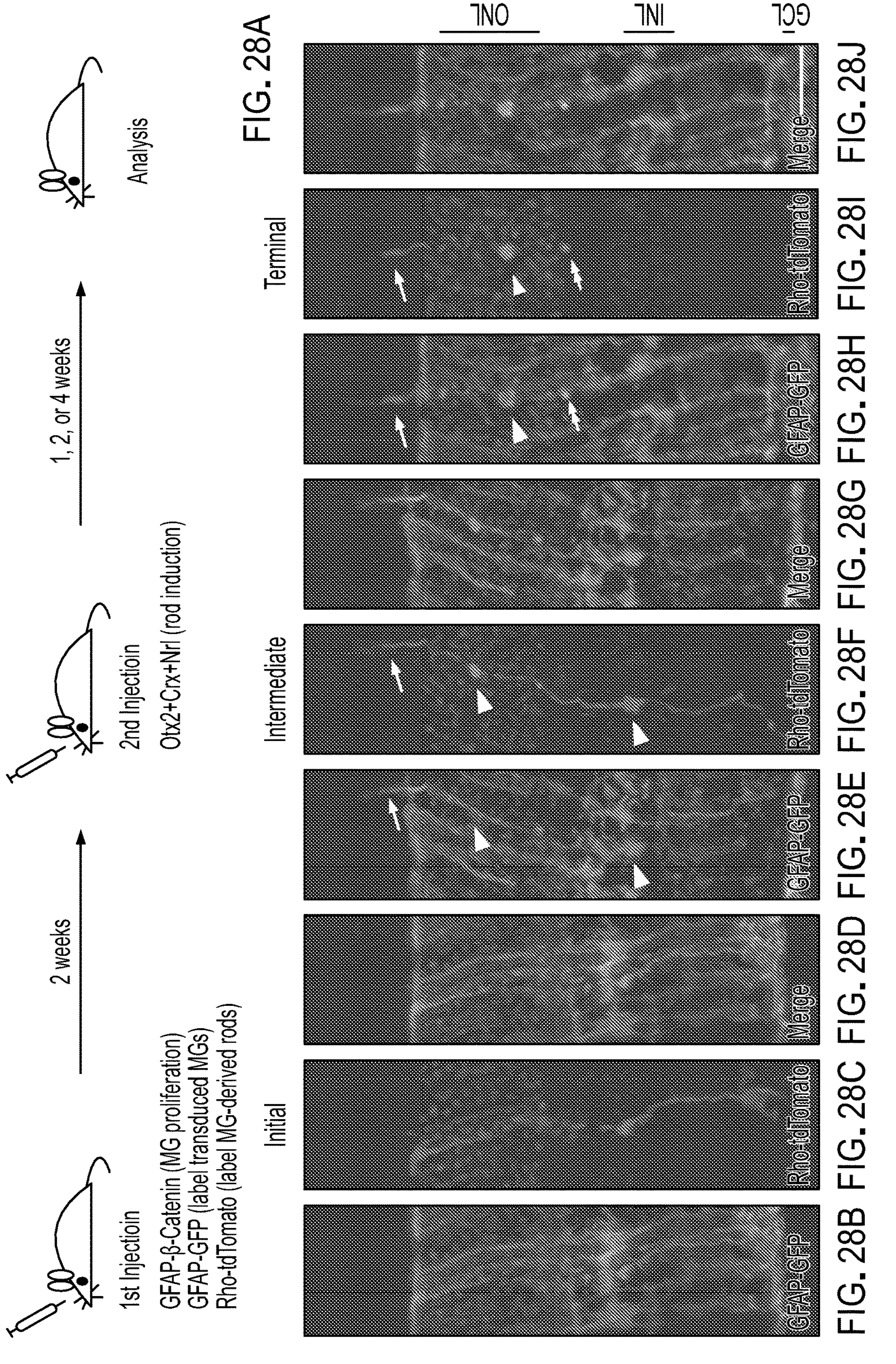
FIG. 28. Generation of rod photoreceptors via reprogramming Müller glial cells (MGs) in the mouse retina, a, A schematic illustration of the two-step reprogramming method to generate rod photoreceptors. b-j, Characterization of MG-derived rod differentiation through the Initial (b-d), Intermediate (e-g), and Terminal (h-j) stages. Arrowheads: cell soma. Arrows: rod outer segments. Double arrows: synaptic terminals. Scale bar: 25 μm. k-m, Quantification of MG-derived rod differentiation at 1 (k), 2 (1), and 4 weeks (m) after the second injection of ShH10-GFAP-mediated gene transfer of Otx2, Crx, and Nrl for rod induction. n and o, Lineage analysis of MG-derived rod photoreceptors. (n) Untreated MG fate mapping mice with MGs labeled by tdTomato. (o) Treated MG fate mapping mice using the two-step reprogramming method. Arrowheads: rod soma. Arrows: rod outer segments. Scale bar: 20 μm. p-t, Quantification of MG-derived rod photoreceptors in the Doral (p), Nasal (q), Temporal (r), Ventral(s) quadrants of retinal flat-mount preparations at 4 weeks after the second injection for rod induction. Scale bar: 20 μm. Data in (t) show mean±SEM, n=4 retinas. Control measurements were combined across quadrants.
Figures 33A, 33B, 33C, 33D, 33E, 33F, 33G, 33H, 33I, 33J, 33K, 33L:
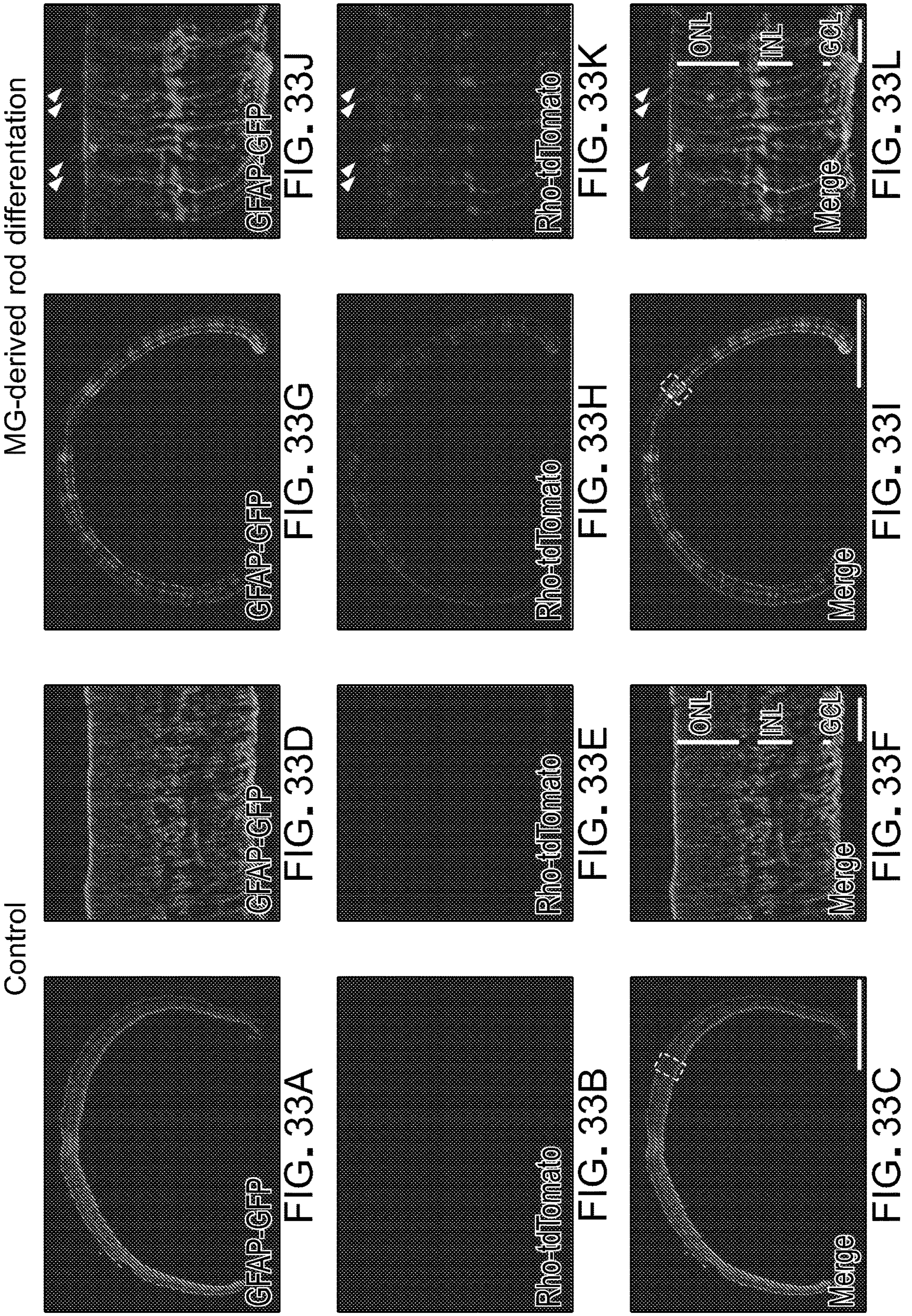
FIG. 33. MG-derived rod differentiation was observed across the whole retinal section. Wild-type retinas at 4 weeks of age were first injected with ShH10-GFAP-GFP (label transduced MGs), and ShH10-Rod-tdTomato (label MG-derived rods) in the absence (a-f) or presence (g-1) of ShH10-GFAP-β-catenin (stimulate MG proliferation), followed 2 weeks later by the second injection of ShH10-GFAP-mediated gene transfer of Otx2, Crx and Nrl for rod induction. Retinal samples were analyzed by confocal microscopy at 10 days after the second injection. The boxed areas in c and i are enlarged in d-f and j-1, respectively. Arrowheads: MG-derived rods. Scale bars: 750 μm in a-c and g-i; 25 μm in d-f and j-1.

To identify MGs that may undergo rod photoreceptor differentiation after the second injection of ShH10-GFAP-mediated gene transfer of Otx2, Crx, and Nrl, we included in the first injection ShH10-Rhodopsin-tdTomato, a 2. 1 kb rhodopsin promoter[25-28] driving the expression of tdTomato, together with ShH10-GFAP-GFP to label all transduced MGs (FIG. 28*a*). Based on the morphological changes observed from different retinal samples after the second injection for rod induction, the progression of MG-derived rod differentiation was categorized into initial, intermediate, and terminal stages. At the initial stage, MGs turned on the expression of Rhodopsin-tdTomato, and the Rhodopsin-tdTomato$^+$ cells appeared morphologically similar to MGs with the upper processes ending at the outer limiting membrane, and the lower processes (MG end feet) extending to the fiber layer of retinal ganglion cells (FIG. 28*b-d*). At the intermediate stage, there was an asymmetric cell division whereby the Rhodopsin-tdTomato$^+$ cell produced two daughter cells with different cell fates (FIG. 28*e-g*). One daughter cell apparently differentiated to a rod photoreceptor with its soma localized in the outer nuclear layer (ONL), and intriguingly, the MG-derived rod cell generated outer/inner segments, a specialized cellular structure essential for rod phototransduction. The second daughter cell remained in the inner nuclear layer (INL) with a typical MG morphology. At the terminal stage, the Rhodopsin-tdTomato$^+$ cell appeared to have differentiated to a mature rod cell, morphologically very similar to native rods with outer/inner segments and an enlarged synaptic bouton-like terminal (FIG. 28*h-j*). The MG-derived rod differentiation was observed from the center to periphery in the whole retinal section, whereas no Rhodopsin-tdTomato$^+$ cells were observed in control retinas receiving the same treatments except ShH10-GFAP-β-catenin was omitted from the first injection (FIG. 33).

Figure 28K:
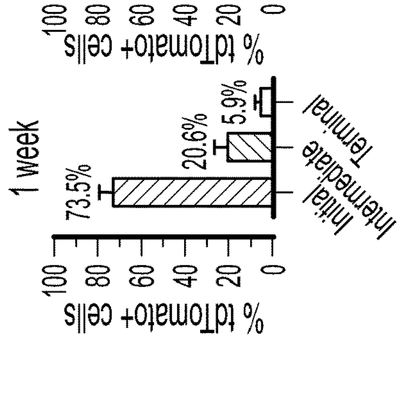
Figure 28L:
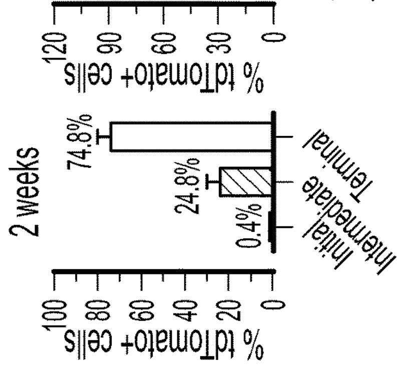
Figures 34A, 34D, 34G, 34J, 34M, 34P:
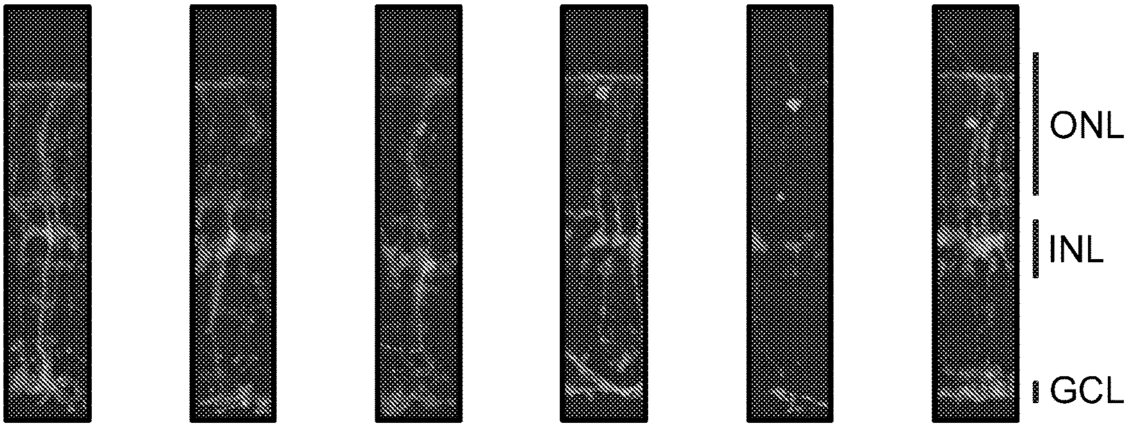
FIG. 34. Additional examples showing the progression of MG-derived rod differentiation. Wild-type retinas at 4 weeks of age were first injected with ShH10-GFAP-β-catenin, ShH10-GFAP-GFP, and ShH10-Rodopsin-tdTomato, followed 2 weeks later by the second injection of ShH10-GFAP-mediated gene transfer of Otx2, Crx and Nrl for rod induction. MG-derived rod differentiation progressed through the initial (a-c), intermediate (d-f, g-i, j-l) and terminal (m-o, p-r) stages. Scale bar: 25 μm.
Figures 34B, 34E, 34H, 34K, 34N, 34Q:
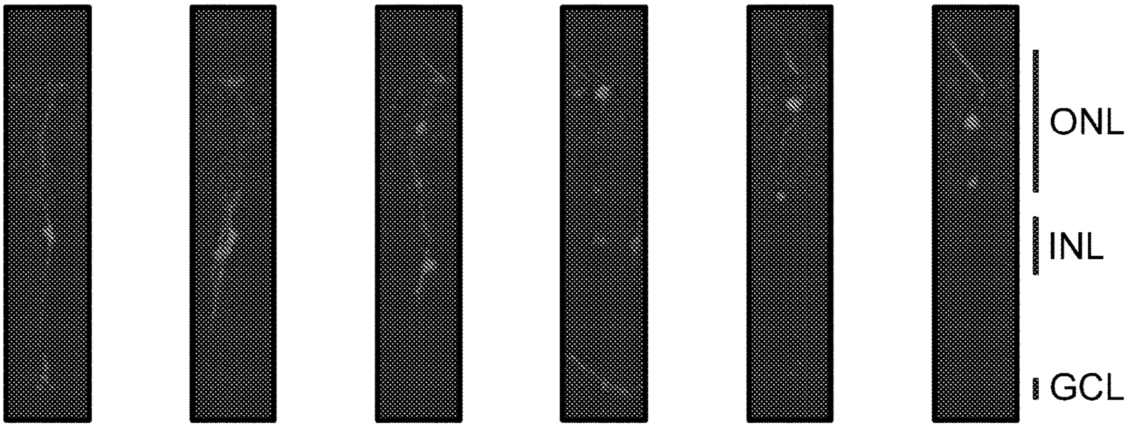
Figures 34C, 34F, 34I, 34L, 34O, 34R:
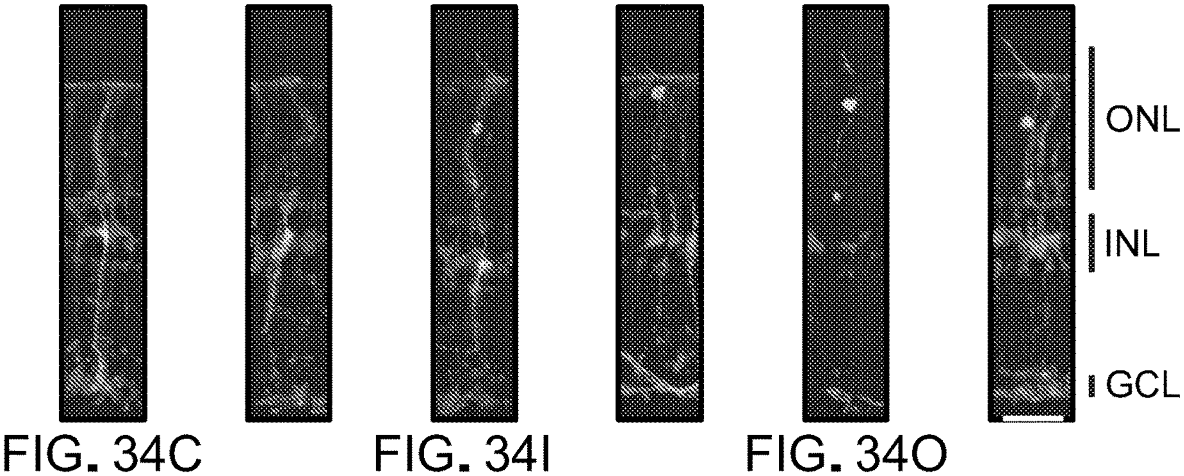
Figure 38:
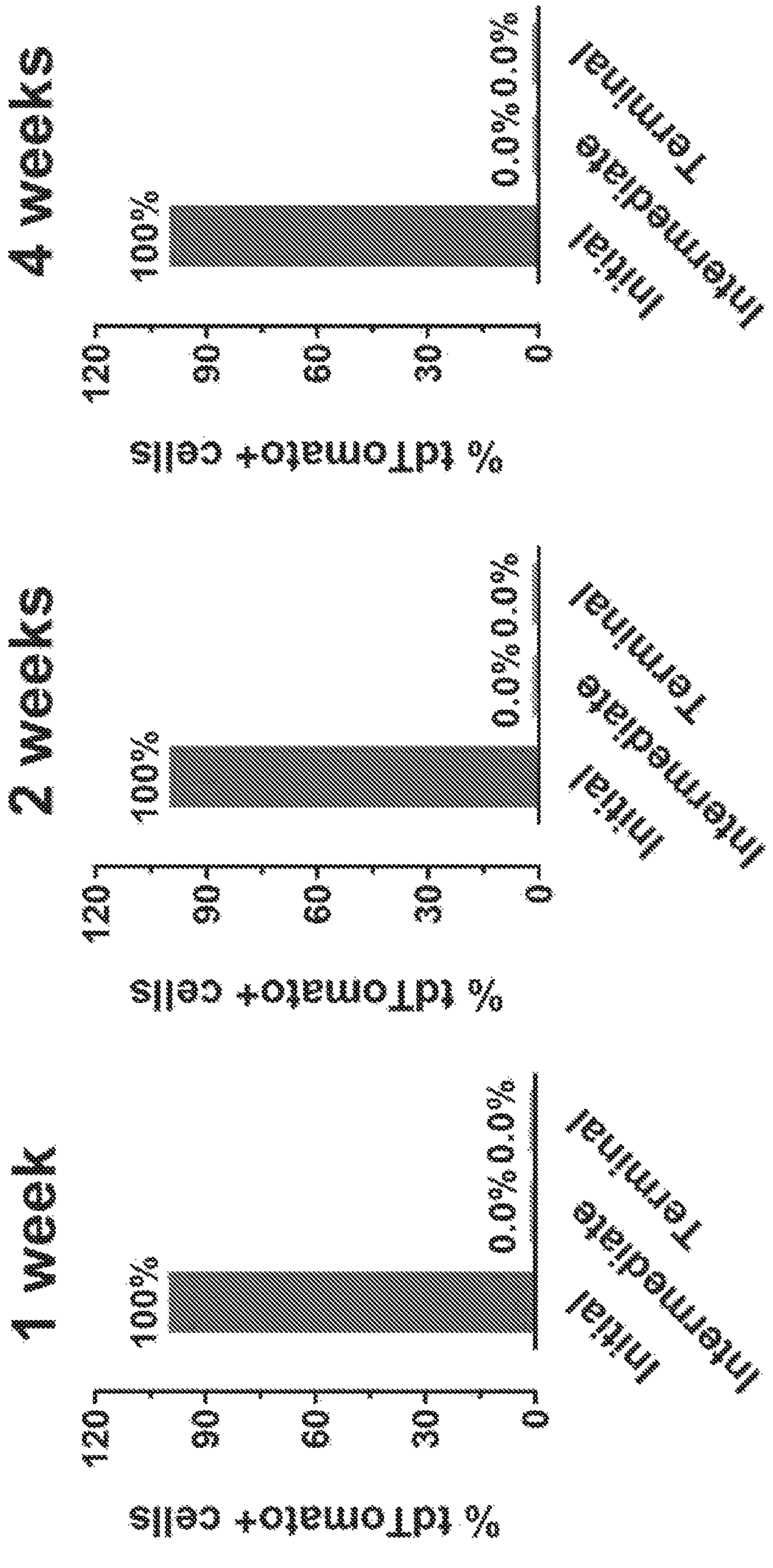
FIG. 38. Time course analysis of MG-derived rod differentiation in wild-type retinas treated with Crx and Nrl. Wild-type retinas at 4 weeks of age were first injected with ShH10-GFAP-β-catenin, ShH10-GFAP-GFP, and ShH10-Rhodopsin-tdTomato, followed 2 weeks later by the second injection of ShH10-GFAP-mediated gene transfer of Crx and Nrl. Rhodopsin-tdTomato$^{+}$ cells were only detected in the initial stage of rod differentiation at 1, 2 and 4 weeks after the second injection. Data are presented as mean±SEM, n=3 retinas at each time point.

We quantified the progression of rod differentiation over time (1,000-1,200 Rhodopsin-tdTomato$^+$ cells, 6-8 retinas for each time point, additional examples of MG-derived rod differentiation are shown in FIG. 34). One week after the second injection (FIG. 28*k*), the majority of Rhodopsin-tdTomato$^+$ cells (73.5%) were in the initial stage, with a smaller number in the intermediate (20.6%) and terminal stages (5.9%). Two weeks after the second injection (FIG. 28*l*), there were almost no Rhodopsin-tdTomato$^+$ cells in the initial stage (0.4%), a small number in the intermediate stage (24.8%) and a majority (74.8%) that had differentiated to mature rods in the terminal stage. Four weeks after the second injection (FIG. 28*m*), nearly all Rhodopsin-tdTomato$^+$ cells differentiated to mature rods in the terminal stage (97.4%). The Rhodopsin-tdTomato$^+$ cells were also positive for GFAP-GFP (FIG. 28*e, h*), indicating that they were indeed derived from MGs, as gene transfer using the ShH10 AAV serotype and GFAP gene promoter should selectively transduce MGs but not photoreceptors[8]. To examine further if native rods could be transduced by the ShH10 serotype, ShH10-rhodopsin-tdTomato was injected together with AAV2/5-CAG-GFP in the subretinal space to maximize the chance for photoreceptor infection. AAV2/5-CAG-GFP acted as a positive control that should transduce photoreceptors and drive GFP expression. While the co-injected AAV2/5-CAG-GFP transduced many photoreceptors in the ONL, no tdTomato signal was detected in the same retinal region (FIG. 35), demonstrating that the ShH10-rhodopsin-mediated gene transfer does not transduce photoreceptors effectively. The expression of GFAP-GFP was eventually turned off in MG-derived rods over time, and no GFP signal was detected in Rhodopsin-tdTomato$^+$ cells 12 weeks after the second injection (FIG. 36). We also tested whether treatment with Otx2, Crx, and Nrl individually or in pairs was sufficient for rod induction (FIG. 37). Four weeks after the second injection, no Rhodopsin-tdTomato$^+$ cells were detected with these treatments except for the combination of Crx and Nrl, which resulted in a few Rhodopsin-tdTomato$^+$ cells detected in the initial stage of rod differentiation at 1, 2, and 4 weeks after the second injection (FIG. 38); however, the level of differentiation in the Crx$^+$Nrl test group was not clinically significant.

Figure 39:
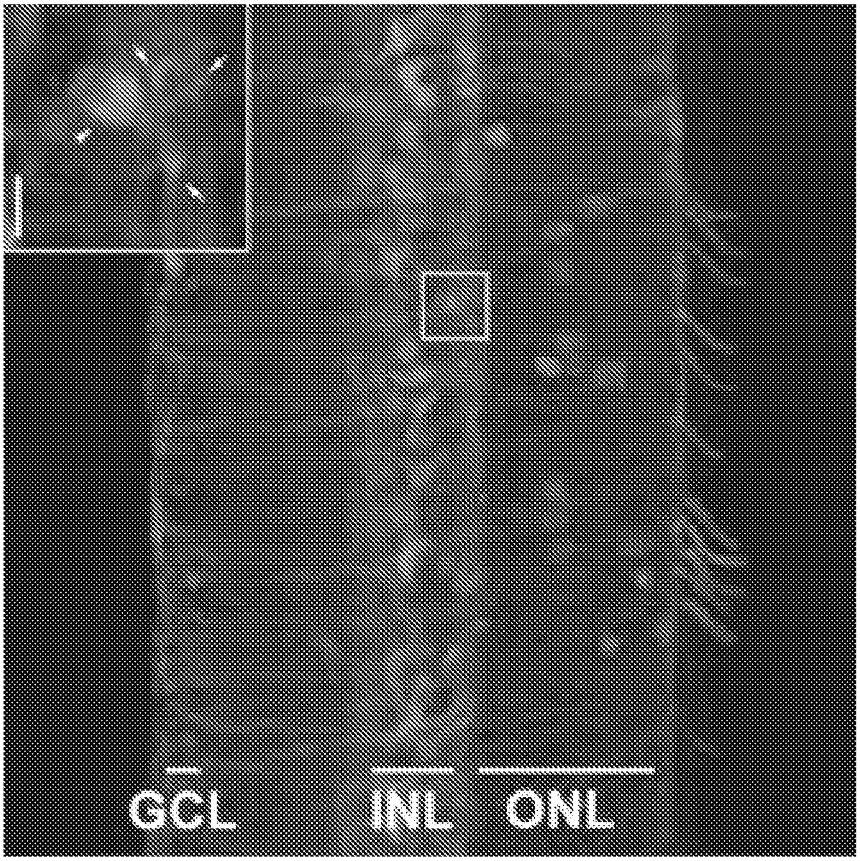
FIG. 39. Fate mapping experiments indicate that the two-step reprogramming method may occasionally produce cells with a horizontal cell morphology. The boxed area is enlarged to show an MG-derived tdTomato$^{+}$ cell with a horizontal cell morphology located in the upper inner nuclear layer. Arrowhead: cell soma. Arrows: cell processes. Scale bar: 5 μm.
Figure 40A:
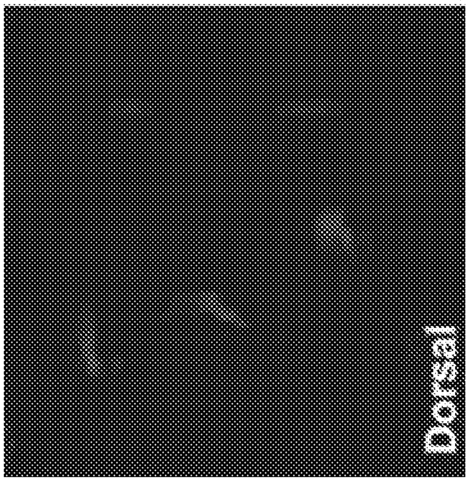
FIG. 40. MG-derived regeneration of rod photoreceptors decreases in aged mice. a-d, Generation of Rhodopsin-tdTomato+MG-derived rod photoreceptors in 7-month-old mouse retinas in the Dorsal (a), Nasal (b), Temporal (c), and Ventral (d) quadrants in retinal flat-mount preparations. Scale bar: 20 μm. e, Quantification of Rhodopsin-tdTomato$^{+}$ MG-derived rods per mm$^{2}$ in the four retinal quadrants. Data are presented as mean±SEM, n=4 retinas.
Figure 40B:
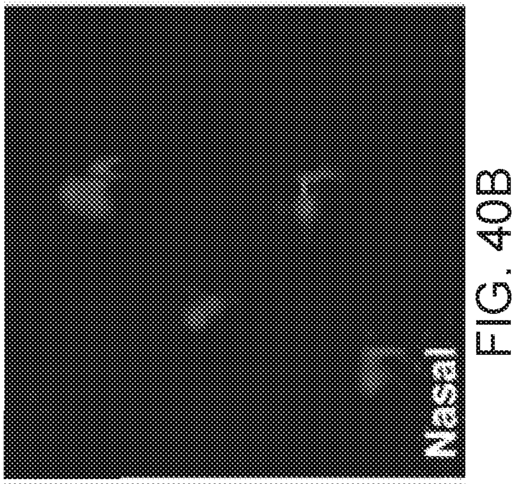
Figure 40C:
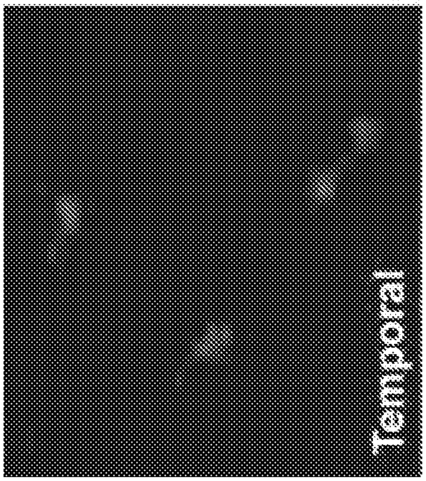
Figure 40D:
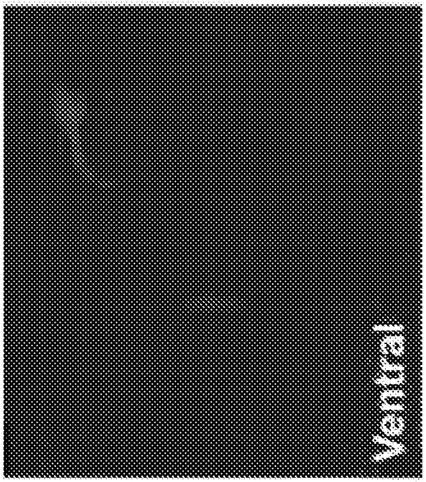
Figure 40E:
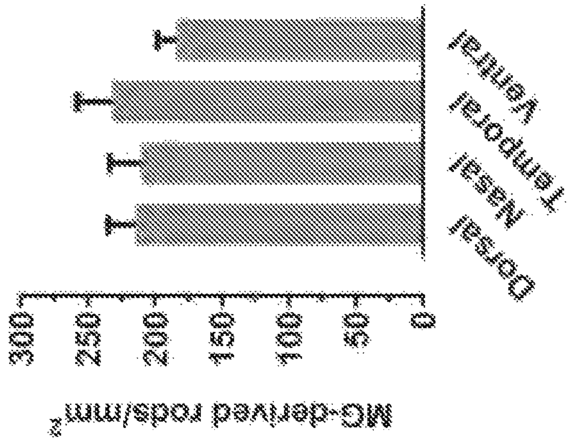
Figure 41A:
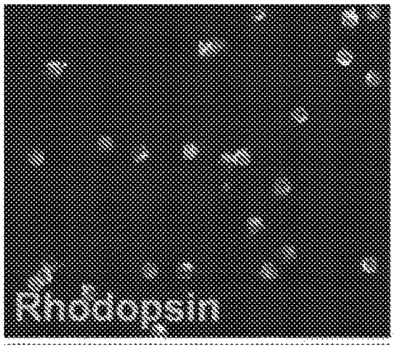
FIG. 41. MG-derived rod photoreceptors express Rhodopsin and Peripherin-2. Wild-type retinas were injected with ShH10-GFAP-β-catenin (MG proliferation) and ShH10-Rhodopsin-tdTomato (label MG-derived rods) at 4 weeks of age, followed 2 weeks later by the second injection of ShH10-GFAP-mediated gene transfer of Otx2, Crx and Nrl for rod induction. Treated retinas were dissociated 4 weeks later after the second injection and analyzed for the expression of Rhodopsin (a-c) and Peripherin-2 (d-f) using immunohistochemistry and confocal microscopy. Arrowheads: MG-derived rods were immunoreactive for Rhodopsin (c) and Peripherin-2 (f). Scale bar: 20 μm.
Figure 41B:
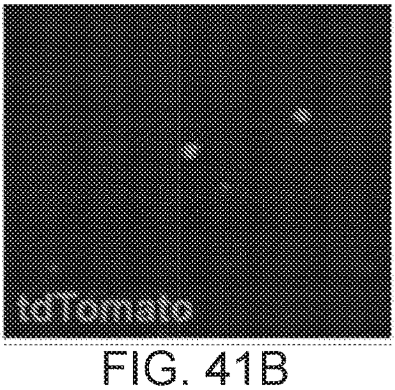
Figure 41C:
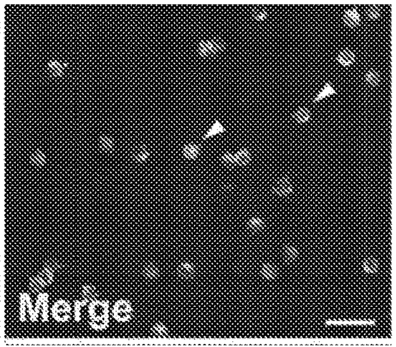
Figure 41D:
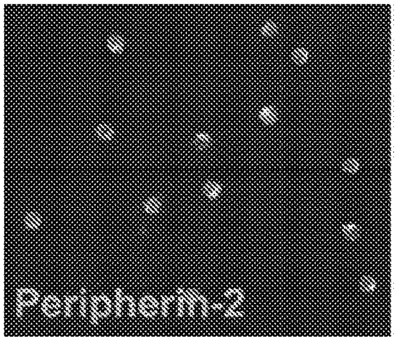
Figure 41E:
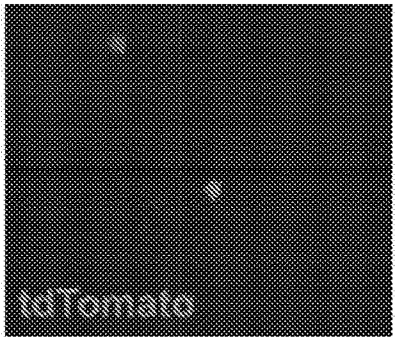
Figure 41F:
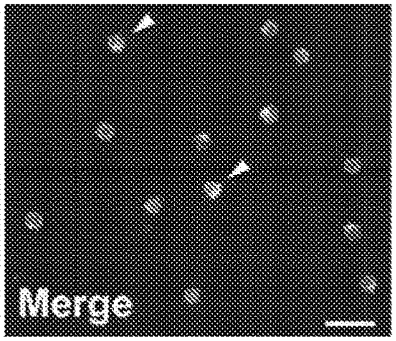

To trace the lineages of MGs following our two-step reprogramming method, we generated a MG fate mapping mouse line by crossing the GFAP-Cre line to the Rosa26-tdTomato reporter line[29,30], resulting in permanent labeling of MGs with tdTomato (FIG. 28*n*)[8]. MG fate mapping mice at 4 weeks of age were first injected with ShH10-GFAP-β-catenin to stimulate MG proliferation, followed two weeks later by ShH10-GFAP-mediated gene transfer of Otx2, Crx, and Nrl for rod induction. Four weeks after the second injection, tdTomato$^+$ cells were observed in the ONL and appeared to have differentiated into mature rods with the formation of outer/inner segments (FIG. 28*o*), further demonstrating that the rod cells were derived from MGs in the treated mouse retina. We occasionally observed MG-derived tdTomato$^+$ cells with a horizontal cell morphology located in the upper inner nuclear layer (FIG. 39). This observation was consistent with a role for Otx2 to promote the fate of photoreceptors and horizontal cells[31].

Figure 28M:
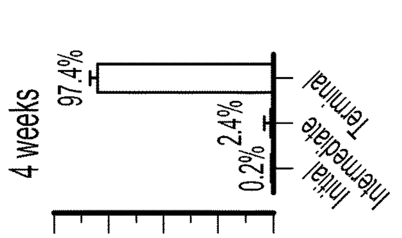
Figure 28N:
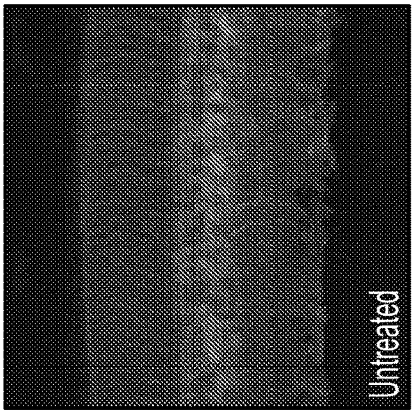
Figure 28O:
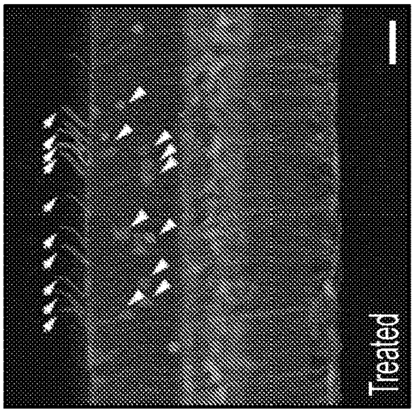
Figure 28P:
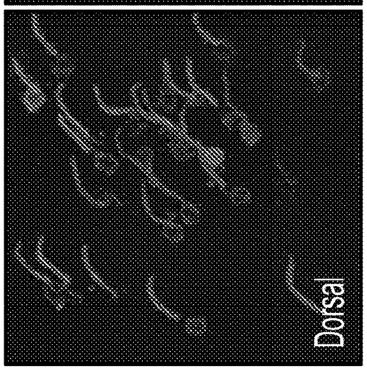
Figure 28Q:
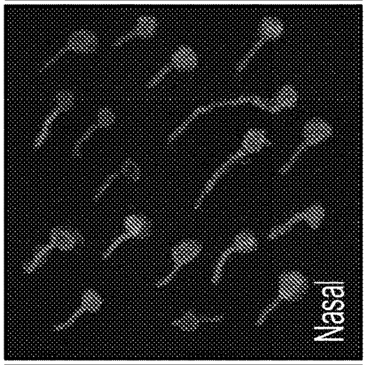
Figure 28R:
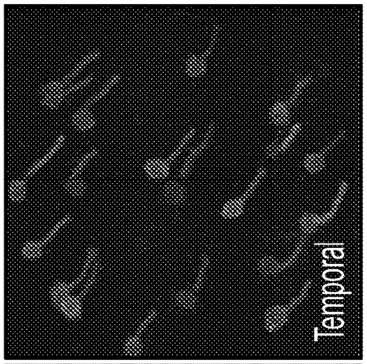
Figure 28S:
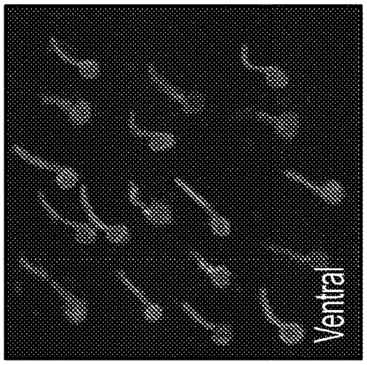
Figure 28T:
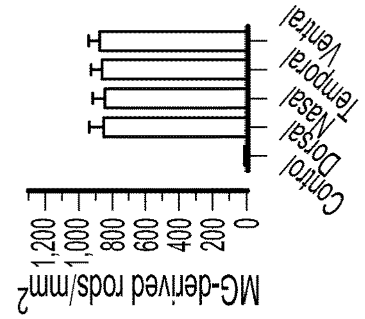

To assess the efficiency of rod induction, we quantified the number of Rhodopsin-tdTomato$^+$ cells in retinal flatmount preparations at 4 weeks after the second injection, when nearly all Rhodopsin-tdTomato$^+$ cells were at the terminal stage of rod differentiation (FIG. 28*m*). The Rhodopsin-tdTomato* cells were evenly distributed across the retina, with over 800 Rhodopsin-tdTomato+ cells per mm$^2$ scored in the dorsal, nasal, temporal, and ventral retina (FIG. 28*p-t*). By contrast, no MG-derived rods were observed in control retinas (ShH10-GFAP-β-catenin omitted from the first injection) from wild-type mice (FIG. 28*t*). We also examined regenerative capability of MGs in 7-month-old mouse retinas. The production of Rhodopsin-tdTomato$^+$ cells was reduced to ~200 per mm$^2$ scored in the dorsal, nasal, temporal, and ventral retina (FIG. 40).

The rod is a primary sensory neuron consisting of specialized cellular structures for detection of photons and communication with downstream neurons, including the outer/inner segments and the synaptic terminal. Using confocal microscopy and immunohistochemistry, we examined whether MG-derived rod cells expressed a set of rod genes (Rhodopsin, Gnat1/rod a-transducin, Peripherin-2, Recoverin, and Ribeye) that play important roles in the formation/maintenance of rod cellular structures and are essential for phototransduction. Wild-type mice at 4 weeks of age were first injected with ShH10-GFAP-β-catenin (stimulate MG proliferation) and ShH10-Rhodopsin-tdTomato (label MG-derived rods). Four weeks after the second injection for ShH10-GFAP-mediated gene transfer of Otx2, Crx, and Nrl, we observed that the Rhodopsin-tdTomato+ cells expressed Rhodopsin and Peripherin-2 in the rod outer segment (FIG. 29*a-d*, 29*e-h*), Gnat-1 and Recoverin in the rod soma and processes (FIG. 29*i-l*, 29*m-p*), and Ribeye in the rod synaptic terminal (FIG. 29*q-t*), which was enlarged to form a synaptic bouton in close apposition to the post-synaptic specialties of PKCα$^+$ rod bipolar cell dendrites (FIG. 29*u-x*). As the immunoreactivity for Rhodopsin and Peripherin-2 were present at high density and in close proximity to native rods, we also dissociated retinal cells and detected the expression of Rhodopsin and Peripherin-2 in Rhodopsin-tdTomato+ cells (FIG. 41). The rod outer segment (ROS) consists of densely packed membrane discs housing the visual pigment and essential proteins for rod phototransduction. The rod inner segment (RIS) is filled with long thin mitochondria providing a main energy source to meet the high metabolic needs of rod photoreceptors. Synthesized proteins and membranes are trafficked from the RIS to ROS via the connecting cilium (CC), a microtubule-based structure crucial for the function and survival of rod photoreceptors. Rods communicate with second-order neurons, bipolar and horizontal cells, through a highly specialized triad synaptic structure. Ultrastructural analysis using transmission electron microscopy showed that the MG-derived rods correctly formed the ROS (FIG. 29*y*), RIS (FIG. 29*z*), CC (FIGS. 29*z*' and 29*z*"), and classic triad synapse (FIG. 29*z*"), which were morphologically similar to native rods.

Figures 30A, 30B, 30C, 30D, 30E, 30F, 30G, 30H, 30I, 30J, 30K:
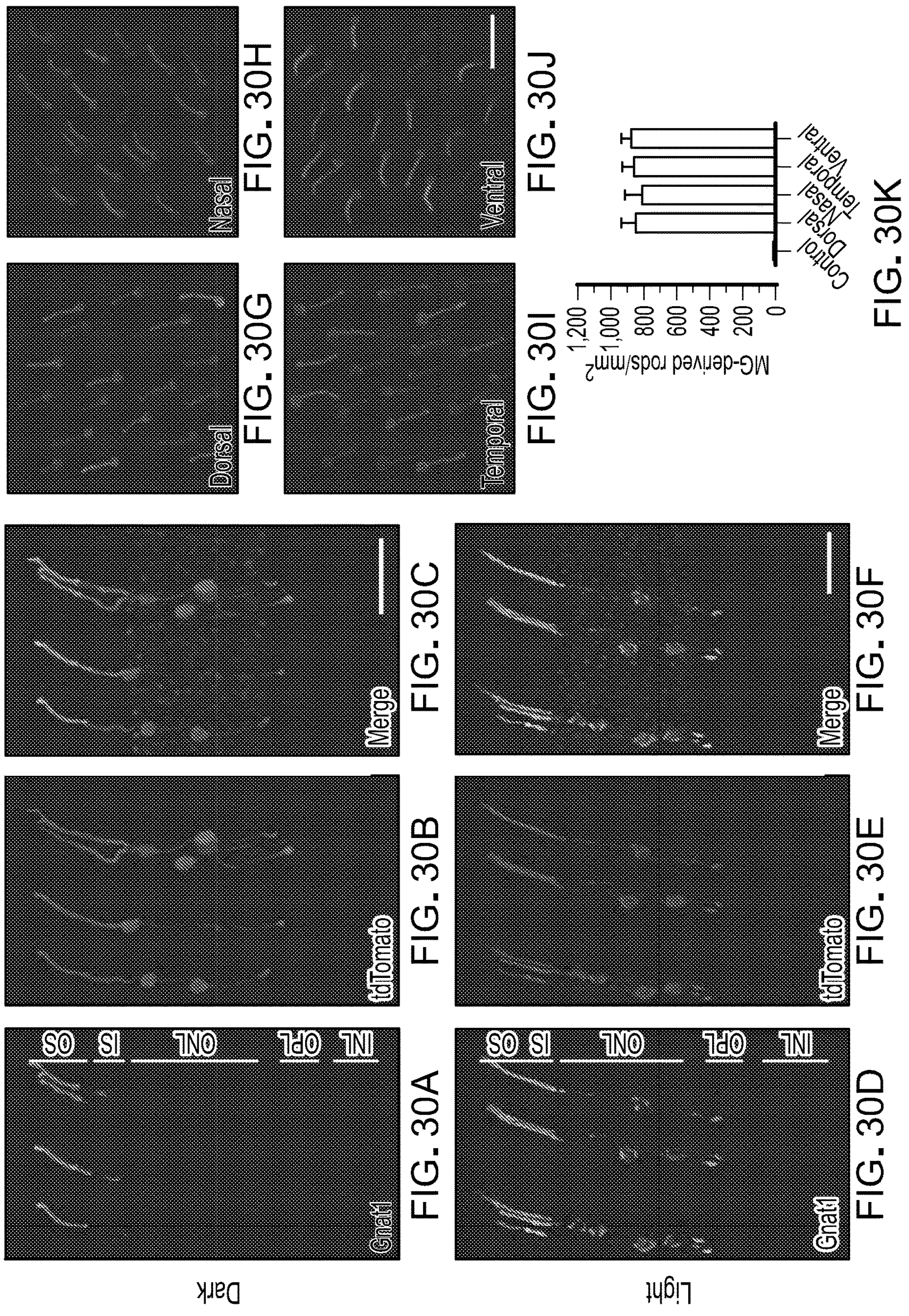
Figure 35A:
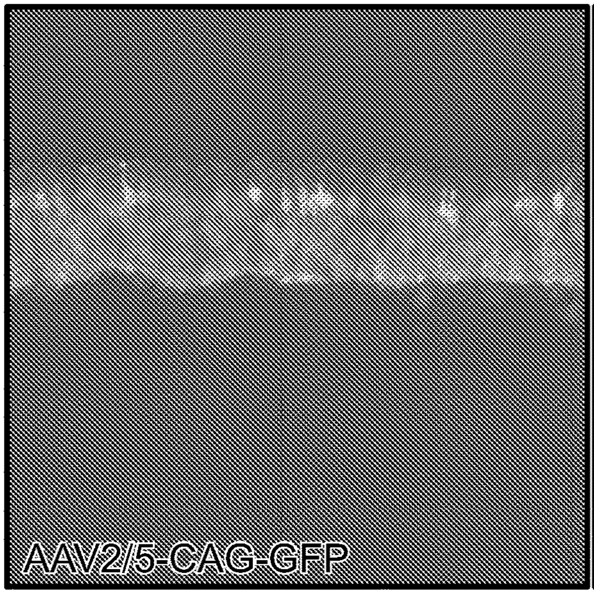
FIG. 35. ShH10-rhodopsin-mediated gene transfer does not transduce photoreceptors even through the subretinal injection route. AAV2/5-CAG-GFP and ShH10-Rhodopsion-tdTomato were co-injected into the subretinal space of the wild-type mouse retina at 4-weeks of age, and the expression of GFP and tdTomato was analyzed 4 weeks later by confocal microscopy in retinal sections. a, Detection of AAV2/5-CAG-GFP. b, Detection of ShH10-rhodopsin-tdTomato. Scale bar: 20 μm.
Figure 35B:
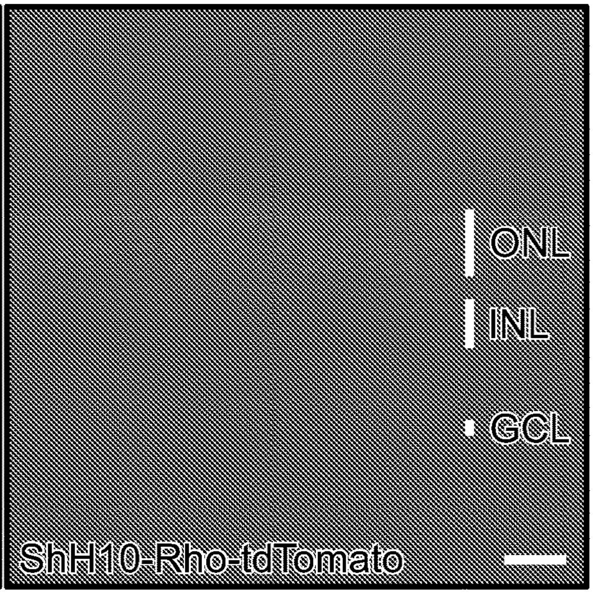
Figure 36A:
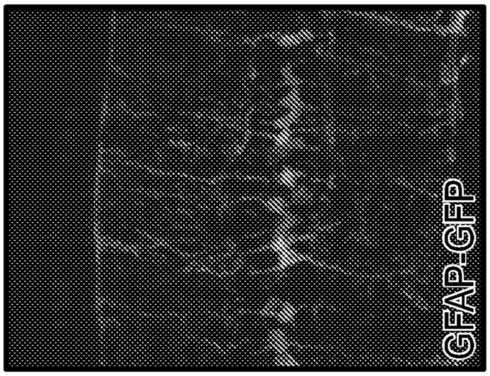
FIG. 36. MG-derived rods eventually turned off the expression of GFAP-GFP over time. Wild-type retinas at 4 weeks of age were first injected with ShH10-GFAP-β-catenin, ShH10-GFAP-GFP, and ShH10-Rhodopsin-tdTomato, followed 2 weeks later by the second injection of ShH10-GFAP-mediated gene transfer of Otx2, Crx and Nrl for rod induction. a-c, Retinas were collected 12 weeks after the second injection and analyzed for the expression of GFAP-GFP in MG-derived rods labeled by Rhodopsin-tdTomato. Scale bar: 25 μm. d. Statistical analysis of the percentage of Rhodopsin-tdTomato+ cells expressing GFAP-GFP. Data are presented as mean±SEM, n=7 retinas.
Figure 36B:
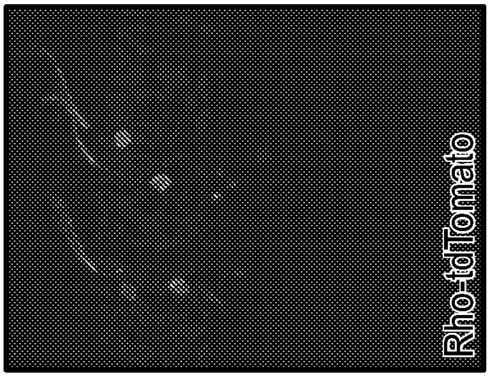
Figure 36C:
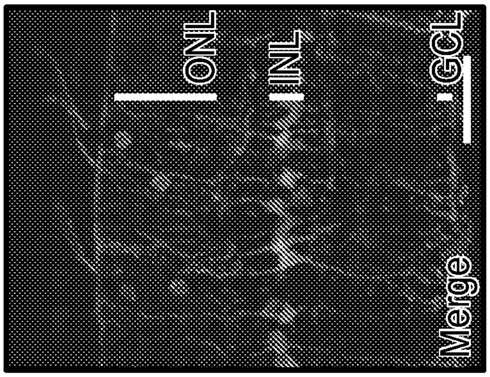
Figure 36D:
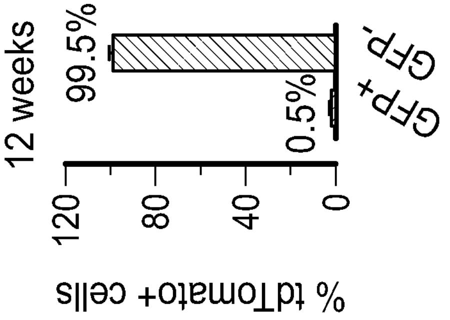
Figure 37A:
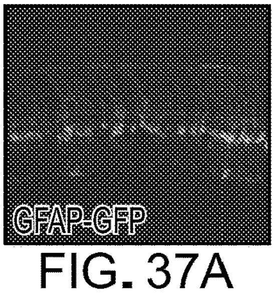
FIG. 37. Treatment with Otx2, Crx, and Nrl individually or in pairs is not sufficient for rod induction. Wild-type retinas were injected with ShH10-GFAP-β-catenin (MG proliferation), ShH10-GFAP-GFP (label transduced MGs), and ShH10-Rhodopsin-tdTomato (label MG-derived rods) at 4 weeks of age, followed 2 weeks later by the second injection of ShH10-GFAP-mediated gene transfer of transcription factors for rod induction. Samples were analyzed by confocal microscopy in retinal sections at 4 weeks after the second injection. a-c, Otx2 treatment. d-f, Crx treatment. g-i, Nrl treatment. j-1, Otx2+Crx treatment. m-o, Otx2+Nrl treatment. p-r, Crx+Nrl treatment. Scale bar: 20 μm.
Figure 37B:
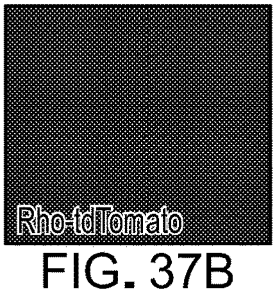
Figure 37C:
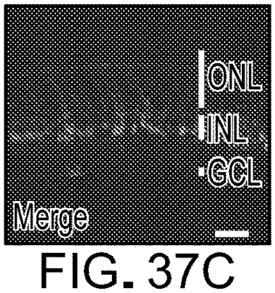
Figure 37D:
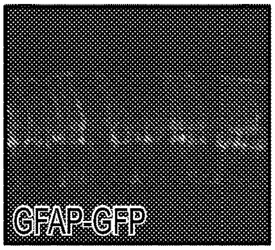
Figure 37E:
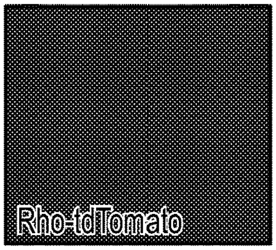
Figure 37F:
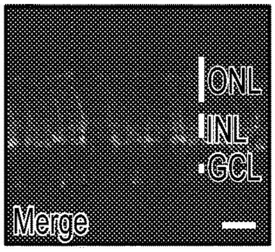
Figure 37G:
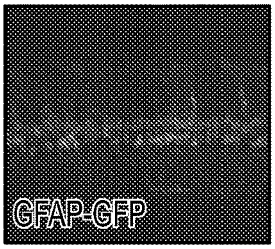
Figure 37H:
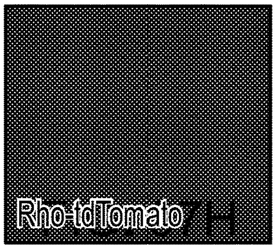
Figure 37I:
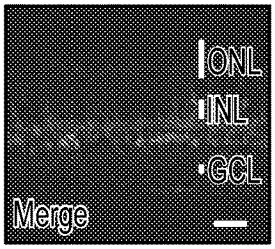
Figure 37J:
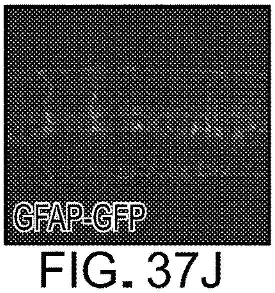
Figure 37K:
Figure 37L:
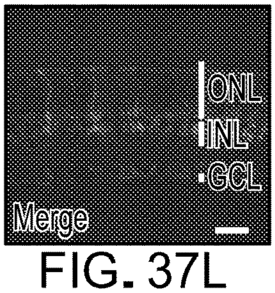
Figure 37M:
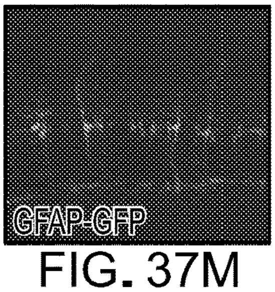
Figure 37N:
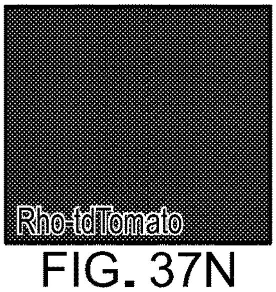
Figure 37O:
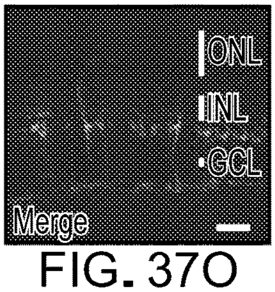
Figure 37P:
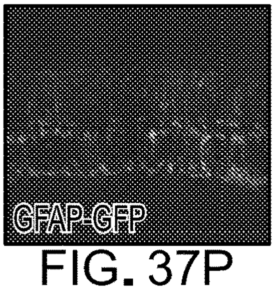
Figure 37Q:
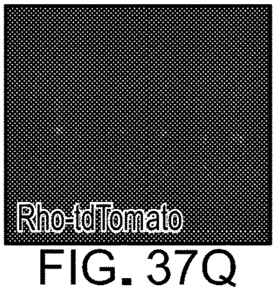
Figure 37R:
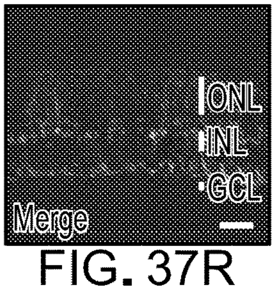

To unambiguously assess the functionality of newly generated rod photoreceptors, we reprogrammed MGs in Gnat1$^{-/-}$:Gnat2$^{cpfl3}$ double mutant mice, which lack photoreceptor-mediated light responses. Gnat1$^{-/-}$ mice lack rod function due to the absence of rod a-transducin, an essential component for rod phototransduction, and are a model of congenital stationary night blindness[9]. Gnat2$^{cpfl3}$ homozygotes have mutated cone a-transducin, with poor cone-mediated responses evident by 3 weeks of age and complete lack of cone-mediated responses at 9 weeks of age[10]. Phototransduction occurs in the outer segment of photoreceptors. Light-driven translocation of Gnat1 allows rods to adapt over a wide range of light intensities[32], and also contributes to rod survival and synaptic transmission to rod bipolar cells[33]. To reconstitute phototransduction in MG-derived rods in Gnat1$^{-/-}$: Gnat2$^{cpfl3}$ mice, we used ShH10-Rhodopsin-mediated gene transfer of the wild-type Gnat1 in MGs, a virus serotype that should not transduce native rods (FIG. 35). Gnat1$^{-/-}$:Gnat2$^{cpl3}$ mice at 4 weeks of age were first injected with ShH10-GFAP-β-catenin (to stimulate MG proliferation), ShH10-Rhodopsin-tdTomato (to label MG-derived rods), and ShH10-Rhodopsin-Gnat1 (to correct the Gnat mutation in MG-derived rods). Four weeks after the second injection for ShH10-GFAP-mediated gene transfer of Otx2, Crx, and Nrl, we observed that Gnat1 was localized to the ROS in the Rhodopsin-tdTomato$^{+}$ MG-derived rods in the dark-adapted retina (FIG. 30*a*). After light stimulation (10,000 lux for 2 hours), Gnat1 translocated towards the inner retina to other cellular compartments including the RIS, rod soma, and synaptic terminal (FIG. 30*d*). However, the co-expressed Rhodopsin-tdTomato, which served as an internal control, was distributed in all cellular compartments regardless of light stimulation (FIG. 30*b, e*). Furthermore, MG-derived rods were generated as effectively in Gnat1$^{-/-}$: Gnat2$^{cpfl3}$ mice as those in wild-type mice, assessed by scoring the number of Rhodopsin-tdTomato$^{+}$ cells in the four quadrants in retinal flatmount preparations (FIG. 30*g-k*). By contrast, no MG-derived rods were observed in control retinas (ShH10-GFAP-β-catenin omitted from the first injection) from Gnat1$^{-/-}$:Gnat2$^{cpfl3}$ mice (FIG. 30*k*).

Figure 31A:
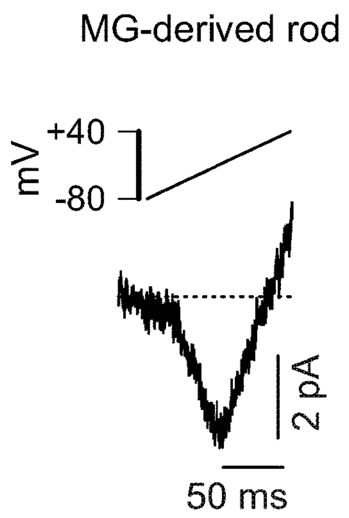
FIG. 31. MG-derived rod photoreceptors integrate into the retinal circuitry and restore visual function in adult $Gnat1^{-/-}$: $Gnat2^{cpfl3}$ mice. a. Evidence of calcium current in MG-derived rods. Figure shows averaged whole-cell current of 11 recordings from 6 MG-derived rods (3 retinas) subjected to a voltage ramp from −80 mV to +40 mV over 120 ms. b-d RGC spike responses to a green light stimulus (1.0-mm diameter) presented on a dark background. Intensity was either 1.3 (control cell) or −1.4 (treated cells) log 10 nW $mm^{-2}$. Spike rate in a response window (horizontal line) was measured relative to two baseline windows (horizontal lines). RGCs from treated retinas showed either an ON response (c) or an OFF response (d). e, Average spike rate to a range of green light stimuli (−1.7 to −0.7 log 10 nW $mm^{-2}$) for 17 control cells (n=7 retinas, 4 animals) and 26 treated cells (n=10 retinas, 6 animals). Treated cells showed significantly higher firing rates (*, p<0.001, t-test). RGCs with responses to the right of the dashed line were categorized as responding cells (n=15). f, Average response (±SEM across cells) of control cells to a range of light intensities (n=11/17 cells tested at a dim/bright range). g, Average response (±SEM across cells) of responding RGCs from treated retinas to a range of light intensities (n=14/9 cells tested at a dim/bright range). Lines show fitted sigmoidal equations that share amplitude (A, 33.8 spikes $s^{-1}$) and exponent (q, 0.705) parameters but have unique semi-saturation constants (σfor green, −2.34 log 10 nW $mm^{-2}$; σfor UV, −1.80 log 10 nW $mm^{-2}$). Cells were ~3.4 times more sensitive to green than UV light, consistent with rod-mediated responses (Lyubarsky et al., 1999; Ke et al., 2014). h, Post-stimulus time histogram (PSTH) showing ON-center RGC spike rate during a light flash in retinas from treated and wild-type (C57/B6; wt) animals. Firing rates are averaged across cells at either high (−1.7 to −0.7 log 10 nW $mm^{-2}$) or low intensities (−3.8 to −3.4 log 10 nW $mm^{-2}$). Shaded regions show ±SEM across cells as a function of time. i, Intensity-response curves for ON RGCs show spike rates (mean±SEM across cells) in treated and wt animals. Over a range of intensities, responses were significantly greater in wt animals (, p<0.002). j, Same format as (h) for OFF-center RGCs. k, Same format as (1) for OFF-center RGCs (*, p<0.05). 1, Example visually-evoked potentials (VEPs) to a light flash (~3.2 log 10 nW $mm^{-2}$ 50 ms) in the primary visual cortex in $Gnat1^{-/-}$:$Gnat2^{epfl3}$ mice in the treatment group (treated), sham group (control) and wt group. For each group, responses from multiple trials in a single animal are superimposed. Responses were absent in the control animal and delayed in the treated animal relative to the wt animal. m, Response amplitude (minimum value of VEP) for n=2-3 animals in each of three groups. Each point represents a single trial, and each box plot shows median±interquartile range; error bars indicate full range (minus outliers). All treated and wt animals showed significant responses (i.e., median response significantly different from zero; ***, p<0.001, Wilcoxin signed-rank test), whereas control mice did not.

Vision is initiated by light-responsive photoreceptors and propagated through synaptic transmission to bipolar cells. Synaptic release from rod photoreceptors requires the calcium current[34,35]. We first examined the calcium current of MG-derived rods in a retinal slice preparation from Gnat1$^{-/-}$:Gnat2$^{cpfl3}$ mice at 4 weeks after the second injection for rod induction. We targeted MG-derived rods (GFAP-GFP$^{+}$ cells) for whole cell voltage clamp using a Cs-based internal solution to reveal voltage-gated calcium currents. Prominent inward currents were recorded with a peak near 0 mV from treated retinas (an average of 11 recordings taken from 6 cells of 3 retinas; FIG. 31*a*), consistent with L-type calcium currents expected in rods[36].

Figure 31B:
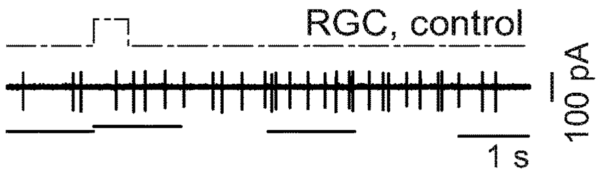
Figure 31C:
Figure 31D:
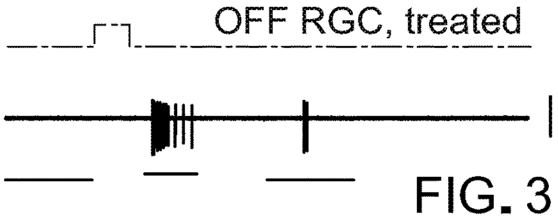
Figure 31E:
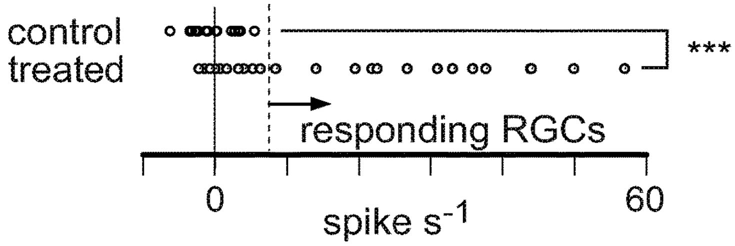
Figure 31F:
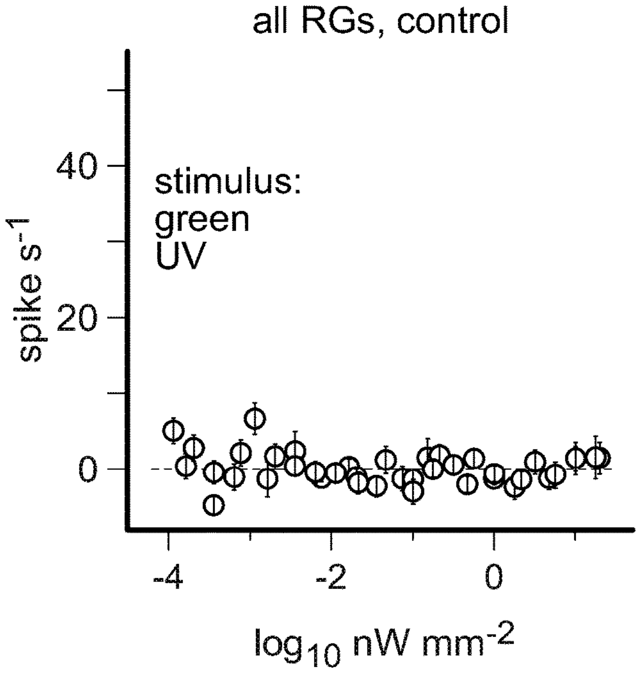
Figure 31G:
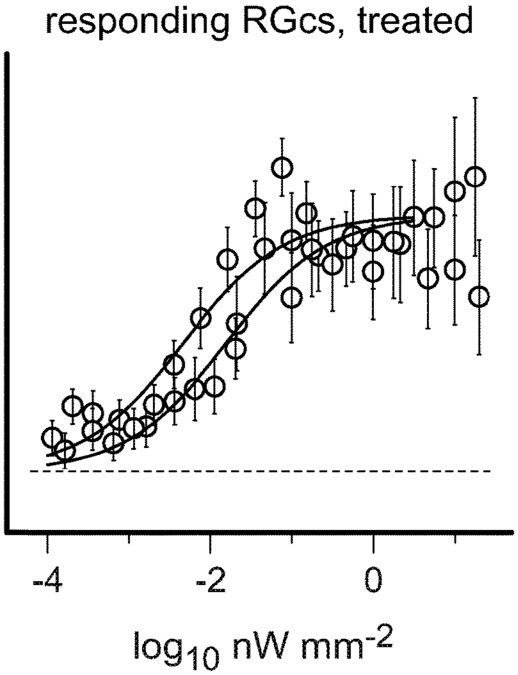
Figure 31H:
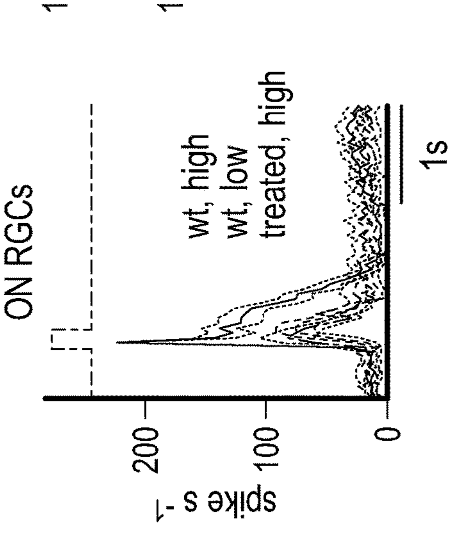
Figure 31I:
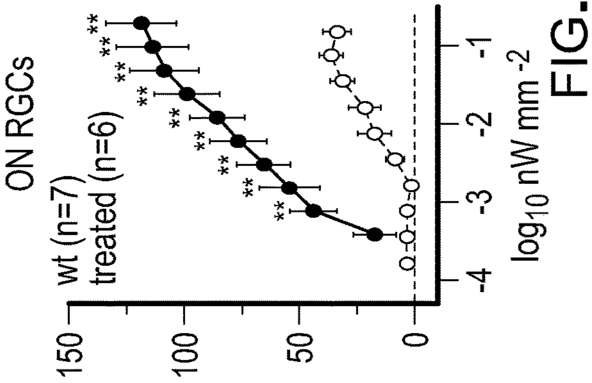
Figure 31J:
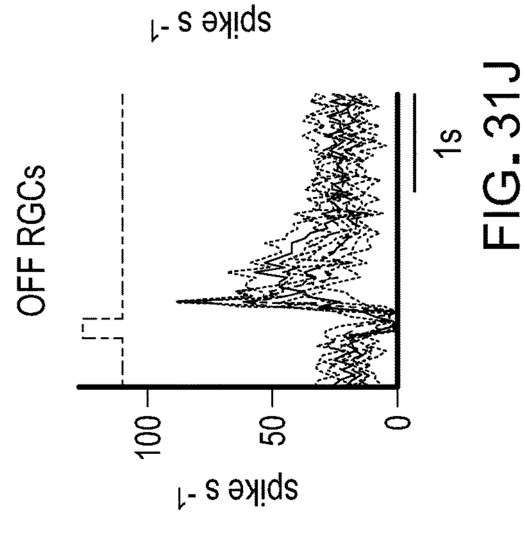
Figure 31K:
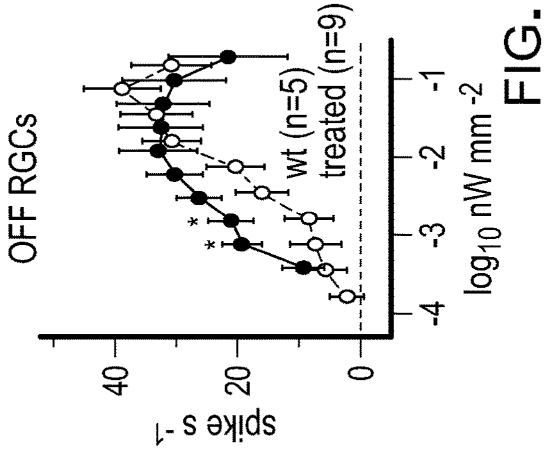

Visual information is integrated by retinal ganglion cells (RGCs), the output neurons of the retina. To examine whether MG-derived rod photoreceptors integrate into retinal circuits, we recorded photoreceptor-mediated light responses from RGCs of Gnat1$^{-/-}$:Gnat2$^{cpfl3}$ mice at 4 weeks after the second injection for rod induction, using an in vitro preparation described previously[37,38]. To distinguish rod- from cone-mediated light responses, we targeted RGCs in the ventral retina, where cones primarily express UV-sensitive cone opsin, with peak sensitivity at 360 nm, whereas rods express the typical green-sensitive rhodopsin with peak at 500 nm37,39-41. Large somas (diameter, >20 μm) in the ganglion cell layer were targeted for loose-patch recordings of action potentials using IR imaging to minimize photobleaching, and subsequently the tissue was exposed to various levels of green and UV light presented within a circular region (1-mm diameter) relative to a dark background. In control retinas (ShH10-GFAP-β-catenin omitted from the first injection), RGCs (n=19 cells from 7 retinas, 4 animals) lacked light responses (FIG. 31*b, e, f*); whereas about half of RGCs from treated retinas (n=15 of 27 cells from 10 retinas, 6 animals) showed clear responses following either light onset (ON cells, n=6; FIG. 31*c*) or light offset (OFF cells, n=9; FIG. 31*d, e, g*). For the entire sample, RGCs from the treated retina showed stronger responses (18.0+/−3.6 spikes $s^{-1}$; mean+/−sem) to green light at an intermediate intensity compared to RGCs from the control retina (−0.03+/−0.76 spikes $s^{-1}$; $p=2.7\times10^{-4}$, FIG. 31*e*). For the responding RGCs from the treated retina (n =15; FIG. 31*e*), the firing rate was ~3.4 times more sensitive to green light as compared to UV light (FIG. 31*g*), consistent with a rod-mediated response[37,38,42]. By comparison, the control cells lacked responses to either green or UV light (FIG. 31*f*). The responding RGCs from treated retinas showed lower sensitivity than RGCs from wild-type (wt; C57/B6 strain) retinas (FIG. 31*h-k*); this was especially evident for ON RGCs (FIG. 31*i*). For both ON and OFF RGCs, responses to a high light level in the treated retina resembled RGC responses to a low light level in the wt retina (FIG. 31*h, j*), which is likely explained by the relatively smaller number of responsive rods in the treated retina.

Figure 31L:
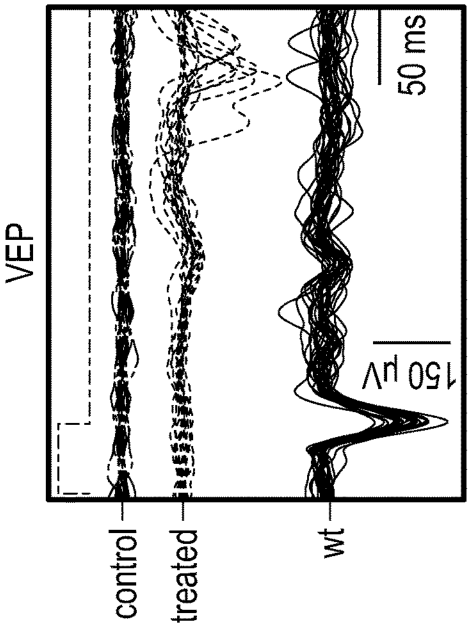
Figure 31M:
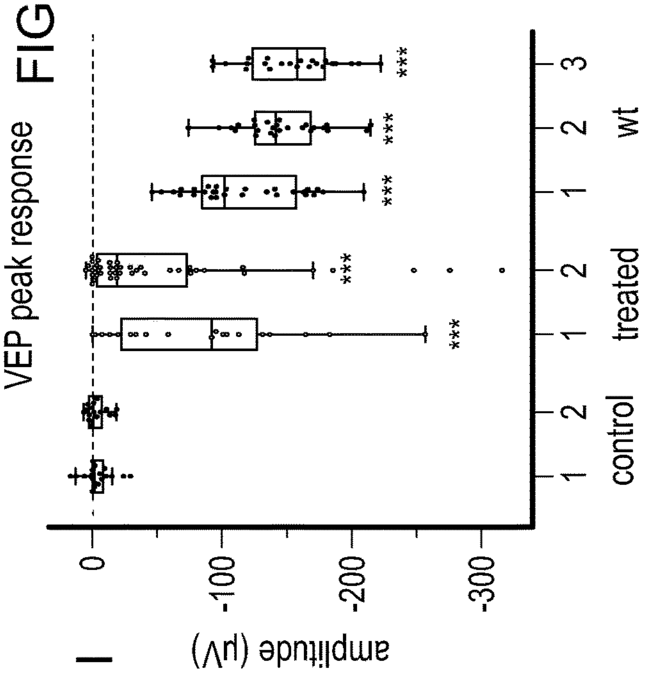
Figure 32A:
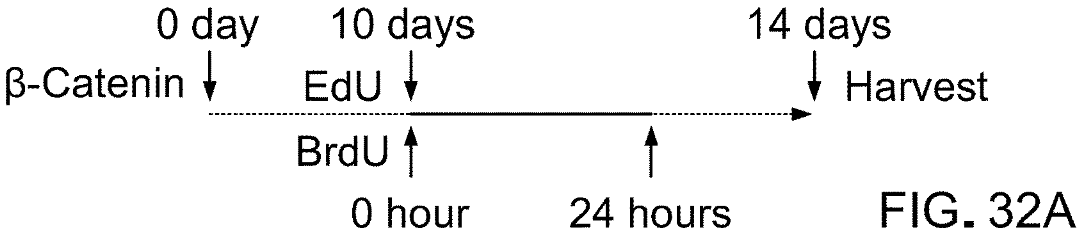
FIG. 32. MGs may undergo only one cell division after β-catenin gene transfer. a, A schematic illustration of EdU/BrdU double-labeling experiment. Wild-type retinas were injected with ShH10-GFAP-β-catenin (0 day), followed by an injection of EdU (10 days). BrdU was either co-injected with EdU (0 hour) or 24 hours later after EdU injection (24 hours). Retinas were harvested 14 days after β-catenin gene transfer. b-g, Detection of EdU and BrdU labeled MGs. Scale bar: 20 μm. b, Statistical analysis of the percentage of MGs labeled by EdU ($EdU^+BrdU^-$), BrdU, or both ($EdU^+$ $BrdU^+$). Data are presented as mean±SEM, n=4 retinas.
Figure 32B:
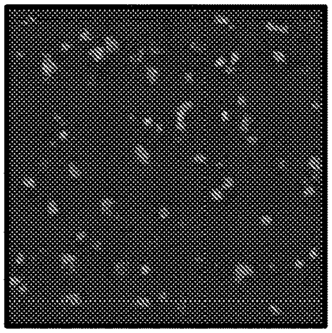
Figure 32E:
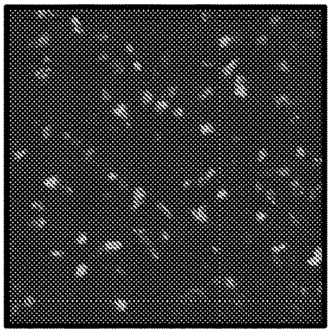
Figure 32C:
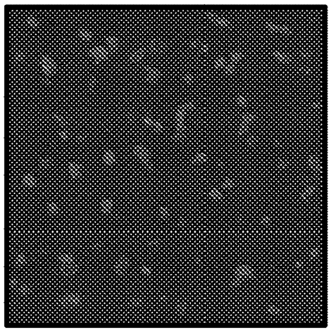
Figure 32F:
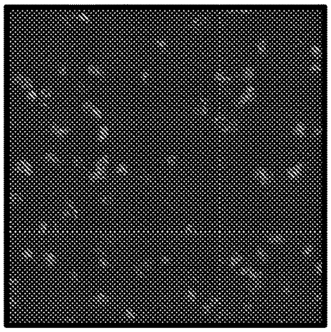
Figure 32D:
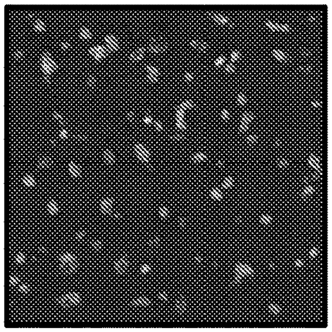
Figure 32G:
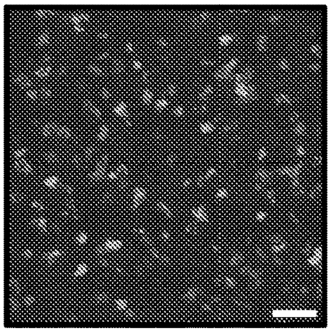
Figure 32H:
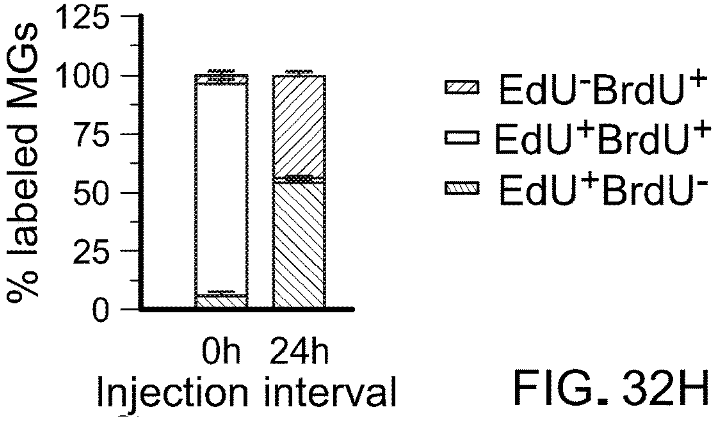

Given the significant photoreceptor-mediated light responses recorded from RGCs of the treated Gnat1−/−: Gnat2$^{epfl3}$ mice in vitro, we reasoned that photoresponses could be transmitted from the retina to the primary visual cortex in the brain in vivo. Visually-evoked potentials (VEPs) were recorded in the primary visual cortices of lightly-anesthetized Gnat1$^{-/-}$:Gnat2$^{cpfl3}$ mice at 4 weeks after the second injection for rod induction from the treated and control (ShH10-GFAP-β-catenin omitted from the first injection) groups. Stimuli were first delivered at low intensity, and the intensity was gradually increased in each session (1.2, 2.8 and 3.2 log 10 nW $mm^{-2}$ at the retina; see Methods). VEPs were identified as negative deflections in the cortical local field potentials (LFPs) following stimulus onset. No response was observed at the dimmest intensity, but gradually stronger responses were observed for the two brighter intensities. At the highest intensity (3.2 log 10 nW $mm^{-2}$), the light stimulus drove a distinctive cortical response in the LFP of the treated group, while no response was recorded in the control group (FIG. 31*l,m*). The responses of the treated group were delayed and smaller relative to responses of C57/B6 wt controls (FIG. 31*l*), perhaps explained by the cortical integration of relatively lower outputs from RGCs in the treated animals. Nevertheless, the significant post-stimulus LFP amplitudes from the treated mice confirmed rescued light response in the primary visual cortices in comparison to the control group (FIG. 31*m*).

Our results demonstrate that MGs, without retinal injury, can be reprogrammed in vivo to generate new rod photoreceptors that integrate into retinal circuits, and restore vision in mammals.

Example 5

Gene Transfer of Ascl1 Stimulates MG Proliferation

Figure 43:
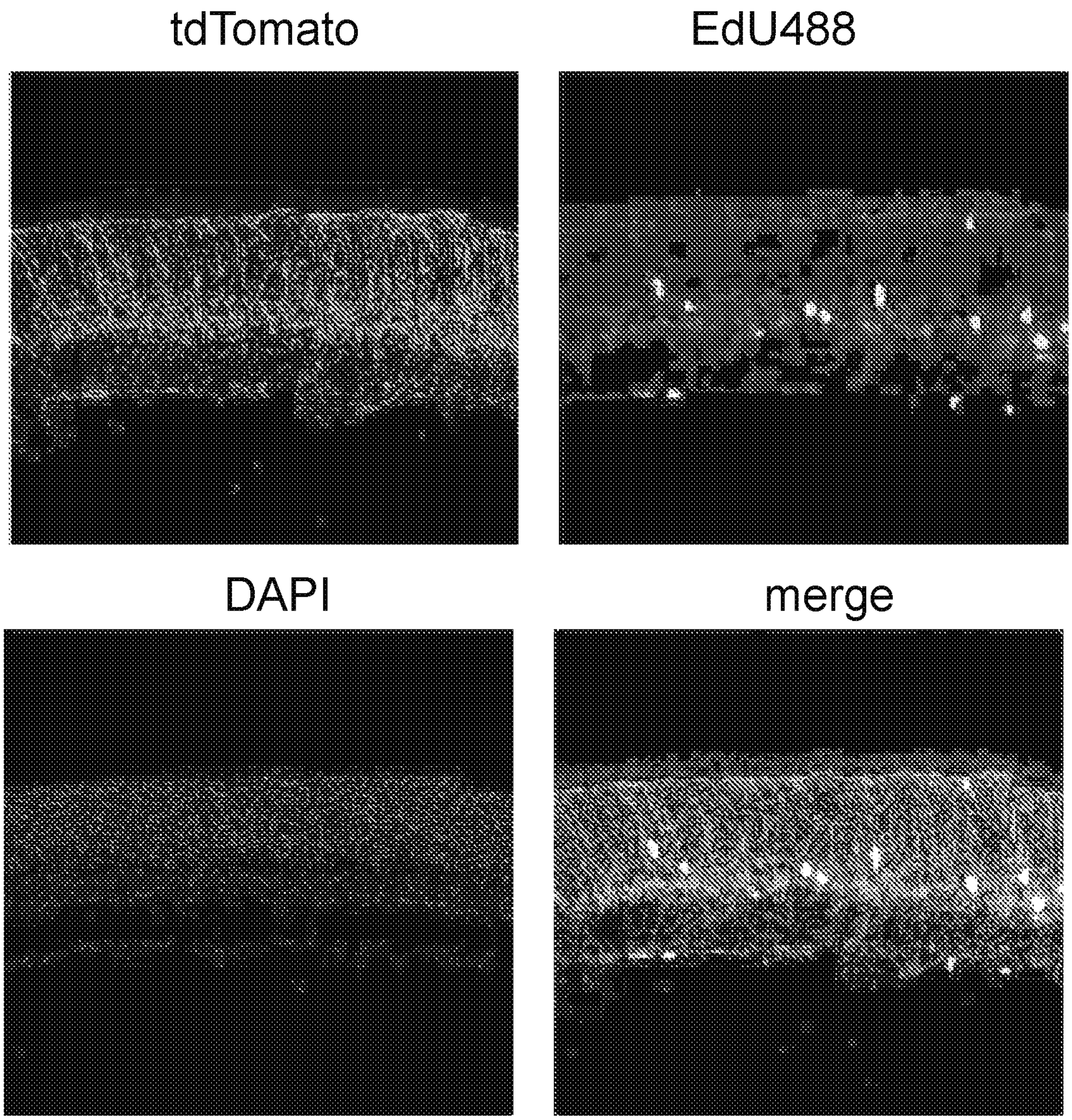
FIG. 43. Stimulation of MG proliferation after AAV-ShH10-GFAP-mediated gene transfer of Ascl 1 in the adult mouse retina. Müller glia are labeled with tdTomato, Proliferative Müller glia are labeled by EdU incorporation assay.

To examine whether Ascl1 expression leads to MG proliferation, EdU incorporation was analyzed following ShH10-GFAP-mediated gene transfer of wild-type Ascl1 in adult mouse retina at 4 weeks of age and MG cell proliferation was performed as described in Example 1. As shown in FIG. 43, ShH10-GFAP-mediate gene transfer of wild-type Ascl1 in adult mouse retina stimulated MG proliferation, as observed by colocalization of MG labeled cells with EdU488.

Methods

Animals

All procedures involving the use of animals in this study were performed in accordance with National Institutes of Health guidelines. Wild-type mice (strain C57BL/6J) and Rosa26-tdTomato reporter mice (strain B6.Cg-Gt(ROSA) $26Sor^{tm14(CAG\text{-}tdTomato)Hze}$/J) were obtained from the Jackson Laboratory (Bar Harbor, ME). $Gnat1^{-/-}$:$Gnat2^{cpfl3}$ double mutant mice were kindly provided by Dr. Bo Chang (The Jackson Laboratory, Bar Harbor, ME). For light adaptation, the mice were placed in the dark for at least 12 hours and the pupils were dilated with 1% tropicamide and 1% atropine before exposure to 10,000 lux white light for 2 hours. For dark adaptation, the mice were maintained in the dark for more than 12 hours and all procedures were performed under infrared illumination.

AAV Production and Intravitreal Injection cDNAs encoding GFP, tdTomato, β-Catenin, Otx2, Crx and Nrl were subcloned and inserted into a AAV vector backbone where the expression was driven by the GFAP promoter (a gift from Dr. Lin Tian at UC Davis), or the Rhodopsin promoter (subcloned from pRho-DsRed (Addgene ±11156). The Gnat1 cDNA, reversely transcribed and amplified from mouse retinal RNAs, was used to replace tdTomato in pAAV-Rho-tdTomato to build the pAAV-Rho-Gnat1 vector. Individual Adeno-associated virus (AAV) was produced by plasmid co-transfection and iodixanol gradient ultracentrifugation. Purified AAVs were concentrated with Amicon Ultra-15 Filter Units (Millipore, Bedford, MA) to a final titer of $1.0\text{-}5.0\times10^{13}$ genome copies/mL (FIG. 42). Intravitreal injection was performed using a microsyringe equipped with a 33-gauge needle. The tip of the needle was passed through the sclera, at the equator and next to the dorsal limbus of the eye, into the vitreous cavity. Injection volume was 1 µl per eye for AAVs.

EdU and BrdU Co-Labeling and Detection

EdU or BrdU solution (1 µL, 1 mg/mL) was intravitreally injected into the vitreous chamber. For BrdU detection, the retinas were rinsed with PBS after fixation with 4% paraformaldehyde and incubated with 2 M HCl for 30 min at room temperature. Rinse the retinas with PBS and incubate with a blocking buffer containing 5% normal donkey serum, 0.1% surfactant TRITON X-100™, and 0.1% NaN3 in PBS for 2 hours at room temperature. Primary antibody for BrdU (Thermo Scientific) was added for overnight incubation at 4° C. Retinas were washed with PBS and incubated with secondary antibody (DyLight™594-conjugated AffiniPure Donkey Anti-Mouse IgG, Jackson ImmunoResearch) for 2 hours at room temperature. Analysis of EdU incorporation was performed using a kit CLICK-IT EDU KIT™ (Thermo Scientific). EdU detection components were re-suspended according to manufacturer's instructions and applied directly to retinal samples. In brief, the solution for each EdU reaction has a total volume of 250 µl composed of 215 µl buffer 1X CLICK-IT™ reaction buffer, 10 µl CuSO4, 0.6 µl dye ALEXA FLUOR™ azide, and 25 µl 1X Reaction buffer additive. After incubation in the reaction solution for 30 min at room temperature, samples were washed with PBS and mounted with Fluoromount-G for detection.

Immunohistochemistry and Imaging

Retinas were fixed with 4% paraformaldehyde in PBS for 30 min at room temperature, and sectioned at 20-µm thickness. Sample slides were washed with PBS before incubation with a blocking buffer containing 5% normal donkey serum, 0.1% surfactant TRITON X-100™, and 0.1% NaN3 in PBS for 2 hours at room temperature. Primary antibodies were added for overnight incubation at 4° C. Primary antibodies used: Rhodopsin (1:250, Thermo Scientific, MS-1233-P1), Peripherin-2 (1:500, Millipore, MABN293), Recoverin (1:500, Millipore, AB5585), Gnat1 (1:1000, Santa Cruz, sc-389), PKCα (1:100, Santa Cruz, sc-8393), and Ribeye (1:500, Synaptic Systems, 192103). Sections were washed with PBS and incubated with secondary antibodies (Jackson ImmunoResearch) for 2 hours at room temperature. Cell nuclei were counterstained with DAPI (Sigma). Confocal Images were acquired using a Zeiss LSM 510 EXCITER microscope.

Transmission Electron Microscopy

The whole eye was fixed in 2.5% gluteraldehyde and 2% paraformaldehyde in 0.1M sodium cacodylate buffer pH7.4 with for 1 hour at room temperature. After the cornea was removed, samples were postfixed in 1% osmium tetroxide for 1 hour, en bloc stained in 2% aqueous uranyl acetate for a further hour then rinsed, dehydrated in ethanol and propylene oxide and infiltrated with Embed 812 (Electron Microscopy Science). The blocks were hardened overnight at 60° C. 60-nm sections were cut with a Leica ultramicrotome and collected on formvar/carbon coated nickel grids. Grids were placed section side down on drops of 1% hydrogen peroxide for 5 minutes, blocked for nonspecific binding on 3% bovine serum albumin in PBS containing 1% surfactant TRITON X™ for 30 minutes. Grids were incubated overnight as a primary antibody with either a rabbit anti-GFP (T. Südhof lab, Stanford University) at 1:200 or rabbit anti-TdTomato at 1:100 (Clontech, 632496), rinsed in buffer and then incubated with the secondary antibody 10 nm protein A gold (Utrecht UMC) for 30 mins. The grids were well rinsed in PBS, fixed in 1% gluteraldehyde for 5 mins, rinsed again, dried and stained using 2% aqueous uranyl acetate and lead citrate. Sample grids were viewed using FEI Tencai Biotwin TEM at 80 kV of accelating voltage. Images were acquired with a Morada CCD camera and iTEM (Olympus) software.

Mouse Retinal Slice Preparation and Calcium Current Recordings

Gnat1−/−:$Gnat2^{cpfl3}$ mice were anaesthetized with isoflurane (Sigma), sacrificed by cervical dislocation, and their eyes enucleated. Whole retinas were isolated and placed on a 0.45-µm cellulose acetate/nitrate membrane filter (Millipore), which was secured with vacuum grease to a glass slide adjacent to the recording chamber. Slices were cut to a thickness of 150 µm using a tissue slicer, and transferred to the recording chamber while remaining submerged. The recording chamber was immediately attached to a perfusion system, and the slices were perfused at a rate of 5 mL min-1 with Ames media bubbled with 95% 02 and 5% $CO_2$. All stages of retinal preparation were carried out at room temperature in a dark room. The standard recording solution for regenerated rods was composed of (in mM): 108 gluconic acid, 5 EGTA, 10 CsCl, 10 TEA, 4 MgATP, 1LIGTP. The pH was adjusted to 7.4 with CsOH. The osmolarity of both extracellular and intracellular solutions was 289-293, with a pH of 7.35-7.40.

Patch pipettes (tip resistance, 10-12 MΩ) were fabricated from borosilicate glass (TWF150-4, WPI) using a two-stage vertical puller (Narishige). Pipettes were coated with Sticky Wax, (Kerr Corp). Whole-cell recordings were obtained using a dual EPC10/2 amplifier (HEKA Instruments). Slices were viewed with a Zeiss Axioskop 2FS plus equipped with a water-immersion 40X DIC objective and using an infrared filter for illumination. Regenerated rods were identified by their shape, GFP fluorescence and position in the slice. Illumination for epifluorescence was performed using an X-Cite 120Q lamp (EXFO) with a 488 nm bandpass excitation filter set for imaging GFP fluorescence or 590 bandpass filter set for imaging RFP. Images were acquired before whole cell recording with Andor iXon camera controlled by a Shutter driver VCM-D1. Data were acquired using PatchMaster (HEKA Instruments), and analysis performed using Igor Pro (WaveMetrics) and Origin 7.5 (Microcal). Currents were elicited at 60-second intervals, collected at 20 kHz, and low-pass filtered at 1 kHz.

RGC Recordings

Retinas from Gnat1$^{-/-}$:Gnat2$^{cpfl3}$ double mutant mice were prepared as described previously (Wang et al., 2011; Ke et al., 2014). After dissecting the retina under infrared light, the tissue was superfused with Ames' medium bubbled with 95% $O_2$ and 5% $CO_2$ in a chamber on a microscope (Olympus BX51WI) stage at ~34 deg C. A patch pipette (tip resistance, ~3-5 MΩ) filled with Ames' medium was used to form a loose seal (~50-200 M (2) on a large soma (>20-μm diameter) to record action potentials. Cells were targeted under microscopic control using infrared light, a 60X water objective lens (NA, 0.9) and an infrared-sensitive camera (Retiga 1300, Qcapture software; Qimaging Corporation). Data were sampled at 10 kHz and recorded on a computer using a MultiClamp 700B amplifier and pClamp9 software (Molecular Devices).

A total of 12 animals were studied, six treated animals, four controls (i.e., beta-catenin delivery omitted from first virus injection) and two C57/B6 wildtype. Of these, six animals (three treated, three controls) were studied in a double blind fashion; the person performing the virus injection was not aware of the identity of the virus condition, and the person performing the recording did not know the treatment group of the animal until the conclusion of all experiments.

Light stimuli were 1-mm-diameter spots generated by green (peak, 530 nm) or ultraviolet (UV; peak, 370 nm) LEDs that were diffused and windowed by the aperture in the microscope's fluorescence port and projected through a 4× objective lens (NA, 0.13) onto the photoreceptor layer. In some experiments, light was attenuated with a 2.0 neutral density filter (NDF; Kodak Wratten, Edmund Optics) that attenuated green and UV light by 130- and 880-fold, respectively. Light was presented as 200-ms flashes on darkness every 10 secs. In one block of trials, green and UV light flashes were alternated for 10 levels, with increasing intensity over time. For some cells, the entire block was repeated both with and without the NDF in place. For some cells with weak or absent responses, light flashes were presented in the brighter range only. For cells with sensitive responses, flashes were presented either in the dimmer range only or in both ranges. Firing rate (spikes s-') was recorded during a response window (300-500 ms) and normalized by subtracting the average firing rate measured during baseline periods before (500 ms) and after the flash (500 ms, FIG. 31*b*-*d*). If there was an obvious response to either light onset or offset, the response window was adjusted accordingly (FIG. 31*c*, *d*). If there was not an obvious response, the window for light onset was used by default (FIG. 31*b*).

RGC responses were quantified by averaging firing rates for green flashes in the intensity range of −1.7 to −0.7 log 10 nW/mm$^2$ (FIG. 31*e*), which included four flash levels for blocks with or without the NDF in place. From these averaged responses, we selected responding cells from the treated group that exceeded the largest response measured in the control group. For responding RGCs in the treated group, we averaged the response across cells and combined data over the dimmer and brighter stimulus ranges (FIG. 31*g*). We fit the flash intensity-response function using the equation:

$$R(I)=AI^q(I^q+\sigma^q)^{-1},$$

where I is intensity (nW mm$^{-2}$), A is the maximum response amplitude (spikes s-1), o is the intensity that drives a half-saturating response, and q determines the slope. The fitted curves shared A and q parameters with unique o parameters for green and UV stimuli. Fitting was performed using least-squares routines in Matlab (Mathworks).

Visually-Evoked Potentials (VEPs) and Multi-Unit Activity (MUA) Recordings

Under isoflurane anesthesia (2%; Baxter, Deerfield IL), an injection of xylocaine/epinephrine (1.0%; AstraZeneca, Wilmington, DE) was delivered beneath the skin overlying the skull. The skull was then exposed, cleaned of tissue, and coated with a thin layer of cyanoacrylate adhesive (VetBond, 3M, St. Paul MN). A second layer of cyanoacrylate adhesive (Maxi-Cure, BSI, Atascadero CA) was used to attach 2 metal bars to the pretreated skull; these bars were then used to secure the head into a custom-built stereotaxic apparatus. A craniotomy was made over primary visual cortex, leaving the dura mater intact. Body temperature was maintained at 36° C. during surgery and experiments via a beating pad placed below the subject. Pupils were dilated with 1% tropicamide and 1% atropine, and the eyes were then coated with a thin layer of silicone oil (Sigma, St. Louis MO) to prevent dehydration.

Neurophysiological signals were collected using a 16-site silicon probe with 4 recording sites on each of 4 shanks (100-μm vertical separation between recording sites; 125-μm horizontal spacing between shanks; 1-2-MΩ impedance; NeuroNexus Technologies, Ann Arbor MI). After the probe was lowered through the dura mater and into the cortex, a layer of agarose (1.5% in ACSF; Sigma) was applied to cover the craniotomy. An insulated silver wire (0.25-mm diameter; Medwire, Mt. Vernon NY) inserted above the cerebellum served as a reference electrode. Signals were preamplified 10× (MPA8I preamplifiers; Multi Channel Systems MCS GmbH, Reutlingen, Germany) before being amplified 200x and band-pass filtered at 0.3-5000 Hz (Model 3500; A-M Systems, Inc., Carlsborg, WA). The amplified and filtered signals were sampled at 25 kHz using a digital interface (Power 1401 mk 2; Cambridge Electronic Design, Cambridge, UK).

After the recording probe was implanted, isoflurane was lowered to 1.0-1.5% and mice were given 30 minutes to adapt to the dimly-lit testing area before visual stimuli were delivered. Stimuli were 50-ms flashes of white light from a light-omitting diode (LED) that was placed 1 cm from the eye. The LED had two peaks, at ~460 and ~550 nm, with an integrated intensity of ~20 μW mm$^2$; taking into account the spectral tuning of Rhodopsin, this corresponded to an equivalent intensity at 500 nm (i.e., the peak sensitivity of Rhodopsin) of ~7.55 μW mm$^2$ at the cornea and ~1.42 μW mm$^{-2}$ (or ~3.2 log 10 nW mm 2) on the retina (assuming a 4-mm$^2$ dilated pupil area and evenly-spread light over the ~21.2 mm$^2$ retinal area). Visually-evoked potentials were identified as negative deflections in the cortical local field potentials (LFPs) following stimulus onset, with greater negative amplitudes in deeper cortical layers than in superficial layers. For LFP analyses, the recording channel with the greatest negative amplitude in response to visual stimulation was used. Maximum negative deflections in the LFP during the 0.5 s following stimulus onset were measured, and, for each animal, we tested whether the median of the response distribution differed from zero (Wilcoxin signed-rank test). Analyses were performed using MATLAB (The Math Works, Inc., Natick, MA), Spike2 (Cambridge Electronic Design) and GraphPad Prism 6 (GraphPad Software, San Diego, CA).

Statistical Analysis

Statistical differences between different experimental groups were typically analyzed by a Student's t-test or one-way ANOVA test except in cases where the data were not normally distributed (e.g., LFP amplitudes), in which case a non-parametric test was used, as described above. Data are presented as mean±SEM, except where data were skewed (e.g., LFP amplitudes), in which case a box plot indicates median #inter-quartile range. A value of $p<0.05$ is considered significant.

REFERENCES

1 Goldman, D. Müller glial cell reprogramming and retina regeneration. Nat Rev Neurosci 15, 431-442, doi: nm3723 [pii] 10.1038/nm3723 (2014).
2 Jorstad, N. L. et al. Stimulation of functional neuronal regeneration from Müller glia in adult mice. Nature 548, 103-107, doi: nature23283 [pii] 10.1038/nature23283 (2017).
3 Karl, M. O. et al. Stimulation of neural regeneration in the mouse retina. Proc Natl Acad Sci USA 105, 19508-19513, doi: 0807453105 [pii] 10.1073/pnas. 0807453105 (2008).
4 Dyer, M. A. & Cepko, C. L. Control of Müller glial cell proliferation and activation following retinal injury. Nat Neurosci 3, 873-880, doi: 10.1038/78774 (2000).
5 Ooto, S. et al. Potential for neural regeneration after neurotoxic injury in the adult mammalian retina. Proc Natl Acad Sci USA 101, 13654-13659, doi: 10.1073/pnas.0402129101 0402129101 [pii] (2004).
6 Close, J. L., Liu, J., Gumuscu, B. & Reh, T. A. Epidermal growth factor receptor expression regulates proliferation in the postnatal rat retina. Glia 54, 94-104, doi: 10.1002/glia.20361 (2006).
7 Ueki, Y. et al. Transgenic expression of the proneural transcription factor Ascl1 in Müller glia stimulates retinal regeneration in young mice. Proc Natl Acad Sci USA 112, 13717-13722, doi: 1510595112 [pii] 10.1073/pnas. 1510595112 (2015).
8 Yao, K. et al. Wnt Regulates Proliferation and Neurogenic Potential of Müller Glial Cells via a Lin28/let-7 miRNA-Dependent Pathway in Adult Mammalian Retinas. Cell Rep 17, 165-178, doi: S2211-1247 (16) 31174-3 [pii] 10.1016/j.celrep.2016.08.078 (2016),
9 Calvert, P. D. et al. Phototransduction in transgenic mice after targeted deletion of the rod transducin alpha-subunit. Proc Natl Acad Sci USA 97, 13913-13918, doi: 10.1073/pnas.250478897 250478897 [pii] (2000).
10 Chang, B. et al. Cone photoreceptor function loss-3, a novel mouse model of achromatopsia due to a mutation in Gnat2. Invest Ophthalmol Vis Sci 47, 5017-5021, doi: 47/11/5017 [pii] 10.1167/iovs.05-1468 (2006).
11 Fausett, B. V. & Goldman, D. A role for alpha1 tubulin-expressing Müller glia in regeneration of the injured zebrafish retina. J Neurosci 26, 6303-6313, doi: 26/23/6303 [pii] 10.1523/JNEUROSCI.0332-06.2006 (2006).
12 Bernardos, R. L., Barthel, L. K., Meyers, J. R. & Raymond, P. A. Late-stage neuronal progenitors in the retina are radial Müller glia that function as retinal stem cells. J Neurosci 27, 7028-7040, doi: 27/26/7028 [pii] 10.1523/JNEUROSCI. 1624-07.2007 (2007).
13 Fimbel, S. M., Montgomery, J. E., Burket, C. T. & Hyde, D. R. Regeneration of inner retinal neurons after intravitreal injection of ouabain in zebrafish. J Neurosci 27, 1712-1724, doi: 27/7/1712 [pii] 10.1523/JNEUROSCI.5317-06.2007 (2007).
14 Thummel, R., Kassen, S. C., Montgomery, J. E., Enright, J. M. & Hyde, D. R. Inhibition of Müller glial cell division blocks regeneration of the light-damaged zebrafish retina. Dev Neurobiol 68, 392-408, doi: 10.1002/dneu.20596 (2008).
15 Ramachandran, R., Reifler, A., Parent, J. M. & Goldman, D. Conditional gene expression and lineage tracing of tubala expressing cells during zebrafish development and retina regeneration. J Comp Neurol 518, 4196-4212, doi: 10.1002/cne.22448 (2010).
16 Qin, Z., Barthel, L. K. & Raymond, P. A. Genetic evidence for shared mechanisms of epimorphic regeneration in zebrafish. Proc Natl Acad Sci USA 106, 9310-9315, doi: 0811186106 [pii] 10.1073/pnas.0811186106 (2009).
17 Wan, J. & Goldman, D. Opposing Actions of Fgf8a on Notch Signaling Distinguish Two Müller Glial Cell Populations that Contribute to Retina Growth and Regeneration. Cell Rep 19, 849-862, doi: S2211-1247 (17) 30484-9 [pii] 10.1016/j.celrep.2017.04.009 (2017).
18 Sahel, J. A. et al. Mitogenic effects of excitatory amino acids in the adult rat retina. Exp Eye Res 53, 657-664 (1991).
19 Nishida, A. et al. Otx2 homeobox gene controls retinal photoreceptor cell fate and pineal gland development. Nat Neurosci 6, 1255-1263 (2003).
20 Chen, S. et al. Crx, a novel Otx-like paired-homeodomain protein, binds to and transactivates photoreceptor cell-specific genes. Neuron 19, 1017-1030 (1997).
21 Furukawa, T., Morrow, E. M. & Cepko, C. L. Crx, a novel otx-like homeobox gene, shows photoreceptor-specific expression and regulates photoreceptor differentiation. Cell 91, 531-541 (1997).
22 Mears, A. J. et al. Nrl is required for rod photoreceptor development. Nat Genet 29, 447-452 (2001).
23 Livesey, F. J. & Cepko, C. L. Vertebrate neural cell-fate determination: lessons from the retina. Nat Rev Neurosci 2, 109-118, doi: 10.1038/35053522 (2001).
24 Ajioka, I. et al. Differentiated horizontal interneurons clonally expand to form metastatic retinoblastoma in mice. Cell 131, 378-390, doi: S0092-8674 (07) 01224-X [pii] 10.1016/j.cell.2007.09.036 (2007).
25 Matsuda, T. & Cepko, C. L. Electroporation and RNA interference in the rodent retina in vivo and in vitro. Proc Natl Acad Sci USA 101, 16-22 (2004).

26 Matsuda, T. & Cepko, C. L. Controlled expression of transgenes introduced by in vivo electroporation. Proc Natl Acad Sci USA 104, 1027-1032 (2007).

27 Chen, B. & Cepko, C. L. HDAC4 regulates neuronal survival in normal and diseased retinas. Science 323, 256-259 (2009).

28 Guo, X. et al. A short N-terminal domain of HDAC4 preserves photoreceptors and restores visual function in retinitis pigmentosa. Nat Commun 6, 8005, doi: ncomms9005 [pii] 10.1038/ncomms9005 (2015).

29 Madisen, L. et al. A robust and high-throughput Cre reporting and characterization system for the whole mouse brain. Nat Neurosci 13, 133-140, doi: nn.2467 [pii] 10.1038/nn.2467 (2010).

30 Kuzmanovic, M., Dudley, V. J. & Sarthy, V. P. GFAP promoter drives Müller cell-specific expression in transgenic mice. Invest Ophthalmol Vis Sci 44, 3606-3613 (2003)

31 Emerson, M. M., Surzenko, N., Goetz, J. J., Trimarchi, J. & Cepko, C. L. Otx2 and Onecut1 promote the fates of cone photoreceptors and horizontal cells and repress rod photoreceptors. Dev Cell 26, 59-72, doi: S1534-5807 (13) 00344-4 [pii] 10.1016/j.devcel.2013.06.005 (2013).

32 Sokolov, M. et al. Massive light-driven translocation of transducin between the two major compartments of rod cells: a novel mechanism of light adaptation. Neuron 34, 95-106, doi: S0896627302006360 [pii] (2002).

33 Majumder, A. et al. Transducin translocation contributes to rod survival and enhances synaptic transmission from rods to rod bipolar cells. Proc Natl Acad Sci USA 110, 12468-12473, doi: 1222666110 [pii] 10.1073/pnas.1222666110 (2013).

34 Schmitz, Y. & Witkovsky, P. Dependence of photoreceptor glutamate release on a dihydropyridine-sensitive calcium channel. Neuroscience 78, 1209-1216, doi: S0306452296006781 [pii] (1997).

35 Thoreson, W. B., Nitzan, R. & Miller, R. F. Reducing extracellular Cl-suppresses dihydropyridine-sensitive Ca2+currents and synaptic transmission in amphibian photoreceptors. J Neurophysiol 77, 2175-2190 (1997).

36 Corey, D. P., Dubinsky, J. M. & Schwartz, E. A. The calcium current in inner segments of rods from the salamander (Ambystoma tigrinum) retina. J Physiol 354, 557-575 (1984).

37 Wang, Y. V., Weick, M. & Demb, J. B. Spectral and temporal sensitivity of cone-mediated responses in mouse retinal ganglion cells. J Neurosci 31, 7670-7681, doi: 31/21/7670 [pii] 10.1523/JNEUROSCI.0629-11.2011 (2011).

38 Ke, J. B. et al. Adaptation to background light enables contrast coding at rod bipolar cell synapses. Neuron 81, 388-401, doi: S0896-6273 (13) 01006-4 [pii] 10.1016/j.neuron.2013.10.054 (2014).

39 Applebury, M. L. et al. The murine cone photoreceptor: a single cone type expresses both S and M opsins with retinal spatial patterning. Neuron 27, 513-523, doi: S0896-6273 (00) 00062-3 [pii] (2000).

40 Nikonov, S. S., Kholodenko, R., Lem, J. & Pugh, E. N., Jr. Physiological features of the S- and M-cone photoreceptors of wild-type mice from single-cell recordings. J Gen Physiol 127, 359-374, doi: jgp.200609490 [pii] 10.1085/jgp.200609490 (2006).

41 Baden, T. et al. A tale of two retinal domains: near-optimal sampling of achromatic contrasts in natural scenes through asymmetric photoreceptor distribution. Neuron 80, 1206-1217, doi: S0896-6273 (13) 00861-1 [pii] 10.1016/j.neuron.2013.09.030 (2013)

42 Lyubarsky, A. L., Falsini, B., Pennesi, M. E., Valentini, P. & Pugh, E. N., Jr. UV- and midwave-sensitive cone-driven retinal responses of the mouse: a possible phenotype for coexpression of cone photopigments. J Neurosci 19, 442-455 (1999)

The disclosures of each and every patent, patent application, and publication cited herein are hereby incorporated herein by reference in their entirety. In case of conflict, the present disclosure controls.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating rod-mediated vision loss or impairment in a subject, comprising:

(a) administering intravitreally to the subject a therapeutically effective amount of a first AAV-ShH10 vector comprising a polynucleotide encoding β-catenin operably linked to a glial fibrillary acidic protein (GFAP) promoter; and (b) at least one week after the administering of step (a), administering intravitreally to the subject a therapeutically effective amount of a second AAV-ShH10 vector comprising a nucleic acid encoding Otx2 operably linked to a GFAP promoter, a third AAV-ShH10 vector comprising a nucleic acid encoding Crx operably linked to a GFAP promoter, and a fourth AAV-ShH10 vector comprising a nucleic acid encoding Nrl operably linked to a GFAP promoter, wherein the expression of β-catenin, Otx2, Crx, and Nrl results in differentiation of mature photoreceptors.

2. The method of claim 1, wherein the subject has a condition selected from age-related macular degeneration (AMD), diabetic retinopathy, retinitis pigmentosa (RP), Bardet-Biedl syndrome, and an eye cancer that causes rod photoreceptor loss.

3. A method of treating rod-mediated vision loss or impairment comprising administering intravitreally to a subject (a) a first AAV-ShH10 vector comprising a polynucleotide encoding β-catenin operably linked to a glial fibrillary acidic protein (GFAP) promoter; and (b) at least two weeks after the administering step in (a), administering intravitreally second AAV-ShH10 vector comprising a nucleic acid encoding Otx2 operably linked to a GFAP promoter, a third AAV-ShH10 vector comprising a nucleic acid encoding Crx operably linked to a GFAP promoter, and a fourth AAV-ShH10 vector comprising a nucleic acid encoding Nrl operably linked to a GFAP promoter; and wherein the expression of β-catenin, Otx2, Crx, and Nrl results in differentiation of mature photoreceptors.

4. The method of claim 3, wherein the subject has a condition selected from age-related macular degeneration (AMD), diabetic retinopathy, retinitis pigmentosa (RP), Bardet-Biedl syndrome, and an eye cancer that causes rod photoreceptor loss.

* * * * *